(12) United States Patent
Babaoglu et al.

(10) Patent No.: US 9,096,586 B2
(45) Date of Patent: Aug. 4, 2015

(54) THERAPEUTIC COMPOUNDS

(71) Applicant: Gilead Sciences, Inc., Foster City, CA (US)

(72) Inventors: Kerim Babaoglu, Lansdale, PA (US); Gediminas Brizgys, San Mateo, CA (US); Hongtao Liu, Cupertino, CA (US); Ryan McFadden, Foster City, CA (US); Michael L. Mitchell, Hayward, CA (US); Yingmei Qi, Sunnyvale, CA (US); Paul A. Roethle, San Francisco, CA (US); Lianhong Xu, Palo Alto, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 138 days.

(21) Appl. No.: 13/867,016

(22) Filed: Apr. 19, 2013

(65) Prior Publication Data
US 2013/0281434 A1  Oct. 24, 2013

Related U.S. Application Data

(60) Provisional application No. 61/636,602, filed on Apr. 20, 2012, provisional application No. 61/718,165, filed on Oct. 24, 2012.

(51) Int. Cl.

| | |
|---|---|
| *A61K 31/425* | (2006.01) |
| *A61K 31/4965* | (2006.01) |
| *A61K 31/497* | (2006.01) |
| *A61K 31/505* | (2006.01) |
| *A61K 31/44* | (2006.01) |
| *A61K 31/415* | (2006.01) |
| *C07D 417/14* | (2006.01) |
| *C07D 417/10* | (2006.01) |
| *A61K 31/4439* | (2006.01) |
| *A61K 31/444* | (2006.01) |
| *A61K 31/506* | (2006.01) |
| *A61K 31/496* | (2006.01) |
| *A61K 31/428* | (2006.01) |
| *C07D 471/04* | (2006.01) |

(Continued)

(52) U.S. Cl.
CPC ............ *C07D 417/14* (2013.01); *A61K 31/428* (2013.01); *A61K 31/437* (2013.01); *A61K 31/4375* (2013.01); *A61K 31/444* (2013.01); *A61K 31/4439* (2013.01); *A61K 31/454* (2013.01); *A61K 31/4709* (2013.01); *A61K 31/4741* (2013.01); *A61K 31/496* (2013.01); *A61K 31/497* (2013.01); *A61K 31/4985* (2013.01); *A61K 31/501* (2013.01); *A61K 31/506* (2013.01); *A61K 31/513* (2013.01); *A61K 31/5377* (2013.01); *A61K 31/5383* (2013.01); *A61K 31/551* (2013.01); *A61K 31/553* (2013.01); *A61K 45/06* (2013.01); *C07D 277/66* (2013.01); *C07D 277/82* (2013.01); *C07D 417/04* (2013.01); *C07D 417/10* (2013.01); *C07D 471/04* (2013.01); *C07D 487/04* (2013.01); *C07D 491/06* (2013.01); *C07D 498/04* (2013.01)

(58) Field of Classification Search
CPC .. C07D 417/02; C07D 417/14; C07D 417/04; C07D 471/14; C07D 471/06; C07D 491/06; A61K 31/428; A61K 31/4436; A61K 31/436; A61K 31/437; A61K 31/4741; A61K 31/496
USPC ............... 514/367, 255.05, 252.14, 269, 303, 514/406, 382; 548/152; 544/367, 333, 114; 546/89
See application file for complete search history.

(56) References Cited

U.S. PATENT DOCUMENTS

| | | | |
|---|---|---|---|
| 3,895,028 | A | 7/1975 | Wada et al. |
| 3,900,486 | A | 8/1975 | Suzuki et al. |

(Continued)

FOREIGN PATENT DOCUMENTS

| | | |
|---|---|---|
| CA | 1144556 A1 | 4/1983 |
| CN | 1123275 A | 5/1996 |

(Continued)

OTHER PUBLICATIONS

Chen, S. et al. (2009). "Design, Synthesis and Biological Evaluation of Novel Quinolone Derivatives as HIV-1 Tat-TAR Interaction Inhibitors," *Bioorganic & Medicinal Chem.* 17:1948-1956.
Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.
Porto, S. et al. (2007). "Chiral Thiols: The Assignment of Their Absolute Configuration by $^1$H NMR," *Organic Letters* 9(24):5015-5018.
Richman, D.D. (2001). "HIV Chemotherapy," *Nature* 410:995-1001.
Sagar, K.S. et al. (Aug. 1, 2004). "Preparation and Anti-HIV Activities of Retrojusticidin B Analogs and Azalignans," *Bioorg. Med. Chem.* 12(15):4045-4054.
Wang, C.Y. et al. (Dec. 2004). "Pharmacokinetic and Metabolic Studies of Retrojusticidin B, a Potential Anti-Viral Lignan, in Rats," *Planta Medica* 70(12):1161-1165.
Willgerodt, C. et al. (1900). "Regarding Quino-α:p-α-Phenyl and Quino-α:p-α Methyl Quinoline-γ-Hydroxy Acid," *Reports of the German Chemical Society* 33(3):2927-2935 (with full English Translation).

(Continued)

*Primary Examiner* — Shengjun Wang

(57) ABSTRACT

Compounds of formula I':

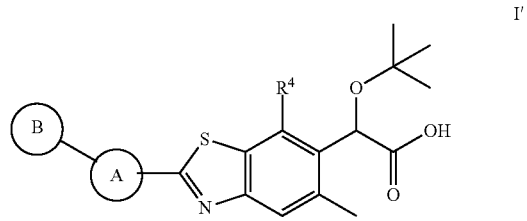

or salts thereof are provided. Pharmaceutical compositions comprising a compound of formula I', processes for preparing compounds of formula I', intermediates useful for preparing compounds of formula I' and therapeutic methods for treating the proliferation of the HIV virus, treating AIDS or delaying the onset of AIDS or ARC symptoms in a mammal are also provided.

20 Claims, No Drawings

(51) Int. Cl.

| | | |
|---|---|---|
| A61K 31/437 | (2006.01) | |
| A61K 31/513 | (2006.01) | |
| A61K 31/5377 | (2006.01) | |
| A61K 31/454 | (2006.01) | |
| C07D 498/04 | (2006.01) | |
| A61K 31/5383 | (2006.01) | |
| A61K 31/4375 | (2006.01) | |
| A61K 31/4709 | (2006.01) | |
| A61K 31/501 | (2006.01) | |
| C07D 487/04 | (2006.01) | |
| A61K 31/4985 | (2006.01) | |
| A61K 31/553 | (2006.01) | |
| A61K 31/551 | (2006.01) | |
| A61K 45/06 | (2006.01) | |
| A61K 31/4741 | (2006.01) | |
| C07D 277/82 | (2006.01) | |
| C07D 491/06 | (2006.01) | |
| C07D 417/04 | (2006.01) | |
| C07D 277/66 | (2006.01) | |

(56) References Cited

U.S. PATENT DOCUMENTS

| | | |
|---|---|---|
| 4,816,570 A | 3/1989 | Farquhar |
| 4,968,788 A | 11/1990 | Farquhar |
| 5,434,188 A | 7/1995 | Boschelli et al. |
| 5,663,159 A | 9/1997 | Starrett, Jr. et al. |
| 5,733,906 A | 3/1998 | Jungheim et al. |
| 5,738,985 A | 4/1998 | Miles et al. |
| 5,792,756 A | 8/1998 | Starrett, Jr. et al. |
| 5,798,365 A | 8/1998 | Kirsch et al. |
| 7,514,233 B2 | 4/2009 | Debyser et al. |
| 8,008,470 B2 | 8/2011 | Debyser et al. |
| 2005/0165052 A1 | 7/2005 | Fakhfakh et al. |
| 2005/0239819 A1 | 10/2005 | Satoh et al. |
| 2005/0261336 A1 | 11/2005 | Mousnier et al. |
| 2006/0035926 A1 | 2/2006 | Lee et al. |
| 2006/0094755 A1 | 5/2006 | Rajagopalan et al. |
| 2006/0275748 A1 | 12/2006 | Debyser et al. |
| 2009/0197862 A1 | 8/2009 | Steinig et al. |
| 2009/0203742 A1 | 8/2009 | Surleraux et al. |
| 2010/0311735 A1 | 12/2010 | Tsantrizos et al. |
| 2011/0223131 A1 | 9/2011 | Jin et al. |
| 2013/0203727 A1 | 8/2013 | Babaoglu et al. |
| 2013/0210801 A1 | 8/2013 | Babaoglu et al. |
| 2013/0231331 A1 | 9/2013 | Pendri et al. |
| 2013/0281433 A1 | 10/2013 | Babaoglu et al. |
| 2014/0031338 A1* | 1/2014 | Chasset et al. ........... 514/211.05 |
| 2014/0045818 A1 | 2/2014 | Mitchell et al. |

FOREIGN PATENT DOCUMENTS

| | | |
|---|---|---|
| CN | 1044117 C | 7/1999 |
| CN | 1466576 A | 1/2004 |
| CR | 20140213 A | 6/2014 |
| DE | 24 03 682 A1 | 7/1974 |
| EP | 0 017 543 A1 | 10/1980 |
| EP | 1 441 228 A1 | 7/2004 |
| EP | 1 541 558 A1 | 6/2005 |
| EP | 1 565 471 B1 | 10/2006 |
| EP | 1 873 238 A1 | 1/2008 |
| EP | 1 873 238 B1 | 1/2008 |
| GB | 2 154 583 A | 9/1985 |
| JP | 3-287558 A | 12/1991 |
| WO | WO-91/19721 A1 | 12/1991 |
| WO | WO-94/23041 A2 | 10/1994 |
| WO | WO-94/23041 A3 | 10/1994 |
| WO | WO-99/52850 A1 | 10/1999 |
| WO | WO-00/63152 A1 | 10/2000 |
| WO | WO-02/18341 A2 | 3/2002 |
| WO | WO-02/18341 A3 | 3/2002 |
| WO | WO-02/083657 A2 | 10/2002 |
| WO | WO-02/083657 A3 | 10/2002 |
| WO | WO-2004/014371 A1 | 2/2004 |
| WO | WO-2004/046115 A1 | 6/2004 |
| WO | WO-2004/087153 A2 | 10/2004 |
| WO | WO-2004/087153 A3 | 10/2004 |
| WO | WO-2005/120508 A1 | 12/2005 |
| WO | WO-2006/001958 A2 | 1/2006 |
| WO | WO-2006/001958 A3 | 1/2006 |
| WO | WO-2006/002185 A1 | 1/2006 |
| WO | WO-2006/045554 A1 | 5/2006 |
| WO | WO-2006/116412 A2 | 11/2006 |
| WO | WO-2006/116412 A3 | 11/2006 |
| WO | WO-2006/124780 A2 | 11/2006 |
| WO | WO-2006/124780 A3 | 11/2006 |
| WO | WO-2007/016392 A2 | 2/2007 |
| WO | WO-2007/016392 A3 | 2/2007 |
| WO | WO-2007/131350 A1 | 11/2007 |
| WO | WO-2007/138472 A2 | 12/2007 |
| WO | WO-2007/138472 A3 | 12/2007 |
| WO | WO-2007/147884 A1 | 12/2007 |
| WO | WO-2008/053478 A2 | 5/2008 |
| WO | WO-2008/071587 A2 | 6/2008 |
| WO | WO-2008/071587 A3 | 6/2008 |
| WO | WO-2009/062285 A1 | 5/2009 |
| WO | WO-2009/062288 A1 | 5/2009 |
| WO | WO-2009/062289 A1 | 5/2009 |
| WO | WO-2009/062308 A1 | 5/2009 |
| WO | WO-2009/095500 A1 | 8/2009 |
| WO | WO-2010/059658 A1 | 5/2010 |
| WO | WO-2010/130034 A1 | 11/2010 |
| WO | WO-2010/130842 A1 | 11/2010 |
| WO | WO-2011/002635 A1 | 1/2011 |
| WO | WO-2011/015641 A1 | 2/2011 |
| WO | WO-2011/047129 A1 | 4/2011 |
| WO | WO-2011/076765 A1 | 6/2011 |
| WO | WO-2011/106445 A1 | 9/2011 |
| WO | WO-2011/149950 A2 | 12/2011 |
| WO | WO-2011/149950 A3 | 12/2011 |
| WO | WO-2012/003497 A1 | 1/2012 |
| WO | WO-2012/003498 A1 | 1/2012 |
| WO | WO-2012/033735 A1 | 3/2012 |
| WO | WO-2012/065963 A2 | 5/2012 |
| WO | WO-2012/065963 A3 | 5/2012 |
| WO | WO-2012/066442 A1 | 5/2012 |
| WO | WO-2012/088365 A1 | 6/2012 |
| WO | WO-2012/102985 A1 | 8/2012 |
| WO | WO-2012/137181 A1 | 10/2012 |
| WO | WO-2012/138669 A1 | 10/2012 |
| WO | WO-2012/138670 A1 | 10/2012 |
| WO | WO-2012/140243 A1 | 10/2012 |
| WO | WO-2012/145728 A1 | 10/2012 |
| WO | WO-2013/002357 A1 | 1/2013 |
| WO | WO-2013/025584 A1 | 2/2013 |
| WO | WO-2013/043553 A1 | 3/2013 |
| WO | WO-2013/058409 A1 | 4/2013 |
| WO | WO-2013/058448 A1 | 4/2013 |
| WO | WO-2013/062028 A1 | 5/2013 |
| WO | WO-2013/103724 A1 | 7/2013 |
| WO | WO-2013/103738 A1 | 7/2013 |
| WO | WO-2013/106643 A2 | 7/2013 |
| WO | WO-2013/106643 A3 | 7/2013 |
| WO | WO-2013/123148 A1 | 8/2013 |
| WO | WO-2013/134113 A1 | 9/2013 |
| WO | WO-2013/134142 A1 | 9/2013 |
| WO | WO-2013/157622 A1 | 10/2013 |
| WO | WO-2013/159064 A1 | 10/2013 |
| WO | WO-2014/009794 A1 | 1/2014 |
| WO | WO-2014/028384 A1 | 2/2014 |
| WO | WO-2014/055603 A1 | 4/2014 |
| WO | WO-2014/055618 A1 | 4/2014 |

OTHER PUBLICATIONS

Palella, F.J. et al. (Mar. 26, 1998). "Declining Morbidity and Mortality Among Patients with Advanced Human Immunodeficiency Virus Infection," *N. Engl. J. Med.* 338(13):853-860.

Pauwels, R. et al. (Jun. 1987). "Sensitive and Rapid Assay on MT-4 Cells for Detection of Antiviral Compounds Against the AIDS Virus," *J. Virol. Methods* 16(3):171-185.

(56) References Cited

OTHER PUBLICATIONS

Zhan, P. et al. (2009). "Synthesis and Anti-HIV Activity Evaluation of 2-(4-(Naphthalen-2-yl)-1,2,3-thiadiazol-5-ylthio)-N-Acetamides as Novel Non-Nucleosides HIV-1 Reverse Transcriptase Inhibitors," *European Journal of Medicinal Chem.* 44:4648-4653.

Zouhiri, F. et al. (2001). "HIV-1 Replication Inhibitors of the Styrylquinoline Class: Incorporation of a Masked Diketo Acid Pharmacophore," *Tetrahedron Letters* 42:8189-8192.

International Search Report mailed on Feb. 21, 2013, for PCT Patent Application No. PCT/US2013/020172 filed on Jan. 3, 2013, four pages.

International Search Report mailed on Sep. 1, 2011, for PCT Patent Application No. PCT/US2011/042880 filed on Jul. 1, 2011, four pages.

International Search Report mailed on Sep. 14, 2011, for PCT Patent Application No. PCT/US2011/042881 filed on Jul. 1, 2011, seven pages.

International Search Report mailed on Mar. 26, 2013, for PCT Patent Application No. PCT/US2013/020151 filed on Jan. 3, 2013, five pages.

International Search Report mailed on Jul. 2, 2012, for PCT Patent Application No. PCT/US2012/034593 filed on Apr. 20, 2012, five pages.

International Search Report mailed on Aug. 5, 2013, for PCT Patent Application No. PCT/US2013/037483 filed on Apr. 19, 2013, three pages.

Written Opinion of the International Searching Authority mailed on Sep. 1, 2011, for PCT Patent Application No. PCT/US2011/042880 filed on Jul. 1, 2011, six pages.

Written Opinion of the International Searching Authority mailed on Sep. 14, 2011, for PCT Patent Application No. PCT/US2011/042881 filed on Jul. 1, 2011, 12 pages.

Written Opinion of the International Searching Authority mailed on Jul. 2, 2012, for PCT Patent Application No. PCT/US2012/034593 filed on Apr. 20, 2012, six pages.

International Preliminary Report on Patentability mailed on Jan. 17, 2013, for PCT Patent Application No. PCT/US2011/042880 filed on Jul. 1, 2011, 7 pages.

European Communication mailed on Oct. 15, 2013 for European Patent Application No. 11738878.5 filed on Jul. 1, 2011, four pages.

U.S. Appl. No. 14/112,473, filed Oct. 17, 2013, by Mitchell et al.

Notice of Allowance mailed on Nov. 7, 2014, for U.S. Appl. No. 13/866,997, filed on Apr. 19, 2013, eight pages.

Costa Rican Opposition submitted by Asociacion De Genericos Farmaceuticos to the Costa Rican Patent Office against Costa Rican Patent Application No. 20140231, filed on Apr. 19, 2013, sixteen pages.

European Office Action mailed on Oct. 20, 2014, for European Patent Application No. 13719355.3, filed on Apr. 19, 2013, four pages.

Benzaria, S. et al. (Dec. 6, 1996). "Synthesis, in Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," *J. Med. Chem.* 39(25):4958-4965.

Bundgaard, H. (1991). "Design and Application of Prodrugs," Chapter 5 in *A Textbook of Drug Design and Development*, Krogsgaard-Larsen, P. et al. eds., Harwood Academic Publishers, Chur, Switzerland, pp. 113-191.

De Lombaert, S. et al. (Feb. 18, 1994). "N-Phosphonomethyl Dipeptides and Their Phosphonate Prodrugs, a New Generation of Neutral Endopeptidase (NEP, EC 3.4.24.11) Inhibitors," *J. Med. Chem.* 37(4):498-511.

Farquhar, D. et al. (Mar. 1983). "Biologically Reversible Phosphate-Protective Groups," *J. Pharm. Sci.* 72(3):324-325.

Khamnei, S. et al. (Sep. 27, 1996). "Neighboring Group Catalysis in the Design of Nucleotide Prodrugs," *J. Med. Chem.* 39(20):4109-4115.

Kocienski, P.J. (May 1994). "Protecting Groups: An Overview," Chapter 1 in *Protecting Groups*, Thieme Publishing Group: New York, NY, pp. 1-20.

Kocienski, P.J. (May 1994). "Hydroxyl Protecting Groups," Chapter 2 in *Protecting Groups*, Thieme Publishing Group: New York, NY, pp. 21-94.

Kocienski, P.J. (May 1994). "Diol Protecting Groups," Chapter 3 in *Protecting Groups*, Thieme Publishing Group: New York, NY, pp. 95-117.

Kocienski, P.J. (May 1994). "Carboxyl Protecting Groups," Chapter 4 in *Protecting Groups*, Thieme Publishing Group: New York, NY, pp. 118-154.

Kocienski, P.J. (May 1994). "Carbonyl Protecting Groups," Chapter 5 in *Protecting Groups*, Thieme Publishing Group: New York, NY, pp. 155-184.

McGinnity, D.F. et al. (Nov. 2004, e-pub. Jul. 30, 2004). "Evaluation of Fresh and Cryopreserved Hepatocytes as in Vitro Drug Metabolism Tools for the Prediction of Metabolic Clearance," *Drug Metab. Dispos.* 32(11):1247-1253.

Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," *J. Chem. Soc. Perkin Trans. II* 2345-2353.

Obach, R.S. et al. (Oct. 1997). "The Prediction of Human Pharmacokinetic Parameters from Preclinical and in Vitro Metabolism Data," *J. Pharmacol. Exp. Ther.* 283(1):46-58.

Puech, F. et al. (Oct. 1993). "Intracellular Delivery of Nucleoside Monophosphates Through a Reductase-Mediated Activation Process," *Antiviral Res.* 22(2-3):155-174.

Spivey, A.C. et al. (1999, e-pub. Dec. 4, 1999). "Configurationally Stable Biaryl Analogues of 4-(Dimethylamino) Pyridine: A Novel Class of Chiral Nucleophilic Catalysts," *J. Org. Chem.* 64(26):9430-9443.

Restriction Requirement mailed on Nov. 8, 2013 for U.S. Appl. No. 13/866,997, filed on Apr. 19, 2013, eight pages.

Bolivian Opposition submitted to the Bolivian Patent Office for Bolivian Patent Application No. SP-0194-2011, filed on Jul. 1, 2011, two pages.

Bolivian Opposition submitted to the Bolivian Patent Office for Bolivian Patent Application No. SP-0195-2011, filed on Jul. 1, 2011, two pages.

Costa Rican Office Action mailed on Aug. 23, 2013 for Costa Rican Patent Application No. 20130045, filed on Jul. 1, 2011, three pages.

Costa Rican Opposition submitted to the Costa Rican Patent Office for Costa Rican Patent Application No. 20130043, filed on Jul. 1, 2011, three pages.

European Communication mailed on Feb. 8, 2013 for European Patent Application No. 11738878.5 filed on Jul. 1, 2011, two pages.

Pakistani Office Action mailed on Nov. 10, 2012 for Pakistani Patent Application No. 4932011, filed on Jul. 1, 2011, two pages.

Pakistani Office Action mailed on Nov. 10, 2012 for Pakistani Patent Application No. 4942011, filed on Jul. 1, 2011, two pages.

Taiwanese Office Action mailed on Nov. 5, 2013 for Taiwanese Patent Application No. 100123357, filed on Jul. 1, 2011, nine pages.

Al-Mawsawi, L.Q. et al. (Feb. 7, 2011; e-pub. Jan. 12, 2011). "Allosteric inhibitor development targeting HIV-1 integrase," *ChemMedChem.* 6(2):228-241.

Balakrishnan, M. et al. (Sep. 9, 2013). "Non-catalytic site HIV-1 integrase inhibitors disrupt core maturation and induce a reverse transcription block in target cells," *PloS One* 8(9):e74163, 12 Total Pages.

Bartholomeeusen, K. et al. (Apr. 24, 2009; e-pub. Feb. 25, 2009). "Lens epithelium-derived growth factor/p75 interacts with the transposase-derived DDE domain of PogZ," *J. Biol. Chem.* 284(17):11467-11477.

Busschots, K. et al. (Feb. 2, 2007; e-pub. Nov. 3, 2006). "Identification of the LEDGF/p75 binding site in HIV-1 integrase," *J. Mol. Biol.* 365(5):1480-1492.

Busschots, K. et al. (Jan. 2009; e-pub. Oct. 16, 2008). "In search of small molecules blocking interactions between HIV proteins and intracellular cofactors," *Mol. Biosyst.* 5(1):21-31.

Chakraborty, A. et al. (Mar. 1, 2013; e-pub. Dec. 25, 2012). "Biochemical interactions between HIV-1 integrase and reverse transcriptase," *FEBS Letters* 587(5):425-429.

(56) References Cited

OTHER PUBLICATIONS

Cherepanov, P. et al. (Jun. 2005; e-pub. May 15, 2005). "Solution structure of the HIV-1 integrase-binding domain in LEDGF/p75," *Nat. Struct. Mol. Biol.* 12(6):526-532.

Cherepanov, P. et al. (Nov. 29, 2005; e-pub. Oct. 31, 2005). "Structural basis for the recognition between HIV-1 integrase and transcriptional coactivator p75," *PNAS* 102(48):17308-17313.

Christ, F. et al. (Aug. 2012; e-pub. Jun. 4, 2012). "Small-molecule inhibitors of the LEDGF/p75 binding site of integrase block HIV replication and modulate integrase multimerization," *Antimicrob. Agents Chemother.* 56(8):4365-4374.

Christ, F. et al. (Jun. 2010; e-pub. May 16, 2010). "Rational design of small-molecule inhibitors of the LEDGF/p75-integrase interaction and HIV replication," *Nat. Chem. Biol.*, 25 total pages.

De Luca, L. et al. (Feb. 2011; e-pub. Dec. 21, 2010). "HIV-1 integrase strand-transfer inhibitors: design, synthesis and molecular modeling investigation," *Eur. J. Med. Chem.* 46(2):756-764.

De Luca, L. et al. (Jul. 2011). "Inhibition of the interaction between HIV-1 integrase and its cofactor LEDGF/p75: a promising approach in anti-retroviral therapy," *Mini Rev. Med. Chem.* 11(8):714-727.

Desimmie, B.A. et al. (May 30, 2013). "LEDGINs inhibit late stage HIV-1 replication by modulating integrase multimerization in the virions," *Retrovirology* 10:57, 16 Total Pages.

Engelman, A. et al. (Mar. 28, 2008). "The lentiviral integrase binding protein LEDGF/p75 and HIV-1 replication," *PloS Pathog.* 4(3):e1000046, 9 Total Pages.

Graham, R.L.J. et al. (2011). "Proteomic Analysis of LEDGF/p75 Interactions with Nuclear Proteins," ASMS Poster, 1 page.

Hauser, F.M. et al. (1978). "Singlet Oxygen and Epoxidation from the Dehydration of Hydrogen Peroxide," *J. Org. Chem.* 43(1):180.

Hayouka, Z. et al. (2010). "Cyclic Peptide Inhibitors of HIV-1 Integrase Derived from the LEDGF/p75 Protein," *Bioorganic & Medicinal Chemistry* 18:8388-8395.

Hombrouck, A. et al. (Mar. 2007). "Virus Evolution Reveals an Exclusive Role for LEDGF/p75 in Chromosomal Tethering," *PloS* 3(3):e47, 13 Total Pages.

Huang, X. et al. (2007). "A Novel Multicomponent Reaction of Arynes, β-Keto Sulfones, and Michael-Type Acceptors: A Direct Synthesis of Polysubstituted Naphthols and Naphthalenes," *J. Org. Chem.* 72:3965-3968.

Johns, B.A. et al. (2013). "HIV Integrase Inhibitors," Chapter 6 in *Successful Strategies for the Discovery of Antiviral Drugs*, Desai, M.C. et al. eds., RSC Publishing, pp. 149-188.

Jurado, K.A. et al. (2013). "Allosteric Integrase Inhibitor Potency is Determined through the Inhibition of HIV-1 Particle Maturation," *PNAS* 110(21):8690-8695.

Kessl, J.J. et al. (2011). "FRET Analysis Reveals Distinct Conformations of IN Tetramers in the Presence of Viral DNA or LEDGF/p75," *Nuc. Acids Res.*, pp. 1-14.

Llano, M. et al. (Sep. 2004). "LEDGF/p75 determines cellular trafficking of diverse lentiviral but not murine oncoretroviral integrase proteins and is a component of functional lentiviral preintegration complexes," *J. Virol.* 78(17):9524-9537.

Llano, M. et al. (Oct. 20, 2006; e-pub. Sep. 7, 2006). "An essential role for LEDGF/p75 in HIV integration," *Science* 314(5798):461-464.

Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," *J. Med. Chem.* 41(15):2846-2857.

Poeschla, E.M. et al. (2008). "Integrase, LEDGF/p75 and HIV Replication," *Cell. Mol. Life Sci.* 65:1403-1424.

Rain, J.C. et al. (2009). "Yeast-Two Hybrid Detection of Integrase-Host Factor Interactions," *Methods*, 7 Total Pages.

Rhodes, D.I. et al. (Oct. 17, 2011; e-pub. Aug. 17, 2011). "Crystal structures of novel allosteric peptide inhibitors of HIV integrase identify new interactions at the LEDGF binding site," *Chembiochem.* 12(15):2311-2315.

Shun, M.C. et al. (Jul. 15, 2007). "LEDGF/p75 functions downstream from preintegration complex formation to effect gene-specific HIV-1 integration," *Genes Dev.* 21(14):1767-1778.

Suzuki, Y. et al. (Mar. 2007). "The road to chromatin—nuclear entry of retroviruses," *Nat. Rev. Microbiol.* 5(3):187-196.

Tsiang, M. et al. (Jun. 15, 2012; e-pub. Apr. 25, 2012). "New class of HIV-1 integrase (IN) inhibitors with a dual mode of action," *J. Biol. Chem.* 287(25):21189-21203.

Vandekerckhove, L. et al. (Feb. 2006). "Transient and stable knockdown of the integrase cofactor LEDGF/p75 reveals its role in the replication cycle of human immunodeficiency virus," *J. Virol.* 80(4):1886-1896.

Walker, M.A. (2009). "New approaches for inhibiting HIV integrase: a journey beyond the active site," *Curr. Opin. Investig. Drugs* 10(2):129-136.

Wenhua, Z. et al. (2003). "Advances on Effects of Natural Products Against AIDS Virus," *Chinese Traditional Patent Medicine* 25(9):750-752 (with English Translation).

Restriction Requirement mailed on Apr. 24, 2014 for U.S. Appl. No. 14/112,473, filed on Oct. 17, 2013, eight pages.

Non-Final Office Action mailed on May 23, 2014 for U.S. Appl. No. 13/866,997, filed on Apr. 19, 2013, eight pages.

Notice of Allowance mailed on Aug. 15, 2014 for U.S. Appl. No. 14/112,473, filed on Oct. 17, 2013, seven pages.

Australian Office Action mailed on Feb. 26, 2014, for Australian Patent Application No. 2011274323, filed on Jul. 1, 2011, three pages.

Australian Office Action mailed on Mar. 7, 2014, for Australian Patent Application No. 2011274322 filed on Jul. 1, 2011, three pages.

Chinese Office Action mailed on Mar. 3, 2014, for Chinese Patent Application No. 201180038442.X filed on Jul. 1, 2011, eight pages.

Chinese Office Action mailed on Mar. 25, 2014 for Chinese Patent Application No. 201180038443.4, filed on Jul. 1, 2011, eight pages.

Costa Rican Opposition filed Apr. 28, 2014 against Costa Rican Patent Application No. 201320102, filed Jul. 1, 2011, sixteen pages.

Columbian Office Action mailed on Feb. 20, 2014, for Columbian Patent Application No. 12236161 filed on Jul. 1, 2011, 10 pages.

Columbian Office Action mailed on Jun. 12, 2014 for Columbian Patent Application No. 12236158, filed on Jul. 1, 2011, twelve pages.

Eurasian Office Action mailed on Mar. 19, 2014, for Eurasian Patent Application No. 201291300 filed on Jul. 1, 2011, four pages.

Eurasian Office Action mailed in Apr. 9, 2014, for Eurasian Patent Application No. 201291301, filed on Jul. 1, 2011, three pages.

Israeli Office Action mailed on Mar. 3, 2014 for Israeli Patent Application No. 223558, filed on Jul. 1, 2011, two pages.

New Zealand Office Action mailed on Aug. 22, 2013 for New Zealand Patent Application No. 604598, filed on Jul. 1, 2011, two pages.

Ecuadoran Opposition filed Apr. 23, 2014 against Ecuadoran Patent Application No. SP1312418, filed Jul. 1, 2011, ten pages.

Ecuadoran Opposition from Jun. of 2014, against Ecuadoran Patent Application No. SP1312417, filed Jul. 1, 2011, nine pages.

Philippine Office Action mailed on Aug. 1, 2014, for Philippine Patent Application No. 12013500011, filed on Jul. 1, 2011, two pages.

Written Opinion of the International Searching Authority mailed on Aug. 5, 2013, for PCT Patent Application No. PCT/US2013/037483 filed on Apr. 19, 2013, seven pages.

Written Opinion of the International Searching Authority mailed on Jul. 17, 2014, for PCT Patent Application No. PCT/US2013/020151 filed on Jan. 3, 2013, six pages.

Written Opinion of the International Searching Authority mailed on Jul. 17, 2014, for PCT Patent Application No. PCT/US2013/020172, filed on Jan. 3, 2013, seven pages.

European Communication mailed on Mar. 12, 2014 for European Patent Application No. 11738878.5 filed on Jul. 1, 2011, eight pages.

(56) References Cited

OTHER PUBLICATIONS

European Communication mailed on Feb. 15, 2013, for European Patent Application No. 11738339.8, filed on Jul. 1, 2011, two pages.
Philippines Office Action mailed on Mar. 14, 2014 for Philippine Patent Application No. 1/2013/500011, filed on Jul. 1, 2011, two pages.

Mexican Office Action mailed on Mar. 13, 2014 for Mexican Patent Application No. MX/a/2012/015293, filed on Jul. 1, 2011, seven pages.

Vietnamese Office Action mailed on Jul. 28, 2014, for Vietnamese Patent Application No. 1-201300326, filed on Jul. 1, 2011, two pages.

* cited by examiner

THERAPEUTIC COMPOUNDS

CROSS REFERENCE TO RELATED APPLICATIONS

This patent application claims the benefit of priority of U.S. Application Ser. No. 61/636,602, filed Apr. 20, 2012 and of U.S. application Ser. No. 61/718,165, filed Oct. 24, 2012. The content of each of these provisional applications is hereby incorporated herein in its entirety.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). Accordingly, there is a need for new agents that inhibit the replication of HIV. There is also a need for agents that are directed against alternate sites in the viral life cycle including agents that target the inhibition of integrase.

SUMMARY OF THE INVENTION

Compounds and methods for the treatment of an HIV infection are disclosed.

One embodiment provides a compound of formula I':

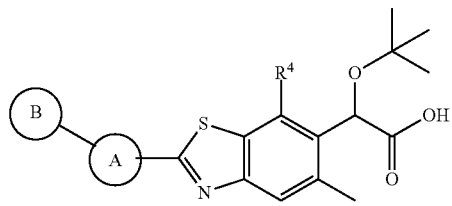

wherein:

$R^4$ is selected from aryl, heterocycle and heteroaryl, wherein any aryl, heterocycle and heteroaryl of $R^4$ is optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —$(C_1-C_6)$alkyl-$(C_3-C_7)$cycloalkyl, —OH, —$O(C_1-C_6)$alkyl, —SH, —$S(C_1-C_6)$alkyl, $NH_2$, —$NH(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo;

A is phenyl, monocyclic heteroaryl or monocyclic heterocycle, wherein any phenyl, monocyclic heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups; or A and B together form a bicyclic aryl, bicyclic heteroaryl or bicyclic heterocycle, wherein bicyclic aryl, bicyclic heteroaryl or bicyclic heterocycle is optionally substituted with one or more $Z^{1b}$ groups;

each $Z^{1a}$ is independently selected from halo, $(C_1-C_3)$alkyl, $(C_2-C_3)$alkenyl, $(C_2-C_3)$alkynyl, $(C_1-C_3)$haloalkyl, $(C_3-C_7)$carbocycle, heterocycle, —$O(C_1-C_3)$alkyl, —$O(C_2-C_3)$alkenyl, —$O(C_2-C_3)$alkynyl, —$NR_cR_d$, —$NR_aC(O)R_a$, —$C(O)OR_b$ and —$C(O)NR_cR_d$, wherein any $(C_3-C_7)$carbocycle or heterocycle of $Z^{1a}$ is optionally substituted with one or more halogen or $(C_1-C_6)$alkyl;

each $Z^{1b}$ is independently selected from halo, CN, $(C_1-C_6)$alkyl, $(C_2-C_6)$alkenyl, $(C_2-C_6)$alkynyl, $(C_1-C_6)$haloalkyl, $(C_3-C_7)$carbocycle, heteroaryl, heterocycle, aryl$(C_1-C_6)$alkyl-, —OH, —$O(C_1-C_6)$alkyl, —$O(C_2-C_6)$alkenyl, —$O(C_2-C_6)$alkynyl, —$NR_cR_d$, —$NR_aC(O)R_a$, —$C(O)OR_b$ and —$C(O)NR_cR_d$, wherein any $(C_3-C_7)$carbocycle or heterocycle of $Z^{1b}$ is optionally substituted with one or more halogen or $(C_1-C_6)$alkyl; and $R_a$, $R_b$, $R_c$ and $R_d$ are each independently H or $(C_1-C_6)$alkyl;

or a salt thereof.

One embodiment provides pharmaceutical compositions comprising a compound disclosed herein (e.g., a compound of formula I, I') or a pharmaceutically acceptable salt thereof, and a pharmaceutically acceptable carrier.

One embodiment provides methods for treating the proliferation of the HIV virus, treating AIDS or delaying the onset of AIDS or ARC symptoms in a mammal (e.g., a human), comprising administering a compound of the invention (e.g., a compound of formula I, I'), or a pharmaceutically acceptable salt thereof, to the mammal.

One embodiment provides methods of treating an HIV infection in a mammal (e.g., a human) comprising administering a compound disclosed herein (e.g., a compound of formula I, I'), or a pharmaceutically acceptable salt thereof, to the mammal.

One embodiment provides methods for treating an HIV infection in a mammal (e.g., a human) comprising administering to the mammal in need thereof a therapeutically effective amount of a compound disclosed herein (e.g., a compound of formula I, I'), or a pharmaceutically acceptable salt thereof, in combination with a therapeutically effective amount of one or more additional therapeutic agents selected from the group consisting HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof, are also disclosed.

One embodiment provides a compound disclosed herein (e.g., a compound of formula I, I'), or a pharmaceutically acceptable salt thereof for use in medical therapy (e.g., for use in treating the proliferation of the HIV virus or AIDS or delaying the onset of AIDS or ARC symptoms in a mammal (e.g., a human)).

One embodiment provides a compound disclosed herein (e.g., a compound of formula I, I'), or a pharmaceutically acceptable salt thereof for use in medical therapy (e.g. for use in treating an HIV infection in a mammal (e.g. a human)).

One embodiment provides a compound disclosed herein (e.g., a compound of formula I, I'), or a pharmaceutically acceptable salt thereof for use in the manufacture of a medicament for treating the proliferation of the HIV virus or AIDS or delaying the onset of AIDS or ARC symptoms in a mammal (e.g., a human).

One embodiment provides a compound disclosed herein (e.g., a compound of formula I, I'), or a pharmaceutically acceptable salt thereof, for use in the prophylactic or therapeutic treatment of the proliferation of the HIV virus or AIDS or for use in the therapeutic treatment of delaying the onset of AIDS or ARC symptoms.

One embodiment provides a compound disclosed herein (e.g., a compound of formula I, I'), or a pharmaceutically acceptable salt thereof, for the manufacture of a medicament for treating an HIV infection in a mammal (e.g., a human).

One embodiment provides a compound disclosed herein (e.g., a compound of formula I, I') or a pharmaceutically acceptable salt thereof, for use in the prophylactic or therapeutic treatment of an HIV infection in a mammal (e.g. a human).

One embodiment provides processes and intermediates disclosed herein that are useful for preparing compounds disclosed herein (e.g. a compound of formula I, I') or salts thereof.

DETAILED DESCRIPTION OF THE INVENTION

Definitions

Unless stated otherwise, the following terms and phrases as used herein are intended to have the following meanings.

When trade names are used herein, applicants intend to independently include the tradename product and the active pharmaceutical ingredient(s) of the tradename product.

"Alkyl" is hydrocarbon containing normal, secondary or tertiary atoms. For example, an alkyl group can have 1 to 20 carbon atoms (i.e., ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl) or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., ($C_1$-$C_{10}$)alkyl), or 1 to 6 carbon atoms (i.e., ($C_1$-$C_6$)alkyl) or 1-3 carbon atoms (i.e., ($C_1$-$C_3$)alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group t to complete halogenation of the alkyl group.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryl or carbocycle). Such bicyclic or multicyclic rings may be optionally substituted with one or more (e.g. 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Exemplary aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl, pyrrolopyridinyl and pyrazolopyridine.

The term "N-heteroaryl" refers to a heteroaryl that contains at least one nitrogen atom within the ring system.

The term "heterocyclyl" or "heterocycle" as used herein refers to a single saturated or partially unsaturated ring or a multiple condensed ring. The term includes single saturated or partially unsaturated ring (e.g. 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g. ring systems comprising 2 or 3 rings) wherein a heterocycle group (as defined above) can be connected to two adjacent atoms (fused heterocycle) with one or more heterocycles (e.g. decahydronapthyridinyl), heteroaryls (e.g. 1,2,3,4-tetrahydronaphthyridinyl), carbocycles (e.g. decahydroquinolyl) or aryls. It is to be understood that the point of attachment of a heterocycle multiple condensed ring, as defined above, can be at any position of the ring including a heterocycle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, tetrahydropyrimidinyl-2-one, imidazolidinyl-2-one, pyrrolidinyl-2-one, 2,3-dihydropyrano[4,3,2-de]quinolonyl, 2,5-benzo[d][1,3]dioxolyl and chromanyl-4-one.

The term "bridged-heterocycle" as used herein refers to a 4, 5, 6, 7 or 8-membered heterocycle as defined herein connected at two non-adjacent atoms of the 4, 5, 6, 7 or 8-membered heterocycle with one or more (e.g. 1 or 2) 3, 4, 5 or 6-membered heterocycles or ($C_3$-$C_7$)carbocycles as defined herein. Such bridged-heterocycles include bicyclic and tricyclic ring systems (e.g. 2-azabicyclo[2.2.1]heptane and 4-azatricyclo[4.3.1.1$^{3,8}$]undecane).

The term "spiro-heterocycle" as used herein refers to a 3, 4, 5, 6, 7 or 8-membered heterocycle as defined herein connected to one or more (e.g. 1 or 2) single atoms of the 3, 4, 5, 6, 7 or 8-membered heterocycle with one or more (e.g. 1 or 2) 3, 4, 5, 6-membered heterocycles or a ($C_3$-$C_7$)carbocycles as defined herein. Such spiro-heterocycles include bicyclic and tricyclic ring systems (e.g. 1,4-dioxaspiro[4.5]dec-7-enyl).

The term "macroheterocycle" as used herein refers to a saturated or partially unsaturated 8, 9, 10, 11 or 12-membered ring comprising about 5 to 11 carbon atoms and about 1 to 3 heteroatoms selected from the group consisting of oxygen, nitrogen and sulfur in the ring which may be optionally fused at two adjacent atoms of the macroheterocycle to one or more (e.g. 1, 2 or 3) aryls, carbocycles, heteroaryls or heterocycles. The macroheterocycle may be substituted with one or more (e.g. 1, 2 or 3) oxo groups and the sulfur and nitrogen atoms may also be present in their oxidized forms.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl ($C_1$-$C_6$)alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrrolidinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a saturated (i.e., cycloalkyl) or partially unsaturated (e.g., cycloalkenyl, cycloalkadienyl, etc.) ring having 3 to 7 carbon atoms as a monocycle or a mutlicyclic ring system. In one embodiment the carbocycle is a monocycle comprising 3-6 ring carbons (i.e. ($C_3$-$C_6$)carbocycle). Carbocycle includes multicyclic carbocycles having 7 to 12 carbon atoms as a bicycle, and up to about 20 carbon atoms as a polycycle provided that the largest single ring of a multicyclic carbocycle is 7 carbon atoms. The term "spiro-bicyclic carbocycle" refers to a carbocycle bicyclic ring system wherein the rings of the bicyclic ring system are connected to a single carbon atom (e.g. spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane). The term "bridged-bicyclic carbocycle" refers to a carbocycle bicyclic ring system wherein the rings of the bicyclic ring system are connected to two non-adjacent carbon (e.g. norbornane, bicyclo[2.2.2]octane, etc). The "carbocycle" or "carbocyclyl" may be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halocarbocycle" as used herein refers to a carbocycle as defined herein, wherein one or more hydrogen atoms are each replaced by a halo substituent. For example, ($C_3$-$C_7$)halocarbocycle is a ($C_3$-$C_7$)carbocycle wherein one or more of the hydrogen atoms have been replaced by a halo substituent. Such a range includes one halo substituent on the carbocycle group to complete halogenation of the carbocycle group.

The term "macrocarbocycle" as used herein refers to a saturated or partially unsaturated 8, 9, 10, 11 or 12-membered ring comprising 8 to 12 carbon atoms which may be optionally fused at two adjacent atoms of the macrocarbocycle to one or more (e.g. 1, 2 or 3) aryls, carbocycles, heteroaryls or heterocycles. The macrocarbocycle may be substituted with one or more (e.g. 1, 2 or 3) oxo groups.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl) ethan-1-yl, and the like, wherein the "carbocyclyl" portion includes any of the carbocyclyl groups described above.

It is to be understood that when a variable is substituted, for example, as described by the phrase "($C_1$-$C_6$)alkyl, either alone or as part of a group, is optionally substituted", the phrase means that the variable ($C_1$-$C_6$)alkyl can be substituted when it is alone and that it can also be substituted when the variable "($C_1$-$C_6$)alkyl" is part of a larger group such as for example an aryl($C_1$-$C_6$)alkyl or a —($C_1$-$C_6$)alkyl-$SO_2$—($C_1$-$C_6$)alkyl-($C_3$-$C_7$)carbocycle group. Similarly, when stated, other variables (e.g. ($C_1$-$C_6$)alkenyl, ($C_1$-$C_6$)alkynyl, aryl, heteroaryl, heterocycle, etc.) can also be substituted "either alone or as part of a group."

It is to be understood that certain variables of formula I that connect two chemical groups may be oriented in either direction. Thus, for the X group of formula I (e.g. O, —C(O)—, —C(O)O—, —S—, —S(O)—, —$SO_2$, —($C_1$-$C_6$)alkylO—, —($C_1$-$C_6$)alkylC(O)—, —($C_1$-$C_6$)alkylC(O)O—, —($C_1$-$C_6$) alkylS—, —($C_1$-$C_6$)alkylS(O)— and —($C_1$-$C_6$)alkyl$SO_2$—) certain values of X that are not symmetric can be oriented in either direction. For example, the —C(O)O—, can be oriented as either —C(O)O— or —OC(O)—, relative to the groups it connects.

It is to be understood that the nitrogen that is included in the core of the compound of formula I can be present in an oxidized form. For example, the thiazole nitrogen of either $G^1$ or $G^2$ of formula I can be an N-oxide. Accordingly, the invention includes a compound of formula I (as defined in the summary of the invention) or a salt or N-oxide thereof.

One skilled in the art will recognize that substituents and other moieties of the compounds disclosed herein should be selected in order to provide a compound which is sufficiently stable to provide a pharmaceutically useful compound which can be formulated into an acceptably stable pharmaceutical composition. Compounds disclosed herein which have such stability are contemplated as falling within the scope of the present invention.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Certain compounds of the invention can exist as atropisomers. For example, it has been discovered that atropisomers exist for certain substituents at the $R^4$ position of compounds of the invention (e.g. compounds of formula I and related formulas described herein) as marked by an asterisk in the formula below.

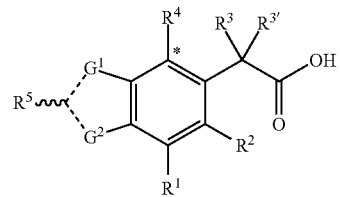

The chirality that results from the atropisomers at the asterisk position is a feature of certain compounds of the invention. Accordingly, the invention includes all atropisomers of compounds of the invention including mixtures of atropisomers and well as mixtures that are enriched in an atropisomer as well as single atropisomers, which mixtures or compounds possess the useful properties described herein.

In one embodiment, the compounds of the invention are greater than 50% a single atropisomer for the $R^4$ substituent at the asterisk position. In one embodiment, the compounds of the invention are at least 60% a single atropisomer for the $R^4$ substituent at the asterisk position. In another embodiment, the compounds of the invention are at least 70% a single atropisomer for the $R^4$ substituent at the asterisk position. In another embodiment, the compounds of the invention are at least 80% a single atropisomer for the $R^4$ substituent at the asterisk position. In another embodiment, the compounds of the invention are at least 90% a single atropisomer for the $R^4$ substituent at the asterisk position. In another embodiment, the compounds of the invention are at least 95% a single atropisomer for the $R^4$ substituent at the asterisk position. In one embodiment the stereochemistry for the $R^4$ substituent at the carbon marked with an asterisk as shown above for a compound of the invention (e.g. compounds of formula I) is the (R) stereochemistry. In another embodiment the stereochemistry for the $R^4$ substituent at the carbon marked with an asterisk as shown above for a compound of the invention (e.g. compounds of formula I) is the (S) stereochemistry.

For certain compounds of the invention the stereochemistry at the carbon bearing the $R^3$ substituent of compounds of the invention (e.g. compounds of formula I) as marked by an asterisk in the formula below is another aspect of the invention.

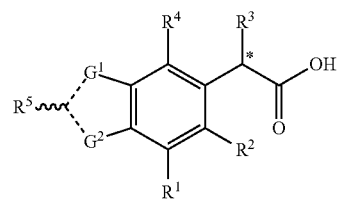

In one embodiment the stereochemistry at the carbon marked with an asterisk as shown in the formula above for a compound of the invention is the (S) stereochemistry. In another embodiment the stereochemistry at the carbon marked with an asterisk as shown in the formula above for a compound of the invention is the (R) stereochemistry.

In one embodiment, the compounds of the invention are greater than 50% a stereoisomer for the carbon at the asterisk position. In another embodiment, the compounds of the invention are at least 60% a single stereoisomer for the carbon at the asterisk position. In another embodiment, the compounds of the invention are at least 70% a single stereoisomer for the carbon at the asterisk position. In another embodiment, the compounds of the invention are at least 80% a single stereoisomer for the carbon at the asterisk position. In another embodiment, the compounds of the invention are at least 90% a single stereoisomer for the carbon at the asterisk position. In another embodiment, the compounds of the invention are at least 95% a single stereoisomer for the carbon at the asterisk position.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present disclosure, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of pharmaceutically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Specific values listed below for radicals, substituents, and ranges in the embodiments of the invention are for illustration only; they do not exclude other defined values or other values within defined ranges for the radicals and substituents.

Isotopes

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be substituted with —$CD_3$.

Compounds of Formula I.

A specific group of compounds of formula I are compounds of formula Ia:

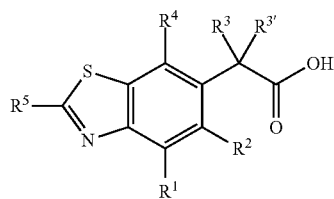

or a salt thereof.

Another specific group of compounds of formula I are compounds of formula Ib:

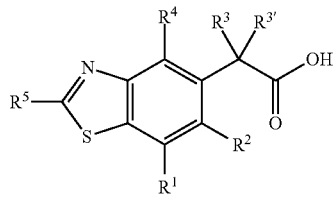

or a salt thereof.

Another specific group of compounds of formula I are compounds of formula Ic:

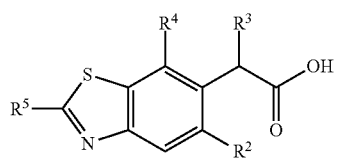

wherein $R^3$ is —$O(C_1$-$C_6)$alkyl or a salt thereof.

Another specific group of compounds of formula I are compounds of formula Ic':

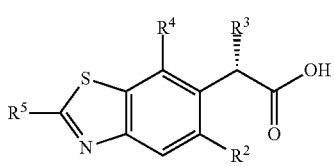

wherein R³ is —O(C₁-C₆)alkyl or a salt thereof.

Another specific group of compounds of formula I are compounds of formula Id:

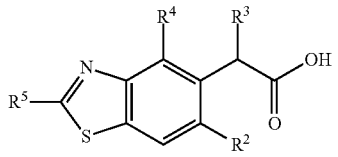

Id wherein R³ is —O(C₁-C₆)alkyl, or a salt thereof.

Another specific group of compounds of formula I are compounds of formula Id':

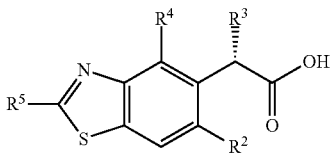

Id' wherein R³ is —O(C₁-C₆)alkyl, or a salt thereof.

Another specific group of compounds of formula I are compounds of formula Ie:

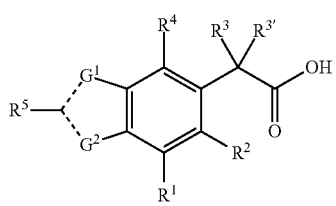

Ie wherein:

G¹ is S; G² is N; the dashed bond connected to G¹ is a single bond and the dashed bond connected to G² is a double bond; or G¹ is N; G² is S; the dashed bond connected to G¹ is a double bond and the dashed bond connected to G² is a single bond; or a salt thereof.

Another specific group of compounds of formula I are compounds of formula Ijf:

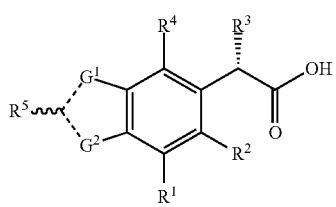

If or a salt thereof.

Specific embodiments of the invention (e.g. embodiments) and specific values listed below are embodiments and values for compounds of formula I including all of the compounds of sub-formulas of formula I (e.g. the compounds of formulas Ia, Ib, Ic, Ic', Id, Id', Ie, If, Ia100-Ia145, I' etc.)

A specific group of compounds of formula I are compounds wherein at least one of R¹, R², R³, R³' or R⁴ is selected from R¹ᵇ, R²ᵇ, R³ᵇ, R³ᵇ' or R⁴ᵇ.

Another specific group of compounds of formula I are compounds wherein at least two of R¹, R², R³, R³' or R⁴ is selected from R¹ᵇ, R²ᵇ, R³ᵇ, R³ᵇ' or R⁴ᵇ.

Another specific group of compounds of formula I are compounds wherein at least three of R¹, R², R³, R³' or R⁴ is selected from R¹ᵇ, R²ᵇ, R³ᵇ, R³ᵇ' or R⁴ᵇ.

Another specific group of compounds of formula I are compounds wherein at least four of R¹, R², R³, R³' or R⁴ is selected from R¹ᵇ, R²ᵇ, R³ᵇ, R³ᵇ' of R⁴ᵇ.

Another specific group of compounds of formula I are compounds wherein at least five of R¹, R², R³, R³' or R⁴ is selected from R¹ᵇ, R²ᵇ, R³ᵇ, R³ᵇ' or R⁴ᵇ.

Another specific group of compounds of formula I are compounds wherein at R¹, R², R³, R³' and R⁴ are R¹ᵇ, R²ᵇ, R³ᵇ, R³ᵇ' and R⁴ᵇ.

A specific value for R¹ is H.

Another specific value for R¹ is H or halo.

Another specific value for R¹ is H or F.

A specific value for R³' is H.

A specific value for R³ is R³ᵇ.

A specific value for R³ᵇ is —OC(CH₃)₂CH₂OH, —OC(CH₃)₂CH₂OH, —O(C₁-C₆)alkyl-O—C(O)—NH₂, —O(C₁-C₆)alkyl-O—C(O)—N(CH₃)₂ or —O(C₁-C₆)alkyl-O—C(O)—NH(phenyl).

Another specific value for R³ᵇ is —(C₁-C₆)alkylOH or —O(C₁-C₆)alkyl-O—C(O)—NR_cR_d.

Another specific value for R³ is R³ᵃ.

A specific value for R³ᵃ is (C₁-C₆)alkyl, (C₂-C₆)alkenyl or —O(C₁-C₆)alkyl wherein any (C₁-C₆)alkyl or (C₂-C₆)alkenyl of R³ᵃ is optionally substituted with one or more groups selected from —O(C₁-C₆)alkyl, halo, oxo and —CN.

Another specific value for R³ᵃ is —OC(CH₃).

A specific value for R³' is R³ᵇ'.

A specific value for R³ᵇ' is (C₁-C₆)alkyl or —O(C₁-C₆)alkyl.

A specific value for R³' is R³ᵃ'.

A specific value for R³ᵃ' is H.

A specific value for R³ is (C₁-C₆)alkyl, (C₂-C₆)alkenyl or —O(C₁-C₆)alkyl, wherein any (C₁-C₆)alkyl or (C₂-C₆)alkenyl of R³ᵃ is optionally substituted with one or more groups selected from —O(C₁-C₆)alkyl, halo, oxo and —CN.

Another specific value for R³ is (C₁-C₆)alkyl, (C₂-C₆)alkenyl or —O(C₁-C₆)alkyl, wherein the (C₁-C₆)alkyl, (C₂-C₆)alkenyl or —O(C₁-C₆)alkyl is branched.

A specific value for R³ is —OC(CH₃)₃.

A specific group of compounds of formula I are compounds wherein R³ᵇ and R³ᵇ' together with the carbon to which they are attached form a (C₃-C₇)carbocycle or heterocycle; wherein the (C₃-C₇)carbocycle or heterocycle is optionally substituted with one or more Z¹ groups.

Another specific group of compounds of formula I are compounds wherein R³ᵇ and R³ᵇ' together with the carbon to which they are attached form a (C₃-C₇)carbocycle or a 4, 5 or 6-membered heterocycle; wherein the (C₃-C₆)carbocycle or the 4, 5 or 6-membered heterocycle is optionally substituted with one or more Z¹ groups.

Another specific group of compounds of formula I are compounds wherein R³ᵇ and R³ᵇ' together with the carbon to which they are attached form a (C₄-C₆)carbocycle or a 5 or 6-membered heterocycle; wherein the (C₄-C₆)carbocycle or the 5 or 6-membered heterocycle is optionally substituted with one or more Z¹ groups.

Another specific group of compounds of formula I are compounds wherein R³ᵇ and R³ᵇ' together with the carbon to which they are attached form a 5 or 6-membered heterocycle; wherein the 5 or 6-membered heterocycle is optionally substituted with one or more $Z^1$ group.

Another specific group of compounds of formula I are compounds wherein $R^{3b}$ and $R^{3b'}$ together with the carbon to which they are attached form a tetrahydropyran or tetrahydrofuran optionally substituted with one or more $Z^1$ groups.

Another specific group of compounds of formula I are compounds wherein $R^{3b}$ and $R^{3b'}$ together with the carbon to which they are attached form:

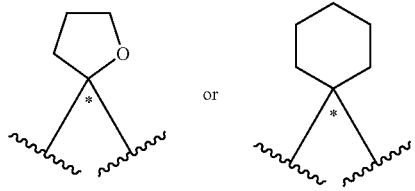 [SMILES: *C1(*)CCCO1 ; "or" ; *C1(*)CCCCC1]

each of which is optionally substituted with one or more $Z^1$ groups; and wherein "*" denotes the point of attachment to the carbon of the compound of formula I.

A specific value for $R^4$ is $R^{4b}$.

A specific value for $R^{4b}$ is $(C_1-C_6)$alkyl, $(C_2-C_6)$alkenyl or $(C_2-C_6)$alkynyl; wherein $(C_1-C_6)$alkyl, $(C_2-C_6)$alkenyl or $(C_2-C_6)$alkynyl are each optionally substituted with one or more $Z^1$ groups.

Another specific value for $R^{4b}$ is:

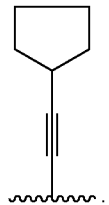 [SMILES: *C#CC1CCCC1]

optionally substituted with one or more $Z^1$ groups.

Another specific value for $R^{4b}$ is $(C_3-C_7)$carbocycle; wherein $(C_3-C_7)$carbocycle is optionally substituted with one or more $Z^1$ groups; or wherein two $Z^1$ groups together with the atom or atoms to which they are attached optionally form a $(C_3-C_6)$carbocycle or 5-6-membered heterocycle.

Another specific value for $R^{4b}$ is:

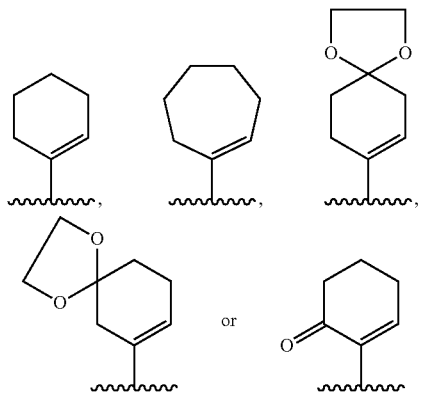

each of which is optionally substituted with one or more $Z^1$ groups.

Another specific value for $R^{4b}$ is aryl, heterocycle or heteroaryl; wherein aryl, heterocycle and heteroaryl are each independently substituted with one or more $Z^7$ groups and optionally substituted with one or more $Z^1$ groups.

Another specific value for $R^{4b}$ is:

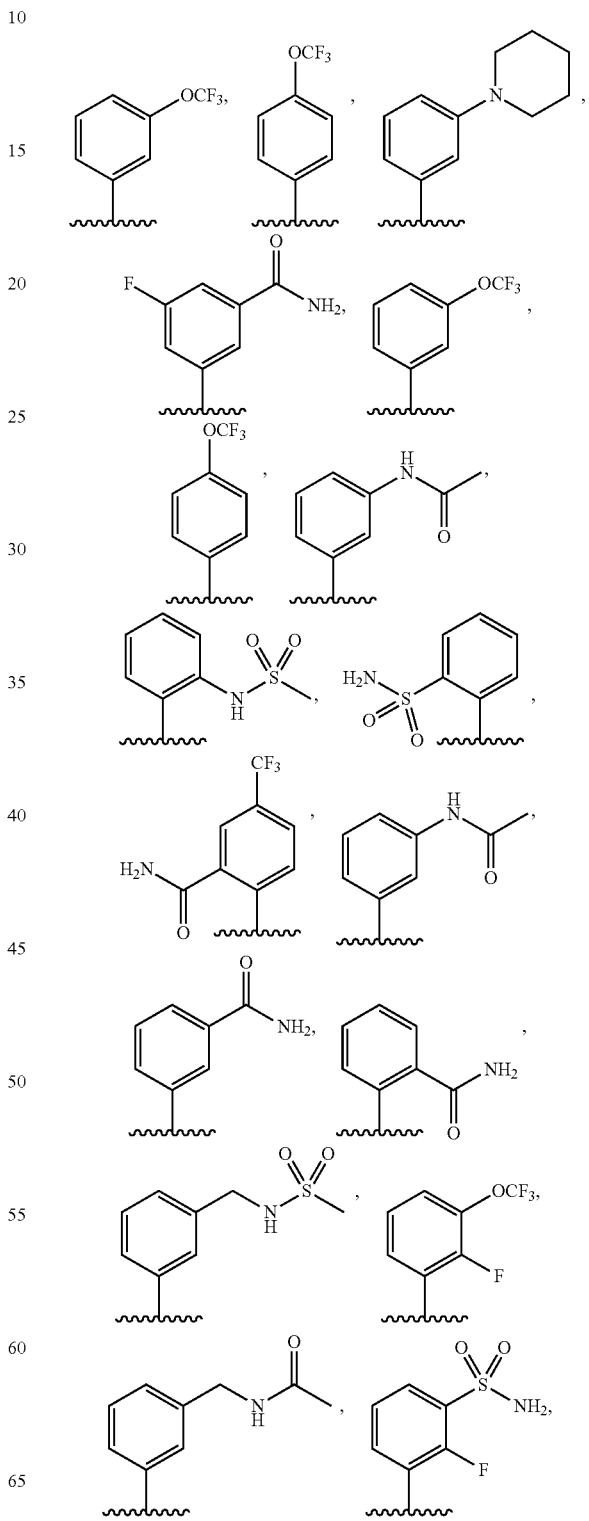

-continued

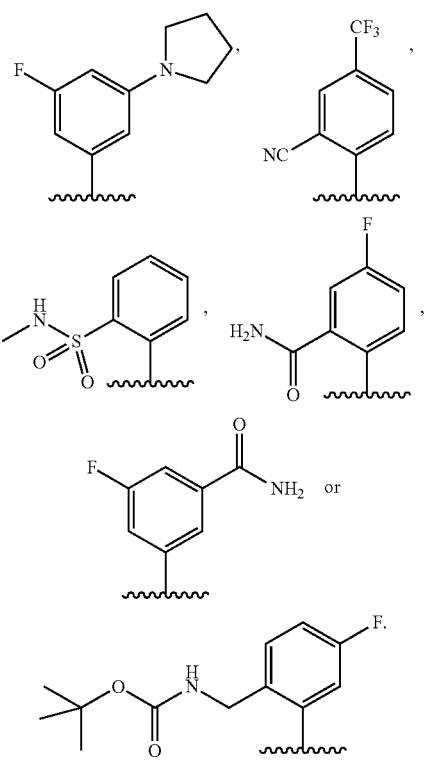

Another specific value for $R^4$ is $R^{4a}$.
A specific value for $R^{4a}$ is:

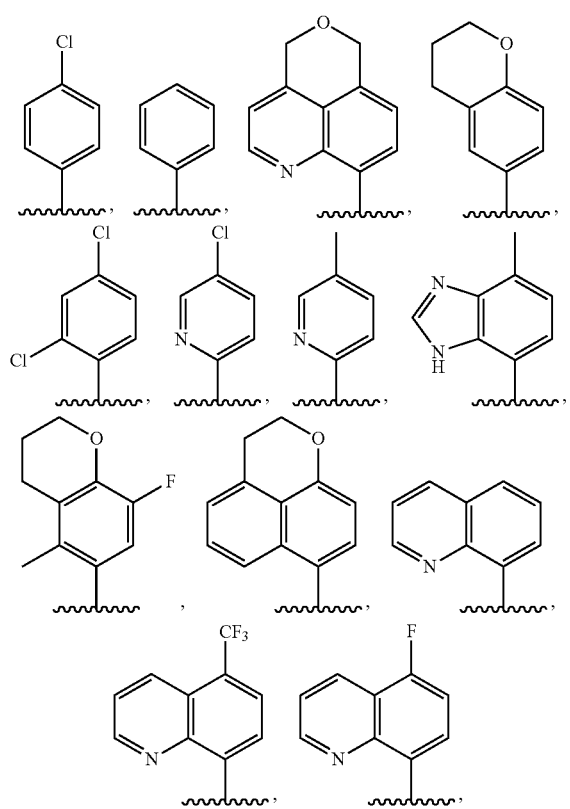

-continued

Another specific value for $R^{4a}$ is:

Another specific value for $R^{4a}$ is:

A specific value for $R^4$ is selected from:
a) aryl, heterocycle and heteroaryl, wherein any aryl, heterocycle and heteroaryl of $R^4$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, —$(C_1-C_6)$alkyl-$(C_3-C_7)$cycloalkyl, —OH, —O($C_1$-$C_6$)alkyl, —SH, —S($C_1$-$C_6$)alkyl, —$NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo; and b) aryl, heteroaryl, spiro-, fused-, or bridged-heterocycle; wherein aryl, heteroaryl, or spiro-, fused-, or bridged-heterocycle are each independently substituted with one or more $Z^7$ groups and optionally substituted with one or more (e.g. 1, 2, 3, 4 or 5) $Z^1$ groups.

Another specific value for $R^4$ is selected from:

a) aryl, heterocycle and heteroaryl, wherein any aryl, heterocycle and heteroaryl of $R^4$ is optionally substituted with one or more (e.g. 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —$NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo; and b) aryl and heteroaryl, wherein aryl and heteroaryl are each independently substituted with one or more $Z^7$ groups and optionally substituted with one or more (e.g. 1, 2, 3, 4 or 5) $Z^1$ groups.

Another specific value for $R^4$ is selected from aryl, heterocycle and heteroaryl, wherein any aryl, heterocycle and heteroaryl of $R^4$ is optionally substituted with one or more (e.g. 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —$NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo.

Another specific value for $R^4$ is:

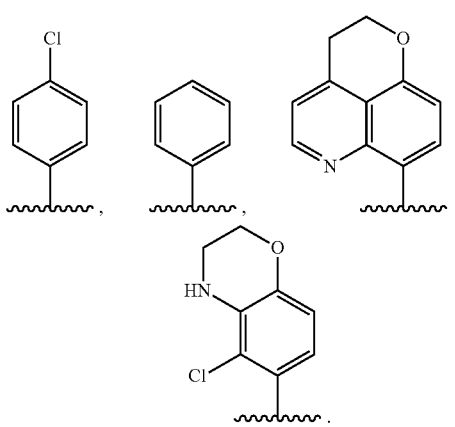

Another specific value for $R^4$ is:

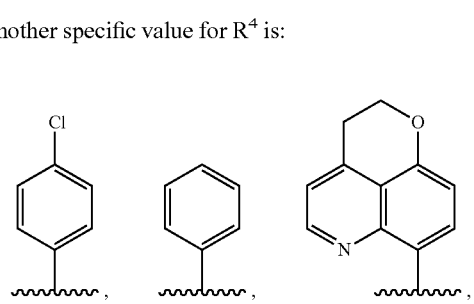

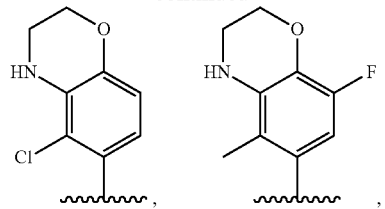

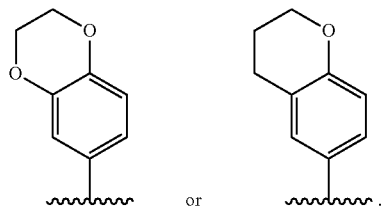

A specific group of compounds of formula I are compounds wherein $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more $Z^1$ groups; and $R^{3'}$ is H, ($C_1$-$C_6$)alkyl or —O($C_1$-$C_6$)alkyl.

Another specific group of compounds of formula I are compounds wherein $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more $Z^1$ groups; and $R^{3'}$ is H.

Another specific group of compounds of formula I are compounds wherein $R^4$ and $R^3$ together with the atoms to which they are attached form the macroheterocycle or a macrocarbocycle which is further fused to a Z group;

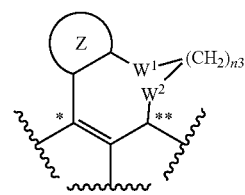

wherein:

Z is aryl, heteroaryl or ($C_3$-$C_6$)carbocycle;

n3 is 2, 3 or 4;

$W^1$ and $W^2$ are each independently O, NH or $CH_2$; and wherein "*" denotes the $R^4$ point of attachment of the macroheterocycle or macrocarbocycle to the compound of formula I and "**" denotes the $R^3$ point of attachment of the macroheterocycle or macrocarbocycle to the compound of formula I; and wherein the macroheterocycle or a macrocarbocycle is optionally substituted with one or more $Z^1$ groups.

Another specific group of compounds of formula I are compounds wherein, $R^4$ and $R^3$ together with the atoms to which they are attached form the macroheterocycle:

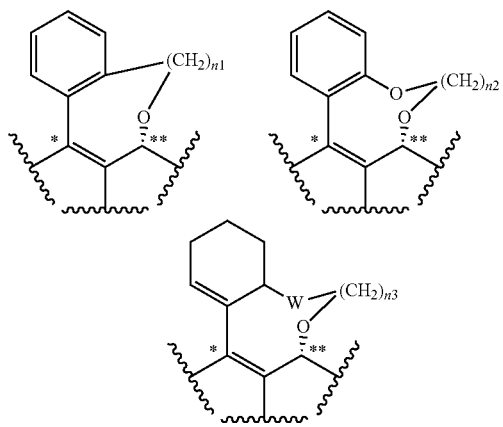

wherein:
n1 is 3 or 4; n2 is 2, 3 or 4; n3 is 2, 3 or 4; W is O, NH or N($C_1$-$C_4$)alkyl; and wherein "*" denotes the $R^4$ point of attachment of the macroheterocycle to the compound of formula I and "**" denotes the $R^3$ point of attachment of the macroheterocycle to the compound of formula I; and wherein the macroheterocycle or a macrocarbocycle is optionally substituted with one or more $Z^1$ groups.

A specific value for $R^2$ is $R^{2b}$.
Another specific value $R^2$ is $R^{2a}$.
A specific value for $R^{2a}$ is H, halo or —$CH_3$.
Another specific value for $R^{2a}$ is Cl.
A specific value for $R^2$ is halo, H or ($C_1$-$C_6$)alkyl.
Another specific value for $R^2$ is halo, H or —$CH_3$.
Another specific value for $R^2$ is H or —$CH_3$.
Another specific value for $R^2$ is H or ($C_1$-$C_6$)alkyl.
Another specific value for $R^2$ is ($C_1$-$C_6$)alkyl.
Another specific value for $R^2$ is —$CH_3$.
Another specific value for $R^5$ is $R^{5a}$.
A specific value for $R^{11}$ is aryl.
Another specific value for $R^{11}$ is carbocycle or aryl.
Another specific value for $R^{11}$ is carbocycle.
A specific value for $R^9$ is H or ($C_1$-$C_6$)alkyl.
A specific value for $R^{10}$ is H or ($C_1$-$C_6$)alkyl.
Another specific value for $R^9$ is H, ($C_1$-$C_6$)alkyl or —C(=O)—$R^{11}$.
Another specific value for $R^{10}$ is H, ($C_1$-$C_6$)alkyl or —C(=O)—$R^{11}$.
A value for $Z^9$ is "each $Z^9$ is independently selected from —($C_1$-$C_6$)alkyl, —O($C_1$-$C_6$)alkyl".
In one embodiment of $R^5$ does not include:

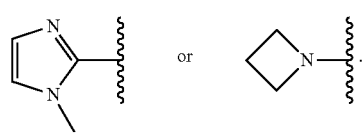

A specific value for $R^5$ is:

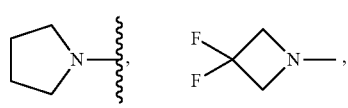

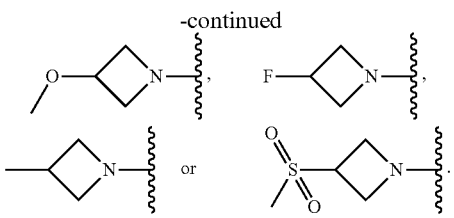

In one embodiment $R^5$ does not include:

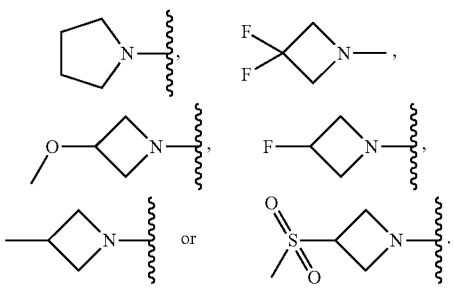

In one embodiment the compounds of the invention do not include compounds 35, 36, 50, 51, 52, 53, 54, 55, 56, 57, 58, 76, and 89.

A specific group of compounds of formula I are compounds wherein $R^{4b}$ is selected from;
a) ($C_1$-$C_6$)alkyl, ($C_2$-$C_6$)alkenyl and ($C_2$-$C_6$)alkynyl, wherein any ($C_1$-$C_6$)alkyl, ($C_2$-$C_6$)alkenyl or ($C_2$-$C_6$)alkynyl is optionally substituted with one or more (e.g. 1, 2, 3, 4 or 5) $Z^1$ groups;
b) ($C_3$-$C_{14}$)carbocycle, wherein ($C_3$-$C_{14}$)carbocycle is optionally substituted with one or more (e.g. 1, 2, 3, 4 or 5) $Z^1$ groups;
c) Spiro-heterocycle or bridged-heterocycle, wherein spiro-heterocycle or bridged-heterocycle is optionally substituted with one or more (e.g. 1, 2, 3, 4 or 5) $Z^1$ groups; and
d) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups.

Another specific group of compounds of formula I are compounds wherein $R^{4b}$ is selected from;
a) ($C_1$-$C_6$)alkyl, ($C_2$-$C_6$)alkenyl and ($C_2$-$C_6$)alkynyl, wherein any ($C_1$-$C_6$)alkyl, ($C_2$-$C_6$)alkenyl or ($C_2$-$C_6$)alkynyl is optionally substituted with one or more (e.g. 1, 2, 3, 4 or 5) $Z^1$ groups;
b) ($C_3$-$C_{14}$)carbocycle, wherein ($C_3$-$C_{14}$)carbocycle is optionally substituted with one or more (e.g. 1, 2, 3, 4 or 5) $Z^1$ groups; wherein two $Z^1$ groups together with the atom or atoms to which they are attached optionally form a ($C_3$-$C_7$) carbocycle or heterocycle; and
c) aryl, heterocycle and heteroaryl, wherein aryl, heterocycle and heteroaryl are each independently substituted with one or more (e.g. 1, 2, 3, 4 or 5) $Z^7$ groups and optionally substituted with one or more (e.g. 1, 2, 3, 4 or 5) $Z^1$ groups.

Another specific group of compounds of formula I are compounds wherein $R^{4b}$ is selected from;
a) ($C_1$-$C_6$)alkyl, ($C_2$-$C_6$)alkenyl and ($C_2$-$C_6$)alkynyl, wherein any ($C_1$-$C_6$)alkyl, ($C_2$-$C_6$)alkenyl or ($C_2$-$C_6$)alkynyl is optionally substituted with one or more (e.g. 1, 2, 3, 4 or 5) $Z^1$ groups;
b) ($C_3$-$C_{14}$)carbocycle, wherein ($C_3$-$C_{14}$)carbocycle is optionally substituted with one or more (e.g. 1, 2, 3, 4 or 5) $Z^1$ groups; and c) aryl, heterocycle and heteroaryl, wherein aryl, heterocycle and heteroaryl are each independently substituted with one or more (e.g. 1, 2, 3, 4 or 5) $Z^7$ groups and optionally substituted with one or more (e.g. 1, 2, 3, 4 or 5) $Z^1$ groups.

In one embodiment, the compounds of the invention do not include the compounds selected from:

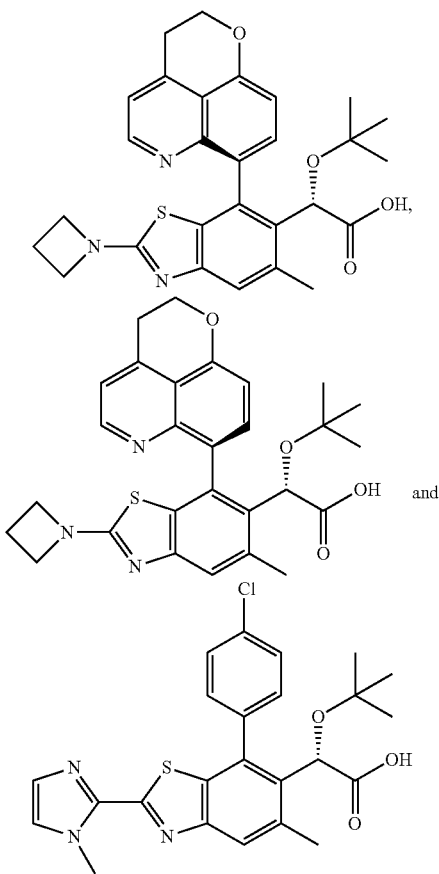

and salts thereof.

A specific value for $R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

A specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups; and $R^{3'}$ is H.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;

$R^2$ is H or $(C_1-C_6)$alkyl; and $R^3$ is —$O(C_1-C_6)$alkyl.

A specific value for $R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heterocycle and heteroaryl, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

A specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups; and $R^{3'}$ is H.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;

$R^2$ is H or $(C_1-C_6)$alkyl; and $R^3$ is —O$(C_1-C_6)$alkyl.

Another specific value for $R^5$ is aryl, heteroaryl, heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

Another specific group of compounds of formula I are compounds wherein:

$R^5$ is selected from aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups; and $R^{3'}$ is H.

Another specific group of compounds of formula I are compounds wherein:

$R^5$ is selected from aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein $R^5$ is selected from aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;

$R^2$ is H or $(C_1-C_6)$alkyl; and $R^3$ is —O$(C_1-C_6)$alkyl.

Another specific value for $R^5$ is selected from:

a) aryl, wherein aryl is optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

Another specific group of compounds of formula I are compounds wherein:

$R^5$ is selected from:

a) aryl, wherein aryl is optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups; and $R^{3'}$ is H.

Another specific group of compounds of formula I are compounds wherein:

$R^5$ is selected from:

a) aryl, wherein aryl is optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, wherein aryl is optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;

$R^2$ is H or $(C_1-C_6)$alkyl; and $R^3$ is —O$(C_1-C_6)$alkyl.

Another specific value for $R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl;

wherein each $Z^{10}$ is independently selected from:
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2$$(C_1-C_6)$alkyl, —NH$_2$, —NH$(C_1-C_6)$alkyl and —N$((C_1-C_6)$alkyl$)_2$;
ii) $(C_1-C_6)$alkyl substituted with —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with halo, $(C_1-C_6)$alkyl or COOH; and
each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl.

Another specific group of compounds of formula I are compounds wherein:
$R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
$R^{3'}$ is H;
each $Z^{10}$ is independently selected from:
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2$$(C_1-C_6)$alkyl, —NH$_2$, —NH$(C_1-C_6)$alkyl and —N$((C_1-C_6)$alkyl$)_2$;
ii) $(C_1-C_6)$alkyl substituted with —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with halo, $(C_1-C_6)$alkyl or COOH; and
each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl.

Another specific group of compounds of formula I are compounds wherein:
$R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
$R^{3'}$ is H; $R^1$ is H;
$R^2$ is H or $(C_1-C_6)$alkyl;
each $Z^{10}$ is independently selected from:
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2$$(C_1-C_6)$alkyl, —NH$_2$, —NH$(C_1-C_6)$alkyl and —N$((C_1-C_6)$alkyl$)_2$;
ii) $(C_1-C_6)$alkyl substituted with —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with halo, $(C_1-C_6)$alkyl or COOH; and
each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl.

Another specific group of compounds of formula I are compounds wherein:
$R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
$R^{3'}$ is H; $R^1$ is H;
$R^2$ is H or $(C_1-C_6)$alkyl;
$R^3$ is —O$(C_1-C_6)$alkyl;
each $Z^{10}$ is independently selected from:
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2$$(C_1-C_6)$alkyl, —NH$_2$, —NH$(C_1-C_6)$alkyl and —N$((C_1-C_6)$alkyl$)_2$;
ii) $(C_1-C_6)$alkyl substituted with —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with halo, $(C_1-C_6)$alkyl or COOH; and
each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl.

Another specific value for $R^5$ is:

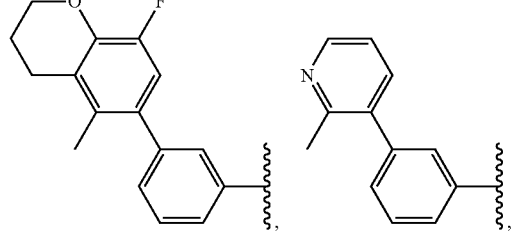

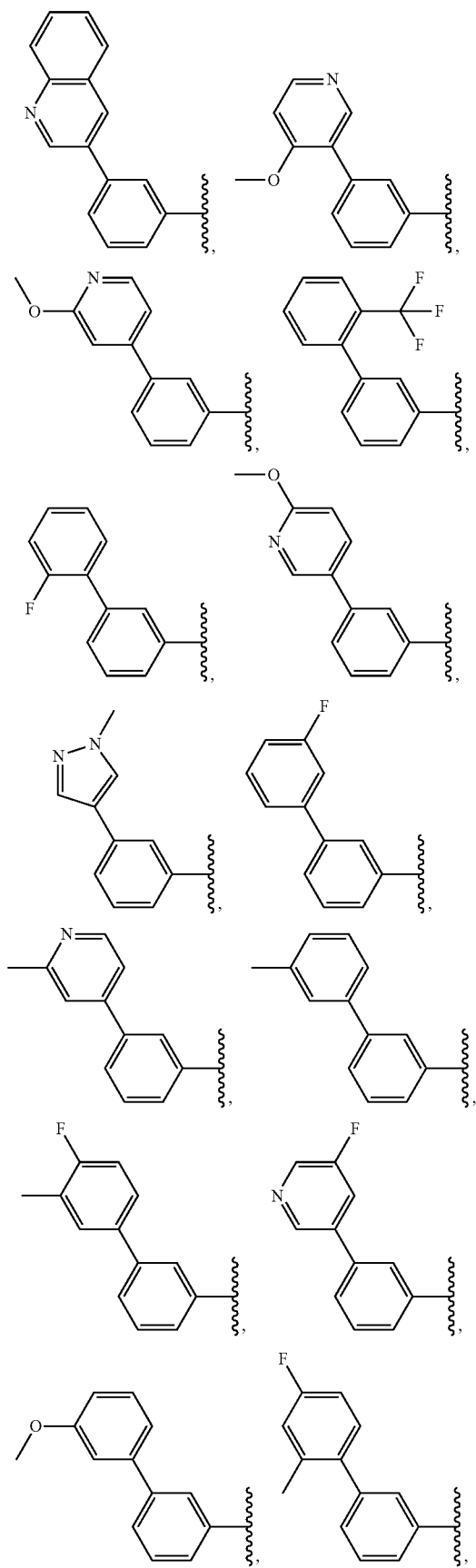
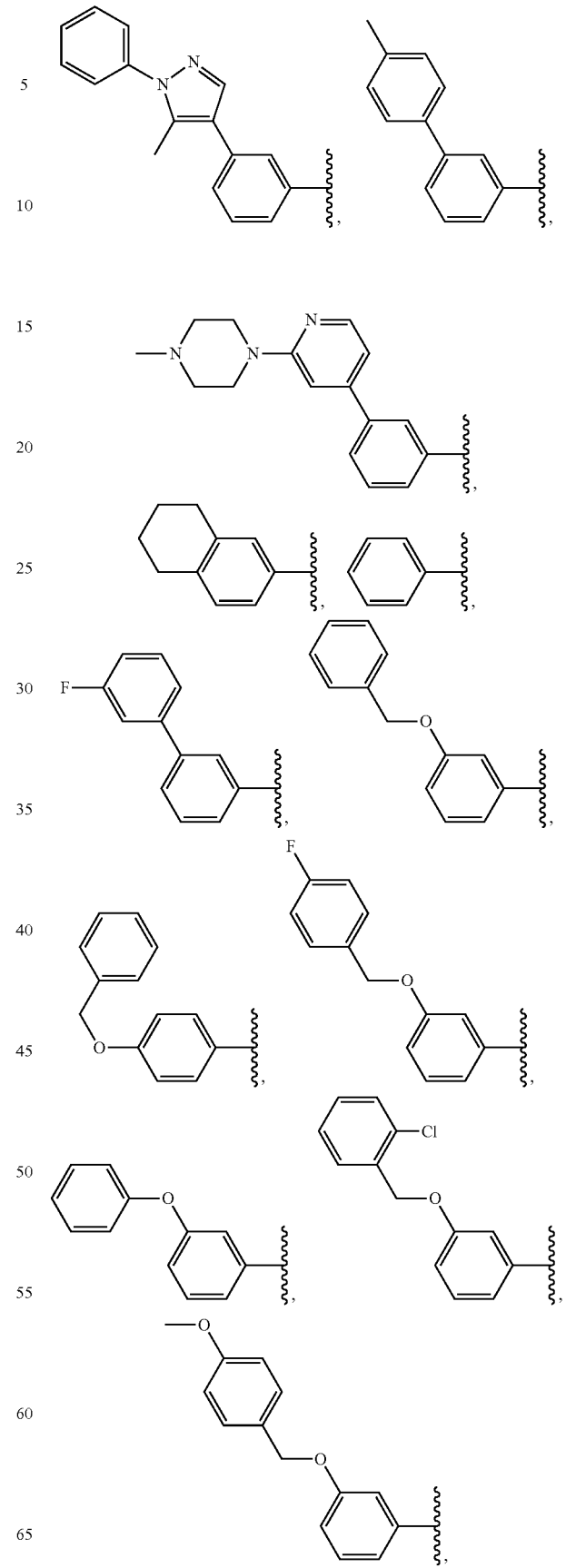

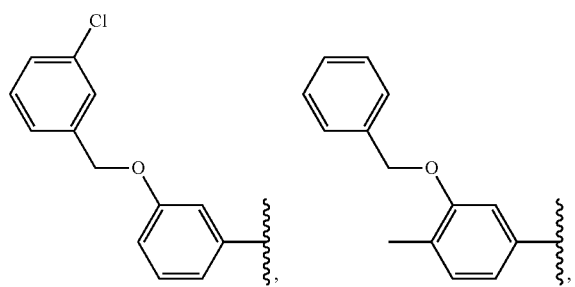
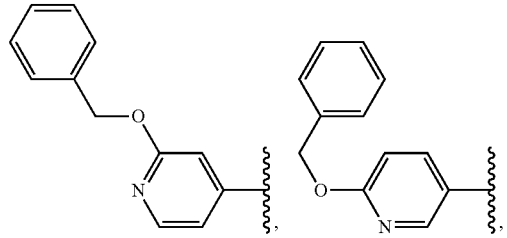
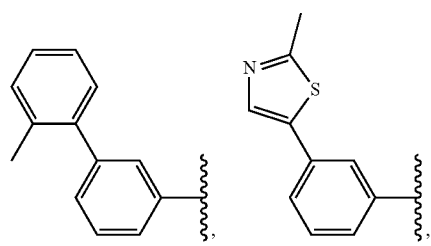
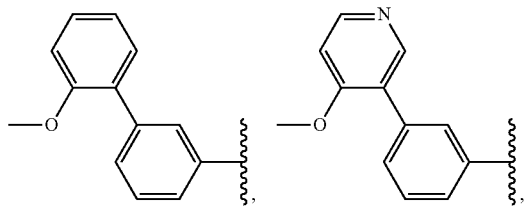
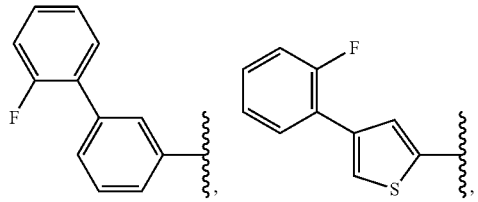
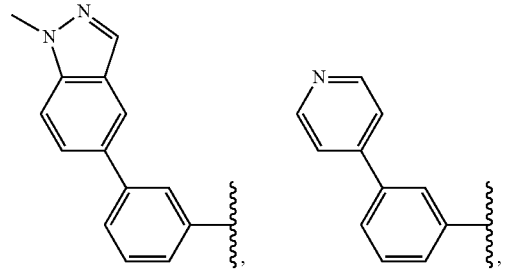
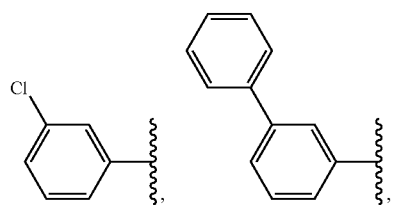
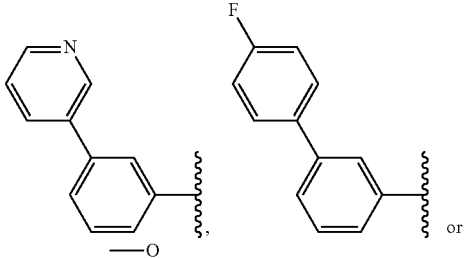
In one embodiment of the invention the compound of formula I is selected from a compound of formulas Ia100-Ia145 (e.g. compounds Ia100, Ia101, Ia102, Ia103, Ia104, Ia105, Ia106, Ia107, Ia108, Ia109, Ia110, Ia111, Ia112, Ia113, Ia114, Ia115, Ia116, Ia117, Ia118, Ia119, Ia120, Ia121, Ia122, Ia123, Ia124, Ia125, Ia126, Ia127, Ia128, Ia129, Ia130, Ia131, Ia132, Ia133, Ia134, Ia135, Ia136, Ia137, Ia138, Ia139, Ia140, Ia141, Ia142, Ia143, Ia144, Ia145):
Ia100
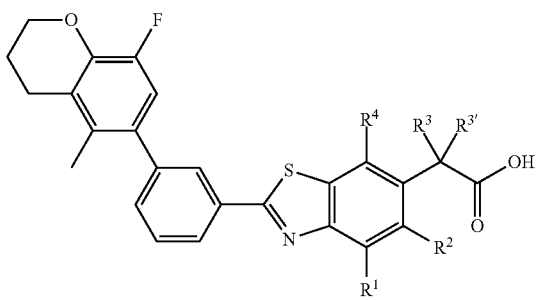
Ia101
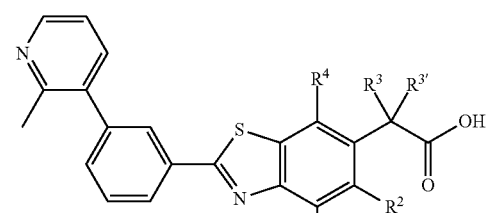
Ia102
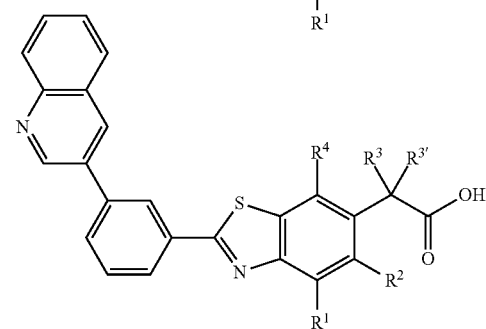

Ia103
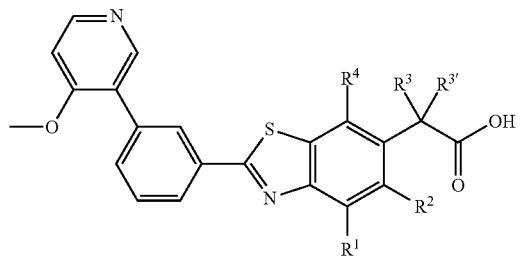
Ia104
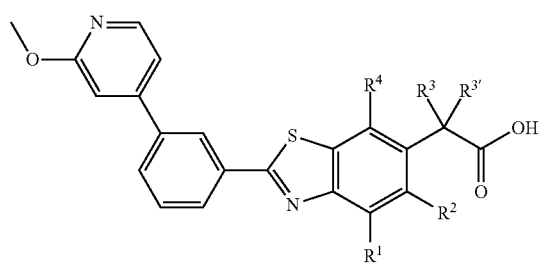
Ia15
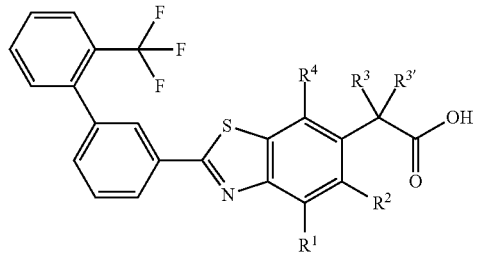
Ia106
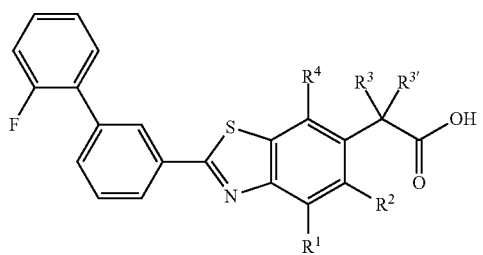
Ia107
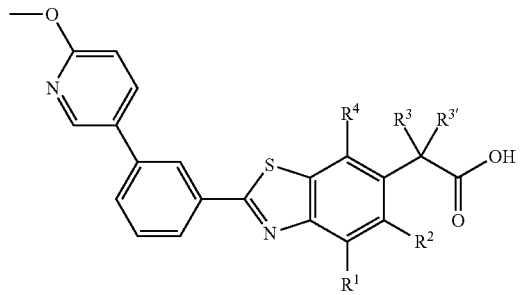
Ia108
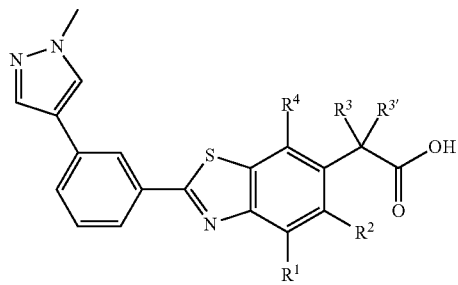
Ia109
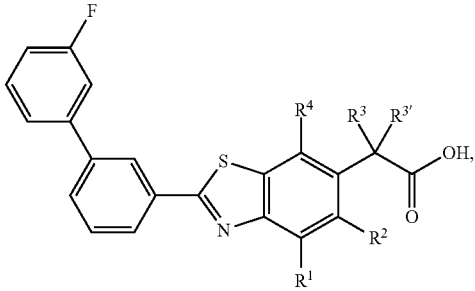
Ia110
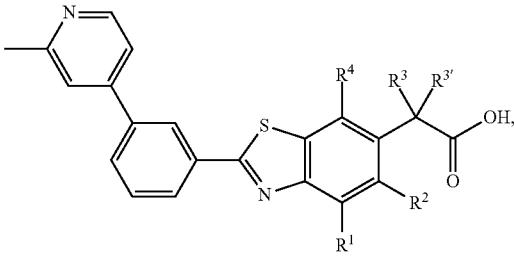
Ia111
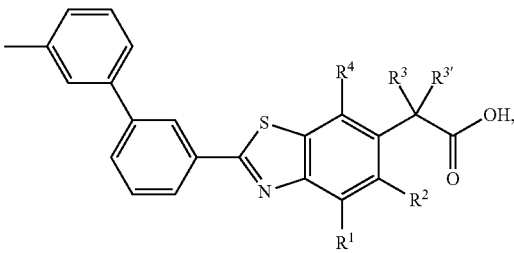
Ia112
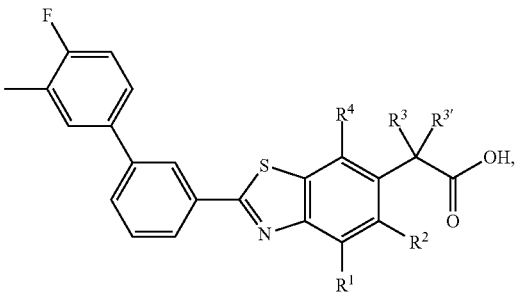

Ia113
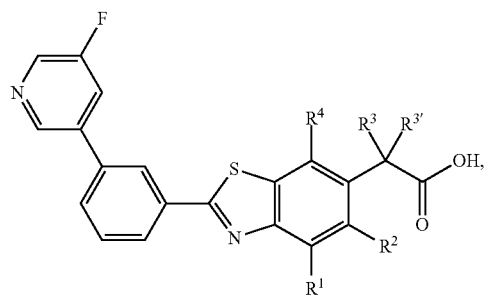
Ia114
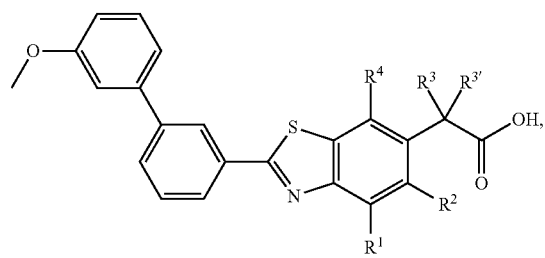
Ia115
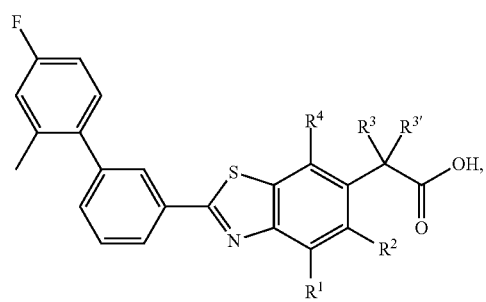
Ia116
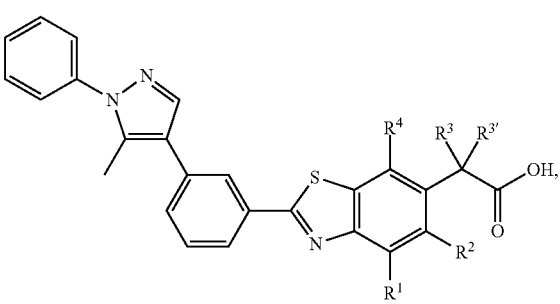
Ia117
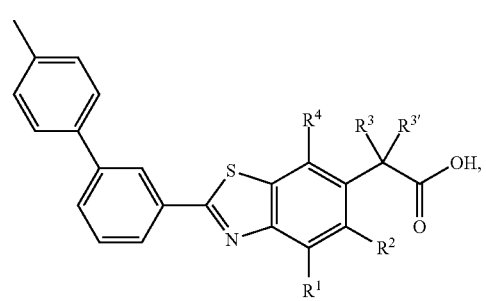
Ia118
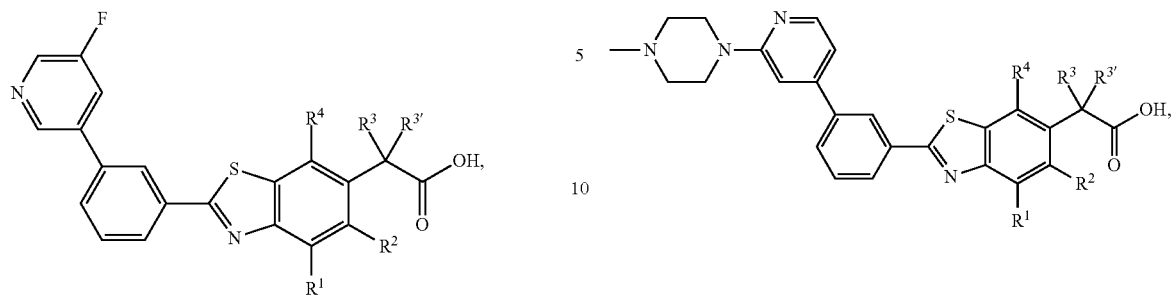
Ia119
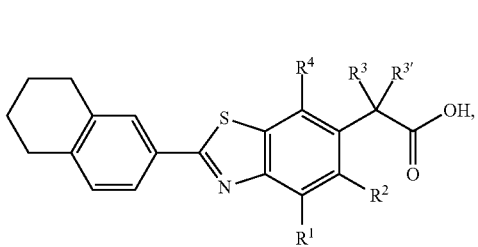
Ia120
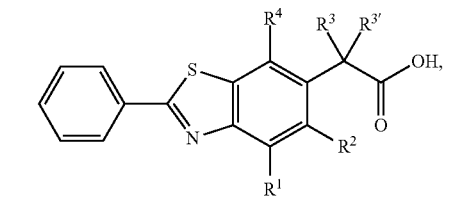
Ia121
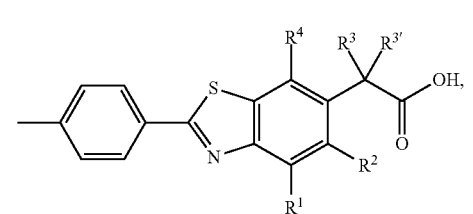
Ia122
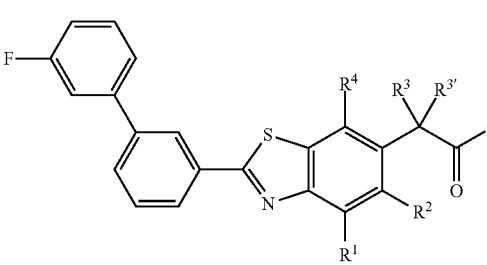
Ia123
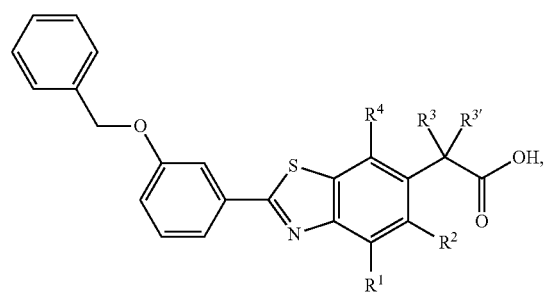

-continued
Ia124
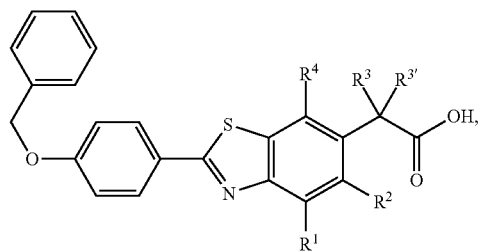
Ia125
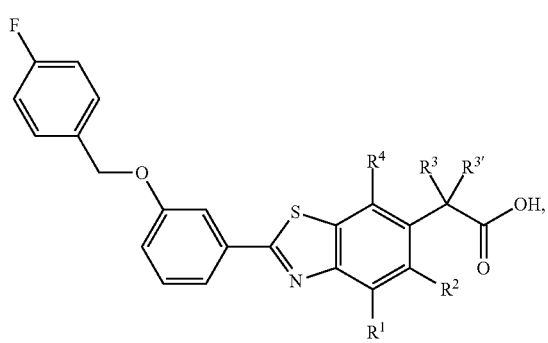
Ia126
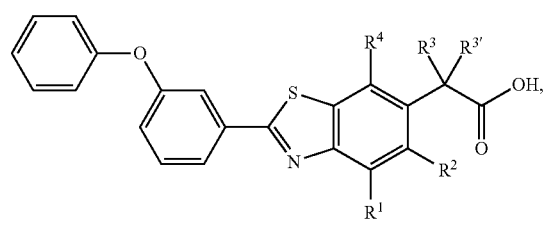
Ia127
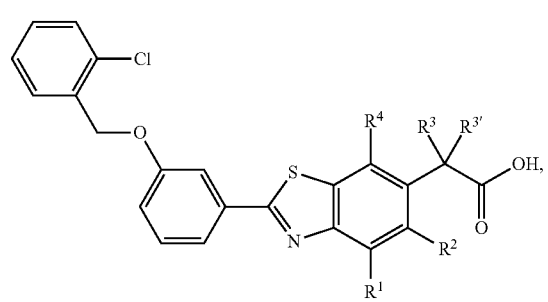
Ia128
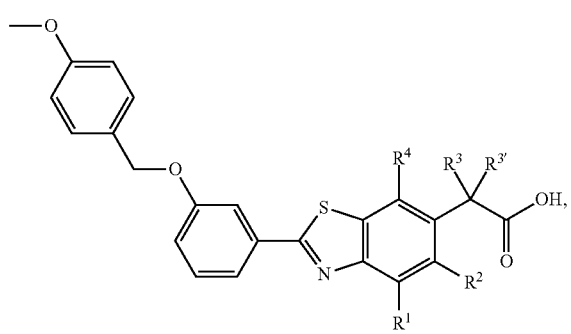
-continued
Ia129
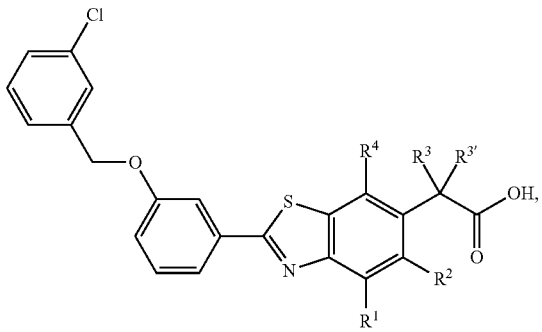
Ia130
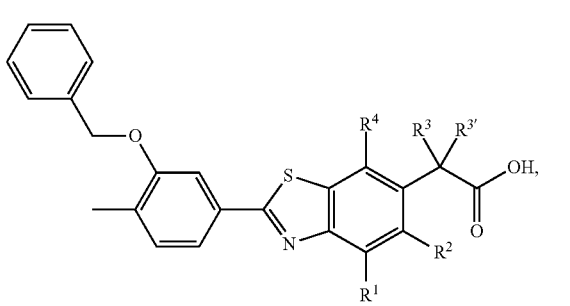
Ia131
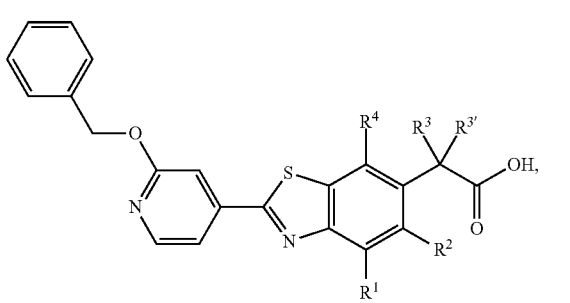
Ia132
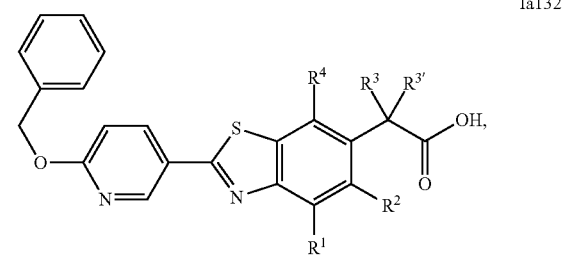
Ia133
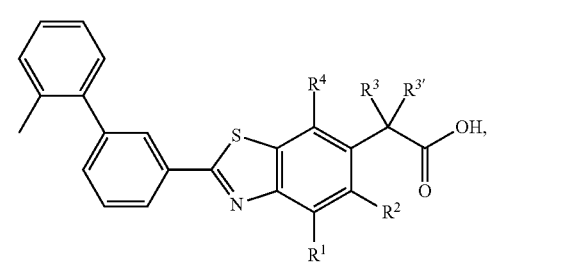

-continued
Ia134
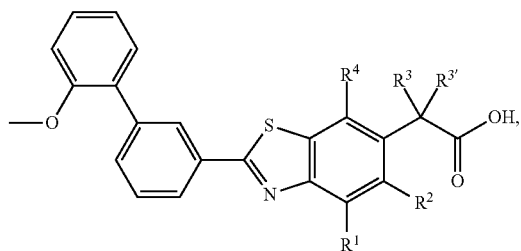
Ia135
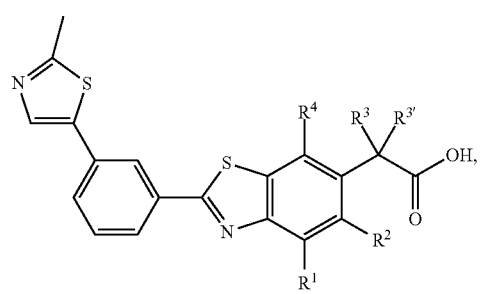
Ia136
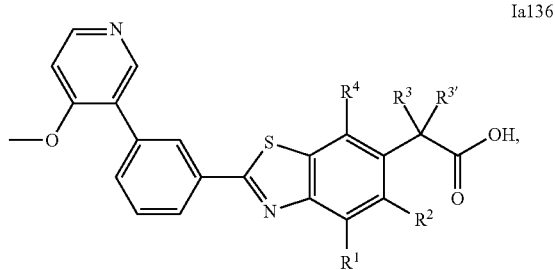
Ia137
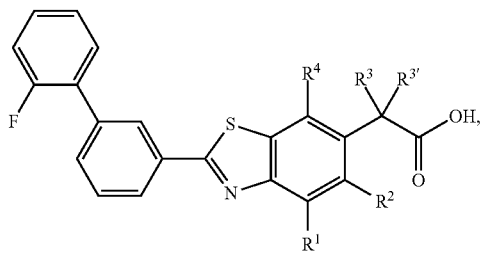
Ia138
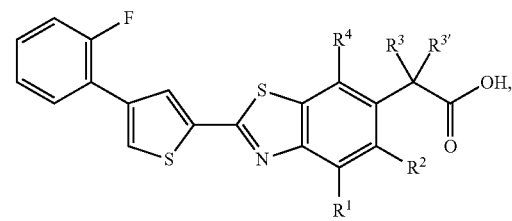
-continued
Ia139
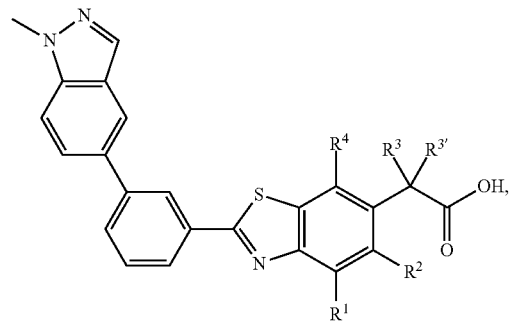
Ia140
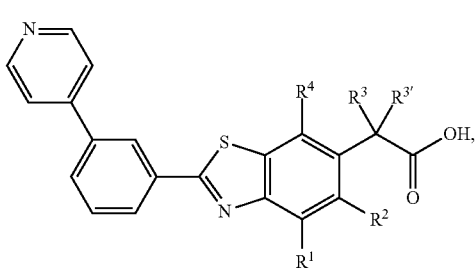
Ia141
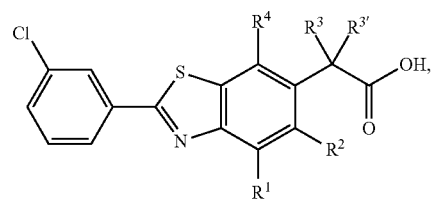
Ia142
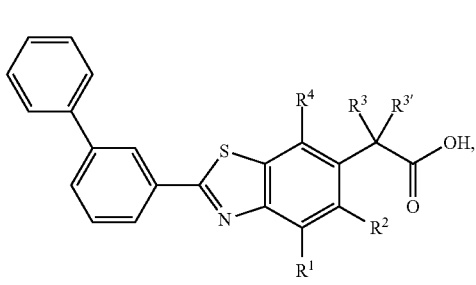
Ia143
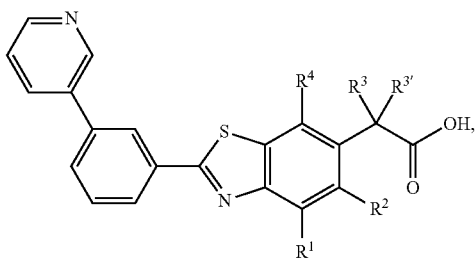

-continued

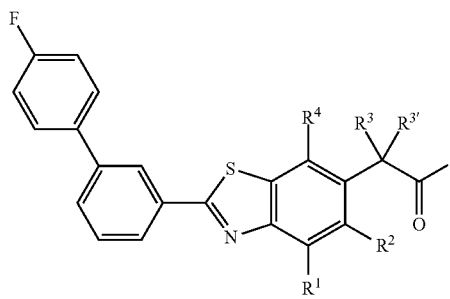
Ia144

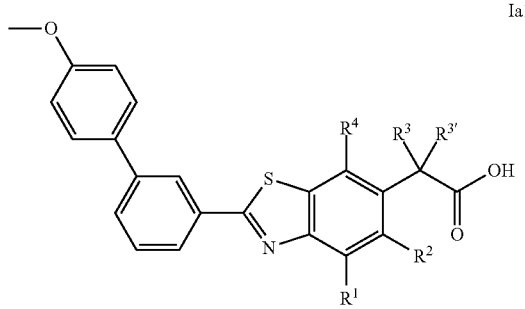
Ia145 and salts thereof.

In one embodiment, the compounds of formula I are selected from the compounds of formulas Ia100-Ia145 wherein:
$R^1$ is H; $R^2$ is methyl, $R^{3'}$ is H; $R^3$ is -OtBu; and
$R^4$ is:

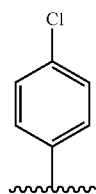

and salts thereof.

In another embodiment, the compounds of formula I are selected from the compounds of formulas Ia100-Ia145 wherein:
$R^1$ is H; $R^2$ is methyl, $R^{3'}$ is H; $R^3$ is -OtBu; and
$R^4$ is:

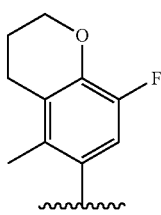 [SMILES: *c1cc(F)c2c(c1C)CCCO2]

and salts thereof.

In another embodiment, the compounds of formula I are selected from the compounds of formulas Ia100-Ia145 wherein:
$R^1$ is H; $R^2$ is methyl, $R^{3'}$ is H; $R^3$ is -OtBu; and
$R^4$ is:

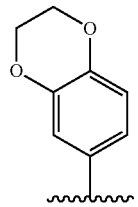

and salts thereof.

In another embodiment of the invention, the compounds of formula I are selected from the compounds of formulas Ia100-Ia145 wherein:
$R^1$ is H; $R^2$ is methyl, $R^{3'}$ is H; $R^3$ is -OtBu; and
$R^4$ is:

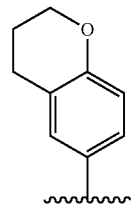

and salts thereof.

In one embodiment of the invention the compounds of formula I are selected from the compounds of formulas Ia100-Ia145 wherein $R^{3'}$ is H; $R^3$ is —O($C_1$-$C_6$)alkyl and the stereochemistry of the carbon bearing the $R^3$ (—O($C_1$-$C_6$)alkyl) group is (S).

In another embodiment of the invention the compounds of formula I are selected from the compounds of formulas Ia100-Ia145 wherein $R^{3'}$ is H; $R^3$ is —O($C_1$-$C_6$)alkyl and the stereochemistry of the carbon bearing the $R^3$ (—O($C_1$-$C_6$)alkyl) group is (R).

In one embodiment of the invention, the compounds of formula I are selected from:

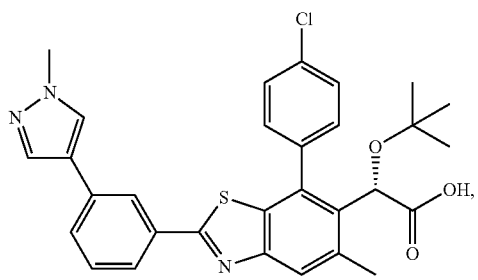

-continued

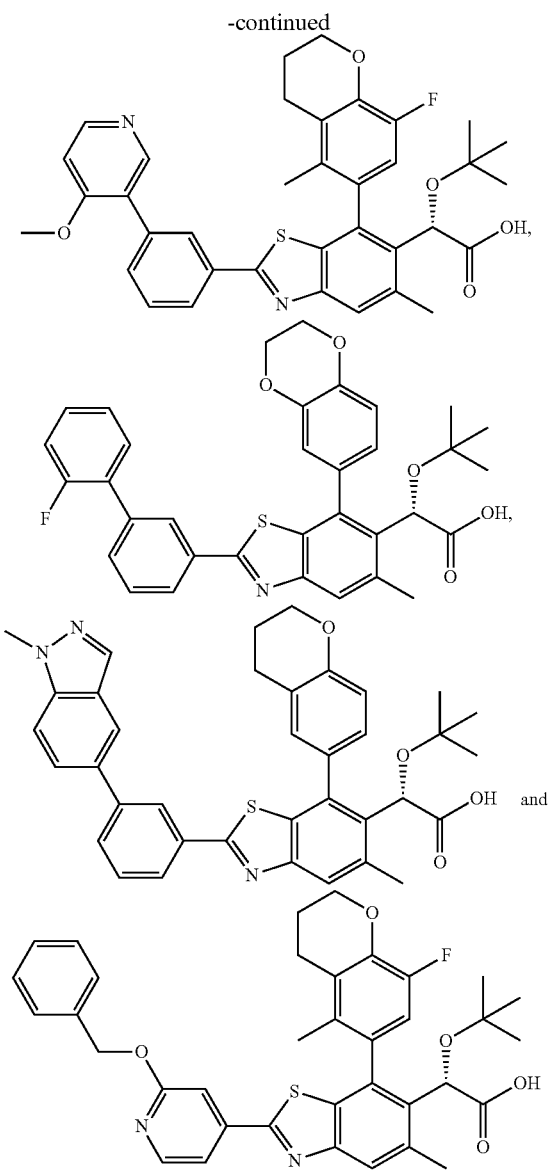

and salts thereof.

In one embodiment, the invention provides a compound of formula I:

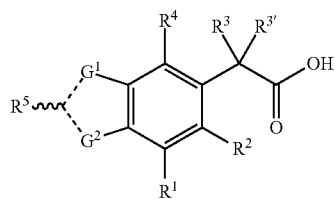

wherein:

$G^1$ is S, $G^2$ is N, the dashed bond connected to $G^1$ is a single bond, the dashed bond connected to $G^2$ is a double bond, and the wavy bond connected to $R^5$ is a single bond; or $G^1$ is N, $G^2$ is S, the dashed bond connected to $G^1$ is a double bond, the dashed bond connected to $G^2$ is a single bond, and the wavy bond connected to $R^5$ is a single bond;

$R^1$ is $R^{1a}$ or $R^{1b}$;
$R^2$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;
$R^{1a}$ is selected from:
a) halo;
b) $R^{11}$, —(=O)—$R^{11}$, —C(=O)—O—$R^{11}$, —O—$R^{11}$, —S—$R^{11}$, —S(O)—$R^{11}$, —SO$_2$—$R^{11}$, —(C$_1$-C$_6$)alkyl-$R^{11}$, —(C$_1$-C$_6$)alkyl-C(=O)—$R^{11}$, —(C$_1$-C$_6$)alkyl-C(=O)—O—$R^{11}$, —(C$_1$-C$_6$)alkyl-O—$R^{11}$, —(C$_1$-C$_6$)alkyl-S—$R^{11}$, —(C$_1$-C$_6$)alkyl-S(O)—$R^{11}$ and —(C$_1$-C$_6$)alkyl-SO$_2$—$R^{11}$, wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle or heteroaryl are each optionally substituted with one or more (e.g. 1, 2 or 3) $Z^{11}$ groups; and
c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C(=O)—N(R$^9$)R$^{10}$ and —(C$_1$-C$_6$)alkyl-SO$_2$—N(R$^9$)R$^{10}$, wherein each $R^9$ is independently selected from H, (C$_1$-C$_6$)alkyl and (C$_3$-C$_7$)cycloalkyl, and each $R^{10}$ is independently selected from $R^{11}$, —(C$_1$-C$_6$)alkyl-$R^{11}$, —SO$_2$—$R^{11}$, —C(=O)—$R^{11}$, —C(=O)OR$^{11}$ and —C(=O)N(R$^9$)R$^{11}$, wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

$R^{1b}$ is selected from:
a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_6$)carbocycle, —(C$_1$-C$_6$)alkyl-SO$_2$—(C$_1$-C$_6$)alkyl-(C$_3$-C$_7$)carbocycle, —(C$_1$-C$_6$)alkyl-SO$_2$—(C$_1$-C$_6$)alkyl-$Z^{13}$, —C(O)—(C$_1$-C$_6$)alkyl-$Z^{13}$, —O—(C$_1$-C$_6$)alkyl-$Z^{13}$, —S—(C$_1$-C$_6$)alkyl-$Z^{13}$, —S(O)—(C$_1$-C$_6$)alkyl-$Z^{13}$, —SO$_2$—(C$_1$-C$_6$)alkyl-$Z^{13}$, —(C$_1$-C$_6$)alkyl-$Z^{14}$, —(C$_1$-C$_6$)alkyl-C(O)—(C$_1$-C$_6$)alkyl-$Z^{13}$, —(C$_1$-C$_6$)alkyl-C(O)—O(C$_1$-C$_6$)alkyl-$Z^{13}$, —(C$_1$-C$_6$)alkyl-O—(C$_1$-C$_6$)alkyl-$Z^{13}$, —(C$_1$-C$_6$)alkyl-S—(C$_1$-C$_6$)alkyl-$Z^{13}$, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl —(C$_2$-C$_6$)alkynyl-heterocycle, —(C$_3$-C$_7$)carbocycle-$Z^1$ or —(C$_1$-C$_6$)haloalkyl-$Z^3$, wherein any (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl, either alone or as part of a group, is optionally substituted with one or more (e.g. 1, 2, 3, 4 or 5) $Z^1$ groups;
b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z^1$ groups, or wherein two $Z^1$ groups together with the atom or atoms to which they are attached optionally form a carbocycle or heterocycle wherein the carbocycle or heterocycle is optionally substituted with one or more (e.g. 1, 2, 3, 4 or 5) $Z^1$ groups;
c) (C$_1$-C$_6$)alkyl, wherein (C$_1$-C$_6$)alkyl is substituted with one or more (e.g. 1, 2, 3, 4 or 5) $Z^2$ groups and optionally substituted with one or more (e.g. 1, 2, 3, 4 or 5) $Z^1$ groups;
d) —X(C$_1$-C$_6$)alkyl, —X(C$_1$-C$_6$)haloalkyl, —X(C$_2$-C$_6$)alkenyl, —X(C$_2$-C$_6$)alkynyl and —X(C$_3$-C$_7$)carbocycle, wherein —X(C$_1$-C$_6$)alkyl and —X(C$_1$-C$_6$)haloalkyl are each independently substituted with one or more $Z^3$ groups and optionally substituted with one or more $Z^1$ groups, and wherein —X($C_2$-$C_6$)alkenyl, —X($C_2$-$C_6$)alkynyl and —X($C_3$-$C_7$)carbocycle, are each independently substituted with one or more (e.g. 1, 2, 3, 4 or 5) $Z^4$ groups and optionally substituted with one or more $Z^1$ groups;

e) aryl, heteroaryl, heterocycle, —Xaryl, —Xheteroaryl and —Xheterocycle; wherein aryl heteroaryl and heterocycle, either alone or as part of a group, are each independently substituted with one or more (e.g. 1, 2, 3, 4 or 5) $Z^5$ groups and optionally substituted with one or more $Z^1$ groups;

f) ($C_1$-$C_6$)haloalkyl, ($C_3$-$C_7$)carbocycle, ($C_2$-$C_6$)alkenyl, and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more $Z^1$ groups;

g) —$NR_eR_f$, —C(O)$NR_eR_f$, —OC(O)$NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$; wherein each ($C_1$-$C_6$)alkyl, as part of a group, is independently substituted with one or more (e.g. 1, 2, 3, 4 or 5) $Z^6$ groups and optionally substituted with one or more $Z^1$ groups; and h) nitro and cyano;

$R^{2a}$ is selected from:

a) halo;

b) $R^{11}$, C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl and heterocycle and heteroaryl, wherein aryl, heterocycle or heteroaryl are each optionally substituted with one or more (e.g. 1, 2 or 3) $Z^{11}$ groups; and c) —N($R^9$)$R^{10}$, —C(=O)—N($R^9$)$R^{10}$, —O—C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$, and —($C_1$-$C_6$)alkyl-$SO_2$—N($R^9$)$R^{10}$, wherein each $R^9$ is independently selected from H, ($C_1$-$C_6$)alkyl and ($C_3$-$C_7$)cycloalkyl, wherein each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl;

$R^{2b}$ is selected from:

a) —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_3$-$C_7$)halocarbocycle, —$NR_aSO_2NR_eR_d$, —$NR_aSO_2O$($C_3$-$C_7$)carbocycle, —$NR_aSO_2$Oaryl, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_3$-$C_7$)carbocycle-$Z^1$ or —($C_1$-$C_6$)haloalkyl-$Z^3$, wherein any ($C_1$-$C_6$)alkyl, —($C_1$-$C_6$)haloalkyl, ($C_3$-$C_7$)carbocycle, ($C_2$-$C_6$)alkenyl, ($C_2$-$C_6$)alkynyl, aryl or heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z^1$ groups, wherein two $Z^1$ groups together with the atom or atoms to which they are attached optionally form a ($C_3$-$C_7$)carbocycle or heterocycle wherein the ($C_3$-$C_6$)carbocycle or heterocycle is optionally substituted with one or more (e.g. 1, 2, 3, 4 or 5) $Z^1$ groups;

c) ($C_1$-$C_6$)alkyl, wherein ($C_1$-$C_6$)alkyl is substituted with one or more $Z^2$ groups and optionally substituted with one or more (e.g. 1, 2, 3, 4 or 5) $Z^1$ groups;

d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle, wherein —X($C_1$-$C_6$)alkyl and X($C_1$-$C_6$)haloalkyl are each independently substituted with one or more $Z^3$ groups and optionally substituted with one or more (e.g. 1, 2, 3, 4 or 5) $Z^1$ groups, and wherein —X($C_2$-$C_6$)alkenyl, —X($C_2$-$C_6$)alkynyl and —X($C_3$-$C_7$)carbocycle are each independently substituted with one or more (e.g. 1, 2, 3, 4 or 5) $Z^4$ groups and optionally substituted with one or more $Z^1$ groups;

e) aryl, heteroaryl, heterocycle, —Xaryl, —Xheteroaryl and —Xheterocycle, wherein aryl heteroaryl and heterocycle, either alone or as part of a group, are each independently substituted with one or more (e.g. 1, 2, 3, 4 or 5) $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl, and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups;

g) —$NR_eR_f$, —C(O)$NR_eR_f$, —OC(O)$NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$ wherein each ($C_1$-$C_6$)alkyl, as part of a group, is independently substituted with one or more (e.g. 1, 2, 3, 4 or 5) $Z^6$ groups and optionally substituted with one or more (e.g. 1, 2, 3, 4 or 5) $Z^1$ groups; and h) nitro and cyano;

or $R^1$ and $R^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are optionally substituted with one or more $Z^1$ groups;

or $R^1$ and $R^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are each independently substituted with one or more (e.g. 1, 2 or 3) $Z^7$ or $Z^8$ groups, or wherein when two $Z^7$ groups are on same atom the two $Z^7$ groups together with the atom to which they are attached optionally form a ($C_3$-$C_7$)carbocycle or 4, 5 or 6-membered heterocycle;

$R^{3a}$ is ($C_1$-$C_6$)alkyl, ($C_1$-$C_6$)haloalkyl, ($C_2$-$C_6$)alkenyl, ($C_2$-$C_6$)alkynyl, —($C_1$-$C_6$)alkyl-($C_3$-$C_7$)cycloalkyl, —($C_1$-$C_6$)alkyl-aryl, —($C_1$-$C_6$)alkyl-heterocycle, —($C_1$-$C_6$)alkyl-heteroaryl, —O($C_1$-$C_6$)alkyl, —O($C_1$-$C_6$)haloalkyl, —O($C_2$-$C_6$)alkenyl, —O($C_2$-$C_6$)alkynyl, —O($C_3$-$C_7$)cycloalkyl, —Oaryl, —O($C_1$-$C_6$)alkyl-($C_3$-$C_7$)cycloalkyl, —O($C_1$-$C_6$)alkyl-aryl, —O($C_1$-$C_6$)alkyl-heterocycle and —O($C_1$-$C_6$)alkyl-heteroaryl, wherein any ($C_1$-$C_6$)alkyl, ($C_1$-$C_6$)haloalkyl, ($C_2$-$C_6$)alkenyl, ($C_2$-$C_6$)alkynyl, —($C_1$-$C_6$)alkyl-($C_3$-$C_7$)cycloalkyl, —($C_1$-$C_6$)alkyl-aryl, —($C_1$-$C_6$)alkyl-heterocycle, —($C_1$-$C_6$)alkyl-heteroaryl, —O($C_1$-$C_6$)alkyl, —O($C_1$-$C_6$)haloalkyl, —O($C_2$-$C_6$)alkenyl, —O($C_2$-$C_6$)alkynyl, —O($C_3$-$C_7$)cycloalkyl, —Oaryl, —O($C_1$-$C_6$)alkyl-($C_3$-$C_7$)cycloalkyl, —O($C_1$-$C_6$)alkyl-aryl, —O($C_1$-$C_6$)alkyl-heterocycle or —O($C_1$-$C_6$)alkyl-heteroaryl of $R^{3a}$ is optionally substituted with one or more (e.g. 1, 2 or 3) groups selected from ($C_1$-$C_6$)alkyl, —O($C_1$-$C_6$)alkyl, halo, oxo and —CN; and $R^{3a'}$ is H;

$R^{3b}$ is —($C_3$-$C_7$)carbocycle, aryl, heteroaryl, heterocycle, —($C_1$-$C_6$)alkylOH, —($C_1$-$C_6$)alkyl-O—($C_1$-$C_6$)alkyl-$Z^{12}$, —($C_1$-$C_6$)alkyl-O—($C_2$-$C_6$)alkenyl-$Z^{12}$, —($C_2$-$C_6$)alkyl-O—($C_2$-$C_6$)alkynyl-$Z^{12}$, —($C_1$-$C_6$)alkyl-S—($C_1$-$C_6$)alkyl-$Z^{12}$, —($C_1$-$C_6$)alkyl-S—($C_2$-$C_6$)alkenyl-$Z^{12}$, —($C_2$-$C_6$)alkyl-S—($C_2$-$C_6$)alkynyl-$Z^{12}$, —($C_1$-$C_6$)alkyl-S(O)—($C_1$-$C_6$)alkyl-$Z^{12}$, —($C_1$-$C_6$)alkyl-S(O)—($C_2$-$C_6$)alkenyl-$Z^{12}$, —($C_2$-$C_6$)alkyl-S(O)—($C_2$-$C_6$)alkynyl-$Z^{12}$, —($C_1$-$C_6$)alkyl-$SO_2$—($C_1$-$C_6$)alkyl-$Z^{12}$, —($C_1$-$C_6$)alkyl-$SO_2$—($C_2$-$C_6$)alkenyl-$Z^{12}$, —($C_2$-$C_6$)alkyl-$SO_2$—($C_2$-$C_6$)alkynyl-$Z^{12}$, —($C_2$-$C_6$)alkyl-$NR_aR_b$, —($C_2$-$C_6$)alkylOC(O)—$NR_cR_d$, —($C_2$-$C_6$)alkyl-$NR_a$—C(O)—$OR_b$, —($C_2$-$C_6$)alkyl-$NR_a$—C(O)—$NR_aR_b$, —($C_1$-$C_6$)alkyl-$SO_2$($C_1$-$C_6$)alkyl, —($C_1$-$C_6$)alkyl-$SO_2NR_cR_d$, —($C_1$-$C_6$)alkyl-$NR_aSO_2NR_cR_d$, —($C_1$-$C_6$)alkyl-$NR_aSO_2$O($C_3$-$C_7$)carbocycle, —($C_1$-$C_6$)alkyl-$NR_aSO_2$Oaryl, —($C_1$-$C_6$)alkyl-$NR_a$—$SO_2$—($C_1$-$C_6$)alkyl, —($C_1$-$C_6$)alkyl-$NR_a$—$SO_2$—($C_1$-$C_6$)haloalkyl, —($C_1$-$C_6$)alkyl-$NR_a$—$SO_2$—($C_2$-$C_6$)alkenyl, —($C_1$-$C_6$)alkyl-$NR_a$—$SO_2$—($C_2$-$C_6$)alkynyl, —($C_1$-$C_6$)alkyl-$NR_a$—$SO_2$—($C_3$-$C_7$)carbocycle, —($C_1$-$C_6$)alkyl-$NR_a$—$SO_2$—($C_3$-$C_7$)halocarbocycle, —($C_1$-$C_6$)alkyl-$NR_a$—$SO_2$-aryl, —($C_1$-$C_6$)alkyl-$NR_a$—$SO_2$-heteroaryl, —($C_1$-$C_6$)alkyl-$NR_a$—$SO_2$-heterocycle, —O($C_1$-$C_6$)alkyl-$NR_aR_b$, —O($C_1$-$C_6$)alkylOC(O)—$NR_cR_d$, —O($C_1$-$C_6$)alkyl-$NR_a$—C(O)—$OR_b$, —O($C_1$-$C_6$)alkyl-$NR_a$—C(O)—$NR_aR_b$, —O($C_1$-$C_6$)alkyl-$NR_a$—$SO_2$—($C_1$-$C_6$)alkyl, —O($C_1$-$C_6$)alkyl-$NR_a$—$SO_2$—($C_1$-$C_6$)haloalkyl, —O($C_1$-$C_6$)alkyl-$NR_a$—$SO_2$—($C_2$-$C_6$)alkenyl, —O($C_1$-$C_6$)alkyl-$NR_a$—$SO_2$—($C_2$-$C_6$)alkynyl, —O($C_1$-$C_6$)alkyl-$NR_a$—$SO_2$—($C_3$-$C_7$)carbocycle, —O($C_1$-$C_6$)alkyl-$NR_a$—$SO_2$—($C_3$-$C_7$)halocarbocycle, —O($C_1$-$C_6$)alkyl-$NR_a$—$SO_2$-aryl, —O($C_1$-$C_6$)alkyl-$NR_a$—$SO_2$-heteroaryl, —O($C_1$-$C_6$)alkyl-$NR_a$—$SO_2$—$NR_aR_b$, —O($C_1$-$C_6$)alkyl-$NR_a$—$SO_2$—($C_3$-$C_7$)carbocycle, —O($C_1$-$C_6$)alkyl-$NR_a$—$SO_2$—($C_3$-$C_7$)halocarbocycle, —O($C_1$-$C_6$)alkyl-$NR_a$—$SO_2$-aryl, —O($C_1$-$C_6$)alkyl-$NR_aSO_2NR_cR_d$, —O($C_1$-$C_6$)alkyl-$NR_aSO_2$O($C_3$-$C_7$)carbocycle, —O($C_1$-$C_6$)alkyl-$NR_aSO_2$Oaryl, —Oheteroaryl, —Oheterocycle, —Sheteroaryl, —Sheterocycle, —S(O)heteroaryl, —S(O)heterocycle, —$SO_2$heteroaryl or —$SO_2$heterocycle, wherein any ($C_1$-$C_6$)alkyl, ($C_2$-$C_6$)alkenyl, ($C_2$-$C_6$)alkynyl, aryl, ($C_3$-$C_7$)carbocycle, heteroaryl or heterocycle of $R^{3b}$, either alone or as part of a group, is optionally substituted with one or more (e.g. 1, 2, 3, 4 or 5) $Z^1$ groups; and $R^{3b'}$ is H, ($C_1$-$C_6$)alkyl or —O($C_1$-$C_6$)alkyl; or $R^{3b}$ and $R^{3b'}$ together with the carbon to which they are attached form a heterocycle or ($C_3$-$C_7$)carbocycle, which heterocycle or ($C_3$-$C_7$)carbocycle of $R^{3b}$ and $R^{3b'}$ together with the carbon to which they are attached is optionally substituted with one or more (e.g. 1, 2, 3, 4 or 5) $Z^1$ groups;

$R^{4a}$ is selected from aryl, heterocycle and heteroaryl, wherein any aryl, heterocycle and heteroaryl of $R^{4a}$ is optionally substituted with one or more (e.g. 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —$NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo;

$R^{4b}$ is selected from;

a) ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl or ($C_2$-$C_6$)alkynyl are each optionally substituted with one or more (e.g. 1, 2, 3, 4 or 5) $Z^1$ groups;

b) ($C_3$-$C_{14}$)carbocycle, wherein ($C_3$-$C_{14}$)carbocycle is optionally substituted with one or more (e.g. 1, 2, 3, 4 or 5) $Z^1$ groups, or wherein two $Z^1$ groups together with the atom or atoms to which they are attached optionally form a ($C_3$-$C_7$) carbocycle or heterocycle;

c) Spiro-heterocycle or bridged-heterocycle, wherein spiro-heterocycle or bridged-heterocycle is optionally substituted with one or more (e.g. 1, 2, 3, 4 or 5) $Z^1$ groups, or wherein two $Z^1$ groups together with the atom or atoms to which they are attached optionally form a ($C_3$-$C_7$)carbocycle or heterocycle; and d) aryl, heteroaryl, spiro-heterocycle, fused-heterocycle, or bridged-heterocycle, wherein aryl, heteroaryl, spiro-heterocycle, fused-heterocycle and bridged-heterocycle are each independently substituted with one or more $Z^7$ groups and optionally substituted with one or more (e.g. 1, 2, 3, 4 or 5) $Z^1$ groups; or $R^4$ and $R^3$ together with the atoms to which they are attached form a macroheterocycle or a macrocarbocycle, wherein any macroheterocycle or macrocarbocycle of $R^4$ and $R^3$ together with the atoms to which they are attached may be optionally substituted with one or more (e.g. 1, 2, 3, 4 or 5) $Z^1$ groups; and $R^{3b'}$ is H or ($C_1$-$C_6$)alkyl, —O($C_1$-$C_6$)alkyl;

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl and heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl, heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

each X is independently selected from O, —C(O)—, —C(O)O—, —S—, —S(O)—, —$SO_2$—, —($C_1$-$C_6$)alkylO—, —($C_1$-$C_6$)alkylC(O)—, —($C_1$-$C_6$)alkylC(O)O—, —($C_1$-$C_6$)alkylS—, —($C_1$-$C_6$)alkylS(O)— and —($C_1$-$C_6$)alkylSO$_2$—;

each $Z^1$ is independently selected from halo, —$NO_2$, —OH, =$NOR_a$, —SH, —CN, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)aryl, —S(O)carbocycle, —S(O)heteroaryl, —S(O)heterocycle, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$ ($C_3$-$C_7$)halocarbocycle, —$SO_2$aryl, —$SO_2$heteroaryl, —$SO_2$heterocycle, —$SO_2NR_cR_d$, —$NR_aR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3$-$C_7)$carbocycle, —$NR_aSO_2Oaryl$, —$OS(O)_2R_a$, —$C(O)R_a$, —$C(O)OR_b$, —$C(O)NR_cR_d$, and —$OC(O)NR_cR_d$, wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^1$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle or —$S(O)_2NR_cR_d$;

each $Z^2$ is independently selected from —$NO_2$, —CN, spiro-heterocycle, bridge-heterocycle, spiro-bicyclic carbocycle, bridged-bicyclic carbocycle, $NR_aSO_2(C_3$-$C_7)$carbocycle, —$NR_aSO_2aryl$, —$NR_aSO_2heteroaryl$, —$NR_aSO_2NR_cR_d$, —$NR_aSO_2O(C_3$-$C_7)$carbocycle and —$NR_aSO_2Oaryl$;

each $Z^3$ is independently selected from —$NO_2$, —CN, —OH, oxo, =$NOR_a$, thioxo, aryl, -heterocycle, heteroaryl, ($C_3$-$C_7$)halocarbocycle, —O($C_1$-$C_6$)alkyl, —O($C_3$-$C_7$)carbocycle, —O($C_3$-$C_7$)halocarbocycle, —Oaryl, —Oheterocycle, —Oheteroaryl, —S($C_1$-$C_6$)alkyl, —S($C_3$-$C_7$)carbocycle, —S($C_3$-$C_7$)halocarbocycle, —Saryl, —Sheterocycle, —Sheteroaryl, —S(O)($C_1$-$C_6$)alkyl, —S(O)($C_3$-$C_7$)carbocycle, —S(O)($C_3$-$C_7$)halocarbocycle, —S(O)aryl, —S(O)heterocycle, —S(O)heteroaryl, —$SO_2(C_1$-$C_6$)alkyl, —$SO_2(C_3$-$C_7)$carbocycle, —$SO_2(C_3$-$C_7)$halocarbocycle, —$SO_2$aryl, —$SO_2$heterocycle, —$SO_2$heteroaryl, —$NR_aR_b$, —$NR_aC(O)R_b$, —$C(O)NR_cR_d$, —$SO_2NR_cR_d$, —$NR_aSO_2NR_cR_d$, —$NR_aSO_2O(C_3$-$C_7)$carbocycle and —$NR_aSO_2Oaryl$;

each $Z^4$ is independently selected from halogen, —($C_1$-$C_6$)alkyl, ($C_3$-$C_7$)carbocycle, —($C_1$-$C_6$)haloalkyl, —$NO_2$, —CN, —OH, oxo, =$NOR_a$, thioxo, -aryl, -heterocycle, -heteroaryl, —($C_3$-$C_7$)halocarbocycle, —O($C_1$-$C_6$)alkyl, —O($C_3$-$C_7$)carbocycle, —O($C_3$-$C_7$)halocarbocycle, —Oaryl, —Oheterocycle, —Oheteroaryl, —S($C_1$-$C_6$)alkyl, —S($C_3$-$C_7$)carbocycle, —S($C_3$-$C_7$)halocarbocycle, —Saryl, —Sheterocycle, —Sheteroaryl, —S(O)($C_1$-$C_6$)alkyl, —S(O)($C_3$-$C_7$)carbocycle, —S(O)($C_3$-$C_7$)halocarbocycle, —S(O)aryl, —S(O)heterocycle, —S(O)heteroaryl, —$SO_2(C_1$-$C_6$)alkyl, —$SO_2(C_3$-$C_7)$carbocycle, —$SO_2(C_3$-$C_7)$halocarbocycle, —$SO_2$aryl, —$SO_2$heterocycle, —$SO_2$heteroaryl, —$NR_aR_b$, —$NR_aC(O)R_a$, —$C(O)NR_cR_d$, —$SO_2NR_cR_d$, —$NR_aSO_2NR_cR_d$, —$NR_aSO_2O(C_3$-$C_7)$carbocycle and —$NR_aSO_2Oaryl$;

each $Z^5$ is independently selected from —$NO_2$, —CN, —$NR_aSO_2NR_cR_d$, —$NR_aSO_2O(C_3$-$C_7)$carbocycle, —$NR_aSO_2Oaryl$, —$NR_aSO_2(C_1$-$C_6)$alkyl, —$NR_aSO_2(C_2$-$C_6)$alkenyl, —$NR_aSO_2(C_2$-$C_6)$alkynyl, —$NR_aSO_2(C_3$-$C_7)$carbocycle, —$NR_aSO_2(C_3$-$C_7)$halocarbocycle, —$NR_aSO_2aryl$, —$NR_aSO_2heteroaryl$, —$NR_aSO_2heteroaryl$, —$NR_aSO_2heterocycle$, —$NR_aC(O)$alkyl, —$NR_aC(O)$alkenyl, —$NR_aC(O)$alkynyl, —$NR_aC(O)(C_3$-$C_7)$carbocycle, —$NR_aC(O)(C_3$-$C_7)$halocarbocycle, —$NR_aC(O)$aryl, —$NR_aC(O)$heteroaryl, —$NR_aC(O)$heterocycle, —$NR_aC(O)NR_cR_d$ and —$NR_aC(O)OR_b$;

each $Z^6$ is independently selected from —$NO_2$, —CN, —$NR_aR_a$, $NR_aC(O)R_b$, —$C(O)NR_cR_d$, ($C_3$-$C_7$)halocarbocycle, aryl, heteroaryl, heterocycle, —Oaryl, —Oheteroaryl, —Oheterocycle, —O($C_3$-$C_7$)halocarbocycle, —O($C_1$-$C_6$)alkyl, —O($C_3$-$C_7$)carbocycle, —O($C_1$-$C_6$)haloalkyl, —Saryl, —Sheteroaryl, —Sheterocycle, —S($C_3$-$C_7$)halocarbocycle, —S($C_1$-$C_6$)alkyl, —S($C_3$-$C_7$)carbocycle, —S($C_1$-$C_6$)haloalkyl, —S(O)aryl, —S(O)heteroaryl, —S(O)heterocycle, —S(O)($C_3$-$C_7$)halocarbocycle, —S(O)($C_1$-$C_6$)alkyl, —S(O)($C_3$-$C_7$)carbocycle, —S(O)($C_1$-$C_6$)haloalkyl, —$SO_2$aryl, —$SO_2$heteroaryl, —$SO_2$heterocycle, —$SO_2(C_1$-$C_6$)alkyl, —$SO_2(C_1$-$C_6$)haloalkyl, —$SO_2(C_3$-$C_7$)carbocycle, —$SO_2(C_3$-$C_7$)halocarbocycle, —$SO_2NR_cR_d$, —$NR_aSO_2(C_3$-$C_7$)halocarbocycle, —$NR_aSO_2aryl$, —$NR_aSO_2heteroaryl$, —$NR_aSO_2heteroaryl$, —$NR_aSO_2NR_cR_d$, —$NR_aSO_2O(C_3$-$C_7$)carbocycle and —$NR_aSO_2Oaryl$, wherein any aryl, of $Z^6$, either alone or as part of a group, is optionally substituted with one or more (e.g. 1, 2, 3, 4 or 5) halogen, —OH, —O($C_1$-$C_6$)alkyl, —CN or —($C_1$-$C_6$)alkyl;

each $Z^7$ is independently selected from —$NO_2$, =$NOR_a$, —CN, —($C_1$-$C_6$)alkyl-$Z^{12}$, —($C_2$-$C_6$)alkenyl-$Z^{12}$, —($C_2$-$C_6$)alkenylOH, —($C_2$-$C_6$)alkynyl-$Z^{12}$, —($C_2$-$C_6$)alkynylOH, —($C_1$-$C_6$)haloalkyl-$Z^{12}$, —($C_1$-$C_6$)haloalkylOH, —($C_3$-$C_7$)carbocycle-$Z^{12}$, —($C_3$-$C_7$)carbocycleOH, —($C_3$-$C_7$)halocarbocycle, —($C_1$-$C_6$)alkyl$NR_cR_d$, —($C_1$-$C_6$)alkyl$NR_aC(O)R_a$, —($C_1$-$C_6$)alkyl$NR_aSO_2R_a$, aryl, heteroaryl, heterocycle, —O($C_1$-$C_6$)alkyl-$Z^{12}$, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —O($C_1$-$C_6$)alkyl$NR_cR_d$, —O($C_1$-$C_6$)alkyl$NR_aC(O)R_a$, —O($C_1$-$C_6$)alkyl$NR_aSO_2R_a$, —Oheteroaryl, —Oheterocycle, —S($C_1$-$C_6$)alkyl-$Z^{12}$, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle,—S($C_1$-$C_6$)alkyl$NR_cR_d$,—S($C_1$-$C_6$)alkyl$NR_aC(O)R_a$, —S($C_1$-$C_6$)alkyl$NR_aSO_2R_a$, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2(C_1$-$C_6$)alkyl, —S(O)($C_1$-$C_6$)alkyl$NR_cR_d$, —S(O)($C_1$-$C_6$)alkyl$NR_aC(O)R_a$, —S(O)($C_1$-$C_6$)alkyl$NR_aSO_2R_a$, —S(O)aryl, —S(O)heteroaryl, —S(O)heterocycle, —$SO_2(C_1$-$C_6$)alkyl, —$SO_2(C_2$-$C_6$)alkenyl, —$SO_2(C_2$-$C_6$)alkynyl, —$SO_2(C_1$-$C_6$)haloalkyl, —$SO_2(C_3$-$C_7$)carbocycle, —$SO_2(C_3$-$C_7$)halocarbocycle, —$SO_2$aryl, —$SO_2$heteroaryl, —$SO_2$heterocycle, —$SO_2(C_1$-$C_6$)alkyl$NR_cR_d$, —$SO_2(C_1$-$C_6$)alkyl$NR_aC(O)R_a$, —$SO_2(C_1$-$C_6$)alkyl$NR_aSO_2R_a$, —$SO_2NR_cR_d$, —$NR_aC(O)OR_b$, —$NR_aC(O)NR_cR_d$, —$NR_aSO_2R_b$, —$NR_aSO_2NR_cR_d$, —$NR_aSO_2O(C_3$-$C_7$)carbocycle, —$NR_aSO_2Oaryl$, —$OS(O)_2R_a$, —$C(O)NR_cR_d$, and —$OC(O)NR_cR_d$, wherein any ($C_1$-$C_6$)alkyl, ($C_2$-$C_6$)alkenyl, ($C_2$-$C_6$)alkynyl, ($C_3$-$C_7$)carbocycle, ($C_3$-$C_7$)halocarbocycle, aryl, heteroaryl or heterocycle of $Z^7$, either alone or as part of a group, is optionally substituted with one or more (e.g. 1, 2, 3, 4 or 5) halogen, —OH, —$OR_b$, —CN, —$NR_aC(O)_2R_b$, heteroaryl, heterocycle, —Oheteroaryl, —Oheterocycle, —NHheteroaryl, —NHheterocycle or —$S(O)_2NR_cR_d$;

each $Z^8$ is independently selected from —$NO_2$ or —CN;
each $Z^{10}$ is independently selected from
i) halo, oxo, thioxo, ($C_2$-$C_6$)alkenyl, ($C_1$-$C_6$)haloalkyl, ($C_3$-$C_7$)cycloalkyl, ($C_3$-$C_7$)cycloalkyl-($C_1$-$C_6$)alkyl-, —OH, —O($C_1$-$C_6$)alkyl, —O($C_1$-$C_6$)haloalkyl, —SH, —S($C_1$-$C_6$)alkyl, —SO($C_1$-$C_6$)alkyl, —$SO_2(C_1$-$C_6$)alkyl, —$NH_2$, —NH($C_1$-$C_6$)alkyl and —N(($C_1$-$C_6$)alkyl)$_2$;
ii) ($C_1$-$C_6$)alkyl optionally substituted with —OH, —O—($C_1$-$C_6$)haloalkyl, or —O—($C_1$-$C_6$)alkyl; and
iii) aryl, heterocycle and heteroaryl, which aryl, heterocycle and heteroaryl is optionally substituted with halo, ($C_1$-$C_6$)alkyl or COOH;

each $Z^{11}$ is independently selected from $Z^{10}$, —C(=O)—$NH_2$, —C(=O)—NH($C_1$-$C_4$)alkyl, —C(=O)—N(($C_1$-$C_4$)alkyl)$_2$, —C(=O)-aryl, —C(=O)-heterocycle and —C(=O)-heteroaryl;

each $Z^{12}$ is independently selected from —NO$_2$, =NOR$_a$, thioxo, aryl, heterocycle, heteroaryl, (C$_3$-C$_7$)halocarbocycle, (C$_3$-C$_7$)carbocycle, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_a$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each $Z^{13}$ is independently selected from —NO$_2$, —OH, =NOR$_a$, —SH, —CN, (C$_3$-C$_7$)halocarbocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —S(O)aryl, —S(O)heteroaryl, —S(O)heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_b$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, (C$_3$-C$_7$)halocarbocycle, (C$_3$-C$_7$)carbocycle, (C$_3$-C$_7$)halocarbocycle, aryl, heteroaryl or heterocycle of $Z^{13}$, either alone or as part of a group, is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle, or —S(O)$_2$NR$_c$R$_d$;

each $Z^{14}$ is independently selected from —NO$_2$, =NOR$_a$, —CN, —(C$_3$-C$_7$)halocarbocycle, —O(C$_3$-C$_7$)halocarbocycle, —S(C$_3$-C$_7$)halocarbocycle, —S(O)(C$_3$-C$_7$)halocarbocycle, —SO$_2$(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, wherein any —(C$_3$-C$_7$)halocarbocycle of $Z^{14}$, either alone or as part of a group, is optionally substituted with one or more (e.g. 1, 2, 3, 4 or 5) halogen, —OH, —OR$_b$, —CN, —NR$_a$C(O)$_2$R$_b$, heteroaryl, -heterocycle, —Oheteroaryl, —Oheterocycle, —NHheteroaryl, —NHheterocycle, or —S(O)$_2$NR$_c$R$_d$;

each $Z^{15}$ is independently selected from aryl, heteroaryl, heterocycle, —Oaryl, —Oheteroaryl, —Oheterocycle, —O(C$_1$-C$_6$)alkyl-aryl, —O(C$_1$-C$_6$)alkyl-heteroaryl, —O(C$_1$-C$_6$)alkyl-heterocycle, wherein aryl, heteroaryl and heterocycle are each independently substituted with one or more (e.g. 1, 2, 3, 4 or 5) $Z^{16}$ groups and optionally substituted with one or more (e.g. 1, 2, 3, 4 or 5) $Z^1$ groups, and wherein any —Oaryl, —Oheteroaryl, —Oheterocycle, —O(C$_1$-C$_6$)alkyl-aryl, —O(C$_1$-C$_6$)alkyl-heteroaryl or —O(C$_1$-C$_6$)alkyl-heterocycle is optionally substituted with one or more (e.g. 1, 2, 3, 4 or 5) $Z^1$ groups;

each $Z^{16}$ is independently selected from —NO$_2$, —OH, =NOR$_a$, —SH, —CN, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heteroaryl, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of $Z^{16}$, either alone or as part of a group, is optionally substituted with one or more (e.g. 1, 2, 3, 4 or 5) halogen, (C$_1$-C$_6$)alkyl, —OH, —OR$_b$, —CN, —NR$_a$C(O)$_2$R$_b$, heteroaryl, heterocycle, —Oheteroaryl, —Oheterocycle, —NHheteroaryl, —NHheterocycle or —S(O)$_2$NR$_c$R$_d$;

each R$_a$ is independently H, (C$_1$-C$_6$)alkyl, (C$_2$-C$_6$)alkenyl, (C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_a$, either alone or as part of a group, is optionally substituted with one or more (e.g. 1, 2, 3, 4 or 5) halogen, OH or cyano;

each R$_b$ is independently (C$_1$-C$_6$)alkyl, (C$_2$-C$_6$)alkenyl, (C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_b$, either alone or as part of a group, is optionally substituted with one or more (e.g. 1, 2, 3, 4 or 5) halogen, OH and cyano;

R$_c$ and R$_d$ are each independently selected from H, (C$_1$-C$_6$)alkyl, (C$_2$-C$_6$)alkenyl, (C$_2$-C$_6$)alkynyl, (C$_3$-C$_7$)carbocycle, aryl, aryl(C$_1$-C$_6$)alkyl-, heterocycle, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_c$ or R$_d$, either alone or as part of a group, is optionally substituted with one or more (e.g. 1, 2, 3, 4 or 5) halogen, OH or cyano; or R$_c$ and R$_d$ together with the nitrogen to which they are attached form a heterocycle, wherein any heterocycle of R$_c$ and R$_d$ together with the nitrogen to which they are attached is optionally substituted with one or more (e.g. 1, 2, 3, 4 or 5) halogen, OH or cyano;

each R$_e$ is independently selected from —OR$_a$, (C$_1$-C$_6$)alkyl or (C$_3$-C$_7$)carbocycle, wherein (C$_1$-C$_6$)alkyl and (C$_3$-C$_7$)carbocycle are each independently substituted with one or more (e.g. 1, 2, 3, 4 or 5) $Z^6$ groups and optionally substituted with one or more (e.g. 1, 2, 3, 4 or 5) $Z^1$ groups; (C$_2$-C$_6$)haloalkyl, (C$_2$-C$_6$)alkenyl and (C$_2$-C$_6$)alkynyl, wherein any (C$_2$-C$_6$)haloalkyl, (C$_2$-C$_6$)alkenyl or (C$_2$-C$_6$)alkynyl is optionally substituted with one or more (e.g. 1, 2, 3, 4 or 5) $Z_1$ groups; and aryl, heterocycle and heteroaryl wherein aryl, heterocycle and heteroaryl are each independently substituted with one or more (e.g. 1, 2, 3, 4 or 5) $Z_5$ groups;

each R$_f$ is independently selected from —R$_g$, —OR$_a$, —(C$_1$-C$_6$)alkyl-Z$^6$, —SO$_2$R$_g$, —C(O)R$_g$, C(O)OR$_g$ and —C(O)NR$_e$R$_g$; and each R$_g$ is independently selected from (C$_1$-C$_6$)alkyl, (C$_3$-C$_7$)carbocycle (C$_1$-C$_6$)haloalkyl, (C$_2$-C$_6$)alkenyl, (C$_2$-C$_6$)alkynyl, aryl, heterocycle and heteroaryl, wherein any (C$_1$-

$C_6$)alkyl, ($C_3$-$C_7$)carbocycle —($C_1$-$C_6$)haloalkyl, ($C_2$-$C_6$)alkenyl, ($C_2$-$C_6$)alkynyl, aryl, heterocycle or heteroaryl of $R_g$ is optionally substituted with one or more (e.g. 1, 2, 3, 4 or 5) $Z_1$ groups;

or a salt thereof.

Accordingly, in one embodiment, a compound of the invention which is a compound of formula Ia is disclosed:

Ia wherein:
$R^1$ is H;
$R^2$ is ($C_1$-$C_6$)alkyl;
$R^3$ is —O($C_1$-$C_6$)alkyl;
$R^{3'}$ is H;
$R^4$ is selected from aryl, heterocycle and heteroaryl, wherein any aryl, heterocycle and heteroaryl of $R^4$ is optionally substituted with one or more groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, NH$_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo;
$R^5$ is selected from:
a) aryl, heterocycle and heteroaryl, wherein aryl, heterocycle and heteroaryl are each optionally substituted with one or more (e.g. 1, 2, 3, 4 or 5) $Z^{11}$ groups;
b) aryl, heteroaryl and heterocycle, wherein aryl, heteroaryl and heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl, and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

each $Z^1$ is independently selected from halo, —NO$_2$, —OH, =NOR$_a$, —SH, —CN, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —SO$_2$($C_1$-$C_6$)alkyl, —S(O)aryl, —S(O)carbocycle, —S(O)heterocycle, —S(O)heterocycle, —SO$_2$($C_2$-$C_6$)alkenyl, —SO$_2$($C_2$-$C_6$)alkynyl, —SO$_2$($C_1$-$C_6$)haloalkyl, —SO$_2$($C_3$-$C_7$)carbocycle, —SO$_2$($C_3$-$C_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$—NR$_a$SO$_2$R$_b$, —NR$_a$SO$_2$NR$_c$R$_d$, —NR$_a$SO$_2$O($C_3$-$C_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^1$, either alone or as part of a group, is optionally substituted with one or more halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each $Z^5$ is independently selected from —NO$_2$, —CN, —NR$_a$SO$_2$NR$_c$R$_d$, —NR$_a$SO$_2$O($C_3$-$C_7$)carbocycle, —NR$_a$SO$_2$Oaryl, —NR$_a$SO$_2$($C_1$-$C_6$)alkyl, —NR$_a$SO$_2$($C_2$-$C_6$)alkenyl, —NR$_a$SO$_2$($C_2$-$C_6$)alkynyl, —NR$_a$SO$_2$($C_3$-$C_7$)carbocycle, —NR$_a$SO$_2$($C_3$-$C_7$)halocarbocycle, —NR$_a$SO$_2$aryl, —NR$_a$SO$_2$heteroaryl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)($C_3$-$C_7$)carbocycle, —NR$_a$C(O)($C_3$-$C_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each $Z^{10}$ is independently selected from
i) halo, oxo, thioxo, ($C_2$-$C_6$)alkenyl, ($C_1$-$C_6$)haloalkyl, ($C_3$-$C_7$)cycloalkyl, ($C_3$-$C_7$)cycloalkyl-($C_1$-$C_6$)alkyl-, —OH, —O($C_1$-$C_6$)alkyl, —O($C_1$-$C_6$)haloalkyl, —SH, —S($C_1$-$C_6$)alkyl, —SO($C_1$-$C_6$)alkyl, —SO$_2$($C_1$-$C_6$)alkyl, —NH$_2$, —NH($C_1$-$C_6$)alkyl and —N(($C_1$-$C_6$)alkyl)$_2$;
ii) ($C_1$-$C_6$)alkyl optionally substituted with one or more —OH, —O—($C_1$-$C_6$)haloalkyl, or —O—($C_1$-$C_6$)alkyl; and
iii) aryl, heterocycle and heteroaryl, which aryl, heterocycle and heteroaryl is optionally substituted with one or more halo, ($C_1$-$C_6$)alkyl or COOH;

each $Z^{11}$ is independently selected from $Z^{10}$, —C(=O)—NH$_2$, —C(=O)—NH($C_1$-$C_4$)alkyl, —C(=O)—N(($C_1$-$C_4$)alkyl)$_2$, —C(=O)-aryl, —C(=O)-heterocycle and —C(=O)-heteroaryl;

each $Z^{15}$ is independently selected from aryl, heteroaryl, heterocycle, —Oaryl, —Oheteroaryl, —Oheterocycle, —O($C_1$-$C_6$)alkyl-aryl, —O($C_1$-$C_6$)alkyl-heteroaryl, —O($C_1$-$C_6$)alkyl-heterocycle, wherein aryl, heteroaryl and heterocycle are each independently substituted with one or more $Z^{16}$ groups and optionally substituted with one or more $Z^1$ groups, and wherein any —Oaryl, —Oheteroaryl, —Oheterocycle, —O($C_1$-$C_6$)alkyl-aryl, —O($C_1$-$C_6$)alkyl-heteroaryl or —O($C_1$-$C_6$)alkyl-heterocycle is optionally substituted with one or more $Z^1$ groups;

each $Z^{16}$ is independently selected from —NO$_2$, —OH, =NOR$_a$, —SH, —CN, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, aryl($C_1$-$C_6$)alkyl-, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —SO$_2$($C_1$-$C_6$)alkyl, —S(O)aryl, —S(O)carbocycle, —S(O)heterocycle, —S(O)heterocycle, —SO$_2$($C_2$-$C_6$)alkenyl, —SO$_2$($C_2$-$C_6$)alkynyl, —SO$_2$($C_1$-$C_6$)haloalkyl, —SO$_2$($C_3$-$C_7$)carbocycle, —SO$_2$($C_3$-$C_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O($C_3$-$C_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$) alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^{16}$, either alone or as part of a group, is optionally substituted with one or more halogen, (C$_1$-C$_6$)alkyl, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each R$_a$ is independently H, (C$_1$-C$_6$)alkyl, (C$_2$-C$_6$)alkenyl, (C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_a$, either alone or as part of a group, is optionally substituted with one or more halogen, OH or cyano;

each R$_b$ is independently (C$_1$-C$_6$)alkyl, (C$_2$-C$_6$)alkenyl, (C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_b$, either alone or as part of a group, is optionally substituted with one or more halogen, OH and cyano; and R$_c$ and R$_d$ are each independently selected from H, (C$_1$-C$_6$) alkyl, (C$_2$-C$_6$)alkenyl, (C$_2$-C$_6$)alkynyl, (C$_3$-C$_7$)carbocycle, aryl, aryl(C$_1$-C$_6$)alkyl-, heterocycle, heteroaryl or heteroaryl (C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_c$ or R$_d$, either alone or as part of a group, is optionally substituted with one or more halogen, OH or cyano; or R$_c$ and R$_d$ together with the nitrogen to which they are attached form a heterocycle, wherein any such heterocycle is optionally substituted with one or more halogen, OH or cyano;

or a salt thereof;

provided R$^5$ is not azetidinyl or 1-methyl-imidazo-2-yl.

In one embodiment, the invention provides a compound of formula Ia:

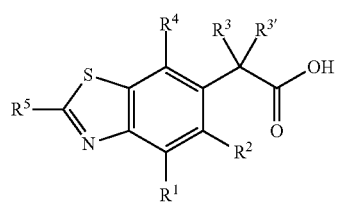

Ia wherein:
R$^1$ is H;
R$^2$ is (C$_1$-C$_6$)alkyl;
R$^3$ is —O(C$_1$-C$_6$)alkyl;
R$^{3'}$ is H;
R$^4$ is selected from aryl, heterocycle and heteroaryl, wherein any aryl, heterocycle and heteroaryl of R$^4$ is optionally substituted with one or more groups each independently selected from halo, (C$_1$-C$_6$)alkyl, (C$_2$-C$_6$)alkenyl, (C$_1$-C$_6$) haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, NH$_2$, —NH(C$_1$-C$_6$)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo;
R$^5$ is selected from:
  a) aryl, heterocycle and heteroaryl, wherein aryl, heterocycle and heteroaryl are each optionally substituted with one or more (e.g. 1, 2 or 3) Z$^{11}$ groups;
  b) aryl, heteroaryl and heterocycle, wherein aryl, heteroaryl and heterocycle, are each independently substituted with one or more (e.g. 1, 2, 3, 4 or 5) Z$^5$ groups and optionally substituted with one or more (e.g. 1, 2, 3, 4 or 5) Z$^1$ groups; and
  c) aryl, heteroaryl, heterocycle, wherein aryl, heteroaryl and heterocycle, are each independently substituted with one or more (e.g. 1, 2, 3, 4 or 5) Z$^{15}$ groups and optionally substituted with one or more (e.g. 1, 2, 3, 4 or 5) Z$^1$ groups;

each Z$^1$ is independently selected from halo, —NO$_2$, —OH, =NOR$_a$, —SH, —CN, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$) halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$) halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$) alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)heterocycle, —S(O)heteroaryl, —S(O) heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$ (C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$) alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^1$, either alone or as part of a group, is optionally substituted with one or more halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each Z$^5$ is independently selected from —NO$_2$, —CN, —NR$_a$SO$_2$NR$_c$R$_d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$) carbocycle, —NR$_a$SO$_2$(C$_3$-C$_7$)halocarbocycle, —NR$_a$SO$_2$aryl, —NR$_a$SO$_2$heteroaryl, —NR$_a$SO$_2$heterocycle, —NR$_a$SO$_2$heterocycle, —NR$_a$C(O) alkyl, —NR$_a$C(O)alkenyl, —NR$_a$C(O)alkynyl, —NR$_a$C(O) (C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each Z$^{10}$ is independently selected from
  i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$) alkyl, —NH$_2$, —NH(C$_1$-C$_6$)alkyl and —N((C$_1$-C$_6$) alkyl)$_2$;
  ii) (C$_1$-C$_6$)alkyl optionally substituted with one or more —OH, —O—(C$_1$-C$_6$)haloalkyl, or —O—(C$_1$-C$_6$)alkyl; and
  iii) aryl, heterocycle and heteroaryl, which aryl, heterocycle and heteroaryl is optionally substituted with one or more halo, (C$_1$-C$_6$)alkyl or COOH;

each Z$^{11}$ is independently selected from Z$^{10}$, —C(=O)—NH$_2$, —C(=O)—NH(C$_1$-C$_4$)alkyl, —C(=O)—N((C$_1$-C$_4$) alkyl)$_2$, —C(=O)-aryl, —C(=O)-heterocycle and —C(=O)-heteroaryl;

each $Z^{15}$ is independently selected from aryl, heteroaryl, heterocycle, —Oaryl, —Oheteroaryl, —Oheterocycle, —O($C_1$-$C_6$)alkyl-aryl, —O($C_1$-$C_6$)alkyl-heteroaryl, —O($C_1$-$C_6$)alkyl-heterocycle, wherein aryl, heteroaryl and heterocycle are each independently substituted with one or more $Z^{16}$ groups and optionally substituted with one or more $Z^1$ groups, and wherein any —Oaryl, —Oheteroaryl, —Oheterocycle, —O($C_1$-$C_6$)alkyl-aryl, —O($C_1$-$C_6$)alkyl-heteroaryl or —O($C_1$-$C_6$)alkyl-heterocycle is optionally substituted with one or more $Z^1$ groups;

each $Z^{16}$ is independently selected from —$NO_2$, —OH, =$NOR_a$, —SH, —CN, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, aryl($C_1$-$C_6$)alkyl-, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)aryl, —S(O)carbocycle, —S(O)heterocycle, —S(O)heterocycle, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3$-$C_7$)carbocycle, —$NR_aSO_2Oaryl$, —$OS(O)_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^{16}$, either alone or as part of a group, is optionally substituted with one or more halogen, ($C_1$-$C_6$)alkyl, —OH, —$OR_b$, —CN, —$NR_aC(O)_2R_b$, -heteroaryl, -heterocycle, —Oheteroaryl, —Oheterocycle, —NHheteroaryl, —NHheterocycle or —$S(O)_2NR_cR_d$;

each $R_a$ is independently H, ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_a$, either alone or as part of a group, is optionally substituted with one or more halogen, OH or cyano;

each $R_b$ is independently ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_b$, either alone or as part of a group, is optionally substituted with one or more halogen, OH and cyano; and $R_c$ and $R_d$ are each independently selected from H, ($C_1$-$C_6$) alkyl, ($C_2$-$C_6$)alkenyl, ($C_2$-$C_6$)alkynyl, ($C_3$-$C_7$)carbocycle, aryl, aryl($C_1$-$C_6$)alkyl-, heterocycle, heteroaryl or heteroaryl ($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_c$ or $R_d$, either alone or as part of a group, is optionally substituted with one or more halogen, OH or cyano; or $R_c$ and $R_d$ together with the nitrogen to which they are attached form a heterocycle, wherein any heterocycle of $R_c$ and $R_d$ together with the nitrogen to which they are attached is optionally substituted with one or more halogen, OH or cyano;

or a salt thereof;

provided $R^5$ is not azetidinyl or 1-methyl-imidazo-2-yl.

In one embodiment, the invention provides a compound of formula Ia:

wherein:
$R^1$ is H;
$R^2$ is ($C_1$-$C_6$)alkyl;
$R^3$ is —O($C_1$-$C_6$)alkyl;
$R^{3'}$ is H;
$R^4$ is selected from aryl, heterocycle and heteroaryl, wherein any aryl, heterocycle and heteroaryl of $R^4$ is optionally substituted with one or more groups each independently selected from halo, ($C_1$-$C_6$)alkyl, ($C_2$-$C_6$)alkenyl, ($C_1$-$C_6$) haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, $NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo;

$R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl and heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl, heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

each $Z^1$ is independently selected from halo, —$NO_2$, —OH, =$NOR_a$, —SH, —CN, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)aryl, —S(O)carbocycle, —S(O)heterocycle, —S(O)heterocycle, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3$-$C_7$)carbocycle, —$NR_aSO_2Oaryl$, —$OS(O)_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^1$, either alone or as part of a group, is optionally substituted with one or more halogen, —OH, —$OR_b$, —CN, —$NR_aC(O)_2R_b$, -heteroaryl, -heterocycle, —Oheteroaryl, —Oheterocycle, —NHheteroaryl, —NHheterocycle or —$S(O)_2NR_cR_d$;

each $Z^5$ is independently selected from —$NO_2$, —CN, —$NR_aSO_2NR_cR_d$, —$NR_aSO_2O(C_3$-$C_7$)carbocycle, —$NR_aSO_2Oaryl$, —$NR_aSO_2(C_1$-$C_6$)alkyl, —$NR_aSO_2(C_2$-$C_6$)alkenyl, —$NR_aSO_2(C_2$-$C_6$)alkynyl, —$NR_aSO_2(C_3$-$C_7$)

carbocycle, —NR$_a$SO$_2$(C$_3$-C$_7$)halocarbocycle, —NR$_a$SO$_2$aryl, —NR$_a$SO$_2$heteroaryl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each Z$^{10}$ is independently selected from
i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;
ii) (C$_1$-C$_6$)alkyl optionally substituted with one or more —OH, —O—(C$_1$-C$_6$)haloalkyl, or —O—(C$_1$-C$_6$)alkyl; and
iii) aryl, heterocycle and heteroaryl, which aryl, heterocycle and heteroaryl is optionally substituted with halo, (C$_1$-C$_6$)alkyl or COOH;

each Z$^{11}$ is independently selected from Z$^{10}$, —C(=O)—NH$_2$, —C(=O)—NH(C$_1$-C$_4$)alkyl, —C(=O)—N((C$_1$-C$_4$)alkyl)$_2$, —C(=O)-aryl, —C(=O)-heterocycle and —C(=O)-heteroaryl;

each Z$^{15}$ is independently selected from aryl, heteroaryl, heterocycle, —Oaryl, —Oheteroaryl, —Oheterocycle, —O(C$_1$-C$_6$)alkyl-aryl, —O(C$_1$-C$_6$)alkyl-heteroaryl, —O(C$_1$-C$_6$)alkyl-heterocycle, wherein aryl, heteroaryl and heterocycle are each independently substituted with one or more Z$^{16}$ groups and optionally substituted with one or more Z$^1$ groups, and wherein any —Oaryl, —Oheteroaryl, —Oheterocycle, —O(C$_1$-C$_6$)alkyl-aryl, —O(C$_1$-C$_6$)alkyl-heteroaryl or —O(C$_1$-C$_6$)alkyl-heterocycle is optionally substituted with one or more Z$^1$ groups;

each Z$^{16}$ is independently selected from —NO$_2$, —OH, =NOR$_a$, —SH, —CN, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heteroaryl, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^{16}$, either alone or as part of a group, is optionally substituted with one or more halogen, (C$_1$-C$_6$)alkyl, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each R$_a$ is independently H, (C$_1$-C$_6$)alkyl, (C$_2$-C$_6$)alkenyl, (C$_2$-C$_6$)alkynyl, (C$_3$-C$_7$)carbocycle, heterocycle, aryl, aryl (C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_a$, either alone or as part of a group, is optionally substituted with one or more halogen, OH or cyano;

each R$_b$ is independently (C$_1$-C$_6$)alkyl, (C$_2$-C$_6$)alkenyl, (C$_2$-C$_6$)alkynyl, (C$_3$-C$_7$)carbocycle, heterocycle, aryl, aryl (C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_b$, either alone or as part of a group, is optionally substituted with one or more halogen, OH and cyano; and R$_c$ and R$_d$ are each independently selected from H, (C$_1$-C$_6$)alkyl, (C$_2$-C$_6$)alkenyl, (C$_2$-C$_6$)alkynyl, (C$_3$-C$_7$)carbocycle, aryl, aryl(C$_1$-C$_6$)alkyl-, heterocycle, heteroaryl or heteroaryl (C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_c$ or R$_d$, either alone or as part of a group, is optionally substituted with one or more halogen, OH or cyano; or R$_c$ and R$_d$ together with the nitrogen to which they are attached form a heterocycle, wherein any heterocycle of R$_c$ and R$_d$ together with the nitrogen to which they are attached is optionally substituted with one or more halogen, OH or cyano;

or a salt thereof.

In one embodiment, the invention provides a compound of formula I':

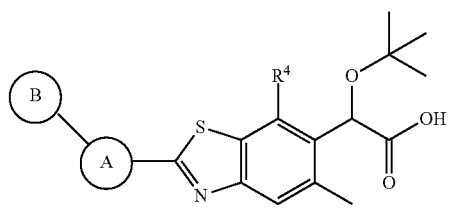

wherein:

R$^4$ is selected from aryl, heterocycle and heteroaryl, wherein any aryl, heterocycle and heteroaryl of R$^4$ is optionally substituted with one or more groups each independently selected from halo, (C$_1$-C$_6$)alkyl, (C$_2$-C$_6$)alkenyl, (C$_1$-C$_6$)haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, NH$_2$, —NH(C$_1$-C$_6$)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo;

A is phenyl, monocyclic heteroaryl or monocyclic heterocycle, wherein any phenyl, monocyclic heteroaryl or monocyclic heterocycle of A is optionally substituted with one or more Z$^{1a}$ groups, and B is aryl, heteroaryl or heterocycle, wherein any aryl, heteroaryl or heterocycle of B is optionally substituted with one or more Z$^{1b}$ groups; or A and B together form a bicyclic aryl, bicyclic heteroaryl or bicyclic heterocycle, wherein bicyclic aryl, bicyclic heteroaryl or bicyclic heterocycle is optionally substituted with one or more Z$^{1b}$ groups;

each Z$^{1a}$ is independently selected from halo, (C$_1$-C$_3$)alkyl, (C$_2$-C$_3$)alkenyl, (C$_2$-C$_3$)alkynyl, (C$_1$-C$_3$)haloalkyl, (C$_3$-C$_7$)carbocycle, heterocycle, —O(C$_1$-C$_3$)alkyl, —O(C$_2$-C$_3$)alkenyl, —O(C$_2$-C$_3$)alkynyl, —NR$_c$R$_d$, —NR$_a$C(O)R$_a$, —C(O)OR$_b$ and —C(O)NR$_c$R$_d$, wherein any (C$_3$-C$_7$)carbocycle or heterocycle of Z$^{1a}$, either alone or as part of a group, is optionally substituted with one or more halogen or (C$_1$-C$_6$)alkyl;

each Z$^{1b}$ is independently selected from halo, CN, (C$_1$-C$_6$)alkyl, (C$_2$-C$_6$)alkenyl, (C$_2$-C$_6$)alkynyl, (C$_1$-C$_6$)haloalkyl, ($C_3$-$C_7$)carbocycle, heteroaryl, heterocycle, aryl($C_1$-$C_6$)alkyl-, —OH, —O($C_1$-$C_6$)alkyl, —O($C_2$-$C_6$)alkenyl, —O($C_2$-$C_6$)alkynyl, —$NR_cR_d$, —$NR_aC(O)R_a$, —C(O)$OR_b$, and —C(O)$NR_cR_d$, wherein any ($C_3$-$C_7$)carbocycle or heterocycle of $Z^{1b}$, either alone or as part of a group, is optionally substituted with one or more halogen or ($C_1$-$C_6$)alkyl; and $R_a$, $R_b$, $R_c$ and $R_d$ are each independently H or ($C_1$-$C_6$)alkyl;

or a salt thereof.

A specific value for A is phenyl, monocyclic heteroaryl or monocyclic heterocycle, wherein any phenyl, monocyclic heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is phenyl, monocyclic N-heteroaryl or monocyclic heterocycle, wherein any phenyl, monocyclic N-heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic heteroaryl or monocyclic heterocycle, wherein any monocyclic heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic N-heteroaryl or monocyclic heterocycle, wherein any monocyclic N-heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic heteroaryl, wherein monocyclic heteroaryl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic N-heteroaryl, wherein monocyclic N-heteroaryl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic heterocycle, wherein monocyclic heterocycle is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl, pyrimidinyl, pyrazinyl, pyridinyl-2-one, tetrahydropyrimidinyl-2-one, imidazolidinyl-2-one, pyrrolidinyl-2-one or pyrrolidinyl, wherein pyridinyl, pyrimidinyl, pyrazinyl, pyridinyl-2-one, tetrahydropyrimidinyl-2-one, imidazolidinyl-2-one, pyrrolidinyl-2-one or pyrrolidinyl is optionally substituted with one or more $Z^{1a}$ groups, and B is aryl, heteroaryl or heterocycle wherein any aryl, heteroaryl or heterocycle of B is optionally substituted with one or more $Z^{1b}$ groups.

Another specific value for A is pyridinyl, pyrimidinyl or pyrazinyl wherein pyridinyl, pyrimidinyl or pyrazinyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl, wherein pyridinyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridin-4-yl, wherein pyridin-4-yl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl-2-one, tetrahydropyrimidinyl-2-one, imidazolidinyl-2-one, pyrrolidinyl-2-one or pyrrolidinyl, wherein pyridinyl-2-one, tetrahydropyrimidinyl-2-one, imidazolidinyl-2-one, pyrrolidinyl-2-one or pyrrolidinyl is optionally substituted with one or more $Z^{1a}$ groups, and B is aryl, heteroaryl or heterocycle wherein any aryl, heteroaryl or heterocycle of B is optionally substituted with one or more $Z^{1b}$ groups.

A specific group of compounds of formula I' are compounds wherein A is not substituted with $Z^{1a}$.

A specific value for B is phenyl, pyridinyl, pyrazolyl, pyrimidinyl, indazolyl, pyrazolopyridine or benzimidazolyl, wherein any phenyl, pyridinyl, pyrazolyl, pyrimidinyl, indazolyl, pyrazolopyridine or benzimidazolyl, of B is optionally substituted with one or more $Z^{1b}$ groups.

Another specific value for B is phenyl or indazolyl, wherein any phenyl or indazolyl of B is optionally substituted with one or more $Z^{1b}$ groups.

A specific group of compounds or formula I' are compounds wherein A and B together form a bicyclic aryl, bicyclic heteroaryl or bicyclic heterocycle, wherein bicyclic aryl, bicyclic heteroaryl or bicyclic heterocycle is optionally substituted with one or more $Z^{1b}$ groups.

Another specific group of compounds or formula I' are compounds wherein A and B together form a bicyclic heteroaryl, wherein bicyclic heteroaryl is optionally substituted with one or more $Z^{1b}$ groups.

Another specific group of compounds or formula I' are compounds wherein A and B together form a pyrrolopyridinyl, pyrazolopyridine or indazolyl wherein pyrrolopyridinyl or indazolyl is optionally substituted with one or more $Z^{1b}$ groups.

Another specific value for A is phenyl, wherein phenyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

A specific value for $Z^{1a}$ is halo.

Another specific value for $Z^{1a}$ is fluoro or chloro.

Another specific value for B is phenyl, pyridinyl, pyrazolyl, pyrimidinyl, indazolyl or pyrazolopyridine, wherein any phenyl, pyridinyl, pyrazolyl, pyrimidinyl, indazolyl or pyrazolopyridine of B is optionally substituted with one or more $Z^{1b}$ groups.

A specific group of compounds of formula I' are compounds wherein each $Z^{1b}$ is independently selected from methyl, isobutyl, isopropyl, cyclopropyl, cyclobutyl, cyclopentyl, N-methylpiperazinyl, morpholinyl, tetrazolyl, —$OCH_3$, t-butyl, —C(O)OH, —$NH_2$, —N($CH_3$)$_2$, —OH, —C(O)$NH_2$, benzyl and CN.

Another specific group of compounds of formula I' are compounds wherein each $Z^{1b}$ independently selected from methyl, cyclopropyl, cyclobutyl, N-methylpiperazinyl, morpholinyl, tetrazolyl, —$OCH_3$, —C(O)OH, —OH, —C(O)$NH_2$, $NH_2$ and CN.

Another specific group of compounds of formula I' are compounds wherein each $Z^{1b}$ is independently selected from methyl, cyclopropyl, cyclobutyl, N-methylpiperazinyl, morpholinyl, tetrazolyl, —OCH₃, —C(O)OH, —OH, —C(O)NH₂ and CN.

Another specific group of compounds of formula I' are compounds wherein each $Z^{1b}$ is independently selected from methyl and NH₂.

Another specific group of compounds of formula I' are compounds wherein each $Z^{1b}$ is independently selected from methyl, isobutyl, isopropyl, cyclopentyl, N-methylpiperazinyl, —OCH₃, t-butyl, —N(CH₃)₂, —OH and benzyl.

A specific group of compounds of formula I' are compounds wherein A-B is selected from:

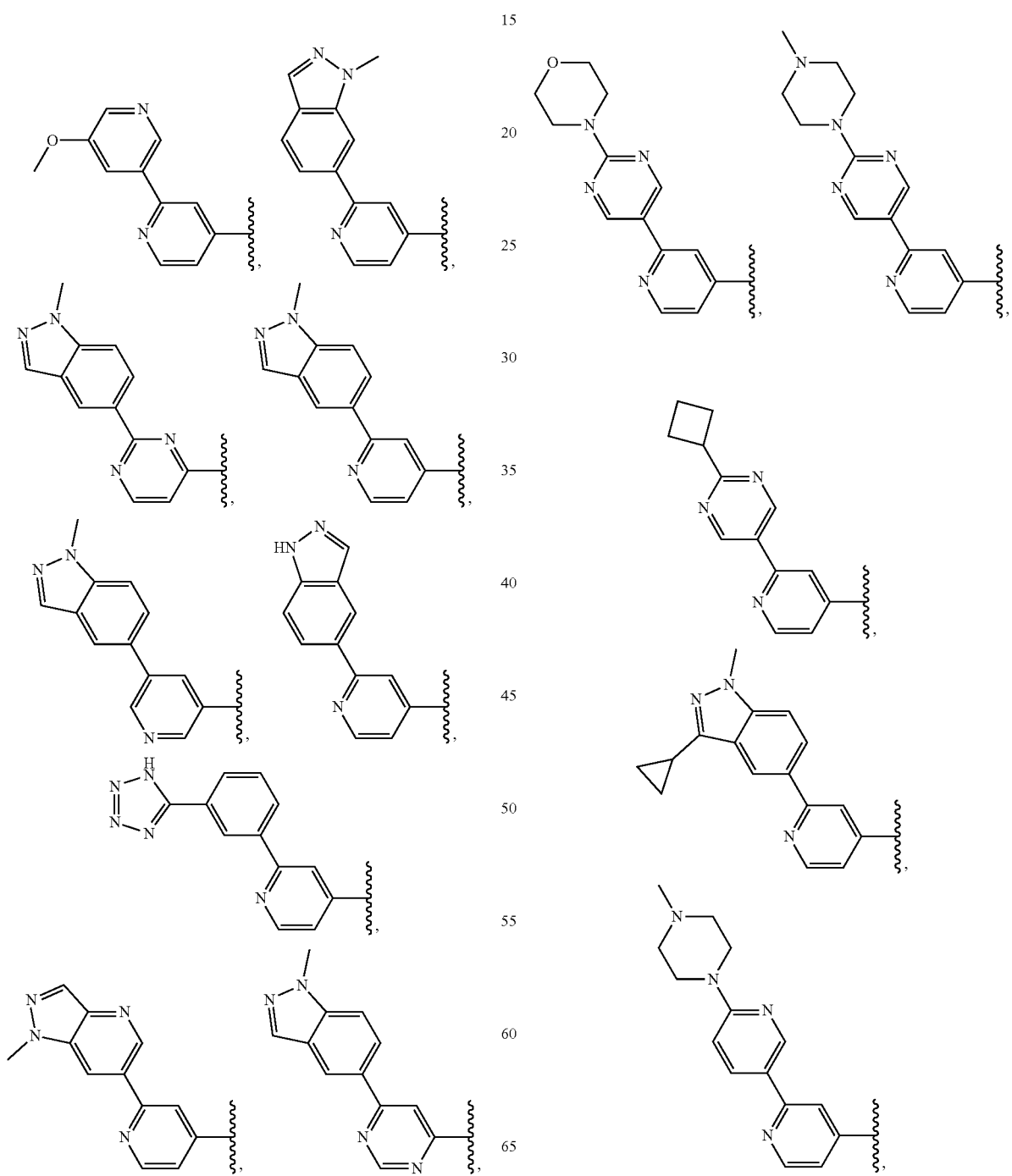

-continued

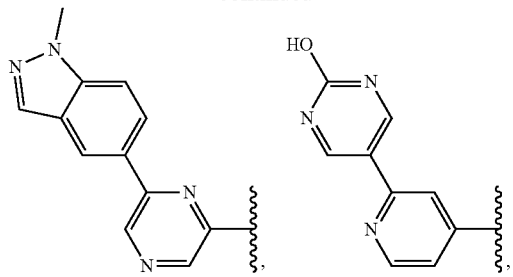

65
-continued
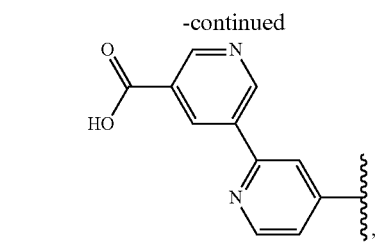
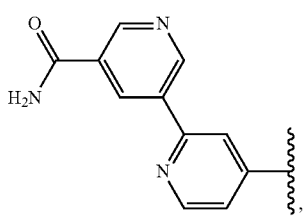
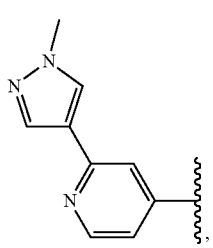 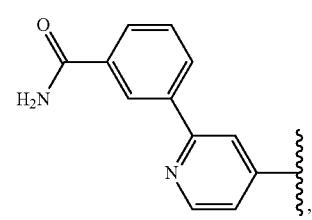
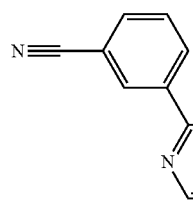 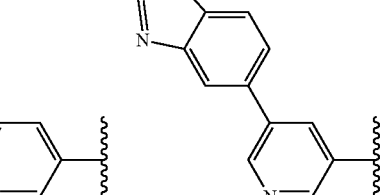
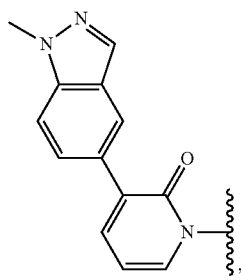 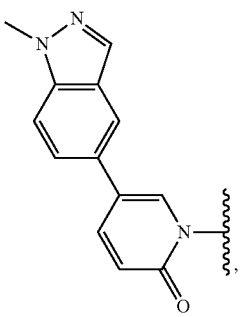
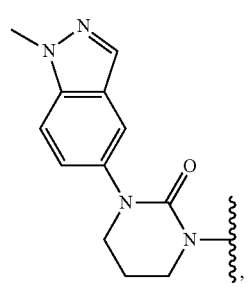 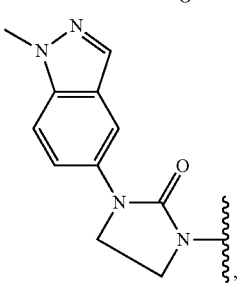
66
-continued
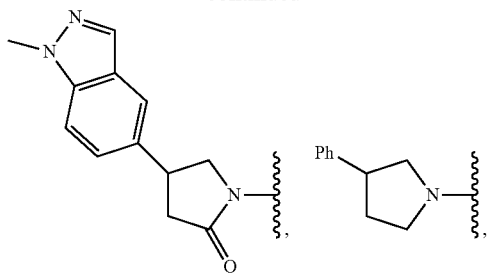
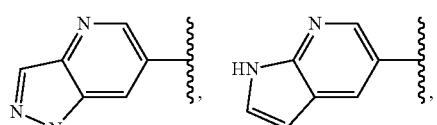
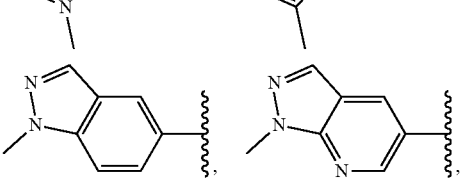
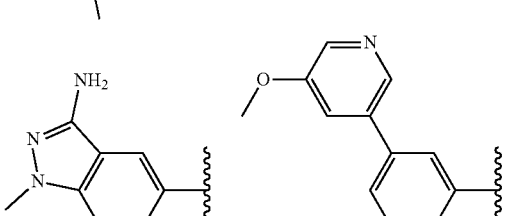
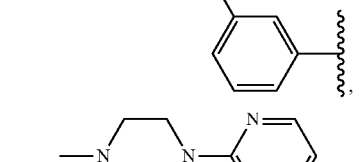
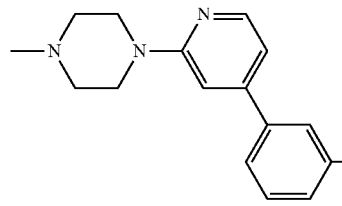
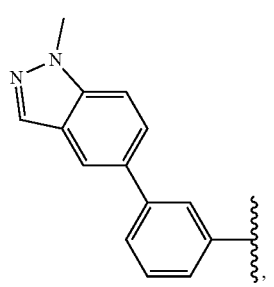 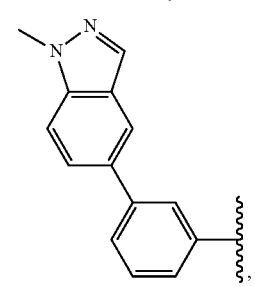

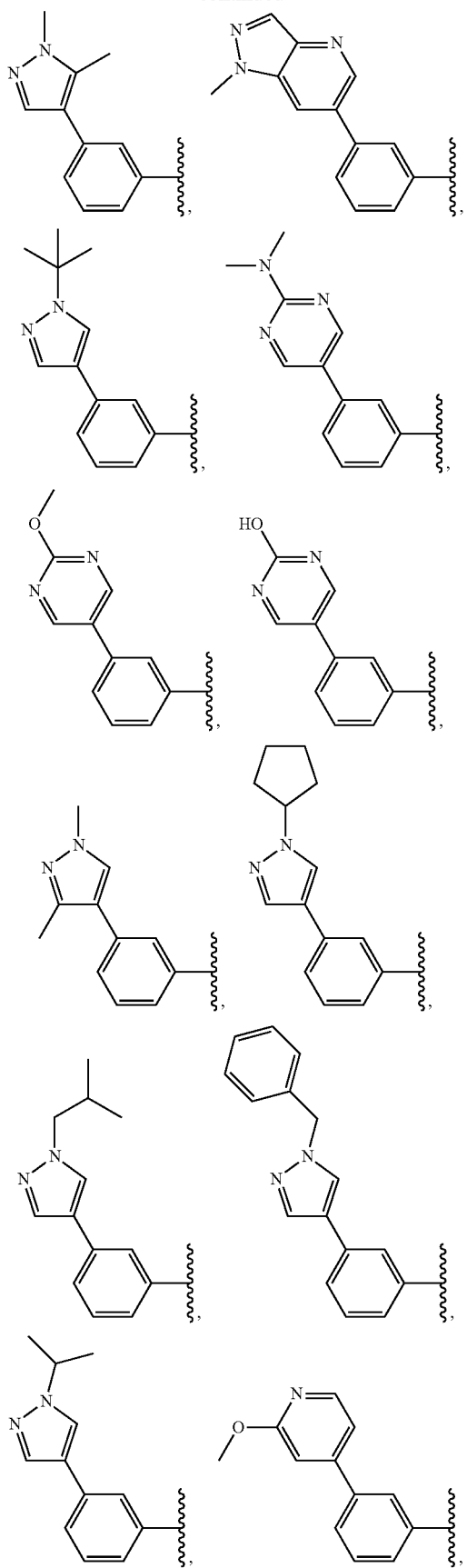

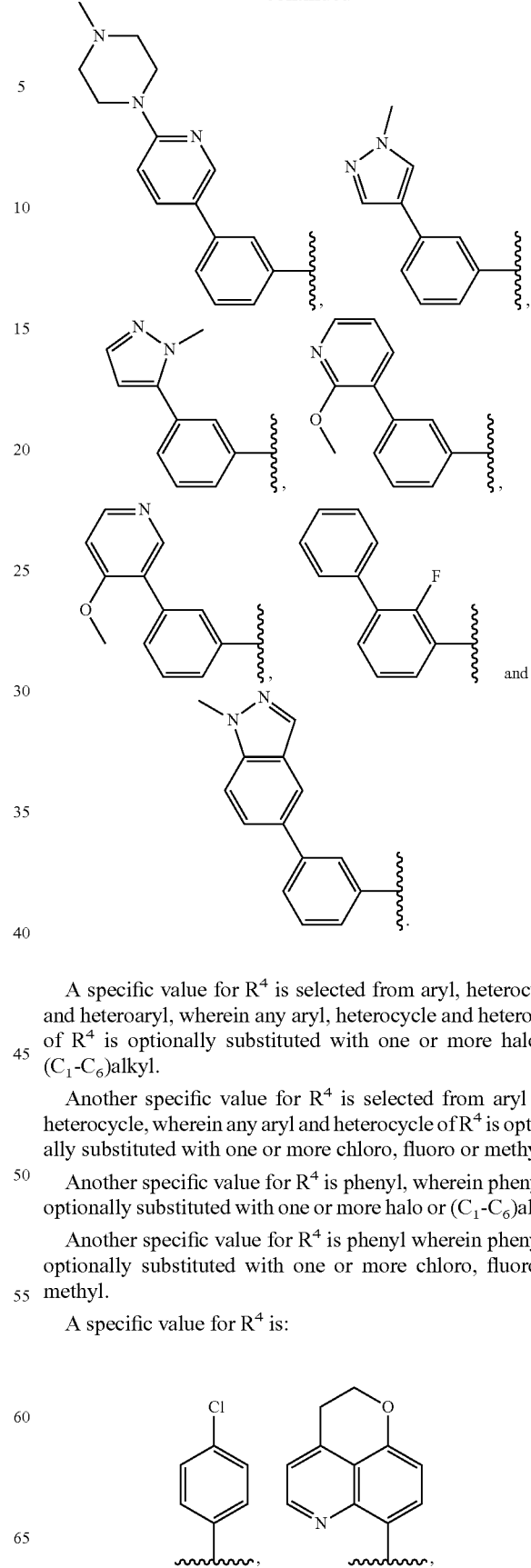

A specific value for $R^4$ is selected from aryl, heterocycle and heteroaryl, wherein any aryl, heterocycle and heteroaryl of $R^4$ is optionally substituted with one or more halo or $(C_1\text{-}C_6)$alkyl.

Another specific value for $R^4$ is selected from aryl and heterocycle, wherein any aryl and heterocycle of $R^4$ is optionally substituted with one or more chloro, fluoro or methyl.

Another specific value for $R^4$ is phenyl, wherein phenyl is optionally substituted with one or more halo or $(C_1\text{-}C_6)$alkyl.

Another specific value for $R^4$ is phenyl wherein phenyl is optionally substituted with one or more chloro, fluoro or methyl.

A specific value for $R^4$ is:

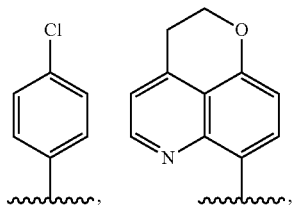

-continued

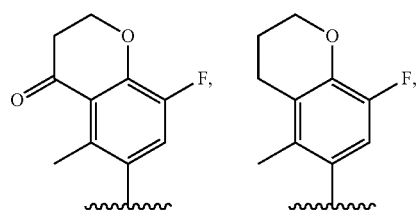 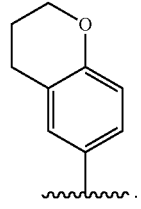

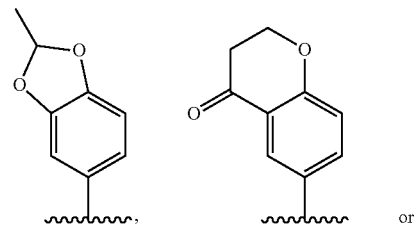, or

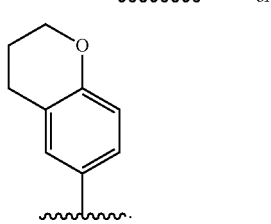.

Another specific value for R⁴ is:

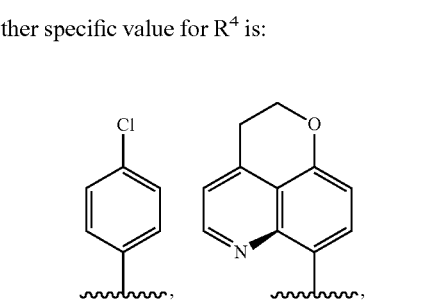

-continued

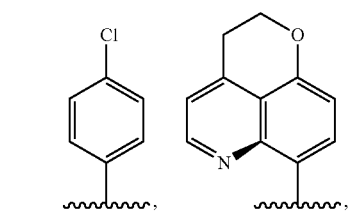.

Another specific value for R⁴ is:

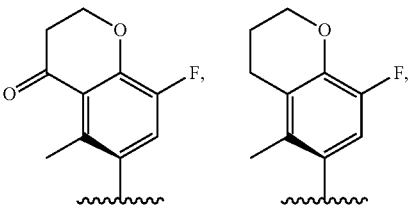,

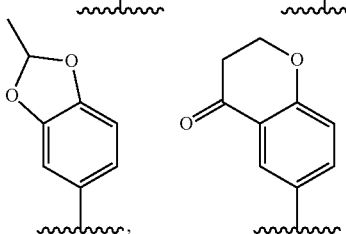, or

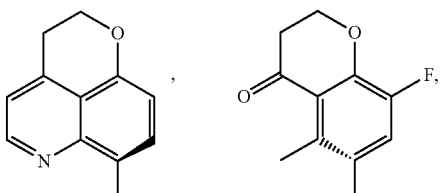,

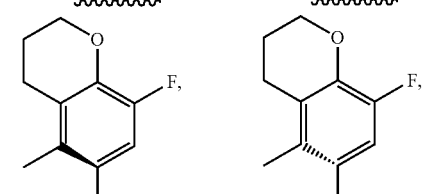,

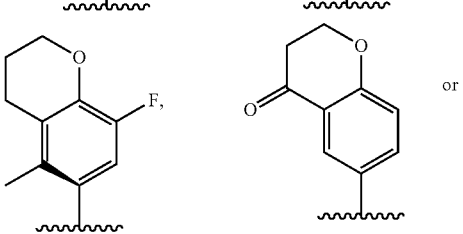 or

A specific group of compounds of the invention are compounds wherein the configuration of the R³ group of formula I is the (S) stereochemistry.

A specific group of compounds of the invention are compounds wherein the configuration of the —OC(CH₃)₃ group as shown in formula I' is the (S) stereochemistry.

In one embodiment a compound of the invention is selected from:

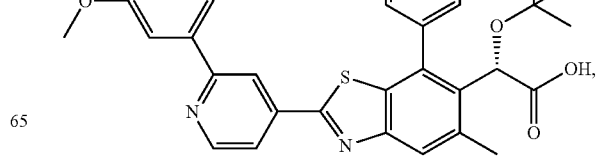

| 71 -continued | 72 -continued |
|---|---|
| 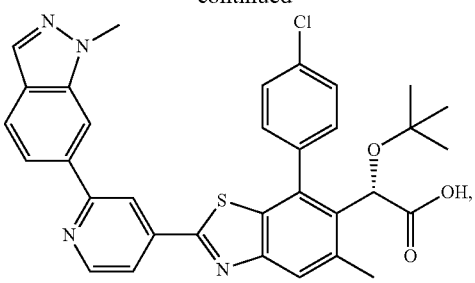 | 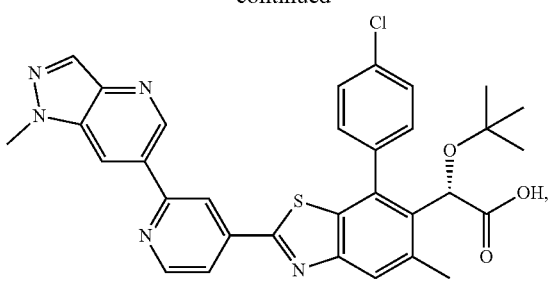 |
| 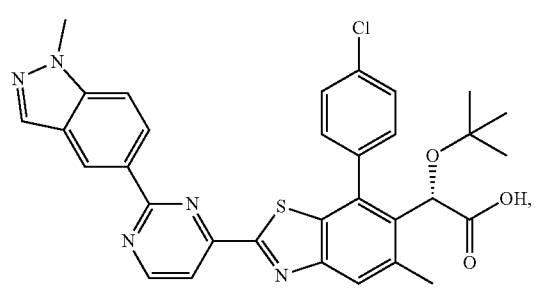 | 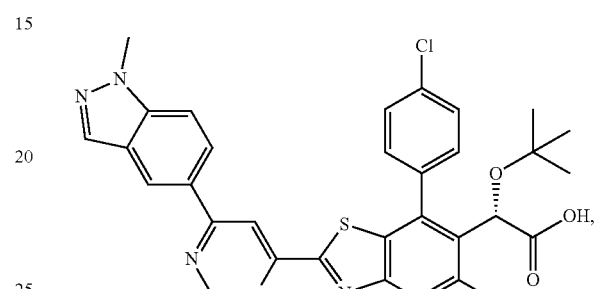 |
| 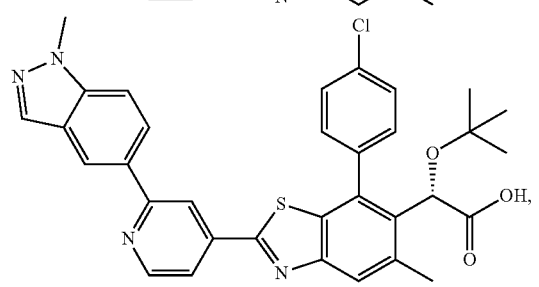 | 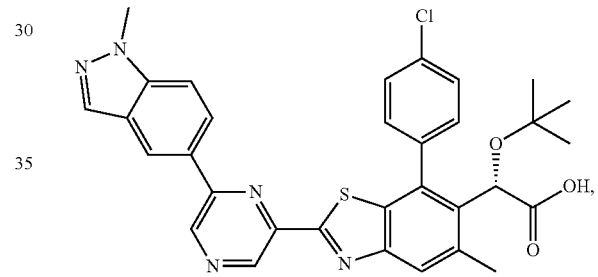 |
| 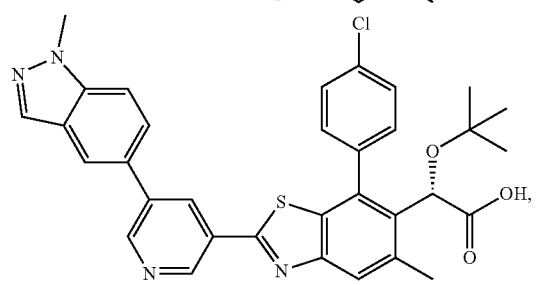 | 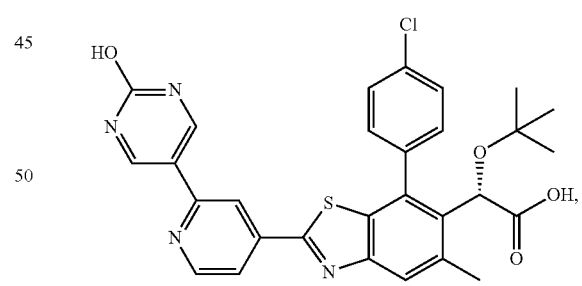 |
| 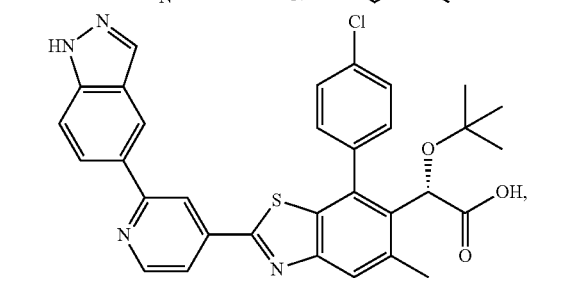 | 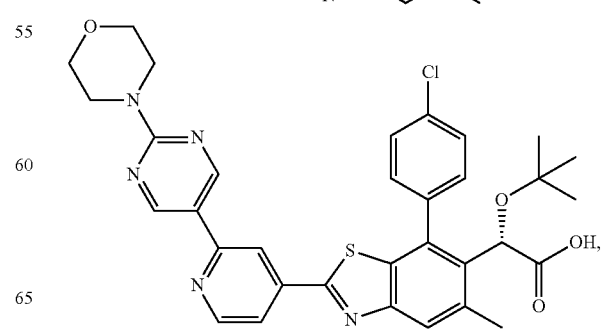 |

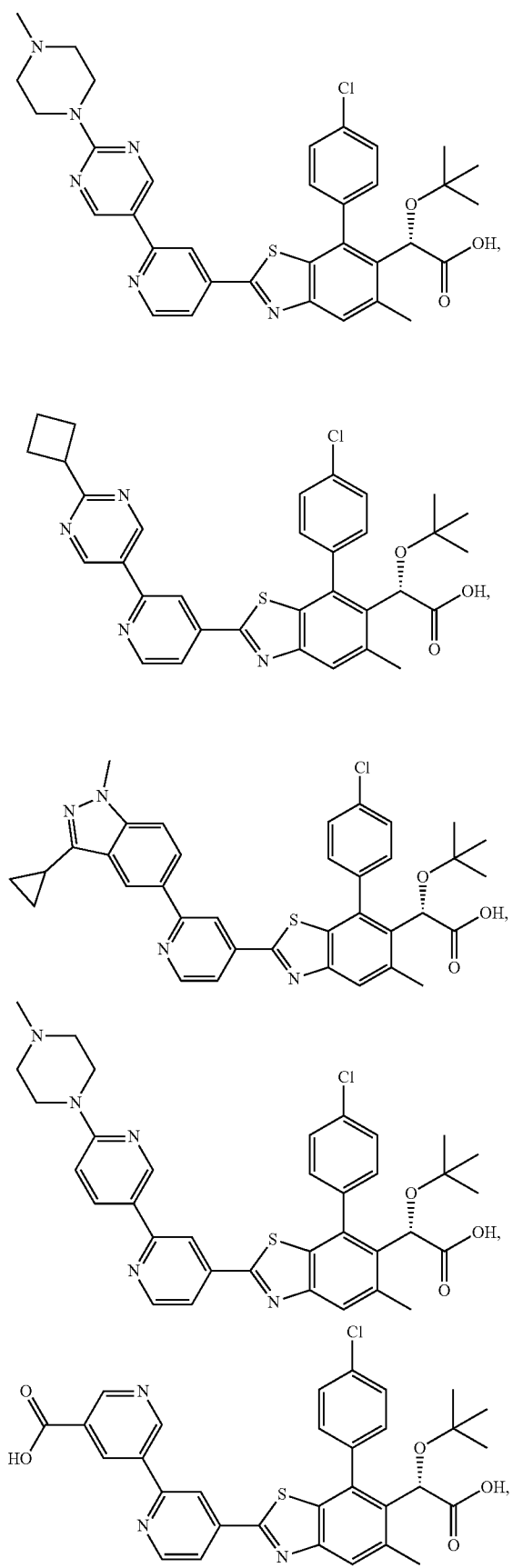
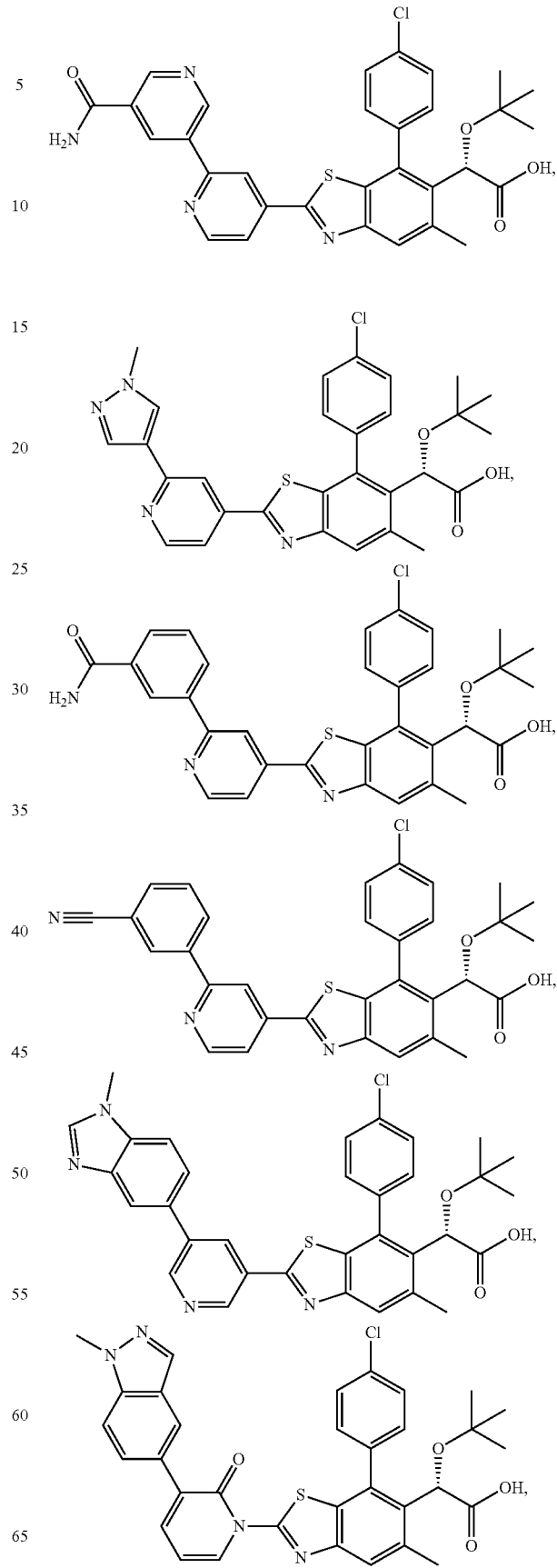

75
-continued
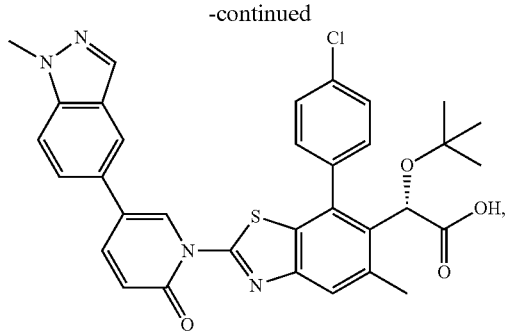
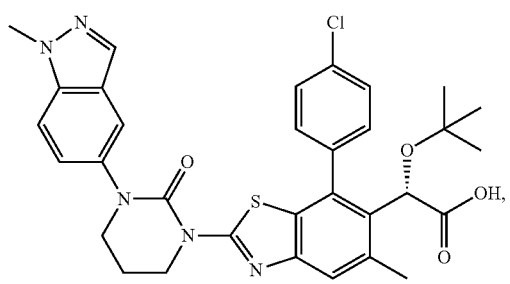
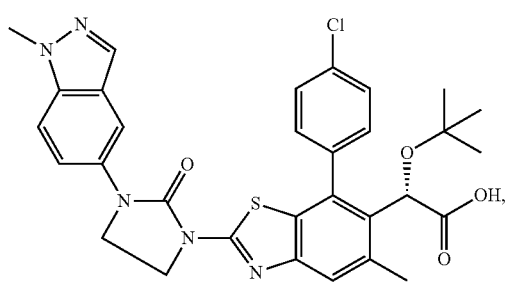
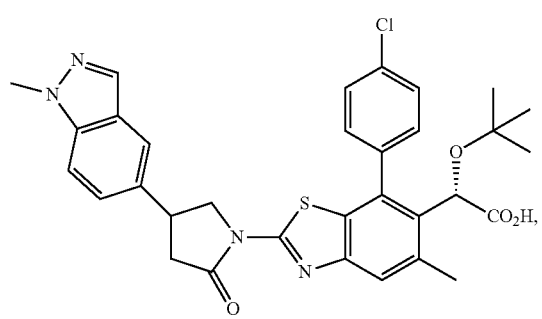
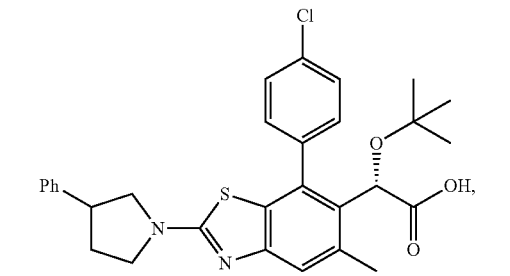
76
-continued
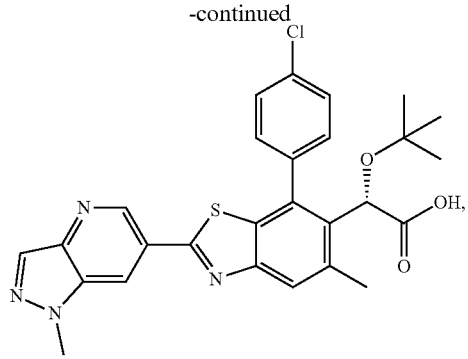
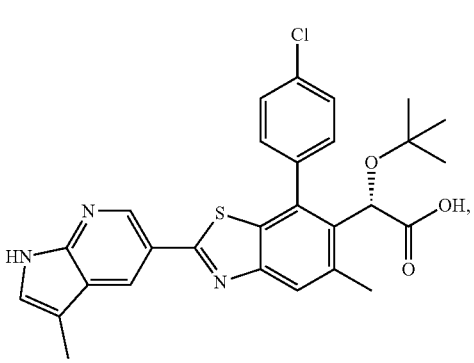
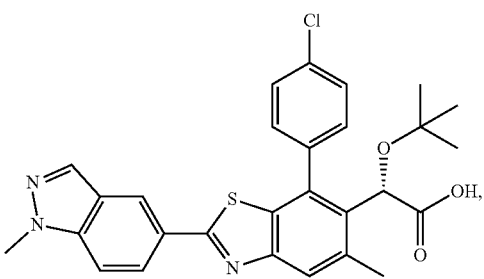
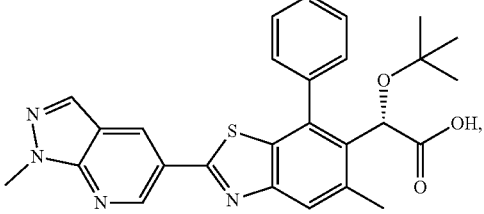
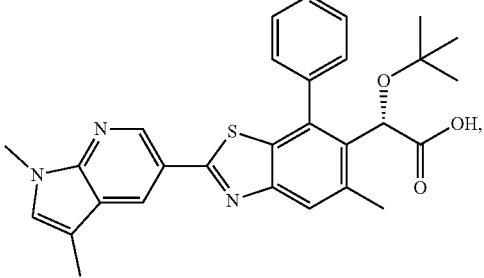

77
-continued
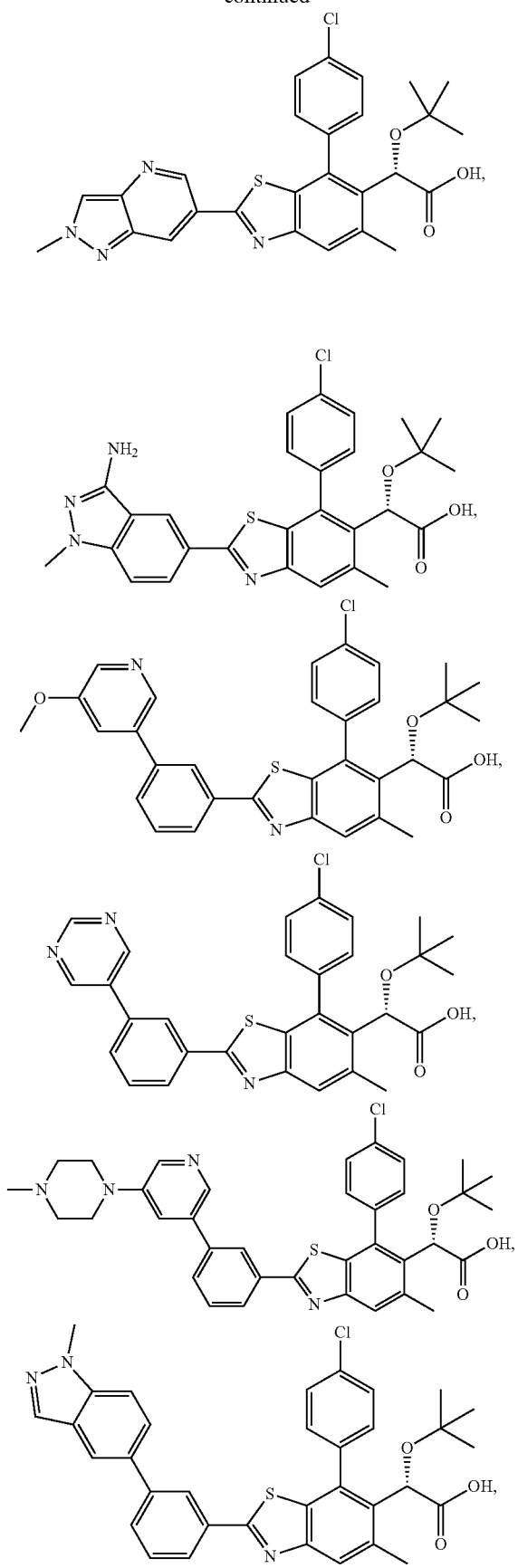
78
-continued
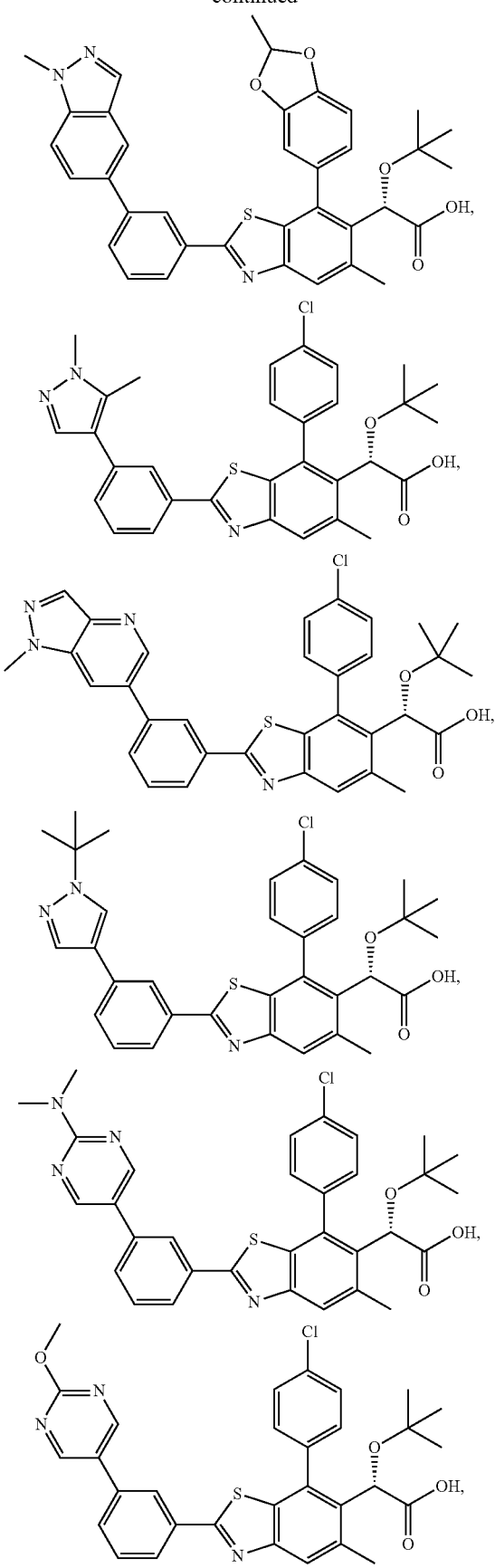

79
-continued
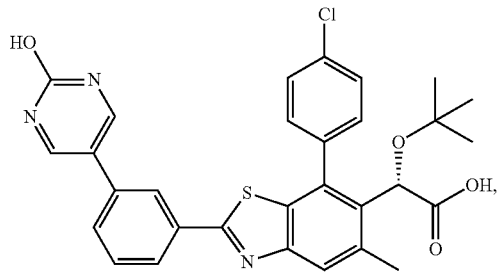
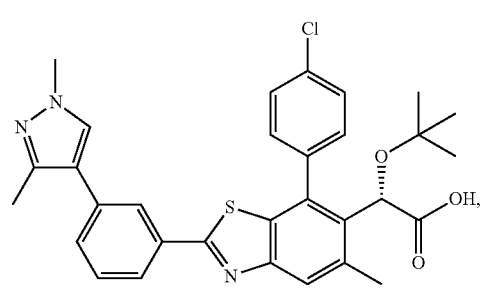
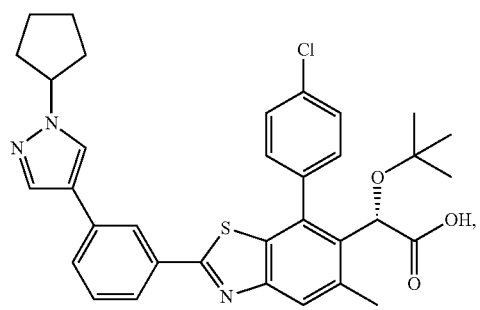
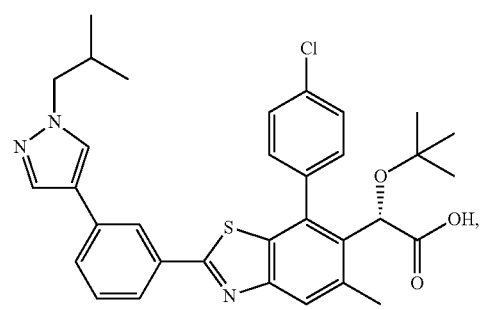
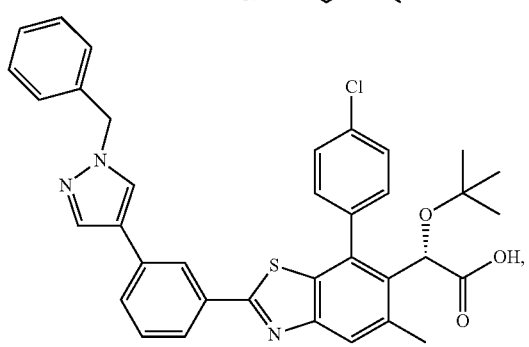
80
-continued
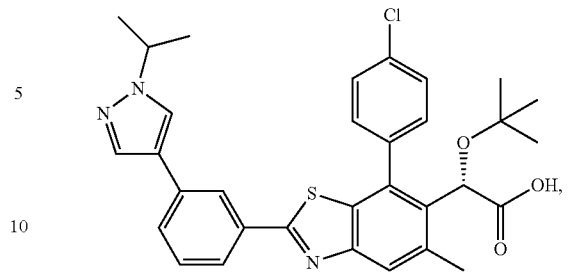
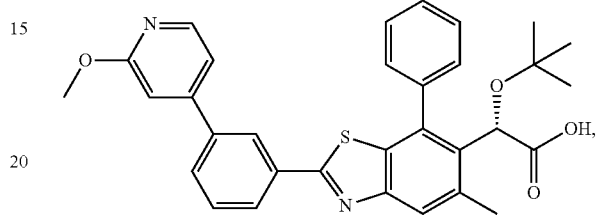
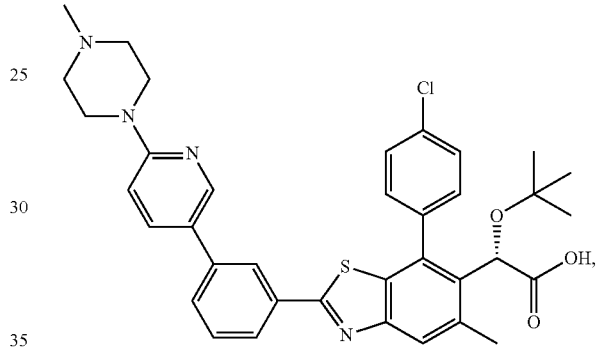
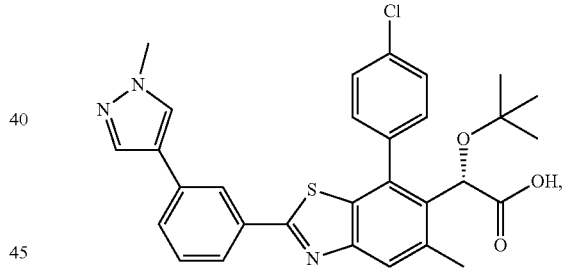
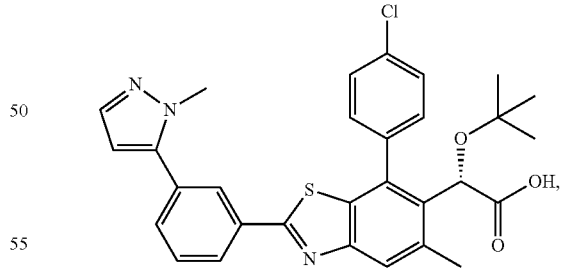
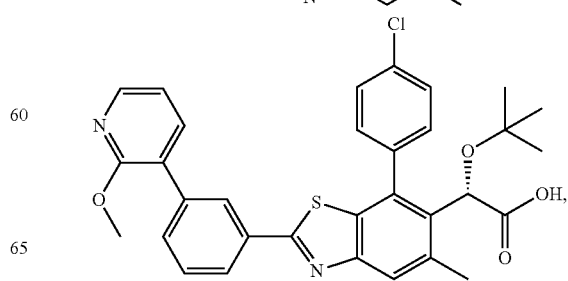

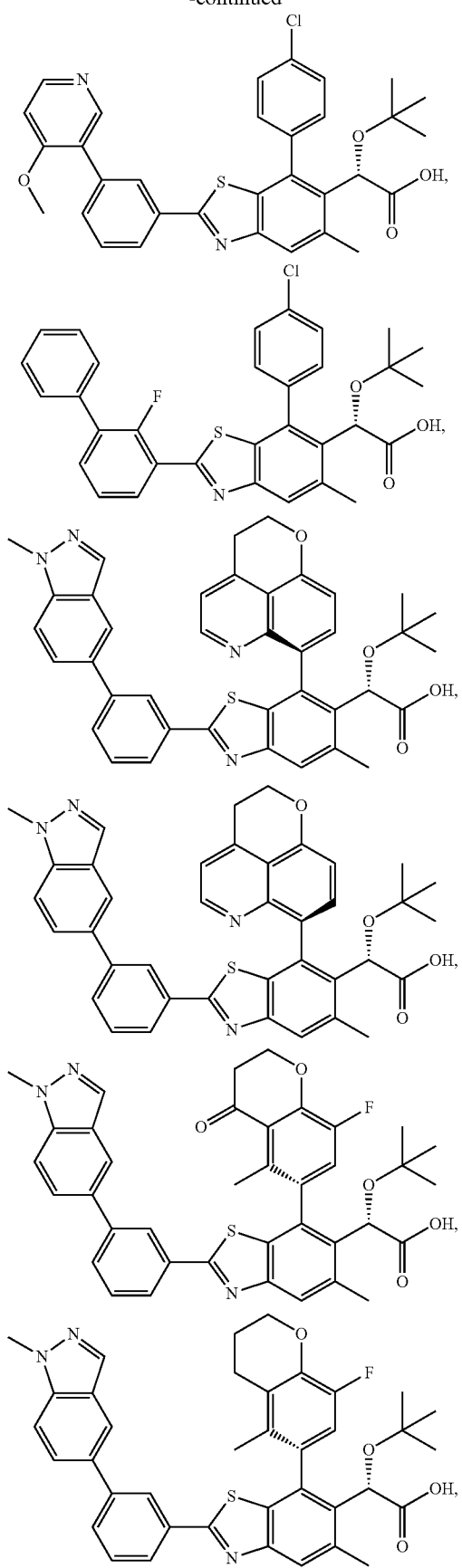
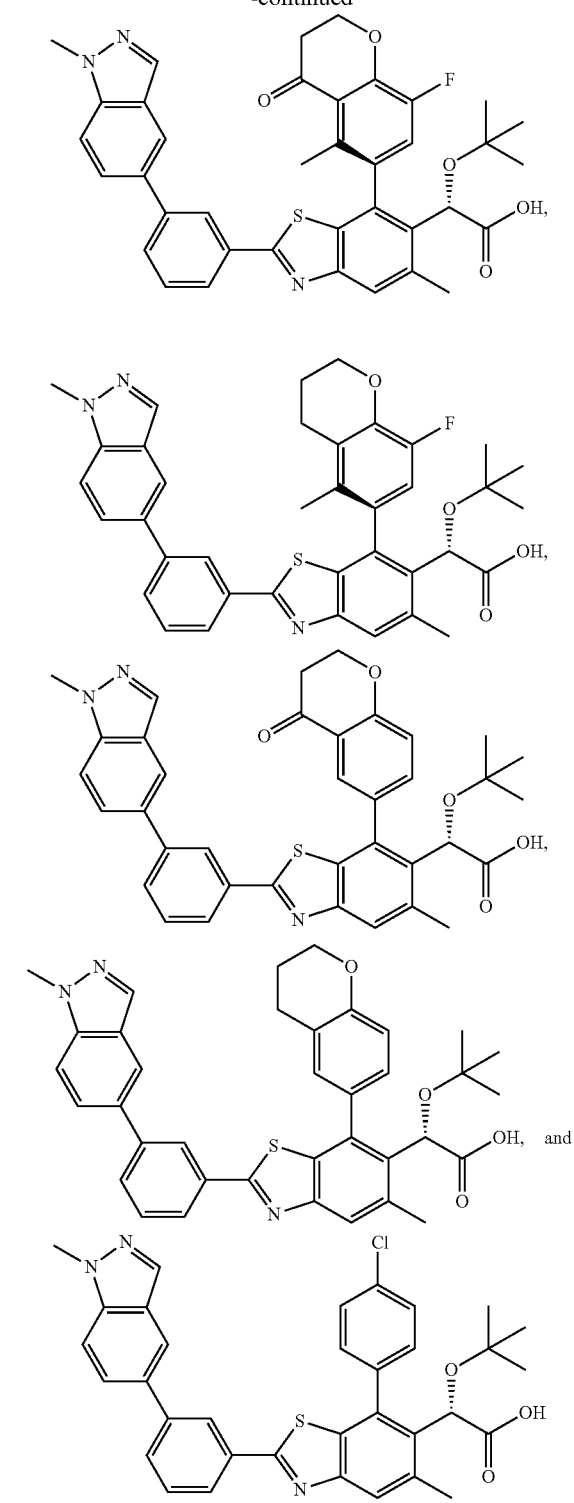
and salts thereof.
In one embodiment the compounds of the invention do not include compounds wherein A is thiophene.
In another embodiment the compounds of the invention do not include compounds wherein A is thiophenyl and B is phenyl, wherein phenyl is optionally substituted with one or $Z^{1b}$ groups.

In another embodiment the compounds of the invention do not include compounds wherein A-B is:

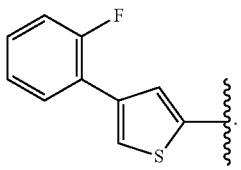 [SMILES: *c1cc(-c2ccccc2F)cs1]

In another embodiment the compounds of the invention do not include the compounds of the following formula:

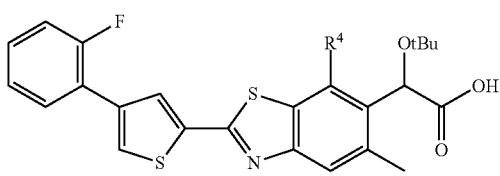

wherein R⁴ is:

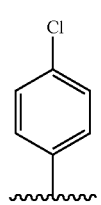 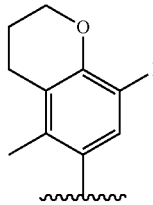 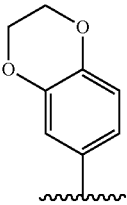 or

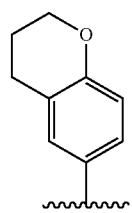

or salts thereof.

General Synthetic Procedures

Schemes 1-15 are provided as further embodiments of the invention and illustrate general methods which were used to prepare compounds of the invention and which can be used to prepare additional compounds of the invention.

Scheme 1

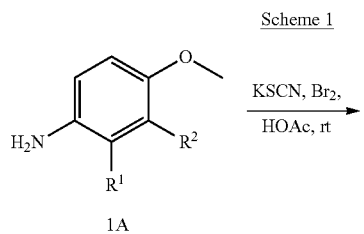

1A

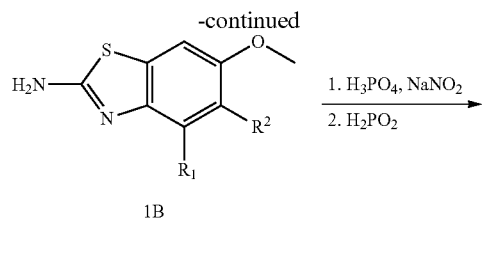

1B

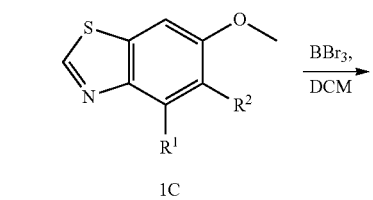

1C

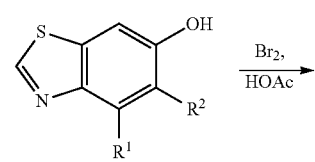

1D

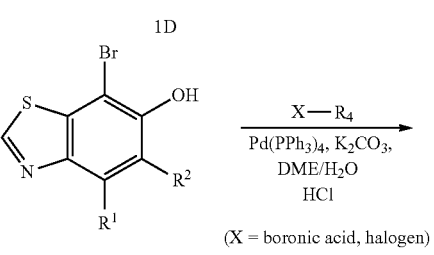

(X = boronic acid, halogen)

1E

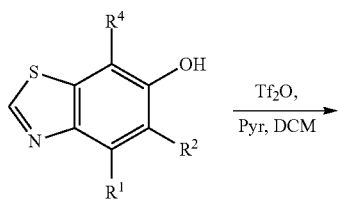

1F

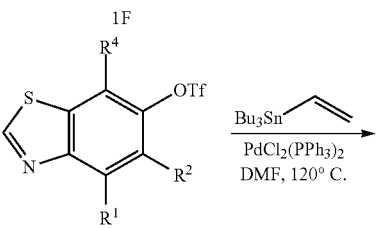

1G

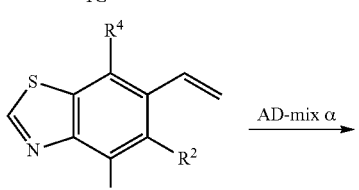

1H

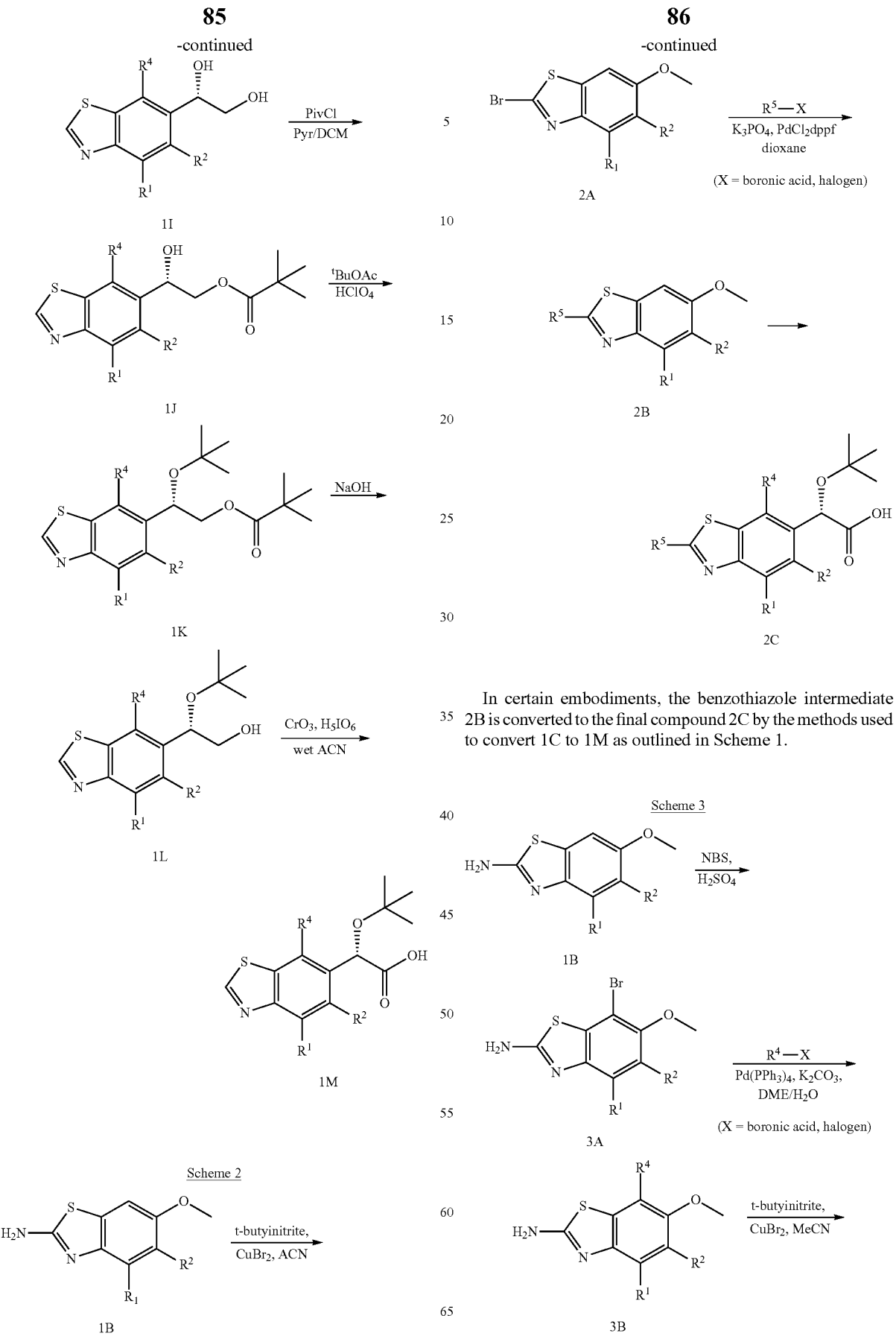
In certain embodiments, the benzothiazole intermediate 2B is converted to the final compound 2C by the methods used to convert 1C to 1M as outlined in Scheme 1.

87

-continued

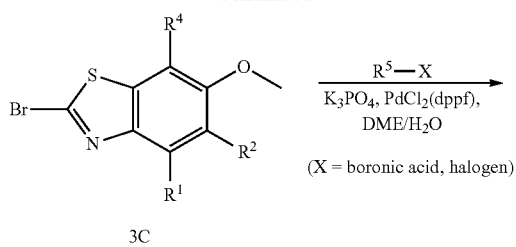
3C

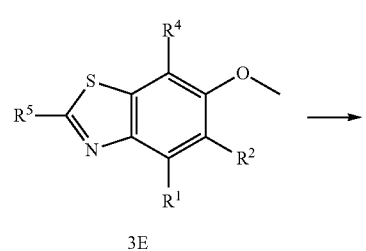
3E

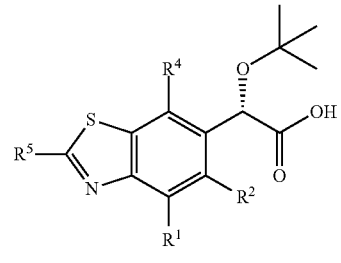
2C

In certain embodiments, the benzothiazole intermediate 3E is converted to the final compound 2C by the methods used to convert 1C to 1D and 1F to 1M as outlined in Scheme 1.

Scheme 4

3C

4A

88

-continued

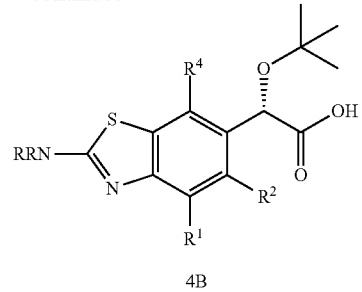
4B

In certain embodiments the benzothiazole intermediate 4A is converted to the final compound 4B by the methods used to convert 1C to 1D and 1F to 1M as outlined in Scheme 1 wherein HNRR a heterocycle (i.e., when R and R taken together with the nitrogen to which they are attached form a ring).

Scheme 5

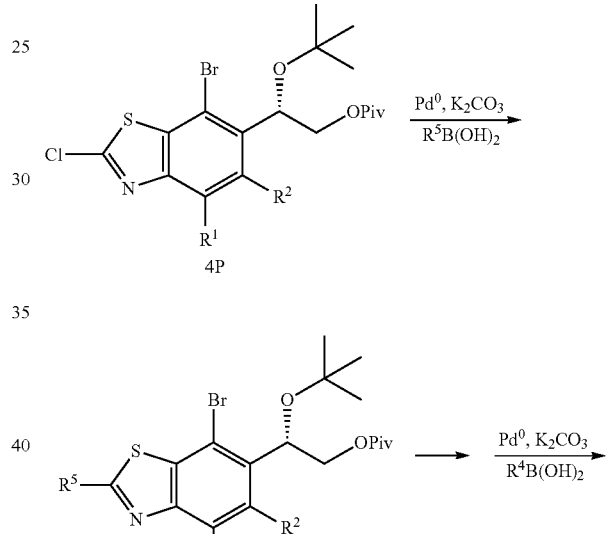

4P

4U

4V

4W

In certain embodiments the benzothiazoline intermediate 4V is converted to the final compound 4W by the methods used to convert 1C to 1M as outlined in Scheme 1.

Scheme 6

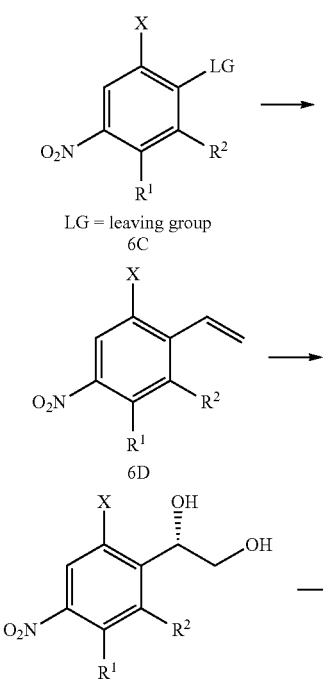

6A

X = halogen
6B

LG = leaving group
6C

6D

6E

PG = protection group
6F

6G

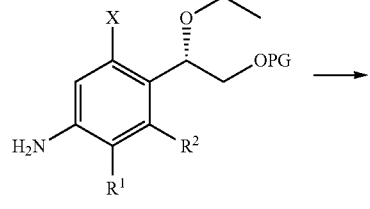

6H

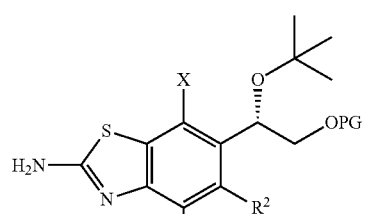

6I

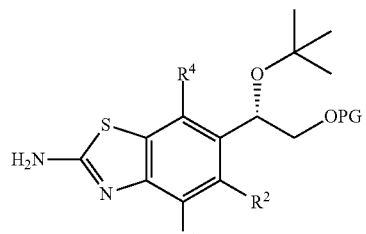

6J

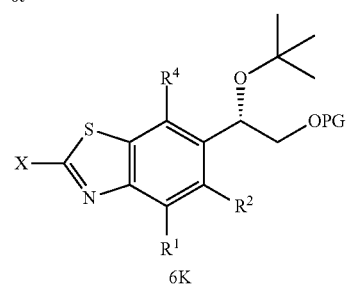

6K

In certain embodiments, an appropriately substituted phenol 6A is halogenated by the treatment of dihalide, for example bromine, in a suitable solvent such as, for example acetic acid. The phenol 6B is converted to a leaving group (e.g., triflate) known to undergo cross-coupling reactions. The corresponding activated phenol 6C undergoes a selective cross-coupling reaction such as, for example Stille cross-coupling using a tin reagent such as tributyl(vinyl)tin and a palladium catalyst such as bis(triphenylphosphine) palladium(II) dichloride to give the corresponding cross-coupled naphthalene such as styrene 6D. The styrene is dihydroxylated to provide 6E by methods known to those skilled in the art such as, Sharpless asymmetric dihydroxylation using, for example, commercially available AD mix-α. The resulting diol 6E is protected at the primary hydroxyl by suitable protecting groups such as pivaloyl ester using pivaloyl chloride and pyridine to provide 6F. The secondary hydroxyl is converted to the corresponding ether such as tert-butyl ether using methods known to those skilled in the art such as, tert-butyl acetate and perchloric acid to provide 6G.

The nitro group of 6G is reduced to the corresponding aniline 6H by catalytic hydrogenation using platinum on carbon, for example, under a hydrogen atmosphere. Benzothiazole 6I is formed by methods known to those skilled in the art such as potassium thiocyanate and pyridinium perbromide, for example. The resulting benzothiazole undergoes cross-coupling reaction such as Suzuki cross-coupling using a boronic acid or ester and a palladium catalyst such as tetrakis(triphenylphosphine)palladium(0) to give the corresponding cross-coupled benzothiazole 6J. The corresponding halobenzothiazole 6K is formed by methods known to those skilled in the art such as tert-butyl nitrite and a copper(II) halide such as copper(II) bromide, for example.

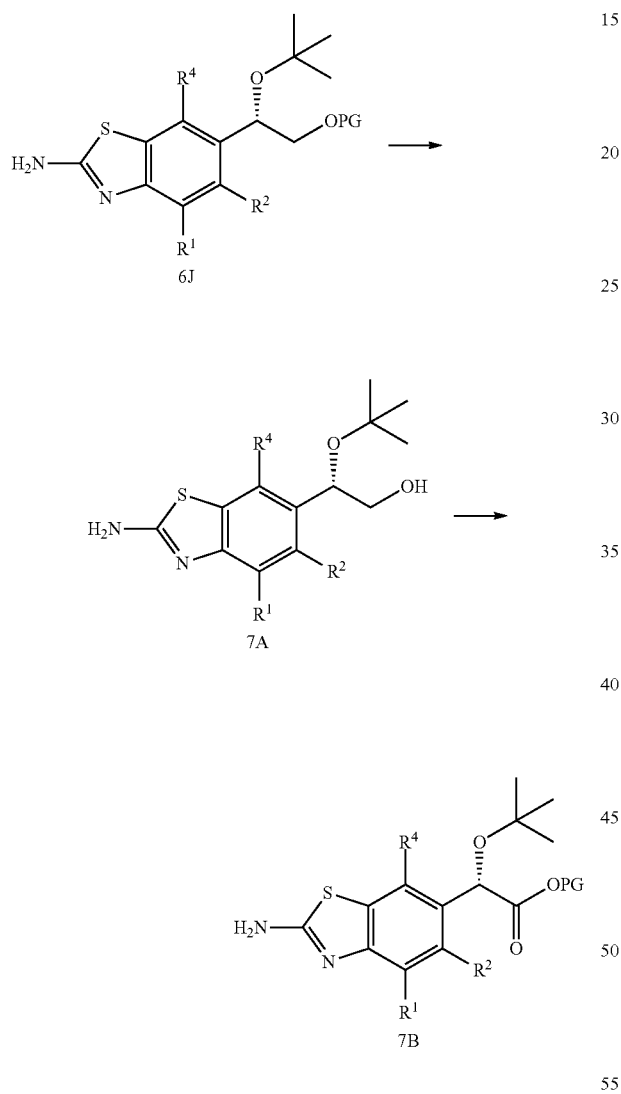

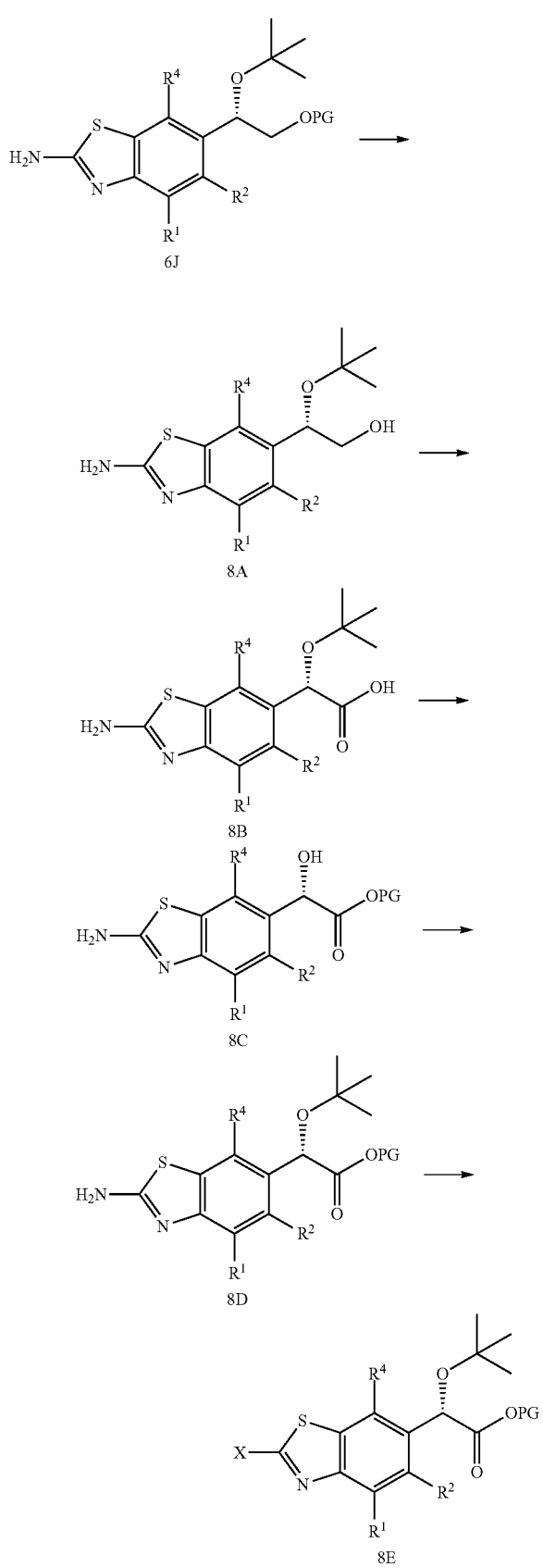

In certain embodiments the protected primary hydroxyl 6J is deprotected by methods known to those skilled in the art such as the deprotection of a pivalate protecting group under basic conditions for example, using sodium hydroxide, to give the corresponding primary hydroxyl compound 7A. The primary hydroxyl is oxidized to the corresponding carboxylic acid 7B by methods known to those skilled in the art such as, for example, periodic acid and chromium trioxide. The resulting carboxylic acid is protected by formation of corresponding carboxylic ester 7B with treatment of, for example, trimethylsilyldiazomethane, to form the corresponding methyl ester.

In certain embodiments the protected primary hydroxyl 6J is deprotected by methods known to those skilled in the art such as the deprotection of a pivalate protecting group under basic conditions for example, using sodium hydroxide, to give the corresponding primary hydroxyl compound 8A. The primary hydroxyl is oxidized to the corresponding carboxylic acid 8B by periodic acid and chromium trioxide, for example. The carboxylic acid is protected as, for example, a methyl ester by treatment with sulfuric acid in methanol. The tert-butyl ether is re-installed by treating 8C with tert-butyl acetate and perchloric acid, for example, to provide 8D. The corresponding halobenzothiazole 8E is formed by methods known to those skilled in the art such as tert-butyl nitrite and a copper(II)halide such as copper(II)bromide, for example.

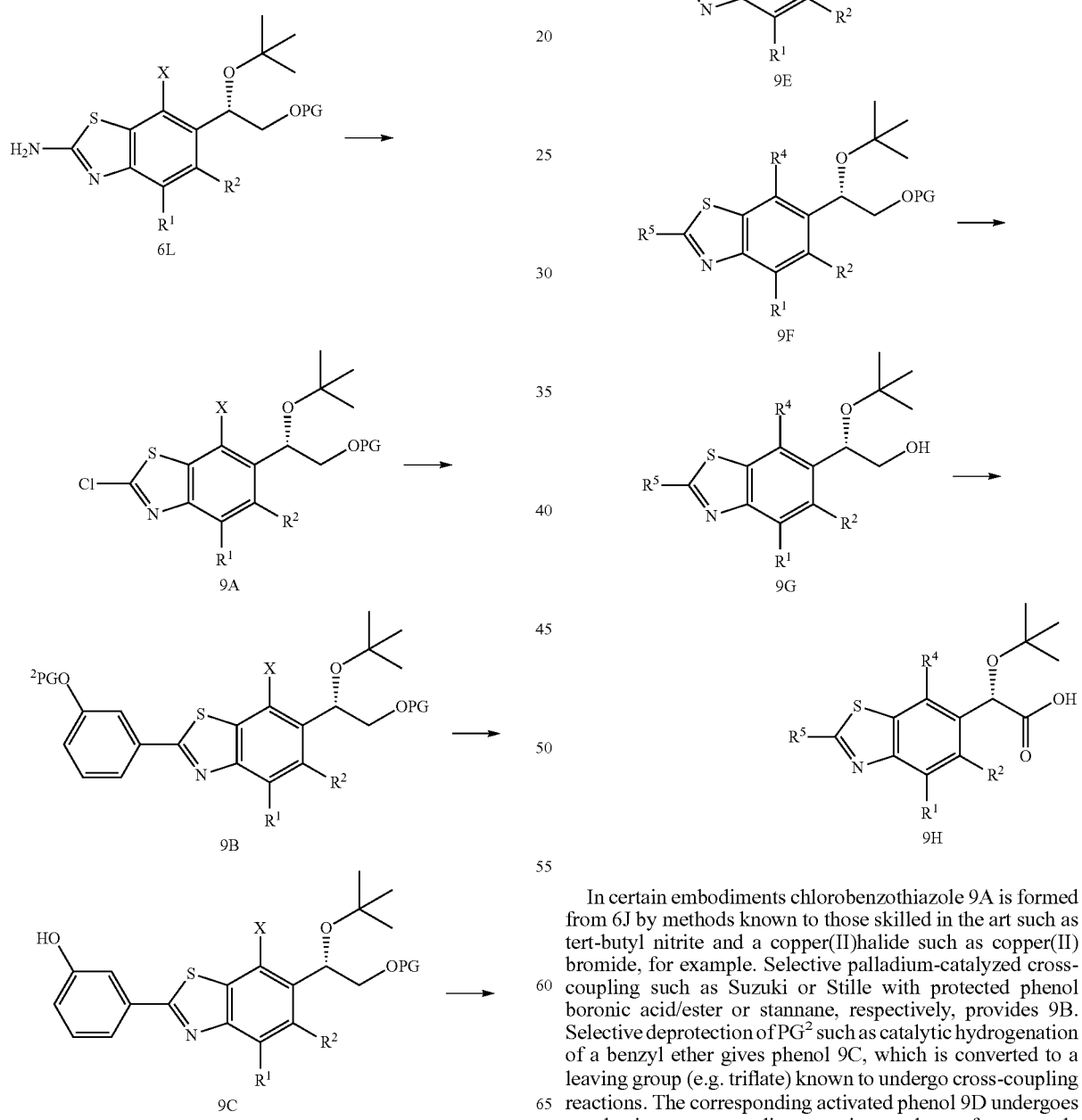

Scheme 9

In certain embodiments chlorobenzothiazole 9A is formed from 6J by methods known to those skilled in the art such as tert-butyl nitrite and a copper(II)halide such as copper(II) bromide, for example. Selective palladium-catalyzed cross-coupling such as Suzuki or Stille with protected phenol boronic acid/ester or stannane, respectively, provides 9B. Selective deprotection of PG² such as catalytic hydrogenation of a benzyl ether gives phenol 9C, which is converted to a leaving group (e.g. triflate) known to undergo cross-coupling reactions. The corresponding activated phenol 9D undergoes a selective cross-coupling reaction such as, for example Suzuki cross-coupling using a boronic acid or ester and a palladium catalyst such as tetrakis(triphenylphosphine)palladium(0) to give the corresponding cross-coupled benzothiazole 9E.

In certain embodiments the R⁴ moiety is introduced by cross-coupling reaction such as, for example Suzuki cross-coupling using a boronic acid or ester and a palladium catalyst such as tetrakis(triphenylphosphine)palladium(0) to give the corresponding cross-coupled benzothiazole 9F. The protected primary hydroxyl 9F is deprotected by methods known to those skilled in the art such as the deprotection of a pivalate protecting group under basic conditions for example, using sodium hydroxide, to give the corresponding primary hydroxyl compound 9G. The primary hydroxyl is oxidized to the corresponding carboxylic acid 9H by periodic acid and chromium trioxide, for example.

Scheme 10

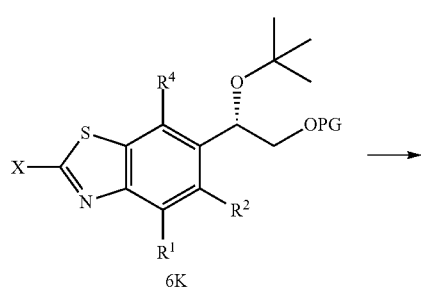

6K

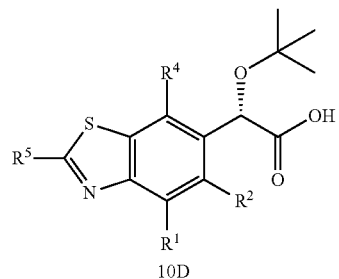

10D

In certain embodiments halobenzothiazole 6K undergoes selective palladium-catalyzed cross-coupling such as Suzuki or Stille with a boronic acid/ester or stannane that also contains a leaving group such as for example, a chloropyridylboronic acid, known to undergo cross-coupling reactions to give 10A. The activated moiety 10A undergoes a cross-coupling reaction such as, for example Suzuki or Stille cross-coupling using a boronic acid/ester or stannane, respectively and a palladium catalyst such as tetrakis(triphenylphosphine)palladium(0) to give the corresponding cross-coupled benzothiazole 10B. The protected primary hydroxyl 10B is deprotected by methods known to those skilled in the art such as the deprotection of a pivalate protecting group under basic conditions for example, using sodium hydroxide, to give the corresponding primary hydroxyl compound 10C. The primary hydroxyl is oxidized to the corresponding carboxylic acid 10D by periodic acid and chromium trioxide, for example.

Scheme 11

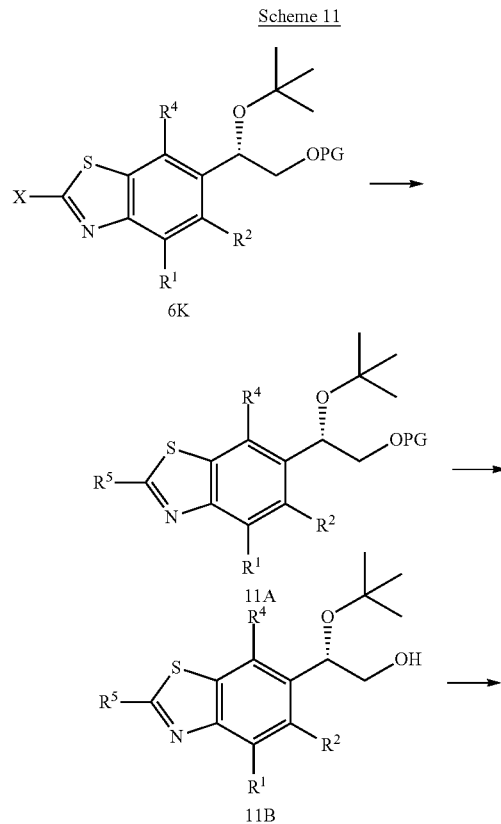

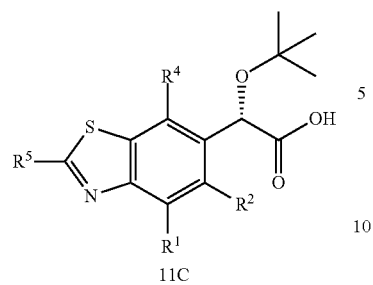

11C

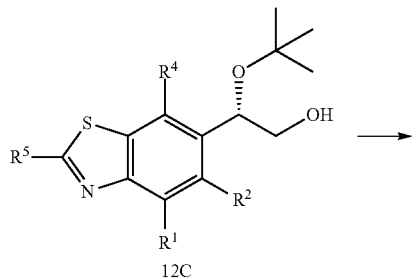

12C

In certain embodiments halobenzothiazole 6K undergoes palladium-catalyzed cross-coupling such as Suzuki with a boronic acid or ester; Stille with a stannane; palladium-catalyzed carbonylation using carbon monoxide, for example in the presence of an amine; copper(I)halide catalyzed or Buchwald-Hartwig amination; palladium-catalyzed amidation; $S_NAr$ with an amine; to introduce the $R^5$ moiety in 11A. The protected primary hydroxyl of 11A is deprotected by methods known to those skilled in the art such as the deprotection of a pivalate protecting group under basic conditions for example, using sodium hydroxide, to give the corresponding primary hydroxyl compound 11B. The primary hydroxyl is oxidized to the corresponding carboxylic acid 11C by periodic acid and chromium trioxide, for example.

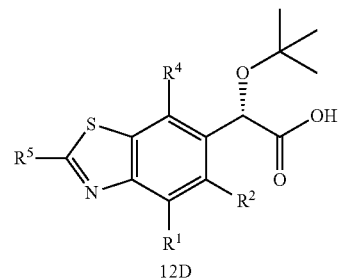

12D

In certain embodiments chlorobenzothiazole 9A undergoes selective palladium-catalyzed cross-coupling such as Suzuki or Stille with protected phenol boronic acid/ester or stannane, respectively, to provide 12A. The $R^4$ moiety is introduced by cross-coupling reaction such as, for example Suzuki cross-coupling using a boronic acid or ester and a palladium catalyst such as tetrakis(triphenylphosphine)palladium(0) to give the corresponding cross-coupled benzothiazole 12B. The protected primary hydroxyl in 12B is deprotected by methods known to those skilled in the art such as the deprotection of a pivalate protecting group under basic conditions for example, using sodium hydroxide, to give the corresponding primary hydroxyl compound 12C. The primary hydroxyl is oxidized to the corresponding carboxylic acid 12D by periodic acid and chromium trioxide, for example.

Scheme 12

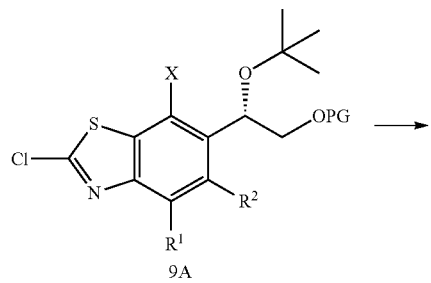

9A

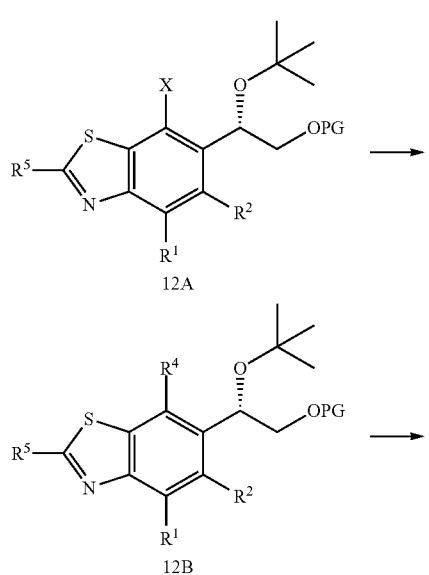

12A

12B

Scheme 13

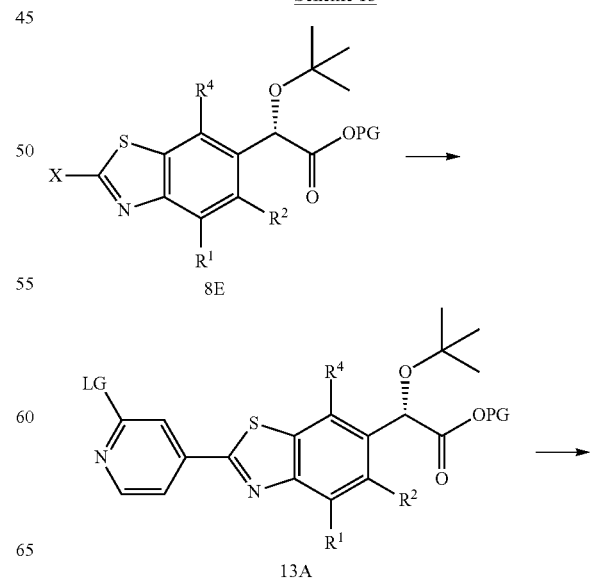

8E

13A

-continued

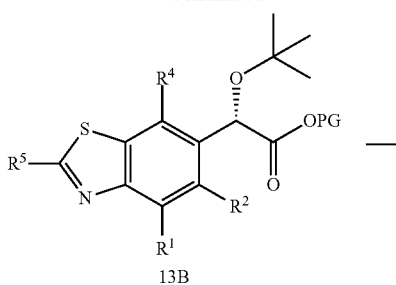
13B

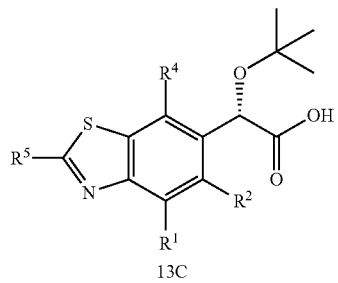
13C

In certain embodiments halobenzothiazole 8E undergoes selective palladium-catalyzed cross-coupling such as Suzuki or Stille with a boronic acid/ester or stannane that also contains a leaving group such as for example, a chloropyridylboronic acid, known to undergo cross-coupling reactions to give 13A. The activated moiety 13A undergoes across-coupling reaction such as, for example Suzuki or Stille cross-coupling using a boronic acid/ester or stannane, respectively and a palladium catalyst such as tetrakis(triphenylphosphine)palladium(0) to give the corresponding cross-coupled benzothiazole 13B. The protected carboxylic acid 13B is deprotected by methods known to those skilled in the art such as the deprotection of a carboxylic ester under basic conditions for example, using sodium hydroxide, to give the corresponding carboxylic acid 13C.

Scheme 14

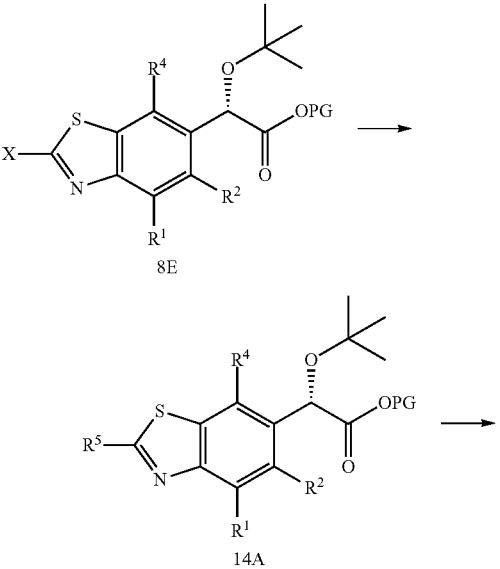
8E

14A

-continued

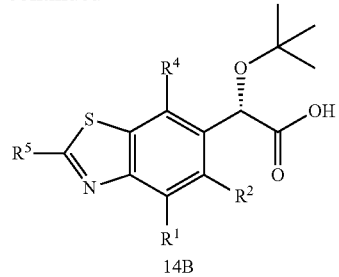
14B

In certain embodiments halobenzothiazole 8E undergoes palladium-catalyzed cross-coupling such as Suzuki with a boronic acid or ester; Stille with a stannane; palladium-catalyzed carbonylation using carbon monoxide, for example in the presence of an amine; copper(I)halide catalyzed or Buchwald-Hartwig amination; palladium-catalyzed amidation; $S_NAr$ with an amine or alcohol; to introduce the $R^5$ moiety in 14A. The protected carboxylic acid 14A is deprotected by methods known to those skilled in the art such as the deprotection of a carboxylic ester under basic conditions for example, using sodium hydroxide, to give the corresponding carboxylic acid 14B.

Scheme 15

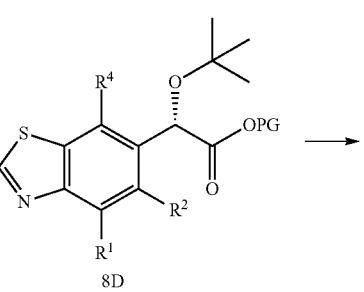
8D

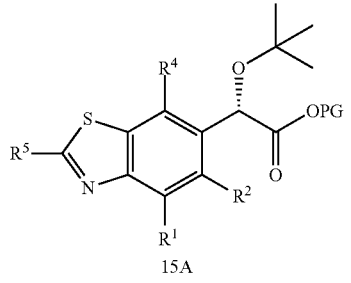
15A

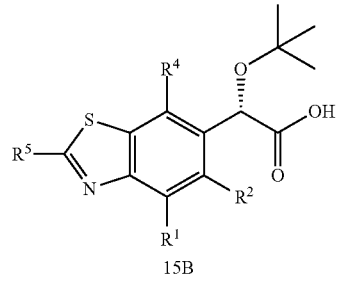
15B

In certain embodiments aminobenzothiazole 8D undergoes reactions known to those skilled in the art such as amide formation using carboxylic acid EDCI, for example; sulfonamide formation using a sulfonyl chloride; urea formation using CDI in the presence of an amine; to introduce the $R^5$ moiety in 15A. The protected carboxylic acid 15A is deprotected by methods known to those skilled in the art such as the deprotection of a carboxylic ester under basic conditions for example, using sodium hydroxide, to give the corresponding carboxylic acid 15B.

Prodrugs

In one embodiment, the invention provides for a prodrug of a disclosed herein including a compound of the invention. The term "prodrug" as used herein refers to any compound that when administered to a biological system generates a compound of the invention that inhibits the replication of HIV ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2C(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 24; also U.S. Pat. Nos. 4,816,570, 4,968,788, 5663159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans.* 112345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Combination Therapy

In one embodiment, the invention provides for a method for treating an HIV infection, comprising administering to a patient in need thereof a therapeutically effective amount of a compound of the invention, or a pharmaceutically acceptable salt, thereof, in combination with a therapeutically effective amount of one or more additional therapeutic agents which are suitable for treating an HIV infection.

In one embodiment, the invention provides pharmaceutical compositions comprising a compound of the present invention, or a pharmaceutically acceptable salt thereof, in combination with at least one additional therapeutic agent, and a pharmaceutically acceptable carrier. For example, the therapeutic agent used in combination with the compound of the present invention can be any anti-HIV agent.

In one embodiment, the invention provides pharmaceutical compositions comprising a compound of the present invention, or a pharmaceutically acceptable salt thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV, and combinations thereof, and a pharmaceutically acceptable carrier.

In another embodiment, the invention provides pharmaceutical compositions comprising a compound of the present invention, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5 mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In another embodiment, the invention provides pharmaceutical compositions comprising a compound of the present invention, or a pharmaceutically acceptable salt thereof, in combination with two, three, four or more additional therapeutic agents. For example, a compound of the present invention, or a pharmaceutically acceptable salt, thereof, is combined with two, three, four or more additional therapeutic agents selected from the classes of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drug for treating HIV. The two, three four or more additional therapeutic agents can be different therapeutic agents selected from the same class of therapeutic agents, or they can be selected from different classes of therapeutic agents.

In one embodiment, the invention provides for a combination pharmaceutical agent comprising:

a) a compound of the invention (e.g. a compound of Formula I), or a pharmaceutically acceptable salt, thereof; and b) at least one additional active agent which is suitable for treating an HIV infection.

In another embodiment, the invention provides a combination pharmaceutical agent comprising:

a) a compound of the invention (e.g. a compound of Formula I), or a pharmaceutically acceptable salt thereof; and b) at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drugs for treating HIV.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

It is also possible to co-administer a compound of the invention with one or more other active therapeutic agents.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In yet another embodiment, the present application provides a method for treating an HIV infection comprising administering to a patient in need thereof a therapeutically effective amount of a compound of the present invention, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV.

In yet another embodiment, the present application provides a method for treating an HIV infection comprising administering to a patient in need thereof a therapeutically effective amount of a compound of the present invention, or a pharmaceutically acceptable salt, thereof, in combination with a therapeutically effective amount of one or more additional therapeutic agents selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5 mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

Pharmaceutical Formulations

The compounds disclosed herein (e.g., compounds of the invention) are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound disclosed herein may be determined using Test A described below.

Test A: Antiviral Assays in MT4 Cells

For the antiviral assay utilizing MT-4 cells, 0.4 µL of 189× test concentration of 3-fold serially diluted compound in DMSO was added to 40 µL of cell growth medium (RPMI 1640, 10% FBS, 1% penicilline/Streptomycine, 1% L-Glutamine, 1% HEPES) in each well of 384-well assay plates (10 concentrations) in quadruplicate.

1 mL aliquots of 2×10e6 MT-4 cells are pre-infected for 1 and 3 hrs respectively, @ 37° C. with 25 uL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 uL of 2000 (for MT4) cells is added to each well of the assay plates.

Assay plates were then incubated in a 37° C. incubator. After 5 days of incubation, 25 µl of 2× concentrated CellTiter-Glo™ Reagent (catalog #G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds disclosed herein demonstrate antiviral activity in this assay (Test A) as depicted in the table below. Accordingly, the compounds disclosed herein (e.g. compound of the invention) may be useful for treating the proliferation of the HIV virus, treating AIDS or delaying the onset of AIDS or ARC symptoms.

| Compound Number | EC50 (nM) |
| --- | --- |
| 50 | 52.8 |
| 51 | 5250 |
| 52 | 53.4 |
| 53 | 37500 |
| 54 | 274 |
| 55 | 53000 |

-continued

| Compound Number | EC50 (nM) |
|---|---|
| 56 | 62.4 |
| 57 | 147 |
| 58 | 3520 |
| 76 | 26 |
| 78 | 726 |
| 89 | 36.6 |
| 104 | 42 |
| 105 | 16 |
| 106 | 103 |
| 107 | 46 |
| 108 | 33 |
| 109 | 82 |
| 110 | 14 |
| 111 | 8 |
| 112 | 28 |
| 113a | 16 |
| 113b | 18 |
| 114 | 13 |
| 115 | 13 |
| 116 | 19 |
| 117 | 14 |
| 118 | 101 |
| 119 | 237 |
| 120 | 23 |
| 121 | 27 |
| 122 | 5518 |
| 123 | 18 |
| 124 | 21 |
| 126 | 722 |
| 130 | 100 |
| 131 | 8 |
| 132 | 12 |
| 133 | 18 |
| 134 | 3226 |
| 135 | 17 |
| 136 | 12 |
| 137 | 21 |
| 138 | 65 |
| 139 | 61 |
| 140 | 5 |
| 141 | 77 |
| 142 | 48 |
| 143 | 24 |
| 144 | 2608 |
| 145 | 34 |
| 146 | 92 |
| 147 | 59 |
| 148 | 2698 |
| 149 | 153 |
| 150 | 91 |
| 151 | 32 |
| 152 | 46 |
| 153 | 15 |
| 154 | 16 |
| 155 | 66 |
| 156 | 26 |
| 157 | 29 |
| 158 | 17 |
| 159 | 46 |
| 160 | 136 |
| 161 | 116 |
| 162 | 350 |
| 163 | 18 |
| 164 | 483 |
| 167 | 39 |
| 168 | 42 |
| 169 | 33 |
| 170 | 35 |

In certain embodiments, the compounds demonstrate an EC50 of <50 µM. In certain embodiments, the compounds demonstrate an EC50 of <30 µM. In certain embodiments, the compounds demonstrate an EC50 of <10 µM. In certain embodiments, the compounds demonstrate an EC50 of <1 µM.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting examples of compounds of the invention and intermediates useful for preparing compounds of the invention.

Example 1

Preparation of Intermediates 24-32

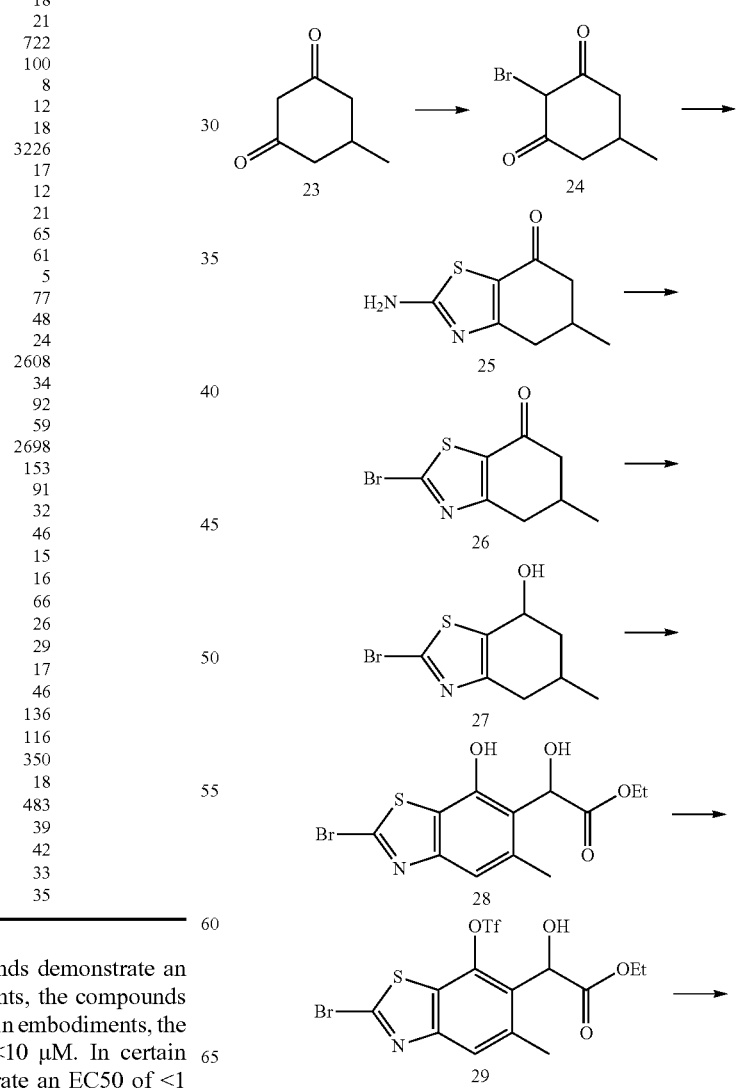

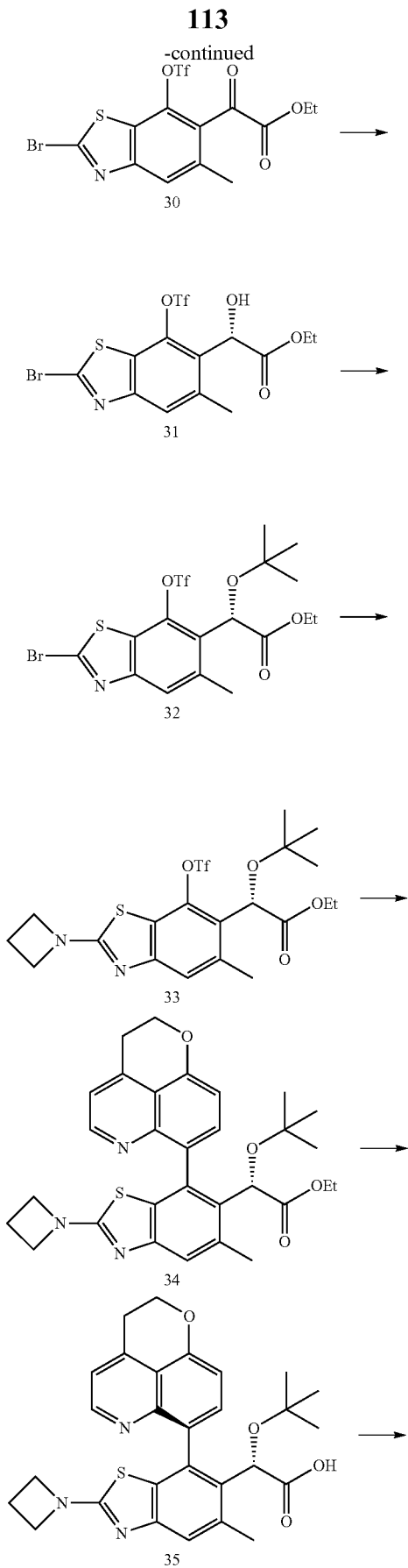

To a solution of 34 (23 mg, 0.043 mmol) in THF (1 mL) and MeOH (1 mL) was added a solution of NaOH (2 M, ~400 μL). The reaction mixture was heated at 70° C. for 4 h. The reaction was brought to ~pH 5 with TFA and was then purified by reverse phase HPLC (MeCN/H$_2$O containing 0.1% TFA) to give 6 mg of compound 35 and 10 mg of compound 36.

Compound 35: $^1$H-NMR: 400 MHz, (CD$_3$OD) δ: 8.75 (d, J=2.6 Hz, 1H), 7.80 (d, J=4.0 Hz, 1H), 7.72 (d, J=2.6 Hz, 1H), 7.47 (s, 1H), 7.34 (d, J=4.0 Hz, 1H), 5.13 (s, 1H), 4.67-4.65 (m, 2H), 4.17 (t, J=7.6 Hz, 4H), 3.59-3.58 (m, 2H), 2.66 (s, 3H), 2.52-2.50 (m, 2H), 0.88 (s, 9H). LCMS-ESI$^+$: calc'd for C$_{28}$H$_{29}$N$_3$O$_4$S: 504.2 (M+H$^+$); Found: 504.0 (M+H$^+$).

Compound 36: $^1$H-NMR: 400 MHz, (CD$_3$OD) δ: 8.67 (d, J=2.2 Hz, 1H), 8.01 (d, J=4.0 Hz, 1H), 7.49 (d, J=2.6 Hz, 1H), 7.40 (s, 1H), 7.27 (d, J=4.2 Hz, 1H), 5.18 (s, 1H), 4.60-4.57 (m, 2H), 4.27 (t, J=7.8 Hz, 4H), 3.48-3.45 (m, 2H), 2.61 (s, 3H), 2.58-2.54 (m, 2H), 0.80 (s, 9H). LCMS-ESI$^+$: calc'd for C$_{28}$H$_{29}$N$_3$O$_4$S: 504.2 (M+H$^+$); Found: 504.1 (M+H$^+$).

Preparation of (2S)-ethyl 2-(2-(azetidin-1-yl)-7-(2,3-dihydropyrano[4,3,2-de]quinolin-7-yl)-5-methyl-benzo[d]thiazol-6-yl)-2-tert-butoxyacetate (34)

Step 1.
Preparation of 2-bromo-5-methylcyclohexane-1,3-dione (24). To a solution of 5-methyl-1,3-cyclohexanedione (23) (45.4 g, 360 mmol) in acetic acid (540 mL) was added bromine (19.4 mL, 378 mmol) over 5 min. After 30 min of stirring (with mechanical stirrer), the reaction mixture was filtered. The solid was left under high vacuum overnight and used in the subsequent step without further purification.
Step 2.
Preparation of 2-amino-5-methyl-5,6-dihydrobenzo[d]thiazol-7(4H)-one (25). To a solution of 24 in acetic acid (540 mL) was added sodium acetate (44.3 g, 540 mmol) and thiourea (28.8 g, 378 mmol). The reaction mixture was stirred with a mechanical stirrer at 100° C. for 3 h. The reaction mixture was partially concentrated in vacuo. EtOAc was added (500 mL). The mixture was made basic with 1 M NaOH, and the layers were separated. The aqueous layer was extracted with EtOAc (2×300 mL). The combined organic layers were dried, filtered, and concentrated in vacuo to give 49.3 g of 25, which was taken on without further purification. LCMS-ESI$^+$: calc'd for C$_8$H$_{11}$N$_2$OS: 183.1 (M+H$^+$); Found: 183.1 (M+H$^+$).
Step 3.
Preparation of 2-bromo-5-methyl-5,6-dihydrobenzo[d]thiazol-7(4H)-one (26). To a solution of 25 (53.9 g, 296 mmol) in MeCN (600 mL) at 0° C., while mechanically stirred), was added copper (II) bromide (79.2 g, 355 mmol) then t-butyl nitrite (46.8 mL, 355 mmol). The reaction mixture was stirred from 0° C. to room temperature over 2 h and was then partially concentrated. EtOAc (400 mL) and a 0.5 M HCl solution were added. The layers were separated, and the organic layer was washed with a brine solution. The combined organic layers were dried, filtered, and concentrated in vacuo. The crude product was adsorbed on ~150 g of silica then run through a plug of silica with 40% EtOAc/hexanes to give 58.3 g of 26. $^1$H-NMR: 400 MHz, (CDCl$_3$) δ: 3.16 (dd, 1H. J=18, 4 Hz), 2.66 (m, 2H), 2.47 (m, 1H), 2.34 (dd, 1H, J=16, 12 Hz), 1.19 (d, 3H, J=7 Hz). LCMS-ESI$^+$: calc'd for C$_8$H$_9$BrNOS: 245.9 (M+H$^+$); Found: 246.1 (M+H$^+$).

Step 4.

Preparation of 2-bromo-5-methylbenzo[d]thiazol-7-ol (27). To a solution of 26 (7.38 g, 30.0 mmol) in CCl$_4$ (90 mL) was added NBS (5.61 g, 31.5 mmol) and dibenzoyl peroxide (727 mg, 3.0 mmol). The reaction was heated at 90° C. in a sealed reaction vessel for about 4 h. Then DBU (6.73 mL, 45.0 mmol) in CH$_2$Cl$_2$ (15 mL) was added. The mixture was heated a reflux for 30 min, then a 1 M HCl solution was added. The layers were separated, and the aqueous layer was extracted with CH$_2$Cl$_2$. The combined organic layers were washed with a brine solution. The organic layer was then dried, filtered, and concentrated in vacuo. The crude product was adsorbed on ~30 g of silica then run through a plug of silica with 40% EtOAc/hexanes to give 5.2 g of 27. $^1$H-NMR: 400 MHz, (CD$_3$OH) δ: 7.25 (s, 1H), 6.69 (s, 1H), 2.40 (s, 3H). LCMS-ESI$^+$: calc'd for C$_8$H$_7$BrNOS: 243.9 (M+H$^+$); Found: 244.1 (M+H$^+$).

Step 5.

Preparation of ethyl 2-(2-bromo-7-hydroxy-5-methylbenzo[d]thiazol-6-yl)-2-hydroxyacetate (28). To a solution of 27 (3.90 g, 16.0 mmol) in CH$_2$Cl$_2$ (80 mL) at 0° C. was added triethylamine (2.45 mL, 16.8 mmol) then a solution of titanium tetrachloride in CH$_2$Cl$_2$ (1.0 M, 16.8 mL, 16.8 mmol). After 15 min, ethyl glyoxalate (50% in toluene, 3.49 mL, 17.6 mmol) was added. The reaction mixture was stirred for 2 h while warming to room temperature. Water (50 mL) and a saturated solution of potassium sodium tartrate (50 mL) were added. The mixture was stirred vigorously for 2 h. The layers were separated, and the aqueous layer was extracted with CH$_2$Cl$_2$. The combined organic layers were dried, filtered, and concentrated in vacuo. The crude material was purified by column chromatography to give 2.48 g of 28 and recovered ~500 mg of 27. $^1$H-NMR: 400 MHz, (CD$_3$OH) δ: 7.33 (s, 1H), 5.69 (s, 1H), 4.17 (m, 2H), 2.50 (s, 3H), 1.18 (t, 3H, J=7 Hz). LCMS-ESI$^+$: calc'd for C$_{12}$H$_{13}$BrNO$_4$S: 346.0 (M+H$^+$); Found: 346.1 (M+H$^+$).

Step 6.

Preparation of ethyl 2-(2-bromo-5-methyl-7-(trifluoromethylsulfonyloxy)benzo[d]thiazol-6-yl)-2-hydroxyacetate (29). To a solution of 28 (2.42 g, 7.00 mmol) in CH$_2$Cl$_2$ (30 mL) at −78° C. was added triethylamine (1.02 mL, 7.70 mmol) followed by trifluoromethanesulfonic anhydride (1.24 mL, 7.35 mmol). After 15 min, saturated NH$_4$Cl was added. The layers were separated. The organic layer was dried, filtered, and concentrated in vacuo. The crude material was purified by column chromatography to give 2.17 g of 29. $^1$H-NMR: 400 MHz, (CDCl$_3$) δ: 7.84 (s, 1H), 5.67 (s, 1H), 4.27 (m, 2H), 2.50 (s, 3H), 1.23 (t, 3H, J=7 Hz). LCMS-ESI$^+$: calc'd for C$_{13}$H$_{12}$BrF$_3$NO$_6$S$_2$: 477.9 (M+H$^+$); Found: 478.2 (M+H$^+$).

Step 7.

Preparation of ethyl 2-(2-bromo-5-methyl-7-(trifluoromethylsulfonyloxy)benzo[d]thiazol-6-yl)-2-oxoacetate (30). To a solution of 29 (9.85 g, 20.6 mmol) in CH$_2$Cl$_2$ (100 mL) was added Dess-Martin periodinane (9.61 g, 22.6 mmol). After 30 min, water (75 mL) and saturated Na$_2$S$_2$O$_4$ solution (75 mL) was added. The mixture was stirred vigorously for 30 min. The layers were separated, and the aqueous layer was extracted with CH$_2$Cl$_2$. The combined organic layers were dried, filtered, and concentrated in vacuo. The crude material was purified by column chromatography to give 8.32 g of 30. $^1$H-NMR: 400 MHz, (CDCl$_3$) δ: 7.91 (s, 1H), 4.40 (q, 2H, J=7 Hz), 2.49 (s, 3H), 1.39 (t, 3H, J=7 Hz). LCMS-ESI$^+$: calc'd for C$_{13}$H$_{10}$BrF$_3$NO$_6$S$_2$: 475.9 (M+H$^+$); Found: 476.1 (M+H$^+$).

Step 8.

Preparation of (S)-ethyl 2-(2-bromo-5-methyl-7-(trifluoromethylsulfonyloxy)benzo[d]thiazol-6-yl)-2-hydroxyacetate (31). To a solution of 30 (8.30 g, 17.4 mmol) in toluene (70 mL) was added ((R)-2-methyl-CBS-oxazaborolidine (725 mg, 2.61 mmol). The reaction mixture was then cooled to −35° C. and a solution of catecholborane (freshly distilled) (1 M in toluene, 20.9 mL, 20.9 mmol) was added via addition funnel over 30 min. The reaction was stirred for 20 min while warming to −20° C. A 2 M solution of Na$_2$CO$_3$ was added (50 mL). The layers were separated, and the organic layer was washed with additional Na$_2$CO$_3$ solution (3×25 mL). The organic layer was dried, filtered, and concentrated in vacuo to give 31, which had analytical data to match 29. The compound was taken on to the next step without further purification.

Step 9.

Preparation of (S)-ethyl 2-(2-bromo-5-methyl-7-(trifluoromethylsulfonyloxy)benzo[d]thiazol-6-yl)-2-tert-butoxyacetate (32). To a solution of 31 (~17 mmol) in t-butylacetate (70 mL) was added perchloric acid (1.23 mL, 20.4 mmol). After 3 h, water was added (50 mL). The layers were separated. The organic layer was washed with a saturated solution of NaHCO$_3$. The organic layer was dried, filtered, and concentrated in vacuo. The crude material was purified by column chromatography (EtOAc/hexanes) to give 7.22 g of 32 and 1.58 g of 31. $^1$H-NMR: 400 MHz, (CD$_3$OH) δ: 7.82 (s, 1H), 5.59 (s, 1H), 4.08-4.25 (m, 2H), 2.55 (s, 3H), 1.20 (s, 9H), 1.16 (t, 3H, J=7 Hz). LCMS-ESI$^+$: calc'd for C$_{17}$H$_{20}$BrF$_3$NO$_6$S$_2$: 534.0 (M+H$^+$); Found: 534.1 (M+H$^+$).

Step 10.

Preparation of (S)-ethyl 2-(2-(azetidin-1-yl)-5-methyl-7-(trifluoromethylsulfonyloxy)benzo[d]thiazol-6-yl)-2-tert-butoxyacetate (33). To a solution of 32 (50 mg, 0.094 mmol) in THF (1 mL) was added azetidine (20 μL). The reaction mixture was heated at 70° C. for 30 min. A saturated solution of NH$_4$Cl (3 mL) was added, and the layers were separated. The aqueous layer was extracted with EtOAc. The combined organic layer were dried, filtered, and concentrated in vacuo. The crude material was purified by column chromatography (EtOAc/hexanes) to give 38 mg of 33. LCMS-ESI$^+$: calc'd for C$_{20}$H$_{25}$F$_3$N$_2$O$_6$S$_2$: 511.1 (M+H$^+$); Found: 511.0 (M+H$^+$).

Step 11.

Preparation of (2S)-ethyl 2-(2-(azetidin-1-yl)-7-(2,3-dihydropyrano[4,3,2-de]quinolin-7-yl)-5-methylbenzo[d]thiazol-6-yl)-2-tert-butoxyacetate (34). To a solution of 33 (38 mg, 0.075 mmol) in freshly distilled DME (1 mL) was added 2,3-dihydropyrano[4,3,2-de]quinolin-7-ylboronic acid hydrochloride (24 mg, 0.097 mmol), chloro(2-dicyclohexylphosphino-2',6'-dimethoxy-1,1'-biphenyl)[2-(2-aminoethylphenyl)]palladium(II) methyl-t-butylether adduct, [SPhos Palladacycle] (5 mg, 0.0075 mmol), and cesium fluoride (46 mg, 0.3 mmol). The reaction mixture was heated in the microwave at 110° C. for 45 min. A saturated solution of NaHCO$_3$ (3 mL) was added, and the layers were separated. The aqueous layer was extracted with EtOAc. The combined organic layer were dried, filtered, and concentrated in vacuo. The crude material was purified by column chromatography (EtOAc/hexanes) to give 21 mg of 34. LCMS-ESI$^+$: calc'd for $C_{30}H_{33}N_3O_4S$: 532.2 (M+H$^+$); Found: 532.0 (M+H$^+$).

Example 2

Preparation of (S)-2-tert-butoxy-2-((S)-7-(2,3-dihydropyrano[4,3,2-de]quinolin-7-yl)-5-methyl-2-(pyrrolidin-1-yl)benzo[d]thiazol-6-yl)acetic acid (50) and (S)-2-tert-butoxy-2-((R)-7-(2,3-dihydropyrano [4,3,2-de]quinolin-7-yl)-5-methyl-2-(pyrrolidin-1-yl) benzo[d]thiazol-6-yl)acetic acid (51)

Compounds 50 and 51 were prepared from compound 32 according to the procedure used to prepare compound 35 (except that pyrrolidine was used instead of azetidine) in Example 10.

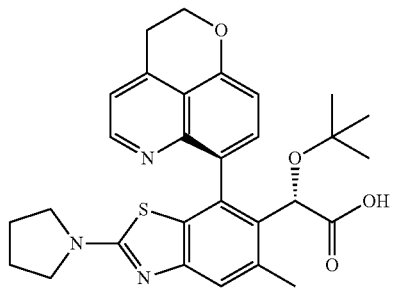

50

Compound 50: $^1$H-NMR: 400 MHz, (CD$_3$OD) δ 8.76 (d, J=5.3 Hz, 1H), 7.80 (d, J=8.1 Hz, 1H), 7.69 (d, J=5.1 Hz, 1H), 7.50 (s, 1H), 7.33 (d, J=8.0 Hz, 1H), 5.15 (s, 1H), 9.03-0.64 (m, 79H), 4.70-4.60 (m, 2H), 3.56 (dd, J=13.8, 7.7 Hz, 6H), 2.68 (s, 3H), 2.10 (t, J=6.7 Hz, 4H), 0.89 (s, 10H). LCMS-ESI$^+$ (m/z): [M+H]$^+$ calcd for $C_{29}H_{32}N_3O_4S$: 518.21 (M+H$^+$); Found: 517.99, 518.97 (M+H$^+$).

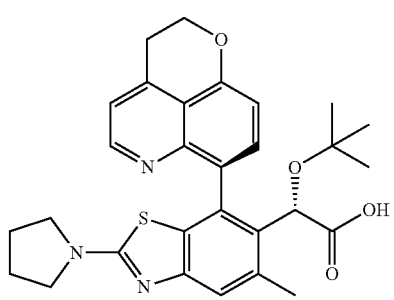

51

Compound 51: $^1$H-NMR: 400 MHz, (CD$_3$OD) δ 8.67 (d, J=4.7 Hz, 1H), 8.01 (d, J=8.1 Hz, 1H), 7.46 (d, J=4.8 Hz, 1H), 7.44 (s, 1H), 7.27 (d, J=8.1 Hz, 1H), 5.20 (s, 1H), 4.68-4.50 (m, 2H), 3.57 (s, 3H), 3.45 (t, J=5.8 Hz, 2H), 2.63 (s, 4H), 2.14 (t, J=6.3 Hz, 4H), 0.79 (s, 9H). LCMS-ESI$^+$ (m/z): [M+H]$^+$ calcd for $C_{29}H_{32}N_3O_4S$: 518.21 (M+H$^+$); Found: 518.07, 519.07 (M+H$^+$).

Example 3

Preparation of (S)-2-tert-butoxy-2-((S)-2-(3,3-difluoroazetidin-1-yl)-7-(2,3-dihydropyrano[4,3,2-de] quinolin-7-yl)-5-methylbenzo[d]thiazol-6-yl)acetic acid (52) and (S)-2-tert-butoxy-2-((R)-2-(3,3-difluoroazetidin-1-yl)-7-(2,3-dihydropyrano[4,3,2-de] quinolin-7-yl)-5-methylbenzo[d]thiazol-6-yl)acetic acid (53)

Compounds 52 and 53 were prepared from compound 32 according to the procedure used to prepare compound 35 (except that 2,2-difluoroazetidine was used instead of azetidine) in Example 10.

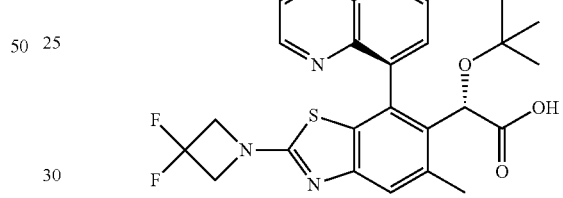

52

Compound 52: $^1$H-NMR: 400 MHz, (CD$_3$OD) δ 8.80 (d, J=5.6 Hz, 1H), 7.87 (d, J=8.2 Hz, 1H), 7.83 (d, J=5.6 Hz, 1H), 7.61 (s, 1H), 7.41 (d, J=8.2 Hz, 1H), 5.17 (s, 1H), 4.76-4.64 (m, 2H), 4.56-4.43 (m, 4H), 3.65 (t, J=5.9 Hz, 2H), 2.69 (s, 3H), 0.91 (s, 9H). $^{19}$F NMR (377 MHz, CD$_3$OD) δ −77.88 (s). LCMS-ESI$^+$ (m/z): [M+H]$^+$ calcd for $C_{28}H_{28}F_2N_3O_4S$: 540.18 (M+H$^+$); Found: 539.96, 540.96 (M+H$^+$).

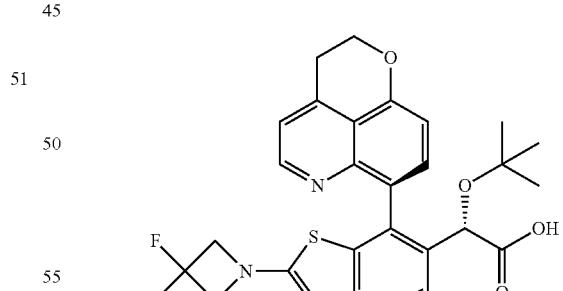

53

Compound 53: $^1$H-NMR: 400 MHz, (CD$_3$OD) δ 8.71 (d, J=5.4 Hz, 1H), 8.14 (d, J=8.2 Hz, 1H), 7.69 (d, J=5.4 Hz, 1H), 7.57 (s, 1H), 7.40 (d, J=8.2 Hz, 1H), 5.21 (s, 1H), 4.72-4.60 (m, 2H), 4.56-4.42 (m, 4H), 3.58 (t, J=6.0 Hz, 2H), 2.65 (s, 3H), 0.91 (s, 9H). LCMS-ESI$^+$ (m/z): [M+H]$^+$ calcd for $C_{28}H_{28}F_2N_3O_4S$: 540.18 (M+H$^+$); Found: 539.98, 541.02 (M+H$^+$).

Example 4

Preparation of (S)-2-tert-butoxy-2-((S)-7-(2,3-dihydropyrano[4,3,2-de]quinolin-7-yl)-2-(3-methoxyazetidin-1-yl)-5-methylbenzo[d]thiazol-6-yl)acetic acid (54) and (S)-2-tert-butoxy-2-((R)-7-(2,3-dihydropyrano[4,3,2-de]quinolin-7-yl)-2-(3-methoxyazetidin-1-yl)-5-methylbenzo[d]thiazol-6-yl)acetic acid (55)

Compounds 54 and 55 were prepared from compound 32 according to the procedure used to prepare compound 35 (except that 2-methoxyazetidine was used instead of azetidine) in Example 10.

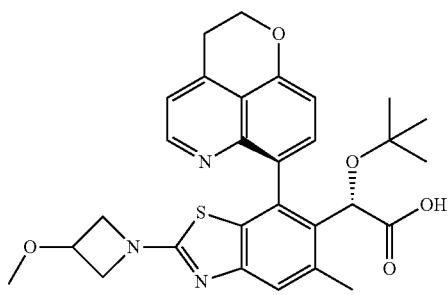

54

Compound 54: $^1$H-NMR: 400 MHz, (CD$_3$OD) δ: 8.78 (d, J=5.5 Hz, 1H), 7.84 (d, J=8.5 Hz, 1H), 7.77 (d, J=6.1 Hz, 1H), 7.52 (s, 1H), 7.37 (d, J=7.8 Hz, 1H), 5.16 (s, 1H), 4.73-4.64 (m, 2H), 4.41 (ddd, J=9.9, 6.2, 3.4 Hz, 1H), 4.31 (td, J=7.7, 1.0 Hz, 2H), 4.02-3.90 (m, 2H), 3.62 (t, J=5.7 Hz, 2H), 2.68 (s, 4H), 0.91 (s, 11H). LCMS-ESI$^+$ (m/z): [M+H]$^+$ calcd for C$_{29}$H$_{32}$N$_3$O$_5$S: 534.21 (M+H$^+$); Found: 533.95, 534.97 (M+H$^+$).

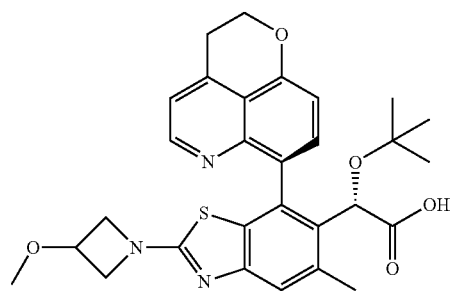

55

Compound 55: $^1$H-NMR: 400 MHz, (CD$_3$OD) δ: 8.67 (d, J=5.1 Hz, 1H), 8.04 (d, J=8.2 Hz, 1H), 7.52 (d, J=4.7 Hz, 1H), 7.43 (s, 1H), 7.30 (d, J=8.1 Hz, 1H), 5.19 (s, 1H), 4.66-4.56 (m, 2H), 4.42 (m, 1H), 4.38-4.32 (m, 2H), 4.08-4.01 (m, 2H), 3.49 (t, J=6.0 Hz, 3H), 2.61 (s, 3H), 0.82 (s, 10H). LCMS-ESI$^+$ (m/z): [M+H]$^+$ calcd for C$_{29}$H$_{32}$N$_3$O$_5$S: 534.21 (M+H$^+$); Found: 534.03, 535.08 (M+H$^+$).

Example 5

Preparation of (S)-2-tert-butoxy-2-((S)-7-(2,3-dihydropyrano[4,3,2-de]quinolin-7-yl)-2-(3-fluoroazetidin-1-yl)-5-methylbenzo[d]thiazol-6-yl)acetic acid (56)

Compound 56 was prepared from compound 32 according to the procedure used to prepare compound 35 (except that 2-fluoroazetidine was used instead of azetidine) in Example 10.

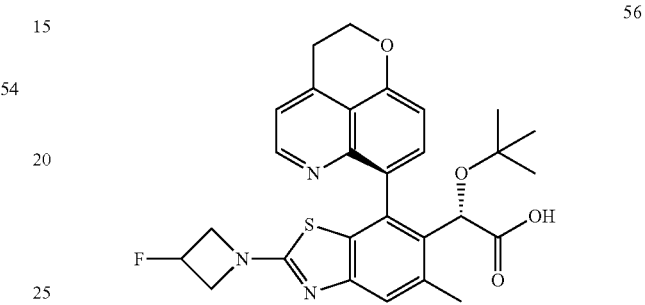

56

Compound 56: $^1$H-NMR: 400 MHz, (CD$_3$OD) δ 8.79 (d, J=5.5 Hz, 1H), 7.85 (d, J=8.1 Hz, 1H), 7.79 (d, J=5.1 Hz, 1H), 7.55 (s, 1H), 7.39 (d, J=7.9 Hz, 1H), 5.58-5.38 (m, 1H), 5.16 (s, 1H), 4.70 (td, J=5.9, 3.1 Hz, 2H), 4.49-4.35 (m, 2H), 4.28-4.12 (m, 2H), 3.63 (t, J=6.0 Hz, 2H), 2.68 (s, 3H), 0.91 (s, 9H). LCMS-ESI$^+$ (m/z): [M+H]$^+$ calcd for C$_{28}$H$_{29}$FN$_3$O$_4$S: 522.19 (M+H$^+$); Found: 521.97, 523.02 (M+H$^+$).

Example 6

Preparation of (S)-2-tert-butoxy-2-((S)-7-(2,3-dihydropyrano[4,3,2-de]quinolin-7-yl)-5-methyl-2-(3-methylazetidin-1-yl)benzo[d]thiazol-6-yl)acetic acid (57)

Compound 57 was prepared from compound 32 according to the procedure used to prepare compound 35 (except that 2-methylazetidine was used instead of azetidine) in Example 10.

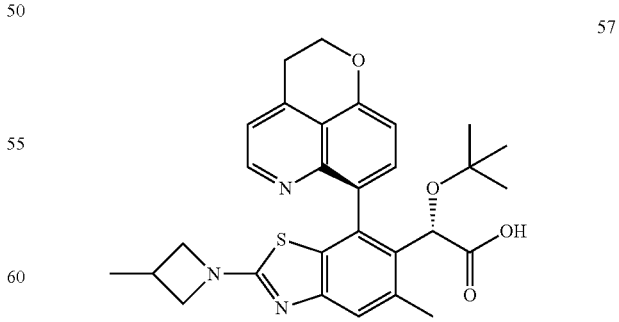

57

Compound 57: $^1$H-NMR: 400 MHz, (CD$_3$OD) δ: δ 8.92 (s, 1H), 7.90 (d, J=7.6 Hz, 2H), 7.56 (s, 1H), 7.44 (d, J=7.3 Hz, 1H), 5.18 (s, 1H), 4.73 (s, 2H), 4.48 (s, 2H), 3.99 (s, 2H), 3.68 (s, 2H), 3.12 (m, 1H), 2.73 (s, 3H), 1.35 (d, J=5.6 Hz, 3H), 0.91 (s, 9H). LCMS-ESI⁺ (m/z): [M+H]⁺ calcd for C$_{29}$H$_{32}$N$_3$O$_4$S: 518.21 (M+H⁺); Found: 518.09, 519.12 (M+H⁺).

Example 7

Preparation of (S)-2-tert-butoxy-2-((S)-7-(2,3-dihydropyrano[4,3,2-de]quinolin-7-yl)-5-methyl-2-(3-(methylsulfonyl)azetidin-1-yl)benzo[d]thiazol-6-yl)acetic acid (58)

Compound 58 was prepared from compound 32 according to the procedure used to prepare compound 35 (except that 2-methylsulfonylazetidine was used instead of azetidine) in Example 10.

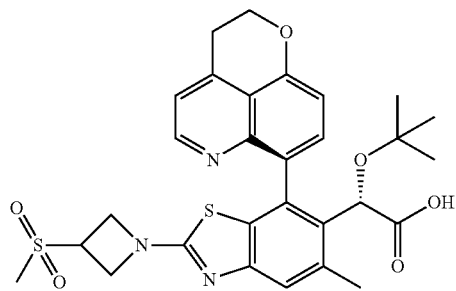

58

Compound 58: ¹H-NMR: 400 MHz, (CD$_3$OD) δ: ¹H NMR (400 MHz, cd$_3$od) δ 8.85 (d, J=5.3 Hz, 1H), 7.89 (t, J=6.7 Hz, 2H), 7.61 (s, 1H), 7.44 (d, J=8.1 Hz, 1H), 5.18 (s, 1H), 4.72 (dd, J=9.0, 6.2 Hz, 2H), 4.59-4.35 (m, 5H), 3.01 (s, 3H), 2.72 (s, 3H), 0.92 (s, 9H). LCMS-ESI⁺ (m/z): [M+H]⁺ calcd for C$_{29}$H$_{32}$N$_3$O$_6$S: 582.17 (M+H⁺); Found: 581.95, 583.02 (M+H⁺).

Example 8

Preparation of (S)-2-((S)-2-(azetidin-1-yl)-7-(2,3-dihydropyrano[4,3,2-de]quinolin-7-yl)-4-fluoro-5-methylbenzo[d]thiazol-6-yl)-2-tert-butoxyacetic acid (76)

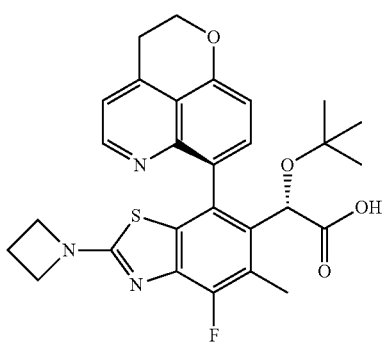

76

Compound 76: ¹H-NMR: 400 MHz, (CD$_3$OD) δ: 8.65 (d, J=4.4 Hz, 1H); 7.70 (d, J=7.6 Hz, 1H); 7.39 (d, J=4.4 Hz, 1H); 7.16 (d, J=7.6 Hz, 1H); 5.04 (s, 1H); 4.57 (t, J=6.0 Hz, 2H); 4.15-4.10 (m, 4H); 3.41 (t, J=6.0 Hz, 2H); 2.50-2.46 (m, 6H); 0.90 (s, 9H). LCMS-ESI⁺ (m/z): [M+H]⁺ calcd for C$_{28}$H$_{29}$FN$_3$O$_4$S: 522.19 (M+H⁺); Found: 521.99, 523.00 (M+H⁺).

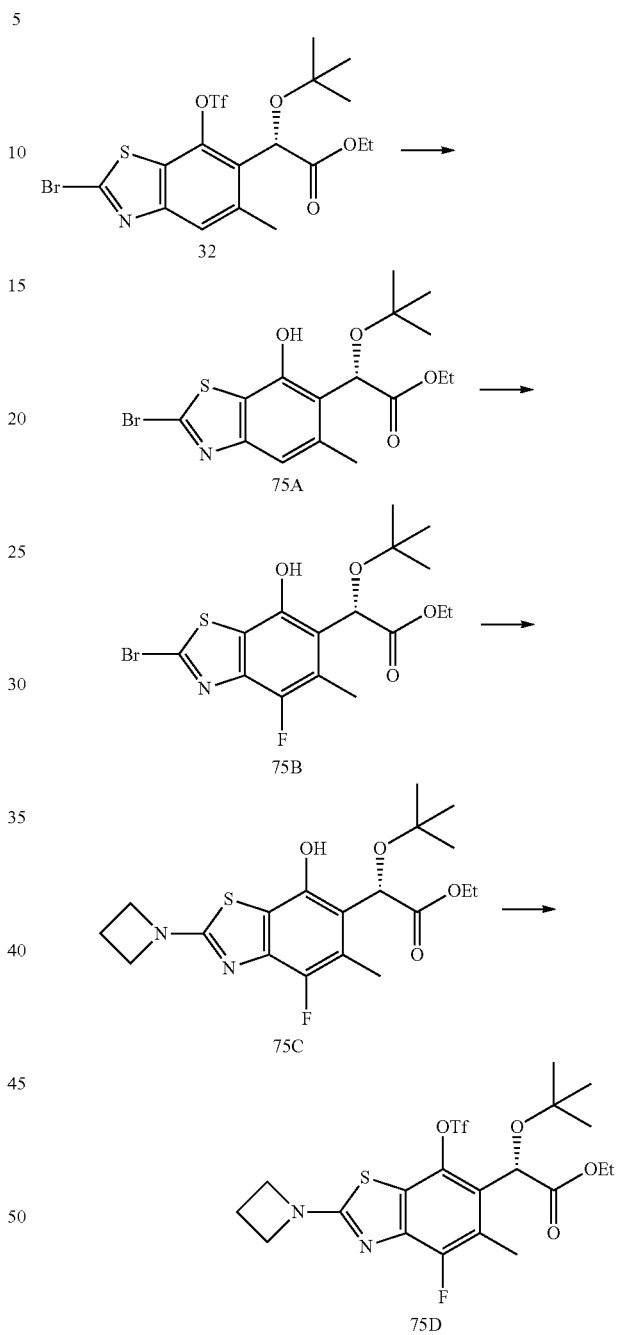

Step 1.

Preparation of (S)-ethyl 2-(2-bromo-7-hydroxy-5-methyl-benzo[d]thiazol-6-yl)-2-tert-butoxyacetate (75A): To a solution of (S)-ethyl 2-(2-bromo-5-methyl-7-(trifluoromethylsulfonyloxy)benzo[d]thiazol-6-yl)-2-tert-butoxyacetate (32): (500 mg, 0.938 mmol) in THF (5 ml) was added TBAF (1.0 M in THF, 4 ml) slowly. The reaction mixture was stirred at rt for 1 h. The reaction mixture was washed by a mixture of H$_2$O (20 ml) and HOAc (200 ul), extracted by EtOAc, the organic phase was washed by sat. NaHCO$_3$, dried over MgSO$_4$, filtered, concentrated down and purified by silica gel column, eluting by 0-40% EtOAc in hexanes to give 75A (380 mg). LCMS-ESI⁺: calc'd for $C_{16}H_{20}BrNO_4S$: 402.0 (M+H⁺); Found: 401.9 (M+H⁺).

Step 2.

Preparation of (S)-ethyl 2-(2-bromo-4-fluoro-7-hydroxy-5-methylbenzo[d]thiazol-6-yl)-2-tert-butoxyacetate (75B): The reaction mixture of (S)-ethyl 2-(2-bromo-7-hydroxy-5-methylbenzo[d]thiazol-6-yl)-2-tert-butoxyacetate (75A) (380 mg, 0.948 mmol), Selectfluor (1.9 g, 4.74 mmol) in acetonitrile (7 ml) was reacted at 0° C. for 5 days. The reaction mixture was washed by 1.5 M $KH_2PO_4$, extracted by EtOAc, the organic phase was dried over $MgSO_4$, filtered, concentrated down and purified by silica gel column, eluting by 0-40% EtOAc in hexanes to give 75B (137 mg, 35%). LCMS-ESI⁺: calc'd for $C_{16}H_{19}FNO_4S$: 420.0 (M+H⁺); Found: 420.1 (M+H⁺).

Step 3.

Preparation of (S)-ethyl 2-(2-(azetidin-1-yl)-4-fluoro-7-hydroxy-5-methylbenzo[d]thiazol-6-yl)-2-tert-butoxyacetate (75C): Prepared by the similar method to make (S)-ethyl 2-(2-(azetidin-1-yl)-5-methyl-7-(trifluoromethylsulfonyloxy)benzo[d]thiazol-6-yl)-2-tert-butoxyacetate (33) in Example 10. LCMS-ESI⁺: calc'd for $C_{19}H_{25}FN_2O_4S$: 397.2 (M+H⁺); Found: 397.0 (M+H⁺).

Step 4.

Preparation of (S)-ethyl 2-(2-(azetidin-1-yl)-4-fluoro-5-methyl-7-(trifluoromethylsulfonyloxy)benzo[d]thiazol-6-yl)-2-tert-butoxyacetate (75D): The reaction mixture of S)-ethyl 2-(2-(azetidin-1-yl)-4-fluoro-7-hydroxy-5-methylbenzo[d]thiazol-6-yl)-2-tert-butoxyacetate (75C) (50 mg, 0.126 mmol), N-phenyl triflate (90 mg, 0.252 mmol), $Cs_2CO_3$ (82 mg, 0.126 mmol) in THF (2 ml) was stirred at rt. After the reaction finished, the reaction was washed by sat $NaHCO_3$, extracted by EtOAc, the organic phase was dried over $MgSO_4$, filtered, concentrated down and purified by silica gel column, eluting by 0-40% EtOAc in hexanes to give 75D (50 mg, 75%). LCMS-ESI⁺: calc'd for $C_{20}H_{24}F_4N_2O_6S_2$: 529.1 (M+H⁺); Found: 529.0 (M+H⁺).

The remainder of the synthesis of compound 76 is analogous to the preparation of compound 35 from compound 33 in example 10.

Example 9

Preparation of (S)-2-((S)-2-(azetidin-1-yl)-7-(2,3-dihydropyrano[4,3,2-de]quinolin-7-yl)-5-methyl-benzo[d]thiazol-6-yl)-2-(tert-pentyloxy)acetic acid (89)

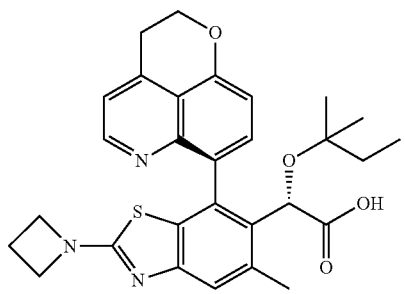

Compound 89: ¹H NMR (400 MHz, $CD_3OD$) δ 8.75 (d, J=5.1 Hz, 1H), 7.82 (d, J=8.3 Hz, 1H), 7.71 (d, J=5.6 Hz, 1H), 7.47 (s, 1H), 7.35 (d, J=8.1 Hz, 1H), 5.09 (d, J=0.6 Hz, 1H), 4.69-4.62 (m, 2H), 4.17 (t, J=7.7 Hz, 4H), 3.61-3.55 (m, 2H), 2.66 (s, 3H), 2.58-2.42 (m, 2H), 0.87 (d, J=2.9 Hz, 6H), 0.59 (t, J=7.0 Hz, 3H). ¹⁹F NMR (377 MHz, $CD_3OD$) δ −77.77. LCMS: calc'd=518.64, observed: 518.08

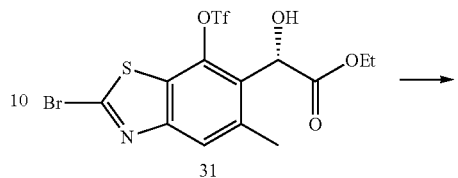

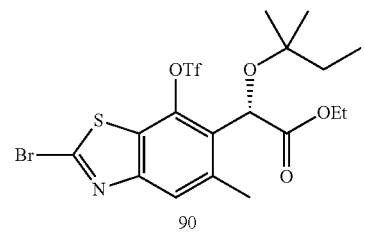

Preparation of 90: A slurry of 31 (740 mg, 1.55 mmol) in tert-amyl acetate (7.0 mL) was treated with 70% aq. $HClO_4$ (5 µL) was added at 23° C. Reaction became cloudy, but LCMS analysis indicated minimal conversion. More 70% aq. $HClO_4$ (50 µL) was introduced. After 2 h, the reaction was added dropwise over 5 min to sat. aq. $NaHCO_3$ (20 mL). $H_2O$ (10 mL) was added, and the system was extracted with DCM (3×20 mL). Combined organic layers were dried ($Na_2SO_4$), filtered, concentrated, and treated with hexane (10 mL). The system was concentrated again to remove some residual t-amyl alcohol. The residue was treated with PhH and loaded onto a 12 gram "gold" ISCO silica gel column. Chromatography (eluent: Hexanes/Ethyl Acetate) gave 90 (134 mg, 16% yield) along with some recovered 31.

¹H-NMR: 400 MHz, ($CDCl_3$) δ: 7.80 (s, 1H), 5.49 (s, 1H), 4.24-4.06 (m, 2H), 2.57 (s, 3H), 1.60-1.40 (m, 2H), 1.17 (s, 3H), 1.16 (t, J=7.0 Hz, 3H), 1.05 (s, 3H), 0.80 (t, J=7.0 Hz, 3H). ¹⁹F-NMR: 376 MHz, ($CDCl_3$) δ: −73.8

The remainder of the synthesis of 89 follows the same route as Example 10 from compound 32.

Example 10

Preparation of (S)-2-(2-amino-7-bromo-5-methyl-benzo[d]thiazol-6-yl)-2-tert-butoxyethyl pivalate (100)

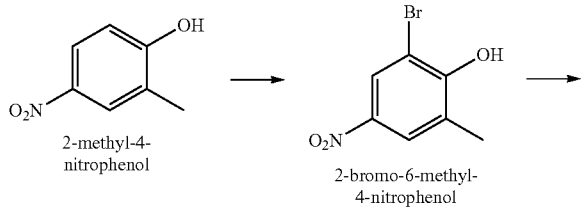

2-methyl-4-nitrophenol 2-bromo-6-methyl-4-nitrophenol

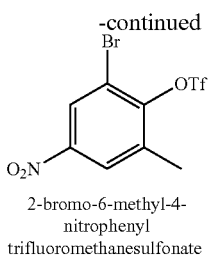

2-bromo-6-methyl-4-
nitrophenyl
trifluoromethanesulfonate

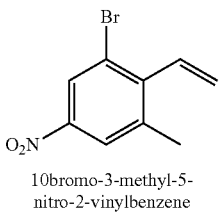

1Obromo-3-methyl-5-
nitro-2-vinylbenzene

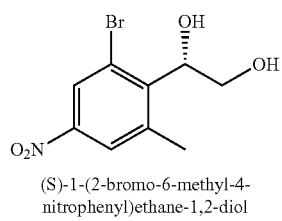

(S)-1-(2-bromo-6-methyl-4-
nitrophenyl)ethane-1,2-diol

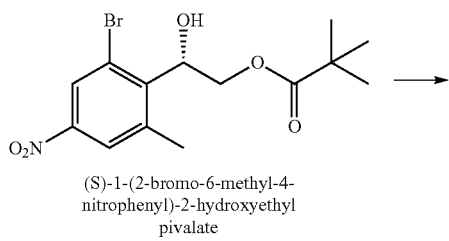

(S)-1-(2-bromo-6-methyl-4-
nitrophenyl)-2-hydroxyethyl
pivalate

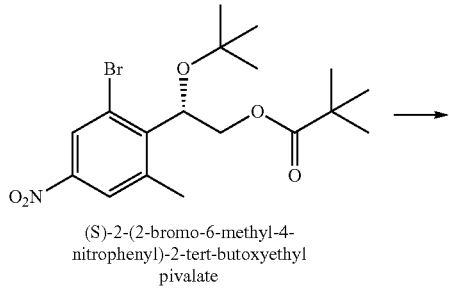

(S)-2-(2-bromo-6-methyl-4-
nitrophenyl)-2-tert-butoxyethyl
pivalate

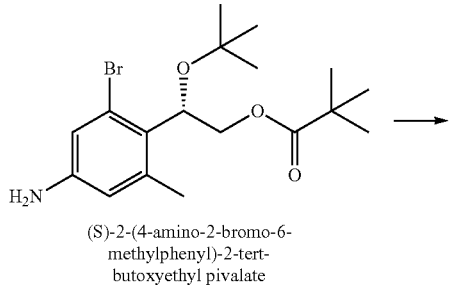

(S)-2-(4-amino-2-bromo-6-
methylphenyl)-2-tert-
butoxyethyl pivalate

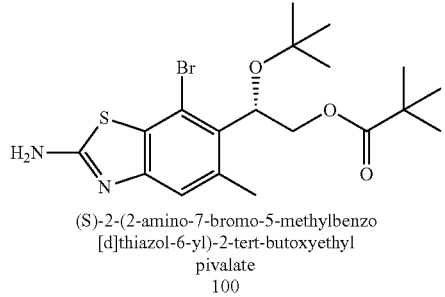 [SMILES: Cc1cc2nc(N)sc2c(Br)c1[C@@H](COC(=O)C(C)(C)C)OC(C)(C)C]

(S)-2-(2-amino-7-bromo-5-methylbenzo
[d]thiazol-6-yl)-2-tert-butoxyethyl
pivalate
100

Preparation of 2-bromo-6-methyl-4-nitrophenol: $Br_2$ (122.2 g, 0.765 mol) was added into a solution of 2-methyl-4-nitrophenol (90.0 g, 0.588 mol) in HOAc (1.17 L) at room temperature. The resulting solution was stirred at room temperature for 4 h. TLC showed the reaction was complete. The solution was added into ice-water (3 L) slowly and filtered. The filter cake was dissolved into EA (2.5 L) and washed with saturated $NaHSO_3$ (3×500 mL). The EtOAc layer was dried over anhydrous $Na_2SO_4$, filtered and concentrated in vacuo to afford 2-bromo-6-methyl-4-nitrophenol (110 g, 80%) as yellow solid. $^1$H-NMR: 400 MHz, $(CDCl_3)$ δ: 8.30 (d, J=2.0 Hz, 1H), 8.05 (s, 1H), 6.22 (s, broad, 1H), 2.41 (s, 3H).

Preparation of 2-Bromo-6-methyl-4-nitrophenyl trifluoromethanesulfonate: To a solution of 2-bromo-6-methyl-4-nitrophenol (110.0 g, 0.474 mol) in DCM (950 mL) at −70° C. was added $Et_3N$ (62.3 g, 0.616 mol) and $Tf_2O$ (147.1 g, 0.521 mol). The resulting solution was stirred at −70° C. for 20 min. TLC showed the reaction was complete. Aqueous HCl (0.5 M, 1 L) was added to quench the reaction. The DCM layers were separated, dried over anhydrous $Na_2SO_4$, filtered, concentrated in vacuo and purified by silica gel column (Petroleum Ether→Petroleum Ether:EtOAc (20:1)) to afford desired 2-Bromo-6-methyl-4-nitrophenyl trifluoromethanesulfonate (146.7 g, 85%) as yellow solid. $^1$H-NMR: 400 MHz, $(CDCl_3)$ δ: 8.41 (d, J=2.0 Hz, 1H), 8.16 (d, J=2.8 Hz, 1H), 2.59 (s, 3H).

Preparation of 1-Bromo-3-methyl-5-nitro-2-vinylbenzene: The reaction mixture of 2-Bromo-6-methyl-4-nitrophenyl trifluoromethanesulfonate (10.0 g, 27.5 mmol), vinyl-tri-n-butyltin (8.7 g, 27.5 mmol), LiCl (1.4 g, 33.0 mmol), $Pd(dppf)Cl_2$ (673 mg, 0.92 mmol) and DMF (50 mL) was stirred at 70° C. for 3 h under $N_2$. Then 2 N aq. NaOH (30 mL) was added and stirred at 70° C. for 10 min. The reaction mixture was cooled down, washed with saturated aqueous $NaHCO_3$ (100 mL), and extracted with EtOAc (3×50 mL). The combined organic layer was dried over anhydrous $Na_2SO_4$, filtered, concentrated in vacuo, and purified by silica gel column (Petroleum Ether→Petroleum Ether:EtOAc (50:1)) to afford 1-Bromo-3-methyl-5-nitro-2-vinylbenzene (2.01 g, 30%) as yellow oil. $^1$H-NMR: 400 MHz, $(CDCl_3)$ δ: 8.29 (d, J=2.0 Hz, 1H), 8.02 (s, 1H), 6.67 (dd, J=17.6, 11.6 Hz, 1H), δ 5.75 (d, J=11.6 Hz, 1H), δ 5.49 (d, J=18.0 Hz, 1H), δ 2.48 (s, 3H).

Preparation of (S)-1-(2-Bromo-6-methyl-4-nitrophenyl) ethane-1,2-diol: The reaction mixture of 1-Bromo-3-methyl-5-nitro-2-vinylbenzene (30.0 g, 0.124 mol), AD-mix α (173.5 g: 0.104 g of $K_2OsO_4.2H_2O$; 1.389 g of $(DHQ)_2PHAL$; 51.038 g of $K_2CO_3$ and 120.99 g of $K_4Fe(CN)_6$), $MeSO_2NH_2$ (11.8 g, 0.124 mol) in t-BuOH (250 mL) and $H_2O$ (250 mL) was stirred at 0° C. for 3 days. $Na_2SO_3$ (15 g) was added and stirred at room temperature for 40 min to quench the reaction. The reaction mixture was treated with water (1 L) and the resulting mixture was extracted with EtOAc (3×200 mL). The combined organic layers were dried over anhydrous Na$_2$SO$_4$, filtered, concentrated in vacuo, and purified by silica gel column (Petroleum Ether:EtOAc (2:1), isocratic) to afford (S)-1-(2-Bromo-6-methyl-4-nitrophenyl)ethane-1,2-diol (17 g, 50%) as yellow solid. $^1$H-NMR: 400 MHz, (CDCl$_3$) δ: 8.26 (s, 1H), 7.99 (s, 1H), 5.56-5.54 (m, 1H), 3.94-3.92 (m, 1H), 3.81-3.78 (m, 1H), 2.82 (d, broad, 1H), 2.67 (s, 3H), 2.18-2.15 (m, 1H).

Preparation of (S)-2-(2-Bromo-6-methyl-4-nitrophenyl)-2-hydroxyethyl pivalate: To a suspension of (S)-1-(2-Bromo-6-methyl-4-nitrophenyl)ethane-1,2-diol (17.0 g, 61.6 mmol) in DCM (435 mL) at 0° C. was added pyridine (18.6 g, 235.4 mmol) and PivCl (13.4 g, 110.8 mmol) slowly. After stirring at 0° C. for 5 min, the system was raised to room temperature and stirred at this temperature for 5 h. TLC showed the reaction was complete. The reaction mixture was treated with saturated aqueous NaHCO$_3$ (500 mL), and the resulting system was extracted with DCM (2×200 mL). The combined organic layer was dried over anhydrous Na$_2$SO$_4$, filtered, concentrated in vacuum, and purified by silica gel column (Petroleum Ether:EtOAc (30:1)) to afford (S)-2-(2-Bromo-6-methyl-4-nitrophenyl)-2-hydroxyethyl pivalate (17 g, 77%) as yellow solid. $^1$H-NMR: 400 MHz, (CDCl$_3$) δ: 8.28 (s, 1H), 8.00 (d, J=2.0 Hz, 1H), 5.70-5.66 (m, 1H), 4.58-4.53 (m, 1H), 4.31-4.26 (m, 1H), 2.84 (d, J=5.6 Hz), 2.68 (s, 3H), 1.22 (s, 9H).

Preparation of (S)-2-(2-Bromo-6-methyl-4-nitrophenyl)-2-tert-butoxyethyl pivalate: To a solution of (S)-2-(2-Bromo-6-methyl-4-nitrophenyl)-2-hydroxyethyl pivalate (13 g, 0.036 mol) in t-BuOAc (300 mL) at 0° C. was added HClO$_4$ (20.7 g, 0.144 mol) slowly. The solution was stirred at 0° C. for 5 min, then warmed to room temperature and stirred at this temperature for 1.5 h. The solution was alkalized by saturated aqueous NaHCO$_3$ until the pH of solution >8. The mixture was extracted with EtOAc (3×1 L). The combined organic layers were dried over anhydrous Na$_2$SO$_4$, filtered, concentrated in vacuo, and purified by silica gel column (Petroleum Ether:EtOAc (50:1)) to afford (S)-2-(2-Bromo-6-methyl-4-nitrophenyl)-2-tert-butoxyethyl pivalate (9.3 g, 62%) as yellow solid. $^1$H-NMR: 400 MHz, (CDCl$_3$) δ: 8.26 (s, 1H), 7.98 (s, 1H), 5.60-5.57 (m, 1H), 4.32-4.27 (m, 1H), 4.18-4.14 (m, 1H), 2.73 (s, 3H), 1.17 (s, 9H), 1.14 (s, 9H).

Preparation of (S)-2-(4-amino-2-bromo-6-methylphenyl)-2-tert-butoxyethyl pivalate: To a solution of (S)-2-(2-Bromo-6-methyl-4-nitrophenyl)-2-tert-butoxyethyl pivalate (9 g, 0.022 mol) in EtOH (50 mL) and EtOAc (50 mL) was added Pt/C (1.4 g), and the reaction was fitted with a balloon of H$_2$. The reaction mixture was stirred at room temperature for 3 h. TLC showed the reaction was complete. The reaction mixture was filtered over Celite. The filtrate was concentrated in vacuo to give (S)-2-(4-amino-2-bromo-6-methylphenyl)-2-tert-butoxyethyl pivalate (7 g, 82%) as brown oil, which was immediately used for next step without further purification. $^1$H-NMR: 400 MHz, (CDCl$_3$) δ: 6.70 (s, 1H), 6.40 (s, 1H), 5.38 (app. s, broad, 1H), 4.22 (app. s, broad, 1H), 4.05 (app. s, broad, 1H), 3.60 (app. s, broad, 2H), 2.47 (s, 3H), 1.17 (s, 9H), 1.13 (s, 9H).

Preparation of (S)-2-(2-amino-7-bromo-5-methylbenzo[d]thiazol-6-yl)-2-tert-butoxyethyl pivalate: To a solution of freshly prepared (S)-2-(4-amino-2-bromo-6-methylphenyl)-2-tert-butoxyethyl pivalate (7 g, 18.1 mmol) in HOAc (90 mL) was added KSCN (1.76 g, 18.1 mmol) at r.t. The reaction mixture was stirred at r.t. for 0.5 h. Pyridinium perbromide (5.79 g, 18.1 mmol) was added slowly over a period of 10 min, and stirred at r.t for 2 h. The mixture was alkalized to pH=8 using saturated aqueous NaHCO$_3$ solution, then extracted with EtOAc (3×600 mL). The combined organic layers were dried over anhydrous Na$_2$SO$_4$, filtered, concentrated in vacuo, and purified by silica gel column (Petroleum Ether:EtOAc (10:1→5:1)) to afford (S)-2-(2-amino-7-bromo-5-methylbenzo[d]thiazol-6-yl)-2-tert-butoxyethyl pivalate (2.74 g, 34.3%) as yellow solid. LCMS-ESI$^+$: calc'd for C$_{19}$H$_{27}$BrN$_2$O$_3$S: 443.1 and 445.1 (M+H$^+$); found: 443.1 and 445.1 (M+H$^+$). $^1$H-NMR: 400 MHz, (CD$_3$OD) δ: 7.15 (s, 1H), 5.53-5.49 (m, 1H), 4.31-4.26 (m, 1H), 4.17-4.13 (m, 1H), 2.64 (s, 3H), 1.15 (s, 9H), 1.11 (s, 9H).

Example 11

Preparation of (S)-2-(2-bromo-7-(4-chlorophenyl)-5-methylbenzo[d]thiazol-6-yl)-2-tert-butoxyethyl pivalate (101)

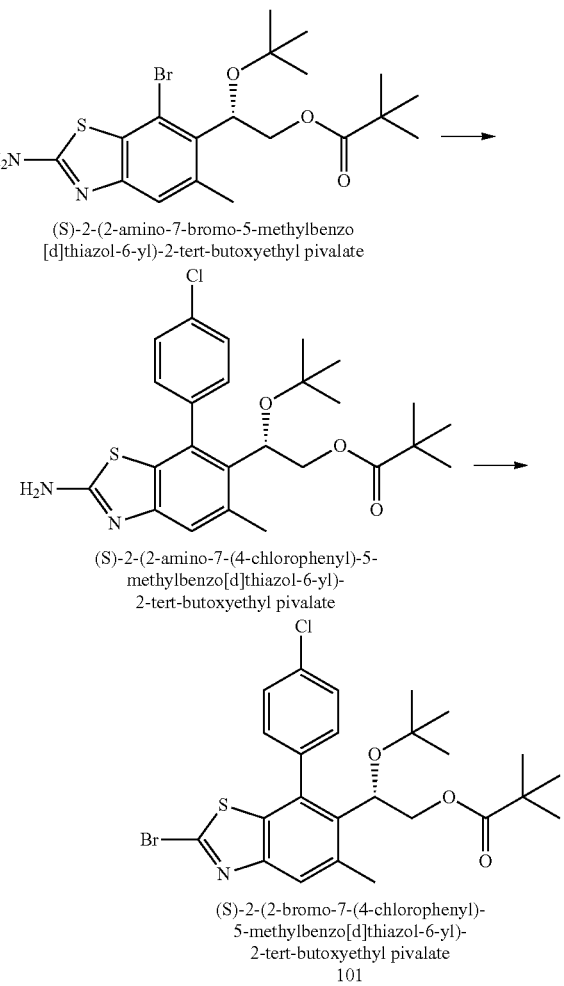

Preparation of (S)-2-(2-Amino-7-(4-chlorophenyl)-5-methylbenzo[d]thiazol-6-yl)-2-tert-butoxyethyl pivalate: 2 separate microwave tubes were each charged with (S)-2-(2-Amino-7-bromo-5-methylbenzo[d]thiazol-6-yl)-2-tert-butoxyethyl pivalate (768 mg, 1.74 mmol), K$_2$CO$_3$ (960 mg, 6.96 mmol), 4-chlorophenylboronic acid (325 mg, 2.09 mmol), Pd(PPh$_3$)$_4$ (200 mg, 0.174 mmol), dioxane (8.0 mL), and H$_2$O (2.0 mL). The two sealed vessels were separately heated at 110° C. for 3 h. The reactions were cooled to 23° C. and combined. H$_2$O (50 mL) was added, and the system was extracted with EtOAc (3×50 mL). The combined extracts were dried (Na$_2$SO$_4$), filtered, and concentrated. The residue was treated with benzene and purified via chromatography on silica gel (80 g "gold" ISCO column; Hex/EtOAc) giving (S)-2-(2-Amino-7-(4-chlorophenyl)-5-methylbenzo[d]thiazol-6-yl)-2-tert-butoxyethyl pivalate (1.55 g, 90% yield). LCMS-ESI$^+$: calc'd for C$_{25}$H$_{31}$ClN$_2$O$_3$S: 475.2 and 477.2 (M+H$^+$); found: 475.3 and 477.3 (M+H$^+$). $^1$H-NMR: 400 MHz, (CDCl$_3$) δ: 7.49-7.41 (m, 2H), 7.36-7.32 (m, 2H), 7.22 (d, J=7.3 Hz, 1H), 5.19 (s, broad, 2H), 4.67 (dd, J=9.0, 2.7 Hz, 1H), 4.36 (dd, J=11.7, 9.0 Hz, 1H), 4.23 (dd, J=11.7, 2.7 Hz, 1H), 2.68 (s, 3H), 1.14 (s, 9H), 0.94 (s, 9H).

Preparation of (S)-2-(2-bromo-7-(4-chlorophenyl)-5-methylbenzo[d]thiazol-6-yl)-2-tert-butoxyethyl pivalate: At 23° C., in a water bath, a solution of (S)-2-(2-amino-7-(4-chlorophenyl)-5-methylbenzo[d]thiazol-6-yl)-2-tert-butoxyethyl pivalate (1.13 g, 2.37 mmol) in CH$_3$CN (22 mL) was treated with solid anhydrous CuBr$_2$ (635 mg, 2.84 mmol). Reaction was fitted with a mineral oil bubbler. A freshly prepared solution of t-butyl nitrite (269 mg, 2.61 mmol) in CH$_3$CN (2.0 mL) was added dropwise over a 5 min period. The water bath was removed. Gas evolution was monitored using the bubbler. At 1 h, gas evolution ceased. The reaction was poured into EtOAc (50 mL) and treated with H$_2$O (50 mL). A brown solid precipitated. The suspension was filtered over Celite, which was thoroughly washed with EtOAc. The filtrate was transferred to a separatory funnel. The organic phase was collected. The aq. phase was extracted with EtOAc. The total organic layers were combined, dried (Na$_2$SO$_4$), filtered, and concentrated. The residue was treated with benzene and purified via chromatography on silica gel (80 g "gold" ISCO column; Hex/EtOAc) giving (S)-2-(2-bromo-7-(4-chlorophenyl)-5-methylbenzo[d]thiazol-6-yl)-2-tert-butoxyethyl pivalate (675 mg, 53% yield). LCMS-ESI$^+$: calc'd for C$_{25}$H$_{29}$BrClNO$_3$S: 538.1, 540.1, and 542.1.1 (M+H$^+$); found: 538.2, 540.2, and 542.2 (M+H$^+$). $^1$H-NMR: 400 MHz, (CDCl$_3$) δ: 7.76 (s, 1H), 7.51 (d, J=8.2 Hz, 1H), 7.47 (d, J=7.8 Hz, 1H), 7.34 (d, J=8.2 Hz, 1H), 7.24 (d, J=7.8 Hz, 1H), 4.76 (dd, J=9.0, 3.5 Hz, 1H), 4.39 (dd, J=11.7, 9.0 Hz, 1H), 4.25 (dd, J=11.7, 3.5 Hz, 1H), 2.76 (s, 3H), 1.14 (s, 9H), 0.94 (s, 9H).

Example 12

Preparation of (S)-methyl 2-(2-amino-7-(4-chlorophenyl)-5-methylbenzo[d]thiazol-6-yl)-2-tert-butoxyacetate (102)

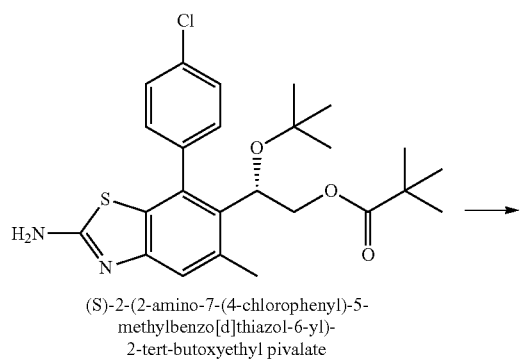

(S)-2-(2-amino-7-(4-chlorophenyl)-5-methylbenzo[d]thiazol-6-yl)-2-tert-butoxyethyl pivalate

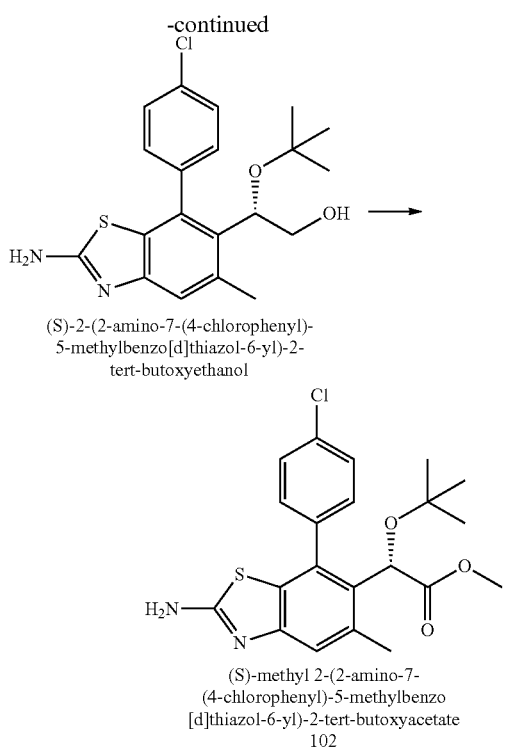

(S)-2-(2-amino-7-(4-chlorophenyl)-5-methylbenzo[d]thiazol-6-yl)-2-tert-butoxyethanol (S)-methyl 2-(2-amino-7-(4-chlorophenyl)-5-methylbenzo[d]thiazol-6-yl)-2-tert-butoxyacetate 102

Preparation of (S)-2-(2-amino-7-(4-chlorophenyl)-5-methylbenzo[d]thiazol-6-yl)-2-tert-butoxyethanol: A flask was charged with (S)-2-(2-Amino-7-(4-chlorophenyl)-5-methylbenzo[d]thiazol-6-yl)-2-tert-butoxyethyl pivalate (2.15 g, 4.52 mmol), LiOH monohydrate (2.00 g, 47.4 mmol), H$_2$O (4 mL), EtOH (absolute, 4.0 mL), and THF (8.0 mL). The reaction was placed under N$_2$ and heated to 100° C. After 2 h, the reaction was cooled to 23° C., diluted with H$_2$O, and extracted with EtOAc several times. The combined organic phases were dried (Na$_2$SO$_4$), filtered, and concentrated. The residue was treated with benzene and purified via chromatography on silica gel (80 g "gold" ISCO column; Hex/EtOAc) giving (S)-2-(2-amino-7-(4-chlorophenyl)-5-methylbenzo[d]thiazol-6-yl)-2-tert-butoxyethanol (1.10 g, 62% yield). LCMS-ESI$^+$: calc'd for C$_{20}$H$_{23}$ClN$_2$O$_2$S: 391.1 and 393.1 (M+H$^+$); found: 391.2 and 393.2 (M+H$^+$). $^1$H-NMR: 400 MHz, (CDCl$_3$) δ: 7.49-7.41 (m, 2H), 7.36-7.32 (m, 2H), 7.20 (d, J=7.3 Hz, 1H), 5.39 (s, broad, 2H), 4.52-4.50 (m, 1H), 3.85-3.70 (m, 2H), 2.63 (s, 3H), 0.99 (s, 9H).

Preparation of (S)-methyl 2-(2-amino-7-(4-chlorophenyl)-5-methylbenzo[d]thiazol-6-yl)-2-tert-butoxyacetate: A solution of (S)-2-(2-amino-7-(4-chlorophenyl)-5-methylbenzo[d]thiazol-6-yl)-2-tert-butoxyethanol (1.10 g, 2.81 mmol) in CH$_3$CN (40 mL) and H$_2$O (10 mL) was treated with H$_5$IO$_6$ (2.00 g, 8.77 mmol) at 0° C. Then solid CrO$_3$ (500 mg, 5.00 mmol) was added in one portion. All solids dissolved initially, then precipitate developed. Reaction was warmed to 23° C. After 1.5 h, the reaction was treated with 1.0 M aq. Na$_2$HPO$_4$ until the pH was ~8. Then 1.0 M aq. NaH$_2$PO$_4$ was added to pH=5. The resulting system was extracted with DCM (50 mL). The organic phase was dried (Na$_2$SO$_4$), filtered, and treated with MeOH (20 mL). Trimethylsilyldiazomethane (2.0 M in hexane, 3.0 mL) was added slowly. The reaction was then stirred for 5 min. Glacial AcOH (300 μL) was added carefully. Saturated aq. Na$_2$HPO$_4$ (50 mL) was added. The organic phase was collected, and the aq. layer was extracted with DCM. Combined organic layers were dried (Na$_2$SO$_4$), filtered, and concentrated. The residue was purified via chromatography on silica gel (80 g "gold" ISCO column; Hex/EtOAc) giving (S)-methyl 2-(2-amino-7-(4-chlorophenyl)-5-methylbenzo[d]thiazol-6-yl)-2-tert-butoxyacetate (206 mg, 19% yield). LCMS-ESI+: calc'd for $C_{21}H_{23}ClN_2O_3S$: 419.1 and 421.1 (M+H+); found: 419.2 and 421.2 (M+H+). $^1$H-NMR: 400 MHz, (CDCl$_3$) δ: 7.50-7.31 (m, 5H), 5.17 (s, broad, 2H), 5.10 (s, 1H), 3.72 (s, 3H), 2.49 (s, 3H), 0.95 (s, 9H).

Example 13

Preparation of (S)-methyl 2-(2-bromo-7-(4-chlorophenyl)-5-methylbenzo[d]thiazol-6-yl)-2-tert-butoxyacetate (103)

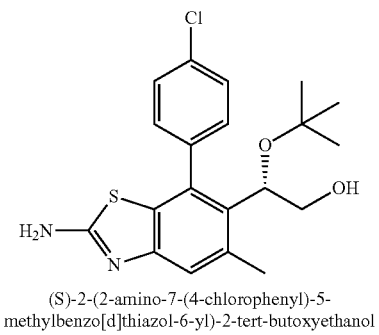

(S)-2-(2-amino-7-(4-chlorophenyl)-5-methylbenzo[d]thiazol-6-yl)-2-tert-butoxyethanol

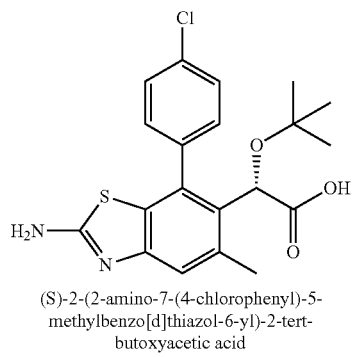

(S)-2-(2-amino-7-(4-chlorophenyl)-5-methylbenzo[d]thiazol-6-yl)-2-tert-butoxyacetic acid

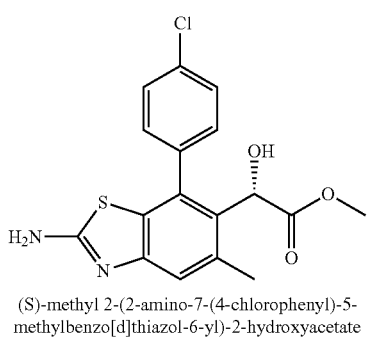

(S)-methyl 2-(2-amino-7-(4-chlorophenyl)-5-methylbenzo[d]thiazol-6-yl)-2-hydroxyacetate

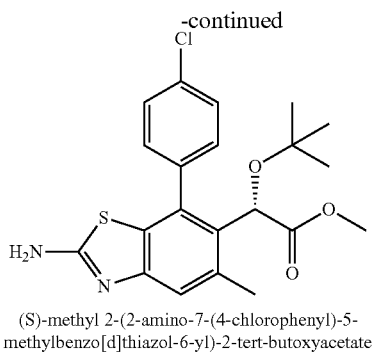

(S)-methyl 2-(2-amino-7-(4-chlorophenyl)-5-methylbenzo[d]thiazol-6-yl)-2-tert-butoxyacetate

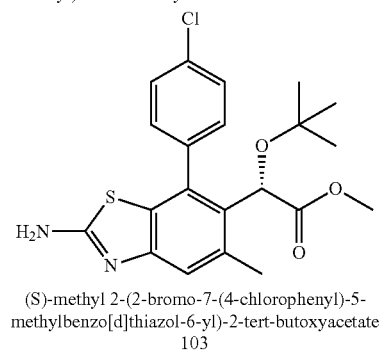

(S)-methyl 2-(2-bromo-7-(4-chlorophenyl)-5-methylbenzo[d]thiazol-6-yl)-2-tert-butoxyacetate
103

Preparation of (S)-2-(2-amino-7-(4-chlorophenyl)-5-methylbenzo[d]thiazol-6-yl)-2-tert-butoxyacetic acid. To a solution of (S)-2-(2-amino-7-(4-chlorophenyl)-5-methylbenzo[d]thiazol-6-yl)-2-tert-butoxyethanol (1.95 g, 5.00 mmol) in acetonitrile (25 mL) and water (1 mL) was added H$_5$IO$_6$ (1.37 g, 6.00 mmol) and CrO$_3$ (1.00 g, 10.0 mmol). The mixture was stirred at rt for 1 h and was diluted with EtOAc (50 mL) and a saturated solution of Na$_2$SO$_3$ (50 mL). The layers were separated, and the aqueous layer was extracted with EtOAc. The crude material was taken on without further purification. $^1$H-NMR: 400 MHz, (CDCl$_3$) δ: 7.42-7.61 (m, 4H), 7.20 (s, 1H), 5.11 (s, 1H), 2.47 (s, 3H), 0.93 (s, 9H).

Preparation of (S)-methyl 2-(2-amino-7-(4-chlorophenyl)-5-methylbenzo[d]thiazol-6-yl)-2-tert-butoxyacetate. To a solution of Preparation of (S)-2-(2-amino-7-(4-chlorophenyl)-5-methylbenzo[d]thiazol-6-yl)-2-tert-butoxyacetic acid from above in MeOH (25 mL) was added H$_2$SO$_4$ (200 μL). The reaction mixture was stirred at rt overnight. EtOAc (20 mL) and saturated NaHCO$_3$ solution (50 mL) were added. The layers were separated, dried, filtered, and concentrated in vacuo. The crude mixture was a mixture of the desired (S)-methyl 2-(2-amino-7-(4-chlorophenyl)-5-methylbenzo[d]thiazol-6-yl)-2-tert-butoxyacetate and (S)-methyl 2-(2-amino-7-(4-chlorophenyl)-5-methylbenzo[d]thiazol-6-yl)-2-hydroxyacetate. t-Butyl acetate was added (20 mL) and perchloric acid (500 μL). The mixture was stirred at rt for 3 hr, where all (S)-methyl 2-(2-amino-7-(4-chlorophenyl)-5-methylbenzo[d]thiazol-6-yl)-2-hydroxyacetate was converted to (S)-methyl 2-(2-amino-7-(4-chlorophenyl)-5-methylbenzo[d]thiazol-6-yl)-2-tert-butoxyacetate. EtOAc (10 mL) and saturated NaHCO$_3$ solution (50 mL) were added. The layers were separated, dried, filtered, and concentrated in vacuo. LCMS-ESI+: calc'd for $C_{21}H_{23}ClN_2O_3S$: 419.1 and 421.1 (M+H+); found: 419.2 and 421.2 (M+H+).

Preparation of (S)-methyl 2-(2-bromo-7-(4-chlorophenyl)-5-methylbenzo[d]thiazol-6-yl)-2-tert-butoxyacetate. To a solution of (S)-methyl 2-(2-amino-7-(4-chlorophenyl)-5-methylbenzo[d]thiazol-6-yl)-2-tert-butoxyacetate from above in acetonitrile (25 mL) was added CuBr$_2$ (1.1 g, 5.0 mmol) and t-butyl nitrite (600 μL, 5.0 mmol). The reaction was stirred at rt for 30 min, and then a saturated solution of Na$_2$SO$_3$ (25 mL) was added. The layers were separated, dried, filtered, and concentrated in vacuo. The crude material was purified by column chromatography (EtOAc/hexanes) to give 642 mg of (S)-methyl 2-(2-bromo-7-(4-chlorophenyl)-5-methylbenzo[d]thiazol-6-yl)-2-tert-butoxyacetate. LCMS-ESI$^+$: calc'd for C$_{21}$H$_{21}$BrClNO$_3$S: 482.0 and 484.0 (M+H$^+$); found: 482.1 and 484.1 (M+H$^+$). $^1$H-NMR: 400 MHz, (CDCl$_3$) δ: 7.70 (s, 1H), 7.41 (br s, 3H), 7.19 (s, 1H), 5.09 (s, 1H), 3.67 (s, 3H), 2.49 (s, 3H), 0.88 (s, 9H).

Example 14

Method B: Preparation of (S)-2-tert-butoxy-2-(7-(4-chlorophenyl)-2-(3-(5-methoxypyridin-3-yl)phenyl)-5-methylbenzo[d]thiazol-6-yl)acetic acid (104)

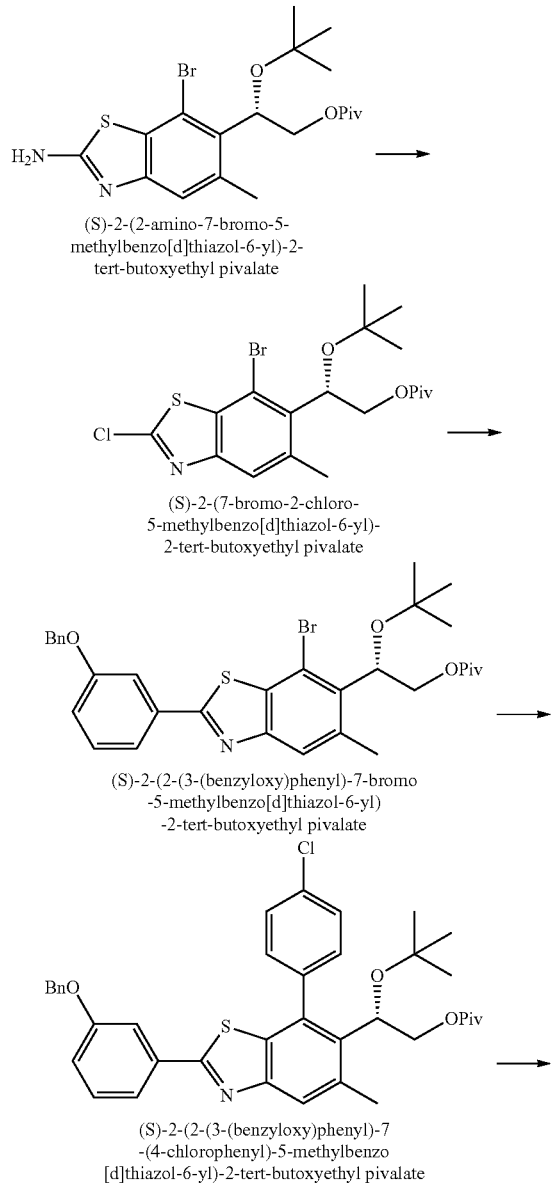

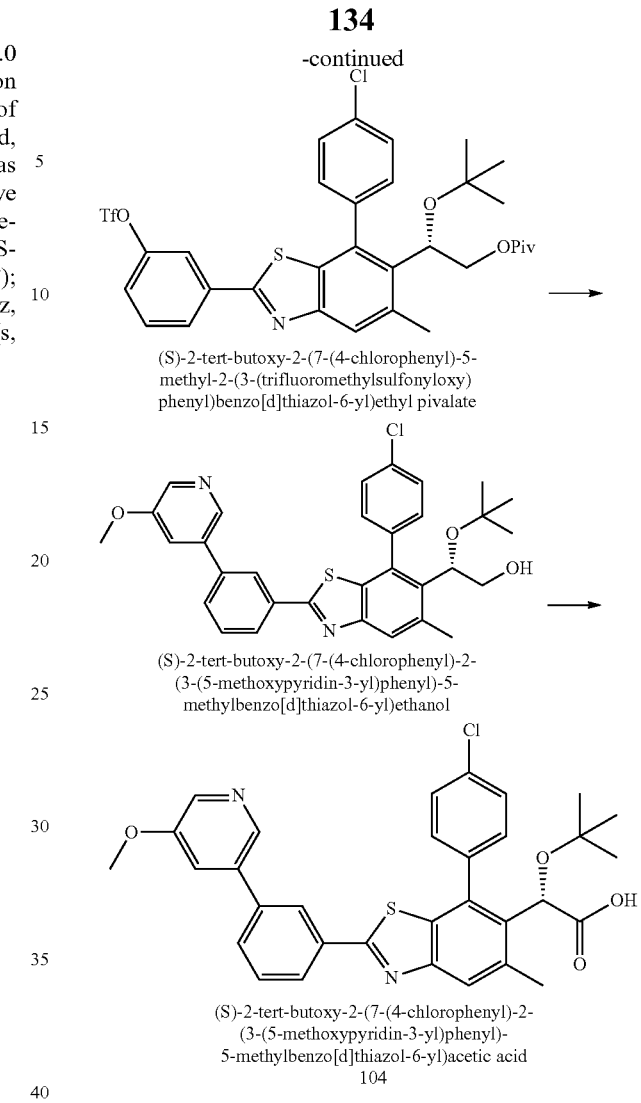

Preparation of (S)-2-(7-bromo-2-chloro-5-methylbenzo[d]thiazol-6-yl)-2-tert-butoxyethyl pivalate: To a solution of (S)-2-(2-amino-7-bromo-5-methylbenzo[d]thiazol-6-yl)-2-tert-butoxyethyl pivalate (1 g, 2.26 mmol) in acetonitrile (15 mL) was added t-butyl nitrite (350 μL, 2.94 mmol) and CuCl$_2$ (364 mg, 2.7 mmol). The reaction mixture was stirred at room temperature for 5 hours. After the reaction finished, the reaction mixture was diluted by EtOAc, washed by water, extracted by EtOAc. The organic phase was dried over MgSO$_4$, filtered, concentrated down and purified by silca gel column, eluting be 0-50% EtOAc in hexanes to give the product (850 mg, 81%). LCMS-ESI$^+$: calc'd for C$_{19}$H$_{25}$BrClNO$_3$S: 462.0 (M+H$^+$); Found: 462.14 (M+H$^+$).

Preparation of (S)-2-(2-(3-(benzyloxy)phenyl)-7-bromo-5-methylbenzo[d]thiazol-6-yl)-2-tert-butoxyethyl pivalate: To a solution of (S)-2-(7-bromo-2-chloro-5-methylbenzo[d]thiazol-6-yl)-2-tert-butoxyethyl pivalate (130 mg, 0.282 mmol) in dioxane, was added 3-benzyloxyphenylboronic acid pinacol ester (105 mg, 0.338 mmol), Pd(PPh$_3$)$_4$ (16 mg, 0.014 mmol), 2N K$_2$CO$_3$ (700 μL). The reaction mixture in sealed tube was heated at 95° C. for 1.5 hs. Then the reaction was cooled down. The reaction mixture was washed by sat. NaHCO$_3$, and extracted by EtOAc. The organic phase was filtered, concentrated down, purified by silica gel column, eluting by 0-50% EtOAc in hexanes to give the product (100 mg, 58%). LCMS-ESI⁺: calc'd for $C_{32}H_{36}BrNO_4S$: 610.2 (M+H⁺); Found: 610.2 (M+H⁺).

Preparation of (S)-2-(2-(3-(benzyloxy)phenyl)-7-(4-chlorophenyl)-5-methylbenzo[d]thiazol-6-yl)-2-tert-butoxyethyl pivalate: The mixture of (S)-2-(2-(3-(benzyloxy)phenyl)-7-bromo-5-methylbenzo[d]thiazol-6-yl)-2-tert-butoxyethyl pivalate (100 mg, 0.164 mmol), 4-chlorophenylboronic acid (38 mg, 0.246 mmol), 2N $K_2CO_3$ (400 μL), Pd(PPh₃)₄ (18 mg, 0.016 mmol) in dioxane in sealed tube was heated at 120° C. After the reaction is finished, the reaction mixture was washed by sat. NaHCO₃, extracted by EtOAc, the organic phase was dried over MgSO₄, filtered, concentrated down and purified by silica gel column (0-50% EtOAc in Hexanes) to give the product (103 mg, 97%). LCMS-ESI⁺: calc'd for $C_{38}H_{40}ClNO_4S$: 642.2 (M+H⁺); Found: 642.3 (M+H⁺).

Preparation of (S)-2-tert-butoxy-2-(7-(4-chlorophenyl)-5-methyl-2-(3-(trifluoromethylsulfonyloxy)phenyl)benzo[d]thiazol-6-yl)ethyl pivalate: To a solution of (S)-2-(2-(3-(benzyloxy)phenyl)-7-(4-chlorophenyl)-5-methylbenzo[d]thiazol-6-yl)-2-tert-butoxyethyl pivalate (410 mg, 0.638 mmol) in EtOH/EtOAc (1:1, 4 mL) was added Pd/C (10%, 600 mg). Then hydrogen balloon was attached to the flask, and the reaction was reacted at room temperature for 1 h. After the reaction was finished, the catalyst was removed over Celite pad and the solution was concentrated down to dryness. The residue was dissolved in DCM (5 mL), to the solution was added pyridine (2 mL), Tf₂O (210 μL, 1.25 mmol) at 0° C. and the reaction was stirred at 0° C. for 1 h. Then the reaction was quenched by sat. NaHCO₃, extracted by DCM, dried over MgSO₄, filtered, concentrated down and purified by silica gel column (0-40% EtOAc in hexanes) to give the product (360 mg, 82%). LCMS-ESI⁺: calc'd for $C_{32}H_{33}ClF_3NO_6S_2$: 684.1 (M+H⁺); Found: 684.1 (M+H⁺).

Preparation of (S)-2-tert-butoxy-2-(7-(4-chlorophenyl)-2-(3-(5-methoxypyridin-3-yl)phenyl)-5-methylbenzo[d]thiazol-6-yl)ethanol: The reaction mixture of (S)-2-tert-butoxy-2-(7-(4-chlorophenyl)-5-methyl-2-(3-(trifluoromethylsulfonyloxy)phenyl)benzo[d]thiazol-6-yl) ethyl pivalate (20 mg, 0.029 mmol), 3-methoxypyridine-5-boronic acid pinacol ester (10 mg, 0.043 mmol), 2N $K_2CO_3$ (70 μL), Pd(PPh₃)₄ (3.3 mg, 0.0029 mmol) in dioxane (1 mL) was heated at 120° C. in sealed tube for 2 hours. After the reaction finished, the reaction was cooled down, to the reaction mixture was added MeOH (1 mL), 2N NaOH (500 μL) and heated at 45° C. for 3 hours. Then reaction mixture was washed by sat. NaHCO₃, extracted by EtOAc, the organic phase was dried over MgSO₄, filtered, concentrated down and purified by silica gel column, eluting by 0-100% EtOAc in hexanes to give the product (10 mg, 62%). LCMS-ESI⁺: calc'd for $C_{32}H_{31}ClN_2O_3S$: 559.2 (M+H⁺); Found: 559.2 (M+H⁺).

Preparation of (S)-2-tert-butoxy-2-(7-(4-chlorophenyl)-2-(3-(5-methoxypyridin-3-yl)phenyl)-5-methylbenzo[d]thiazol-6-yl)acetic acid: To a solution of (S)-2-tert-butoxy-2-(7-(4-chlorophenyl)-2-(3-(5-methoxypyridin-3-yl)phenyl)-5-methylbenzo[d]thiazol-6-yl)ethanol (10 mg, 0.0179 mmol) in wet acetonitrile (0.75 w % $H_2O$, 1 mL), was added stock solution of $H_5IO_6/CrO_3$ (0.439 M in 0.75% $H_2O$ in acetonitrile, 400 μL) at 0° C. for ½ hour. The reaction mixture was filtered and purified by reverse phase HPLC, eluting by 0-100% acetonitrile in $H_2O$ with 0.1% TFA give the product (5 mg, 40%). LCMS-ESI⁺: calc'd for $C_{32}H_{29}ClN_2O_4S$: 573.2 (M+H⁺); Found: 573.2 (M+H⁺). ¹H NMR (400 MHz, CD₃OD): δ 8.59 (s, 1H), 8.40-8.38 (m, 2H), 8.09 (d, J=4.2 Hz, 1H), 7.97 (s, 1H), 7.89-7.88 (m, 2H), 7.70-7.60 (m, 5H), 5.26 (s, 1H), 4.03 (s, 3H), 2.62 (s, 3H), 0.97 (s, 9H).

Example 15

Method C: Preparation of (S)-2-tert-butoxy-2-(7-(4-chlorophenyl)-2-(5'-methoxy-2,3'-bipyridin-4-yl)-5-methylbenzo[d]thiazol-6-yl)acetic acid (105)

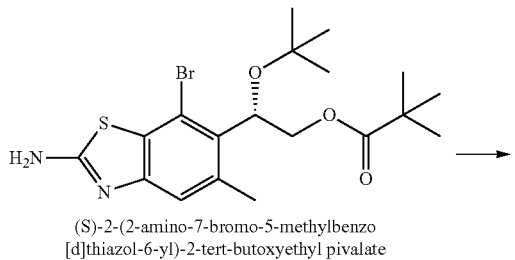

(S)-2-(2-amino-7-bromo-5-methylbenzo[d]thiazol-6-yl)-2-tert-butoxyethyl pivalate

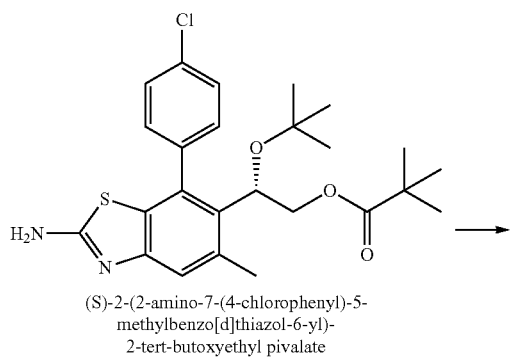

(S)-2-(2-amino-7-(4-chlorophenyl)-5-methylbenzo[d]thiazol-6-yl)-2-tert-butoxyethyl pivalate

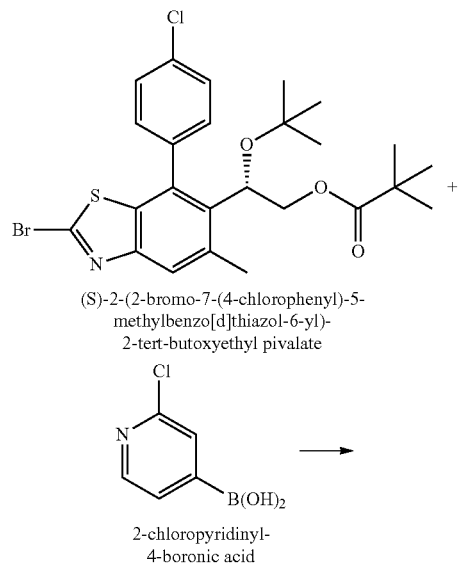

(S)-2-(2-bromo-7-(4-chlorophenyl)-5-methylbenzo[d]thiazol-6-yl)-2-tert-butoxyethyl pivalate 2-chloropyridinyl-4-boronic acid -continued

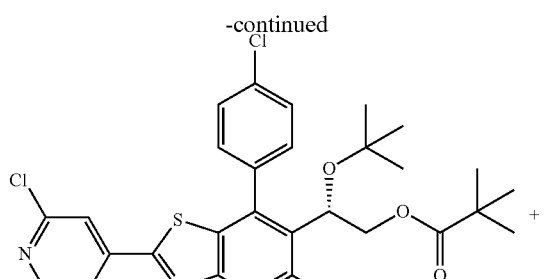

(S)-2-tert-butoxy-2-(7-(4-chlorophenyl)-
2-(2-chloropyridin-4-yl)-5-
methylbenzo[d]thiazol-6-yl)ethyl pivalate

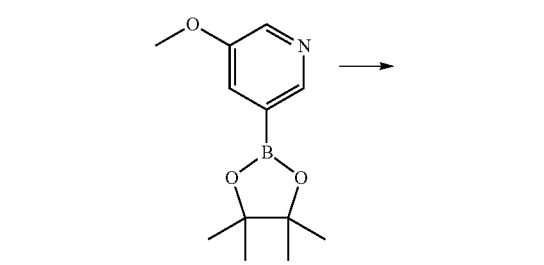

5-methoxy-3-
pyridineboronic
acid pinacol ester

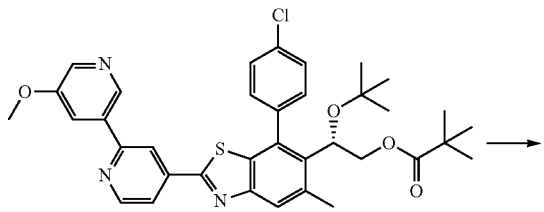

(S)-2-tert-butoxy-2-(7-(4-chlorophenyl)-
2-(5'-methoxy-2,3'-bipyridin-4-yl)-5-
methylbenzo[d]thiazol-6-yl)ethyl pivalate

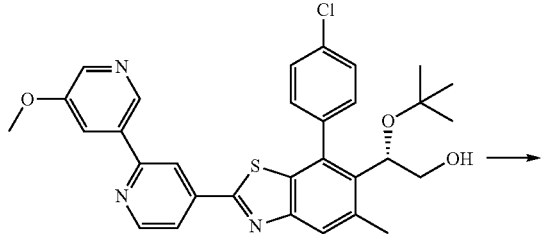

(S)-2-tert-butoxy-2-(7-(4-chlorophenyl)-2-
(5'-methoxy-2,3'-bipyridin-4-yl)-5-
methylbenzo[d]thiazol-6-yl)ethanol

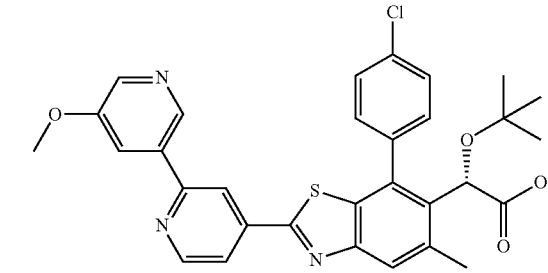

(S)-2-tert-butoxy-2-(7-(4-chlorophenyl)-2-
(5'-methoxy-2-3'-bipyridin-4-yl)-5-
methylbenzo[d]thiazol-6-yl)acetic acid
105

Preparation of (S)-2-(2-Amino-7-(4-chlorophenyl)-5-methylbenzo[d]thiazol-6-yl)-2-tert-butoxyethyl pivalate: 2 separate microwave tubes were each charged with (S)-2-(2-Amino-7-bromo-5-methylbenzo[d]thiazol-6-yl)-2-tert-butoxyethyl pivalate (768 mg, 1.74 mmol), $K_2CO_3$ (960 mg, 6.96 mmol), 4-chlorophenylboronic acid (325 mg, 2.09 mmol), $Pd(PPh_3)_4$ (200 mg, 0.174 mmol), dioxane (8.0 mL), and $H_2O$ (2.0 mL). The two sealed vessels were separately heated at 110° C. for 3 h. The reactions were cooled to 23° C. and combined. $H_2O$ (50 mL) was added, and the system was extracted with EtOAc (3×50 mL). The combined extracts were dried ($Na_2SO_4$), filtered, and concentrated. The residue was treated with benzene and purified via chromatography on silica gel (80 g "gold" ISCO column; Hex/EtOAc) giving (S)-2-(2-Amino-7-(4-chlorophenyl)-5-methylbenzo[d]thiazol-6-yl)-2-tert-butoxyethyl pivalate (1.55 g, 90% yield). LCMS-ESI$^+$: calc'd for $C_{25}H_{31}ClN_2O_3S$: 475.2 and 477.2 (M+H$^+$); found: 475.3 and 477.3 (M+H$^+$). $^1$H-NMR: 400 MHz, (CDCl$_3$) δ: 7.49-7.41 (m, 2H), 7.36-7.32 (m, 2H), 7.22 (d, J=7.3 Hz, 1H), 5.19 (s, broad, 2H), 4.67 (dd, J=9.0, 2.7 Hz, 1H), 4.36 (dd, J=11.7, 9.0 Hz, 1H), 4.23 (dd, J=11.7, 2.7 Hz, 1H), 2.68 (s, 3H), 1.14 (s, 9H), 0.94 (s, 9H).

Preparation of (S)-2-(2-bromo-7-(4-chlorophenyl)-5-methylbenzo[d]thiazol-6-yl)-2-tert-butoxyethyl pivalate: At 23° C., in a water bath, a solution of (S)-2-(2-amino-7-(4-chlorophenyl)-5-methylbenzo[d]thiazol-6-yl)-2-tert-butoxyethyl pivalate (1.13 g, 2.37 mmol) in $CH_3CN$ (22 mL) was treated with solid anhydrous $CuBr_2$ (635 mg, 2.84 mmol). Reaction was fitted with a mineral oil bubbler. A freshly prepared solution of t-butyl nitrite (269 mg, 2.61 mmol) in $CH_3CN$ (2.0 mL) was added dropwise over a 5 min period. The water bath was removed. Gas evolution was monitored using the bubbler. At 1 h, gas evolution ceased. The reaction was poured into EtOAc (50 mL) and treated with $H_2O$ (50 mL). A brown solid precipitated. The suspension was filtered over Celite, which was thoroughly washed with EtOAc. The filtrate was transferred to a separatory funnel. The organic phase was collected. The aq. phase was extracted with EtOAc. The total organic layers were combined, dried ($Na_2SO_4$), filtered, and concentrated. The residue was treated with benzene and purified via chromatography on silica gel (80 g "gold" ISCO column; Hex/EtOAc) giving (S)-2-(2-bromo-7-(4-chlorophenyl)-5-methylbenzo[d]thiazol-6-yl)-2-tert-butoxyethyl pivalate. LCMS-ESI$^+$: calc'd for $C_{25}H_{29}BrClNO_3S$: 538.1, 540.1, and 542.1.1 (M+H$^+$); found: 538.2, 540.2, and 542.2 (M+H$^+$). $^1$H-NMR: 400 MHz, (CDCl$_3$) δ: 7.76 (s, 1H), 7.51 (d, J=8.2 Hz, 1H), 7.47 (d, J=7.8 Hz, 1H), 7.34 (d, J=8.2 Hz, 1H), 7.24 (d, J=7.8 Hz, 1H), 4.76 (dd, J=9.0, 3.5 Hz, 1H), 4.39 (dd, J=11.7, 9.0 Hz, 1H), 4.25 (dd, J=11.7, 3.5 Hz, 1H), 2.76 (s, 3H), 1.14 (s, 9H), 0.94 (s, 9H).

Preparation of (S)-2-tert-butoxy-2-(7-(4-chlorophenyl)-2-(2-chloropyridin-4-yl)-5-methylbenzo[d]thiazol-6-yl)ethyl pivalate: (S)-2-(2-bromo-7-(4-chlorophenyl)-5-methylbenzo[d]thiazol-6-yl)-2-tert-butoxyethyl pivalate (400.0 mg, 0.742 mmol), 2-chloro-4-pyridinylboronic acid (140.2 mg, 0.891 mmol), potassium carbonate (307.7 mg, 2.227 mmol), and $Pd(PPh_3)_4$ (128.7 mg, 0.111 mmol) were placed in a microwave vial and the vial was vacuum pumped and flushed with argon three times. To this mixture was added degassed 1,4-dioxane (3.5 mL) and water (0.7 mL). The reaction mixture was heated at 90° C. for 4.5 h then cooled to rt. The aqueous layer was separated and extracted three times with ethyl acetate. All organic layers were combined, dried over $Na_2SO_4$, and concentrated. Purification by flash column chromatography on silica gel (hexanes/ethyl acetate eluent) provided the final compound. LCMS-ESI$^+$: calc'd for $C_{30}H_{33}O_2N_2O_3S$: 571.2 (M+H$^+$); Found: 571.1 (M+H$^+$); $^1$H NMR (400 MHz, CDCl$_3$) δ 8.49 (d, J=4.9 Hz, 1H), 7.93 (s, 2H), 7.77 (d, J=5.0 Hz, 1H), 7.55 (d, J=9.2 Hz, 1H), 7.50 (d, J=7.4 Hz, 1H), 7.40 (d, J=7.4 Hz, 1H), 7.29 (d, J=8.9 Hz, 1H), 4.82 (dd, J=8.9, 2.7 Hz, 1H), 4.42 (dd, J=11.2, 9.3 Hz, 1H), 4.29 (dd, J=11.5, 3.2 Hz, 1H), 2.80 (s, 3H), 1.14 (s, 9H), 0.97 (s, 9H).

Preparation of (S)-2-tert-butoxy-2-(7-(4-chlorophenyl)-2-(5'-methoxy-2,3'-bipyridin-4-yl)-5-methylbenzo[d]thiazol-6-yl)ethyl pivalate: (S)-2-tert-butoxy-2-(7-(4-chlorophenyl)-2-(2-chloropyridin-4-yl)-5-methylbenzo[d]thiazol-6-yl) ethyl pivalate (40.0 mg, 0.070 mmol), 5-methoxy-3-pyridineboronic acid pinacol ester (19.7 mg, 0.084 mmol), potassium carbonate (29.0 mg, 0.210 mmol), and Pd(PPh$_3$)$_4$ (12.1 mg, 0.010 mmol) were placed in a microwave vial and the vial was vacuum pumped and flushed with argon three times. To this mixture was added degassed 1,4-dioxane (0.8 mL) and water (0.2 mL). The reaction mixture was heated at 110° C. for 1 h then cooled to rt. The aqueous layer was separated and extracted three times with ethyl acetate. All organic layers were combined, dried over Na$_2$SO$_4$, and concentrated. Purification by flash column chromatography on silica gel (hexanes/ethyl acetate eluent) provided the product. LCMS-ESI$^+$: calc'd for C$_{36}$H$_{39}$ClN$_3$O$_4$S: 644.2 (M+H$^+$); Found: 644.1 (M+H$^+$); $^1$H NMR (400 MHz, CDCl$_3$) δ 8.89 (s, 1H), 8.81 (d, J=4.9 Hz, 1H), 8.40 (d, J=2.7 Hz, 1H), 8.35 (s, 1H), 8.02 (s, 1H), 7.95 (s, 1H), 7.83 (d, J=5.2 Hz, 1H), 7.57 (d, J=8.4 Hz, 1H), 7.51 (d, J=8.5 Hz, 1H), 7.43 (d, J=8.4 Hz, 1H), 7.31 (d, J=8.7 Hz, 1H), 4.83 (dd, J=9.4, 2.7 Hz, 1H), 4.43 (dd, J=11.2, 9.5 Hz, 1H), 4.30 (dd, J=12.1, 2.9 Hz, 1H), 3.99 (s, 3H), 2.81 (s, 3H), 1.15 (s, 9H), 0.97 (s, 9H).

Preparation of (S)-2-tert-butoxy-2-(7-(4-chlorophenyl)-2-(5'-methoxy-2,3'-bipyridin-4-yl)-5-methylbenzo[d]thiazol-6-yl)ethanol: To a solution of (S)-2-tert-butoxy-2-(7-(4-chlorophenyl)-2-(5'-methoxy-2,3'-bipyridin-4-yl)-5-methylbenzo[d]thiazol-6-yl)ethyl pivalate (40.5 mg, 0.063 mmol) in THF (0.5 mL) and methanol (0.5 mL) was added NaOH (0.5 mL, 2N solution). The reaction mixture was heated at 40° C. for 4 h, cooled, diluted with satd. aqueous NH$_4$Cl, and extracted with ethyl acetate. The organic layer was dried over Na$_2$SO$_4$, filtered and concentrated to give the crude product which was used without further purification. LCMS-ESI$^+$: calc'd for C$_{31}$H$_{31}$ClN$_3$O$_3$S: 560.2 (M+H$^+$); Found: 560.0 (M+H$^+$).

Preparation of (S)-2-tert-butoxy-2-(7-(4-chlorophenyl)-2-(5'-methoxy-2,3'-bipyridin-4-yl)-5-methylbenzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. To a solution of crude (S)-2-tert-butoxy-2-(7-(4-chlorophenyl)-2-(5'-methoxy-2,3'-bipyridin-4-yl)-5-methylbenzo[d]thiazol-6-yl)ethanol from the previous reaction (assume 0.063 mmol) in 25% water/acetonitrile (1.6 mL) was added sequentially, a stock solution of CrO$_3$/H$_5$IO$_6$ (0.72 mL, 0.439 M solution) and CrO$_3$ (9.4 mg, 0.094 mmol) at room temperature. The reaction was stirred for 1 h and quenched with aqueous Na$_2$SO$_3$ (10% w/v). When the reaction mixture turned green, it was extracted 3 times with ethyl acetate. The combined organic layers were dried over Na$_2$SO$_4$, concentrated, taken up in THF (0.3 mL), methanol (0.3 mL), and water (0.15 mL), filtered, and purified by reverse phase HPLC. Fractions containing the product were pooled and lyophilized to provide the TFA salt of the product. $^1$H NMR (400 MHz, CD$_3$OD) δ 9.03 (s, 1H), 8.84 (d, J=5.1 Hz, 1H), 8.61 (s, 1H), 8.50 (s, 2H), 8.02 (d, J=5.2 Hz, 1H), 7.94 (s, 1H), 7.70 (d, J=9.6 Hz, 1H), 7.64-7.56 (m, 3H), 5.28 (s, 1H), 4.08 (s, 3H), 2.64 (s, 3H), 0.98 (s, 9H). LCMS-ESI$^+$: calc'd for C$_{31}$H$_{29}$ClN$_3$O$_4$S: 574.1 (M+H$^+$); Found: 574.0 (M+H$^+$).

Example 16

Method D: Preparation of (S)-2-tert-butoxy-2-(7-(4-chlorophenyl)-5-methyl-2-(3-(pyrimidin-5-yl)phenyl)benzo[d]thiazol-6-yl)acetic acid (106)

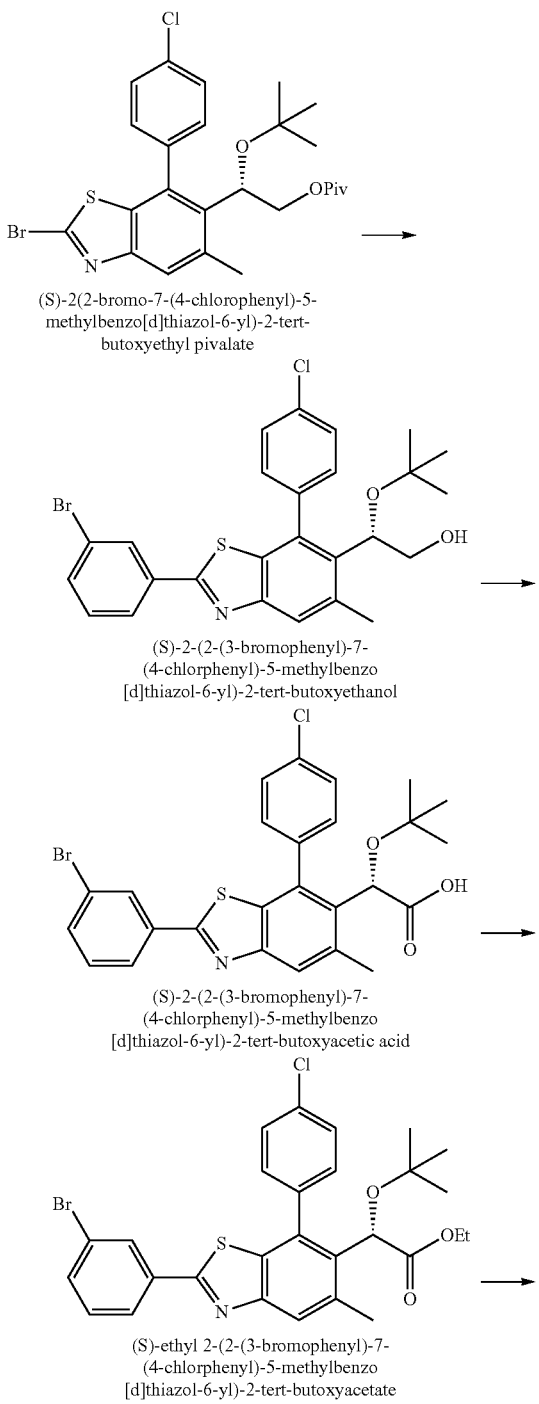

(S)-2(2-bromo-7-(4-chlorophenyl)-5-methylbenzo[d]thiazol-6-yl)-2-tert-butoxyethyl pivalate (S)-2-(2-(3-bromophenyl)-7-(4-chlorphenyl)-5-methylbenzo[d]thiazol-6-yl)-2-tert-butoxyethanol (S)-2-(2-(3-bromophenyl)-7-(4-chlorphenyl)-5-methylbenzo[d]thiazol-6-yl)-2-tert-butoxyacetic acid (S)-ethyl 2-(2-(3-bromophenyl)-7-(4-chlorphenyl)-5-methylbenzo[d]thiazol-6-yl)-2-tert-butoxyacetate -continued

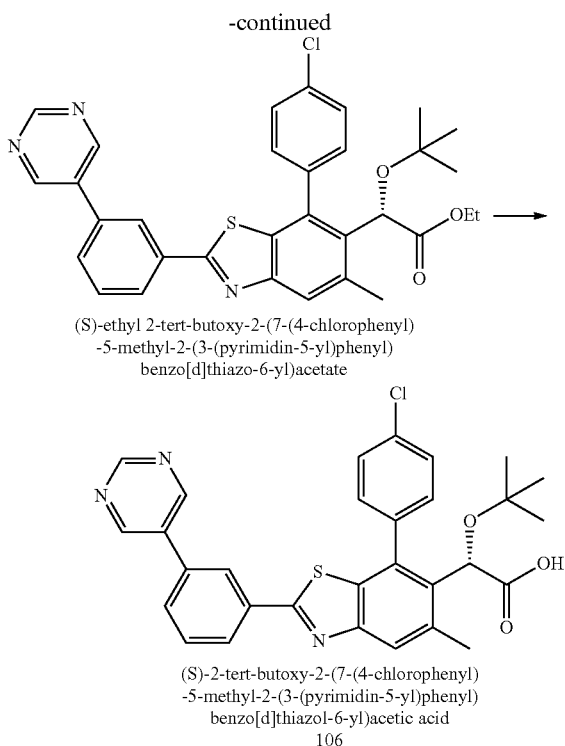

(S)-ethyl 2-tert-butoxy-2-(7-(4-chlorophenyl)
-5-methyl-2-(3-(pyrimidin-5-yl)phenyl)
benzo[d]thiazo-6-yl)acetate (S)-2-tert-butoxy-2-(7-(4-chlorophenyl)
-5-methyl-2-(3-(pyrimidin-5-yl)phenyl)
benzo[d]thiazol-6-yl)acetic acid
106

Preparation of (S)-2-(2-(3-bromophenyl)-7-(4-chlorophenyl)-5-methylbenzo[d]thiazol-6-yl)-2-tert-butoxyethanol: To a solution of (S)-2-(2-bromo-7-(4-chlorophenyl)-5-methylbenzo[d]thiazol-6-yl)-2-tert-butoxyethyl pivalate (310 mg, 0.577 mmol) in dioxane (5 mL), was added 3-bromophenylboronic acid (173 mg, 0.865 mmol), Ph(PPh$_3$)$_4$ (33 mg, 0.029 mmol) 2N K$_2$CO$_3$ (850 μL) in sealed tube. The reaction mixture was heated at 90° C. for 3 hs. Then the reaction was cooled down and to the mixture was added MeOH (5 mL), 2N NaOH (1.5 mL) and heated at 45° C. After the reaction was finished, the reaction was washed by water, extracted by EtOAc. The organic phase was dried over MgSO$_4$, filtered, concentrated down and purified by silica gel column, eluting by 0-50% EtOAc in hexanes to give the product (110 mg, 36%). LCMS-ESI$^+$: calc'd for C$_{26}$H$_{25}$BrClNO$_2$S: 530.0 (M+H$^+$); Found: 530.2 (M+H$^+$).

Preparation of (S)-2-(2-(3-bromophenyl)-7-(4-chlorophenyl)-5-methylbenzo[d]thiazol-6-yl)-2-tert-butoxyacetic acid: To a solution of (S)-2-(2-(3-bromophenyl)-7-(4-chlorophenyl)-5-methylbenzo[d]thiazol-6-yl)-2-tert-butoxyethanol (110 mg, 0.208 mmol) in wet acetonitrile (0.75% H$_2$O, 2.5 mL), was added H$_5$IO$_6$/CrO$_3$ stock solution (0.439 M in wet acetonitrile, 2.4 mL) at 0° C. The reaction was stirred at 0° C. for ½ h. The reaction mixture was washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{26}$H$_{23}$BrClNO$_3$S: 544.0 (M+H$^+$); Found: 544.1 (M+H$^+$).

Preparation of (S)-ethyl 2-(2-(3-bromophenyl)-7-(4-chlorophenyl)-5-methylbenzo[d]thiazol-6-yl)-2-tert-butoxyacetate: To a solution of (S)-2-(2-(3-bromophenyl)-7-(4-chlorophenyl)-5-methylbenzo[d]thiazol-6-yl)-2-tert-butoxyacetic acid (104 mg, 0.191 mmol) in DMF, was added Cs$_2$CO$_3$ (152 mg, 0.467 mmol), ethyl iodide (30 μL, 0.343 mmol). The reaction was stirred at room temperature for 2 hs. The reaction mixture was washed by sat. NaHCO$_3$, extracted by EtOAc, dry over MgSO$_4$, filtered, purified by silica gel column, eluting by 0-50% EtOAc in hexanes to give the product. LCMS-ESI$^+$: calc'd for C$_{28}$H$_{27}$BrClNO$_3$S: 572.1 (M+H$^+$); Found: 572.2 (M+H$^+$).

Preparation of (S)-ethyl 2-tert-butoxy-2-(7-(4-chlorophenyl)-5-methyl-2-(3-(pyrimidin-5-yl)phenyl)benzo[d]thiazol-6-yl)acetate: The reaction mixture of (S)-ethyl 2-(2-(3-bromophenyl)-7-(4-chlorophenyl)-5-methylbenzo[d]thiazol-6-yl)-2-tert-butoxyacetate (12 mg, 0.025 mmol), 5-pyrimidineboronic acid (5 mg, 0.0375 mmol), 2N K$_2$CO$_3$ (60 μL), Pd(PPh$_3$)$_4$ (3 mg, 0.0025 mmol) in dioxane (1 mL) was heated at 120° C. in sealed tube. After the reaction was finished, the reaction was washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{32}$H$_{30}$ClN$_3$O$_3$S: 572.2 (M+H$^+$); Found: 572.2 (M+H$^+$).

Preparation of (S)-2-tert-butoxy-2-(7-(4-chlorophenyl)-5-methyl-2-(3-(pyrimidin-5-yl)phenyl)benzo[d]thiazol-6-yl)acetic acid: The reaction mixture of (S)-ethyl 2-tert-butoxy-2-(7-(4-chlorophenyl)-5-methyl-2-(3-(pyrimidin-5-yl)phenyl)benzo[d]thiazol-6-yl)acetate (9 mg, 0.0157 mmol), excess NaOH, in MeOH/THF (1:1, 2 mL) was heated at 45° C. overnight. After reaction finished, the solvent was removed and the residue was dissolved in MeOH and purified by reverse phase HPLC, eluting by 0-100% acetonitrile in H$_2$O with 0.1% TFA to give the product. LCMS-ESI$^+$: calc'd for C$_{30}$H$_{26}$ClN$_3$O$_3$S: 544.1 (M+H$^+$); Found: 544.2 (M+H$^+$). $^1$H NMR (400 MHz, CD$_3$OD): δ 9.18 (s, 1H), 9.16 (s, 2H), 8.40 (s, 1H), 8.12 (d, J=4 Hz, 1H), 7.91-7.88 (m, 2H), 7.71-7.67 (m, 2H), 7.60-7.58 (m, 3H), 5.26 (s, 1H), 2.62 (s, 3H), 0.97 (s, 9H).

Example 17

Method E: Preparation of (S)-2-tert-butoxy-2-(7-(4-chlorophenyl)-2-(3-(2-chloropyridin-4-yl)phenyl)-5-methylbenzo[d]thiazol-6-yl)acetic acid (107)

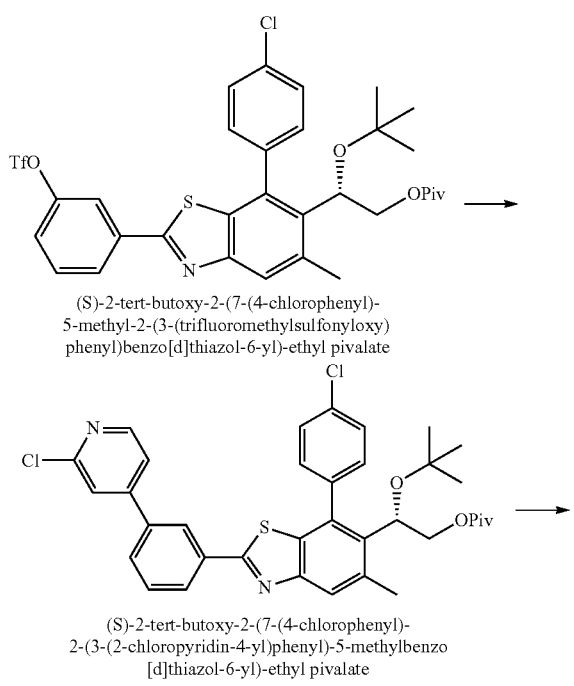

(S)-2-tert-butoxy-2-(7-(4-chlorophenyl)-
5-methyl-2-(3-(trifluoromethylsulfonyloxy)
phenyl)benzo[d]thiazol-6-yl)-ethyl pivalate (S)-2-tert-butoxy-2-(7-(4-chlorophenyl)-
2-(3-(2-chloropyridin-4-yl)phenyl)-5-methylbenzo
[d]thiazol-6-yl)-ethyl pivalate

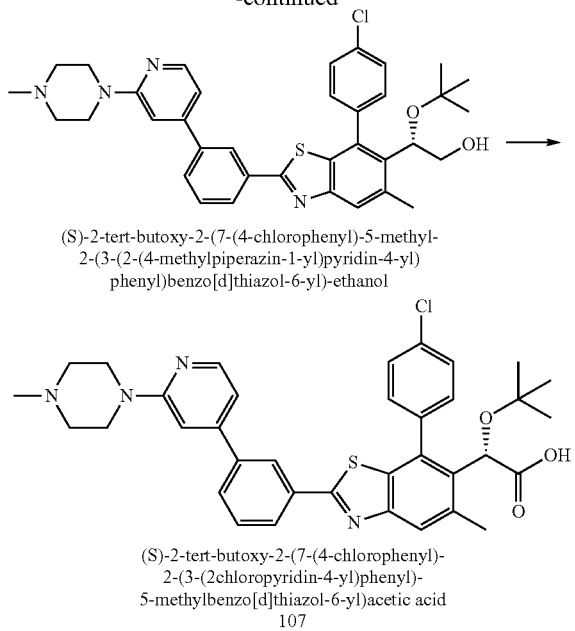

(S)-2-tert-butoxy-2-(7-(4-chlorophenyl)-5-methyl-
2-(3-(2-(4-methylpiperazin-1-yl)pyridin-4-yl)
phenyl)benzo[d]thiazol-6-yl)-ethanol (S)-2-tert-butoxy-2-(7-(4-chlorophenyl)-
2-(3-(2chloropyridin-4-yl)phenyl)-
5-methylbenzo[d]thiazol-6-yl)acetic acid
107

Preparation of (S)-2-tert-butoxy-2-(7-(4-chlorophenyl)-2-(3-(2-chloropyridin-4-yl)phenyl)-5-methylbenzo[d]thiazol-6-yl)ethyl pivalate: The reaction mixture of (S)-2-tert-butoxy-2-(7-(4-chlorophenyl)-5-methyl-2-(3-(trifluoromethylsulfonyloxy)phenyl)benzo[d]thiazol-6-yl) ethyl pivalate (30 mg, 0.0438 mmol), 2-chloropyridine-4-boronic acid (10 mg, 0.0657 mmol), 2N $K_2CO_3$ (100 μL), Pd(PPh$_3$)$_4$ (5.0 mg, 0.0044 mmol) in dioxane (2 mL) was heated at 120° C. in sealed tube for 2 hs. The reaction was washed by sat. NaHCO$_3$, extracted by EtOAc, dried by MgSO$_4$, filtered, concentrated down and purified by silica gel column, eluting by 0-100% EtOAc in hexanes to give the product (LCMS-ESI$^+$: calc'd for $C_{36}H_{36}Cl_2N_2O_3S$: 647.2 (M+H$^+$); Found: 647.3 (M+H$^+$).

Preparation of (S)-2-tert-butoxy-2-(7-(4-chlorophenyl)-5-methyl-2-(3-(2-(4-methylpiperazin-1-yl)pyridin-4-yl)phenyl)benzo[d]thiazol-6-yl)ethanol: The reaction mixture of (S)-2-tert-butoxy-2-(7-(4-chlorophenyl)-2-(3-(2-chloropyridin-4-yl)phenyl)-5-methylbenzo[d]thiazol-6-yl)ethyl pivalate (16 mg, 0.025 mmol), 1-methylpiperazine (1 mL) was heated at 120° C. overnight. Then the reaction mixture was washed by sat. NaHCO$_3$, extracted by EtOAc, the organic phase was dried over MgSO$_4$, filtered, concentrated. To the residue was added THF, MeOH, 2N NaOH, the mixture was heated at 45° C. After the reaction finished, the reaction was washed by sat NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for $C_{36}H_{39}ClN_4O_2S$: 627.2 (M+H$^+$); Found: 627.3 (M+H$^+$).

Preparation of (S)-2-tert-butoxy-2-(7-(4-chlorophenyl)-2-(3-(2-chloropyridin-4-yl)phenyl)-5-methylbenzo[d]thiazol-6-yl)acetic acid: To a solution of (S)-2-tert-butoxy-2-(7-(4-chlorophenyl)-5-methyl-2-(3-(2-(4-methylpiperazin-1-yl) pyridin-4-yl)phenyl)benzo[d]thiazol-6-yl)ethanol in DCM (1 mL) was added Dess-Martin periodinane (8.8 mg, 0.020 mmol). After 1 h, more Dess-Martin periodinane was added (10 mg) and the reaction mixture was reacted at room temperature overnight. The mixture was washed by sat. NaHCO$_3$, 1M Na$_2$S$_2$O$_3$, extracted by DCM, dried over MgSO$_4$, filtered, concentrated down. To the residue was added t-BuOH (600 μL), 1M NaH$_2$PO4 (300 μL), 2-methylbut-2-ene (500 μL) and NaClO$_2$ (14 mg). The reaction mixture was reacted at room temperature. After the reaction finished, the mixture was treated with MeOH, filtered, purified by reverse phase HPLC to give the product. LCMS-ESI$^+$: calc'd for $C_{36}H_{37}ClN_4O_3S$: 641.2 (M+H$^+$); Found: 641.2 (M+H$^+$).

Example 18

Method F: Preparation of (S)-2-tert-butoxy-2-(7-(4-chlorophenyl)-5-methyl-2-(2-(1-methyl-1H-indazol-6-yl)pyridin-4-yl)benzo[d]thiazol-6-yl)acetic acid (108)

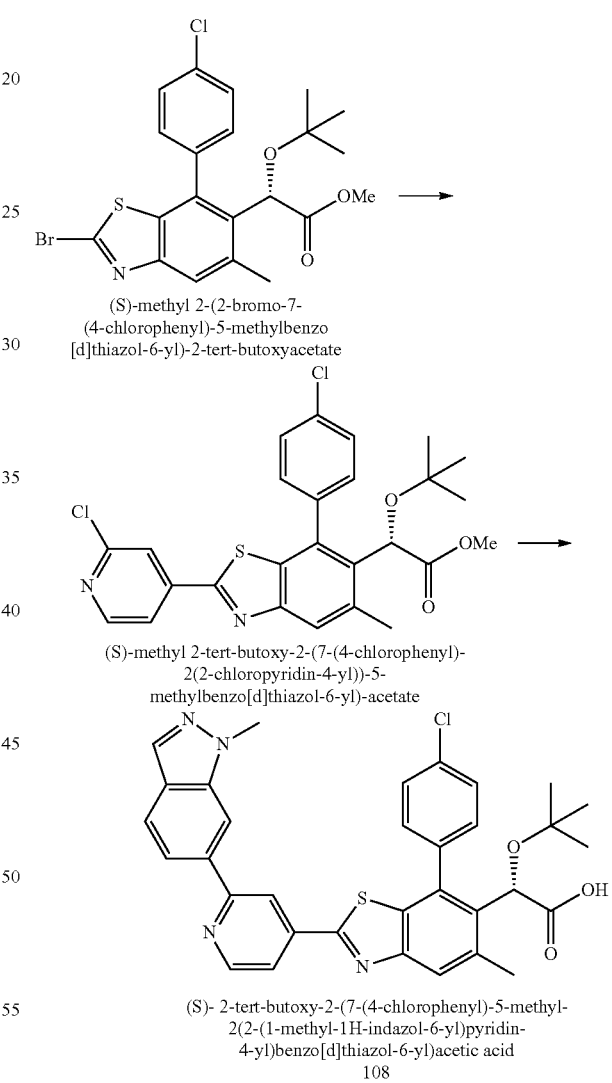

(S)-methyl 2-(2-bromo-7-
(4-chlorophenyl)-5-methylbenzo
[d]thiazol-6-yl)-2-tert-butoxyacetate (S)-methyl 2-tert-butoxy-2-(7-(4-chlorophenyl)-
2(2-chloropyridin-4-yl))-5-
methylbenzo[d]thiazol-6-yl)-acetate (S)- 2-tert-butoxy-2-(7-(4-chlorophenyl)-5-methyl-
2(2-(1-methyl-1H-indazol-6-yl)pyridin-
4-yl)benzo[d]thiazol-6-yl)acetic acid
108

Preparation of (S)-methyl 2-tert-butoxy-2-(7-(4-chlorophenyl)-2-(2-chloropyridin-4-yl)-5-methylbenzo[d]thiazol-6-yl)acetate: The reaction mixture of (S)-methyl 2-(2-bromo-7-(4-chlorophenyl)-5-methylbenzo[d]thiazol-6-yl)-2-tert-butoxyacetate (370 mg, 0.769 mol), 2-chloropyridine-4-boronic acid (157 mg, 0.99 mmol), 2N K$_2$CO$_3$ (1.9 mL), Pd(PPh$_3$)$_4$ (80 mg, 0.077 mmol) in dioxane (10 mL) was heated at 95° C. for 2 hrs. The reaction mixture was diluted by EtOAc, washed by sat. NaHCO₃, extracted by EtOAc, the organic phase was dried over MgSO₄, filtered, concentrated down and purified by silica gel column, eluting by 0-100% EtOAc in hexanes to give the product. LCMS-ESI⁺: calc'd for $C_{26}H_{24}Cl_2N_2O_3S$: 515.1 (M+H⁺); Found: 515.1 (M+H⁺).

Preparation of (S)-2-tert-butoxy-2-(7-(4-chlorophenyl)-5-methyl-2-(2-(1-methyl-1H-indazol-6-yl)pyridin-4-yl)benzo[d]thiazol-6-yl)acetic acid: The reaction mixture of (S)-methyl 2-tert-butoxy-2-(7-(4-chlorophenyl)-2-(2-chloropyridin-4-yl)-5-methylbenzo[d]thiazol-6-yl)acetate (20 mg, 0.039 mmol), 1-methyl-1H-indazole-6-boronic acid (10.3 mg, 0.058 mmol), 2N K₂CO₃ (100 µL, 0.19 mmol), Pd(PPh₃)₄ (4.3 mg, 0.004 mmol) in dioxane (1.5 mL) in sealed tube was heated at 110° C. for 2 h. After the starting material consumed, the reaction was cooled down, to the mixture was added MeOH, excess NaOH, the reaction mixture was heated at 45° C. overnight. Then the reaction mixture was neutralized by acetic acid, concentrated down, then treated by MeOH, and purified by reverse phase HPLC, eluting by 0-100% acetonitrile in H₂O with 0.1% TFA to give the product. LCMS-ESI⁺: calc'd for $C_{33}H_{29}ClN_4O_3S$: 597.2 (M+H⁺); Found: 597.2 (M+H⁺). ¹H NMR (400 MHz, CD₃OD): δ 8.78 (d, J=2.6 Hz, 1H), 8.60 (s, 1H), 8.26 (s, 1H), 8.06 (s, 1H), 8.03-7.82 (m, 4H), 7.71-7.69 (m, 1H), 7.61-7.60 (m, 3H), 5.28 (s, 1H), 4.16 (s, 3H), 2.64 (s, 3H), 0.98 (s, 9H).

Example 19

Method G: Preparation of (S)-2-tert-butoxy-2-(7-(4-chlorophenyl)-5-methyl-2-(3-(1-methyl-1H-indazol-5-yl)phenyl)benzo[d]thiazol-6-yl)acetic acid (109)

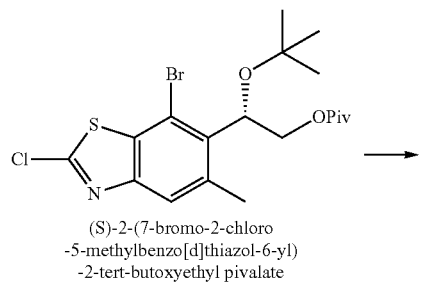

(S)-2-(7-bromo-2-chloro-5-methylbenzo[d]thiazol-6-yl)-2-tert-butoxyethyl pivalate

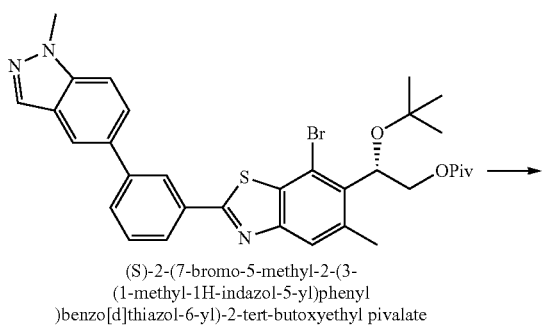

(S)-2-(7-bromo-5-methyl-2-(3-(1-methyl-1H-indazol-5-yl)phenyl)benzo[d]thiazol-6-yl)-2-tert-butoxyethyl pivalate

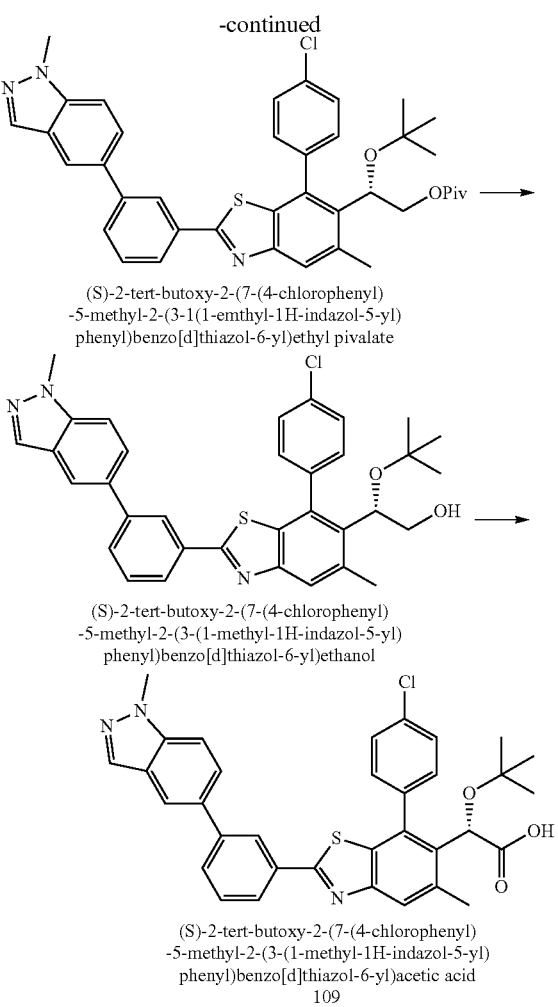

(S)-2-tert-butoxy-2-(7-(4-chlorophenyl)-5-methyl-2-(3-1(1-emthyl-1H-indazol-5-yl)phenyl)benzo[d]thiazol-6-yl)ethyl pivalate (S)-2-tert-butoxy-2-(7-(4-chlorophenyl)-5-methyl-2-(3-(1-methyl-1H-indazol-5-yl)phenyl)benzo[d]thiazol-6-yl)ethanol (S)-2-tert-butoxy-2-(7-(4-chlorophenyl)-5-methyl-2-(3-(1-methyl-1H-indazol-5-yl)phenyl)benzo[d]thiazol-6-yl)acetic acid
109

Preparation of (S)-2-(7-bromo-5-methyl-2-(3-(1-methyl-1H-indazol-5-yl)phenyl)benzo[d]thiazol-6-yl)-2-tert-butoxyethyl pivalate: The reaction mixture of (S)-2-(7-bromo-2-chloro-5-methylbenzo[d]thiazol-6-yl)-2-tert-butoxyethyl pivalate (300 mg, 0.65 mmol), 1-methyl-5-(3-(4,4,5,5-tetramethyl-1,3,2-dioxaborolan-2-yl)phenyl)-1H-indazole (260 mg, 0.78 mmol), Pd(PPh₃)₄ (75 mg, 0.065 mmol), 2N K₂CO₃ (1.6 mL) in dioxane (5 mL) was heated at 95° C. for hours. After the reaction finished, the reaction mixture was diluted by EtOAc, washed by sat. NaHCO₃, extracted by EtOAc, the organic phase was dried over MgSO₄, filtered, concentrated down and purified by silica gel column, eluting by 0-100% EtOAc in hexanes to give the product. LCMS-ESI⁺: calc'd for $C_{33}H_{36}BrN_3O_3S$: 634.2 (M+H⁺); Found: 634.1 (M+H⁺).

Preparation of (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate: The mixture of (S)-2-(7-bromo-5-methyl-2-(3-(1-methyl-1H-indazol-5-yl)phenyl)benzo[d]thiazol-6-yl)-2-tert-butoxyethyl pivalate (24 mg, 0.0379 mmol), 4-chlorophenylboronic acid (9 mg, 0.0568 mmol), 2N NaHCO₃ (100 µL), Pd(PPh₃)₄ (4 mg, 0.0038 mmol) in dioxane (2 mL) was heated at 120° C. for 3 hrs. The reaction mixture was diluted by EtOAc, washed by sat. NaHCO₃, extracted by EtOAc, the organic phase was dried over MgSO₄, filtered, concentrated down and purified by silica gel column, eluting by 0-100% EtOAc in hexanes to give the product. LCMS-ESI⁺: calc'd for $C_{39}H_{40}ClN_3O_3S$: 666.2 (M+H⁺); Found: 666.1 (M+H⁺).

Preparation of (S)-2-tert-butoxy-2-(7-(4-chlorophenyl)-5-methyl-2-(3-(1-methyl-1H-indazol-5-yl)phenyl)benzo[d]thiazol-6-yl)ethanol: The reaction mixture of (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate (10 mg, 0.015 mmol), 2N NaOH (150 µL) in THF/MeOH (1:1, 1 mL) was heated at 40° C. After reaction finished, the reaction mixture was diluted by EtOAc, washed by sat. NaHCO₃, extracted by EtOAc, the organic phase was dried over MgSO₄, filtered, concentrated down and purified by silica gel column, eluting by 0-100% EtOAc in hexanes to give the product. LCMS-ESI⁺: calc'd for $C_{34}H_{32}ClN_3O_2S$: 582.2 (M+H⁺); Found: 582.2 (M+H⁺).

Preparation of (S)-2-tert-butoxy-2-(7-(4-chlorophenyl)-5-methyl-2-(3-(1-methyl-1H-indazol-5-yl)phenyl)benzo[d]thiazol-6-yl)acetic acid: To the solution of (S)-2-tert-butoxy-2-(7-(4-chlorophenyl)-5-methyl-2-(3-(1-methyl-1H-indazol-5-yl)phenyl)benzo[d]thiazol-6-yl)ethanol (6 mg, 0.010 mmol) in wet acetonitrile (0.75 w % H₂O, 1 mL), was added stock solution of H₅IO₆/CrO₃ (0.439 M in wet acetonitrile, 150 µL) at 0° C. for ½ hour. The reaction mixture was filtered and purified by reverse phase HPLC, eluting by 0-100% acetonitrile in H₂O with 0.1% TFA give the product. LCMS-ESI⁺: calc'd for $C_{34}H_{30}ClN_3O_3S$: 596.2 (M+H⁺); Found: 596.2 (M+H⁺). ¹H NMR (300 MHz, CD₃OD): δ 8.24 (s, 1H), 7.95-7.98 (m, 2H), 7.88-7.50 (m, 10H), 5.17 (s, 1H), 4.01 (s, 3H), 2.52 (s, 3H), 0.88 (s, 9H).

Example 20

Method H: Preparation of (S)-2-tert-butoxy-2-(7-(4-chlorophenyl)-5-methyl-2-(2-(1-methyl-1H-indazol-5-yl)pyrimidin-4-yl)benzo[d]thiazol-6-yl)acetic acid (110)

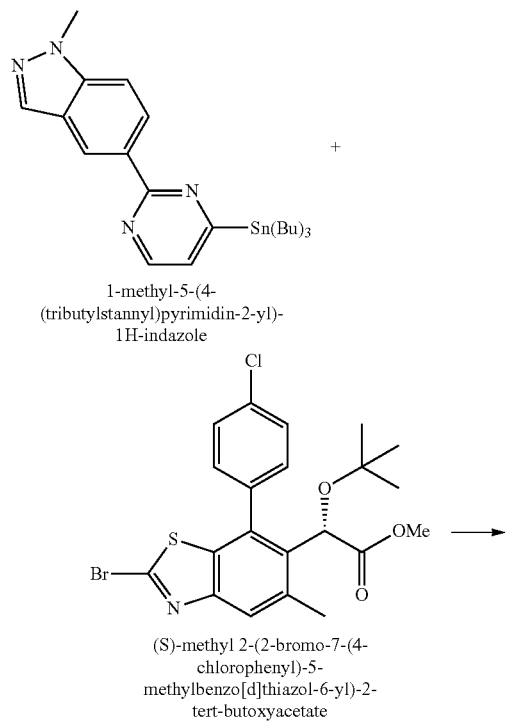

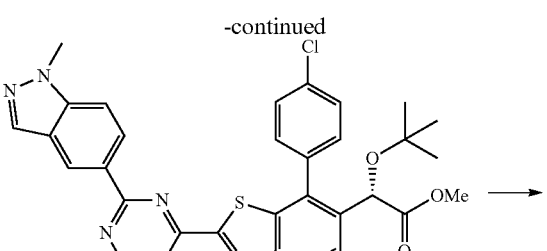

(S)-methyl 2-tert-butoxy-2-(7-(4-chlorophenyl)-5-methyl-2-(2-(1-methyl-1H-indazol-5-yl)pyrimidin-4-yl)benzo[d]thiazol-6-yl)-acetate

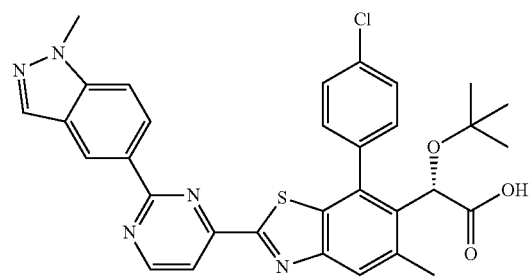

(S)-2-tert-butoxy-2-(7-(4-chlorophenyl)-5-methyl-2-(2-(1-methyl-1H-indazol-5-yl)pyrimidin-4-yl)benzo[d]thiazol-6-yl)-acetic acid
110

Preparation of (S)-methyl 2-tert-butoxy-2-(7-(4-chlorophenyl)-5-methyl-2-(2-(1-methyl-1H-indazol-5-yl)pyrimidin-4-yl)benzo[d]thiazol-6-yl)acetate: (S)-methyl 2-(2-bromo-7-(4-chlorophenyl)-5-methylbenzo[d]thiazol-6-yl)-2-tert-butoxyacetate (17.4 mg, 0.036 mmol), Pd(PPh₃)₄ (2.1 mg, 0.002 mmol), lithium chloride (2.3 mg, 0.054 mmol), and copper(I) iodide (1.0 mg, 0.005 mmol) were taken in a microwave vial and the vial was vacuum pumped and flushed with argon three times. To this mixture was added 1-methyl-5-(4-(tributylstannyl)pyrimidin-2-yl)-1H-indazole (9.0 mg, 0.018 mmol) in degassed 1,4-dioxane (0.5 mL). The reaction mixture was heated at 100° C. for 5 h, cooled, filtered through celite (ethyl acetate eluent), and concentrated. Purification by flash column chromatography on silica gel (hexanes/ethyl acetate eluent) provided the product. LCMS-ESI⁺: calc'd for $C_{33}H_{31}ClN_5O_3S$: 612.2 (M+H⁺); Found: 611.9 (M+H⁺).

Preparation of (S)-2-tert-butoxy-2-(7-(4-chlorophenyl)-5-methyl-2-(2-(1-methyl-1H-indazol-5-yl)pyrimidin-4-yl)benzo[d]thiazol-6-yl)acetic acid: To a solution of (S)-methyl 2-tert-butoxy-2-(7-(4-chlorophenyl)-5-methyl-2-(2-(1-methyl-1H-indazol-5-yl)pyrimidin-4-yl)benzo[d]thiazol-6-yl)acetate (4.8 mg, 0.008 mmol) in THF (0.3 mL) and methanol (0.3 mL) was added NaOH (0.3 mL of a 2N solution). The reaction mixture was heated at 45° C. for 6 h, cooled, filtered, and purified by reverse phase HPLC. Fractions containing the product were pooled and lyophilized to provide the TFA salt of the product. ¹H NMR (400 MHz, CD₃OD) δ 8.94 (d, J=5.1 Hz, 1H), 8.83 (s, 1H), 8.49 (dd, J=9.0, 1.4 Hz, 1H), 8.12 (s, 1H), 8.05 (d, J=5.1 Hz, 1H), 7.87 (s, 1H), 7.76-7.71 (m, 1H), 7.68-7.59 (m, 3H), 7.57 (d, J=8.9 Hz, 1H), 5.29 (s, 1H), 4.07

(s, 3H), 2.63 (s, 3H), 0.99 (s, 9H). LCMS-ESI⁺: calc'd for $C_{32}H_{29}ClN_5O_3S$: 598.2 (M+H⁺); Found: 598.3 (M+H⁺).

Example 21

Method I: Preparation of (S)-2-tert-butoxy-2-(7-(4-chlorophenyl)-5-methyl-2-(1-methyl-1H-pyrazolo[4,3-b]pyridin-6-yl)benzo[d]thiazol-6-yl)acetic acid (111)

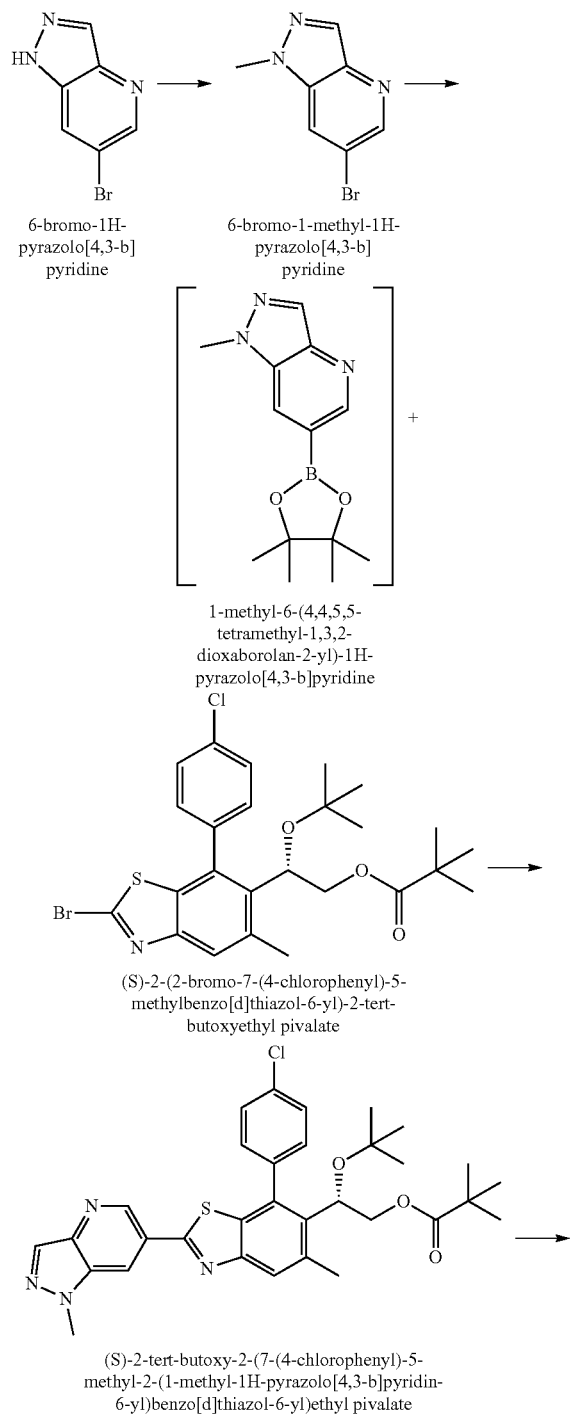

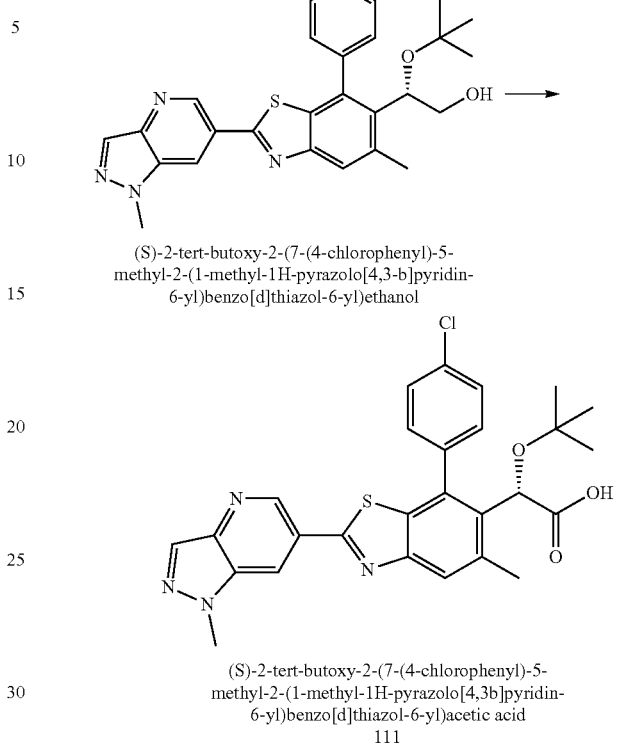

Preparation of 6-bromo-1-methyl-1H-pyrazolo[4,3-b]pyridine: To a solution of 6-bromo-1H-pyrazolo[4,3-b]pyridine (200 mg, 1.01 mmol) in DMF (5 mL) was added cesium carbonate (494 mg, 1.515 mmol). The reaction solution was stirred at room temperature for 5 minutes, iodomethane (215 mg, 1.515 mmol) was added. The reaction solution was stirred for 2 h and quenched with water. Volatiles were removed and the residue partitioned between ethyl acetate and water. The organic phase was washed with brine, dried (MgSO₄), filtered and concentrated to give crude product which was purified by chromatographic column to afford the desired product 6-bromo-1-methyl-1H-pyrazolo[4,3-b]pyridine. LCMS-ESI⁺: calc'd for $C_7H_6BrN_3$: 211.98 (M+H⁺); Found: 212.1 (M+H⁺).

Preparation of (S)-2-tert-butoxy-2-(7-(4-chlorophenyl)-5-methyl-2-(1-methyl-1H-pyrazolo[4,3-b]pyridine-6-yl)benzo[d]thiazol-6-yl)ethyl pivalate: To a solution of 6-bromo-1-methyl-1H-pyrazolo[4,3-b]pyridine (20 mg, 0.094 mmol) in dioxane (2 mL) was added bis(pinacolato)diboron (29 mg, 0.113 mmol), [1,1'-Bis(diphenylphosphino)ferrocene]dichloropalladium(II) complex with dichloromethane (8 mg, 0.0094 mmol), potassium acetate (19 mg, 0.189 mmol). The mixture was degassed and heated at 100° C. for 2 h. The mixture was cooled, and then added (S)-2-(2-bromo-7-(4-chlorophenyl)-5-methylbenzo[d]thiazol-6-yl)-2-tert-butoxyethyl pivalate (25 mg, 0.046 mmol), tetrakis(triphenylphosphine)palladium(0) (6 mg, 0.005 mmol), K₂CO₃ (33 mg, 0.23 mmol) and water (0.3 mL, degassed). The reaction mixture was heated at 90° C. for 1 h, cooled and partitioned between ethyl acetate and brine. The organic layer was separated, dried over Na₂SO₄, filtered and concentrated to give crude product which was purified by chromatographic column to afford the desired product. LCMS-ESI⁺: calc'd for $C_{32}H_{35}ClN_4O_3S$: 591.22 (M+H⁺); Found: 591.2 (M+H⁺).

Preparation of (S)-2-tert-butoxy-2-(7-(4-chlorophenyl)-5-methyl-2-(1-methyl-1H-pyrazolo[4,3-b]pyridin-6-yl)benzo[d]thiazol-6-yl)ethanol: To a solution of (S)-2-tert-butoxy-2-(7-(4-chlorophenyl)-5-methyl-2-(1-methyl-1H-pyrazolo[4,3-b]pyridine-6-yl)benzo[d]thiazol-6-yl)ethyl pivalate: (68 mg, 0.115 mmol) in THF/CH$_3$OH (1.5 mL/1.5 mL) was added 2N NaOH (0.57 mL, 1.15 mmol). The reaction mixture was heated at 45° C. for 2 h and cooled to rt. The reaction solution is quenched with saturated ammonium chloride solution and extracted with ethyl acetate. The organic solution is washed with water, brine, dried and concentrated to give crude product which was carried to next reaction without further purification. LCMS-ESI$^+$: calc'd for C$_{27}$H$_{27}$ClN$_4$O$_2$S: 507.16 (M+H$^+$); Found: 507.2 (M+H$^+$).

Preparation of (S)-2-tert-butoxy-2-(7-(4-chlorophenyl)-5-methyl-2-(1-methyl-1H-pyrazolo[4,3-b]pyridin-6-yl)benzo[d]thiazol-6-yl)acetic acid: To a solution of (S)-2-tert-butoxy-2-(7-(4-chlorophenyl)-5-methyl-2-(1-methyl-1H-pyrazolo[4,3-b]pyridin-6-yl)benzo[d]thiazol-6-yl)ethanol (50 mg, 0.099 mmol) in acetonitrile/water (2 mL/0.5 mL) was added CrO$_3$/H$_5$IO$_6$ (0.439M, 1.1 mL, 0.483 mmol) and CrO$_3$ (20 mg, 0.198 mmol). The reaction solution was stirred at room temperature for 1 h and quenched with 5% Na$_2$S$_2$O$_3$ solution. The mixture was extracted with ethyl acetate, washed with water and brine. The organic solution was dried and concentrated to give crude which was purified by reverse phase HPLC, eluting by 5-100% acetonitrile in H$_2$O with 0.1% TFA to give the desired product. LCMS-ESI$^+$: calc'd for C$_{27}$H$_{25}$ClN$_4$O$_3$S: 521.14 (M+H$^+$); Found: 521.2 (M+H$^+$), $^1$H NMR (400 MHz, CD$_3$OD) δ 9.20 (d, J=8 Hz, 1H), 8.67 (s, 1H), 8.24 (s, 1H), 7.88 (s, 1H), 7.71-7.59 (m, 4H), 5.27 (s, 1H), 4.16 (s, 3H), 2.62 (s, 3H), 0.98 (s, 9H).

Example 22
Method J: Preparation of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetic acid (112)

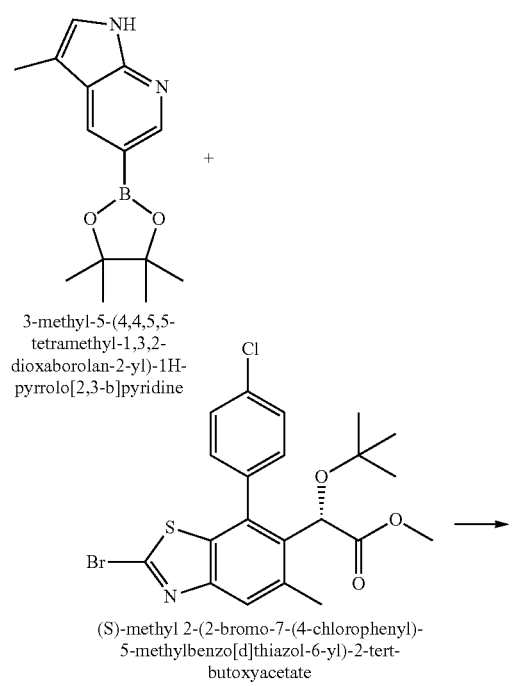

3-methyl-5-(4,4,5,5-tetramethyl-1,3,2-dioxaborolan-2-yl)-1H-pyrrolo[2,3-b]pyridine (S)-methyl 2-(2-bromo-7-(4-chlorophenyl)-5-methylbenzo[d]thiazol-6-yl)-2-tert-butoxyacetate

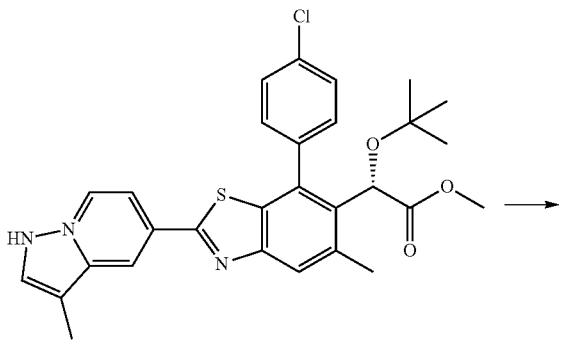

(S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate

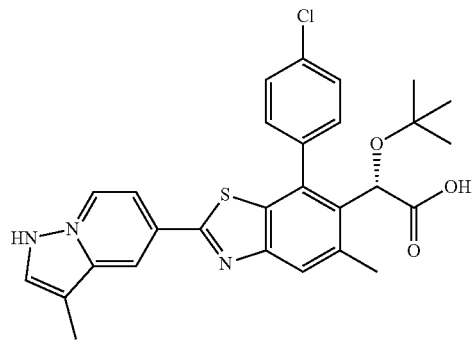

(S)-2-tert-butoxy-2-(7-(4-chlorophenyl)-5-methyl-2-(3-methyl-1H-pyrrolo[2,3-b]pyridin-5-yl)benzo[d]thiazol-6-yl)acetic acid
112

Preparation of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate: To a solution of (S)-methyl-5-(4,4,5,5-tetramethyl-1,3,2-dioxaborolan-2-yl)-1H-pyrrolo[2,3-b]pyridine (22 mg, 0.085 mmol) and (S)-methyl 2-(2-bromo-7-(4-chlorophenyl)-5-methylbenzo[d]thiazol-6-yl)-2-tert-butoxyacetate (20 mg, 0.041 mmol) in dioxane (1.2 mL, degassed) was added tetrakis(triphenylphosphine)palladium(0) (2.4 mg, 0.00207 mmol), K$_2$CO$_3$ (29 mg, 0.207 mmol) and water (0.4 mL, degassed). The reaction mixture was heated at 90° C. for 1 h, cooled and partitioned between ethyl acetate and brine. The organic layer was separated, dried over Na$_2$SO$_4$, filtered and concentrated to give crude which was purified by chromatographic column to afford the desired product. LCMS-ESI$^+$: calc'd for C$_{29}$H$_{28}$ClN$_3$O$_3$S: 534.16 (M+H$^+$); Found: 534.4 (M+H$^+$).

Preparation of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetic acid: To a solution of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate: (8 mg, 0.015 mmol) in THF/CH$_3$OH (0.5 mL/0.5 mL) was added 2N NaOH (75 μL, 0.15 mmol). The reaction mixture was heated at 50° C. for 2 h and the crude was purified by reverse phase HPLC, eluting by 0-100% acetonitrile in H2O with 0.1% TFA to give the product. LCMS-ESI$^+$: calc'd for C$_{28}$H$_{26}$ClN$_3$O$_3$S: 520.14 (M+H$^+$); Found: 520.2 (M+H$^+$). $^1$H NMR (400 MHz, CD$_3$OD): δ 8.86 (d, J=1 Hz, 1H), 8.57 (d, J=1 Hz, 1H), 7.84 (s, 1H), 7.71-7.26 (m, 5H), 5.26 (s, 1H), 2.62 (s, 3H), 2.36 (s, 3H), 0.94 (s, 9H).
Example 23
Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid (113a) and (S)-2-tert-butoxy-2-(7-(4-chlorophenyl)-5-methyl-2-(1-methyl-1H-indazol-5-yl)benzo[d]thiazol-6-yl)acetic acid (113b)
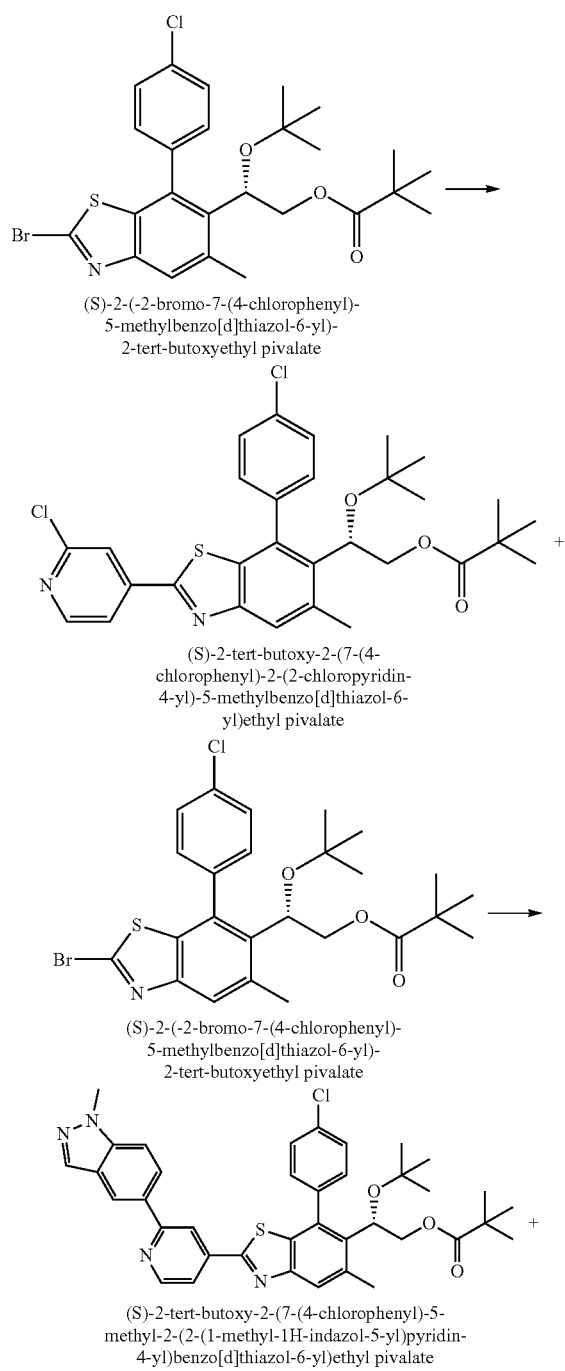
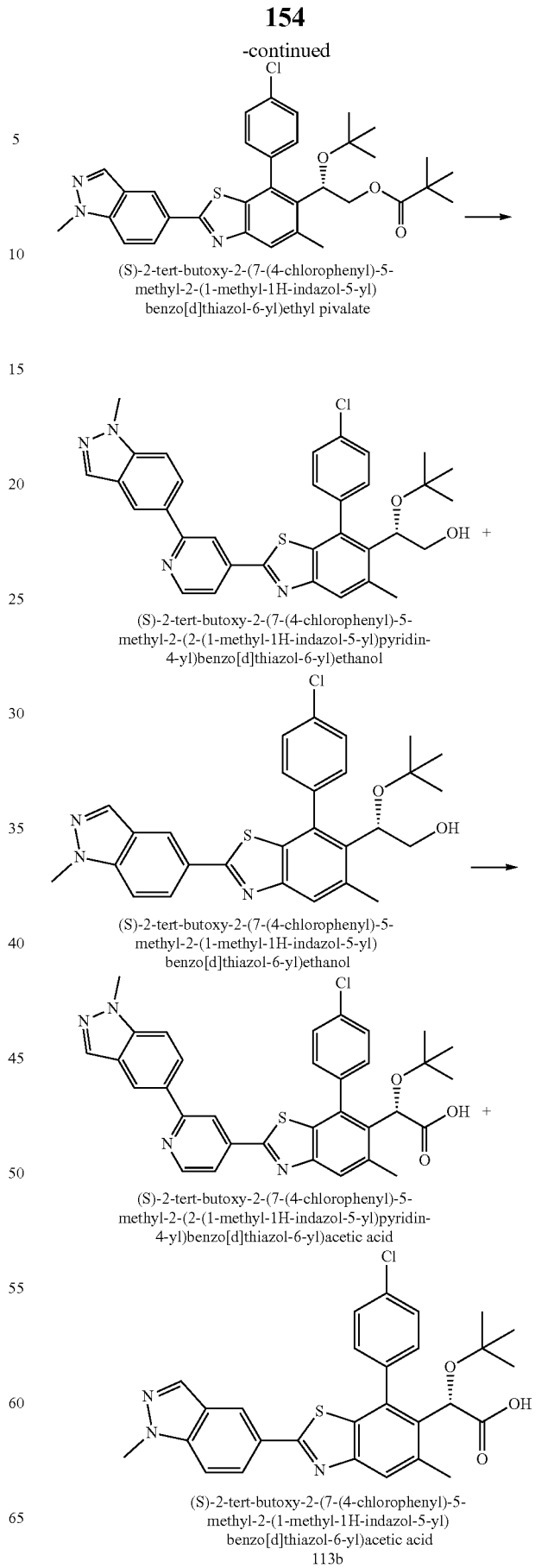

Preparation of (S)-2-tert-butoxy-2-(7-(4-chlorophenyl)-5-methyl-2-(2-(1-methyl-1H-indazol-6-yl)pyridin-4-yl)benzo[d]thiazol-6-yl)ethanol: A mixture of (S)-2-(2-bromo-7-(4-chlorophenyl)-5-methylbenzo[d]thiazol-6-yl)-2-tert-butoxyethyl pivalate (0.190 g, 0.35 mmol), 2-chloropyridin-4-ylboronic acid (0.66 g, 0.42 mmol), Pd(PPh$_3$)$_4$ (0.020 g, 0.0175, aq. 2M potassium carbonate solution (0.7 mL, 1.4 mmol) in degassed dioxane (2.0 mL) was heated at 90° C. for 3 hr. LC/MS indicated a 1.5:1 ratio of (S)-2-tert-butoxy-2-(7-(4-chlorophenyl)-2-(2-chloropyridin-4-yl)-5-methylbenzo[d]thiazol-6-yl)ethyl pivalate to (S)-2-(2-bromo-7-(4-chlorophenyl)-5-methylbenzo[d]thiazol-6-yl)-2-tert-butoxyethyl pivalate. Reaction mixture was used in next step without further purification.

(S)-2-tert-butoxy-2-(7-(4-chlorophenyl)-2-(2-chloropyridin-4-yl)-5-methylbenzo[d]thiazol-6-yl)ethyl pivalate: LCMS-ESI$^+$: calc'd for C$_{30}$H$_{33}$Cl$_2$N$_2$O$_3$S: 571.2 (M+H$^+$); found: 571.2 (M+H$^+$).

(S)-2-(2-bromo-7-(4-chlorophenyl)-5-methylbenzo[d]thiazol-6-yl)-2-tert-butoxyethyl pivalate: LCMS-ESI$^+$: calc'd for C$_{25}$H$_{29}$BrClNO$_3$S: 538.1, 540.1, and 542.1.1 (M+H$^+$); found: 538.2, 540.2, and 542.2 (M+H$^+$).

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate and (S)-2-tert-butoxy-2-(7-(4-chlorophenyl)-5-methyl-2-(1-methyl-1H-indazol-5-yl)benzo[d]thiazol-6-yl)ethyl pivalate: One-half of above reaction mixture containing S)-2-tert-butoxy-2-(7-(4-chlorophenyl)-2-(2-chloropyridin-4-yl)-5-methylbenzo[d]thiazol-6-yl)ethyl pivalate to (S)-2-(2-bromo-7-(4-chlorophenyl)-5-methylbenzo[d]thiazol-6-yl)-2-tert-butoxyethyl pivalate (1.5:1 ratio) was telescoped into the subsequent reaction. 1-Methyl-1H-indazol-5-ylboronic acid was added to the previous reaction mixture and reaction continued was heated at 120° C. for 30 minutes to give (S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate and (S)-2-tert-butoxy-2-(7-(4-chlorophenyl)-5-methyl-2-(1-methyl-1H-indazol-5-yl)benzo[d]thiazol-6-yl)ethyl pivalate.

(S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate: LCMS-ESI$^+$: calc'd for C$_{38}$H$_{40}$ClN$_4$O$_3$S: 667.2 (M+H$^+$); found: 667.4 (M+H$^+$).

(S)-2-tert-butoxy-2-(7-(4-chlorophenyl)-5-methyl-2(1-methyl-1H-indazol-5-yl)benzo[d]thiazol-6-yl)ethyl pivalate: LCMS-ESI$^+$: calc'd for C$_{33}$H$_{36}$ClN$_3$O$_3$S: 590.2 (M+H$^+$); found: 590.2 (M+H$^+$).

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)ethanol and (S)-2-tert-butoxy-2-(7-(4-chlorophenyl)-5-methyl-2-(1-methyl-1H-indazol-5-yl)benzo[d]thiazol-6-yl)ethanol: (S)-2-tert-butoxy-2-(7-(4-chlorophenyl)-5-methyl-2-(2-(1-methyl-1H-indazol-6-yl)pyridin-4-yl)benzo[d]thiazol-6-yl)ethyl pivalate and (S)-2-tert-butoxy-2-(7-(4-chlorophenyl)-5-methyl-2-(1-methyl-1H-indazol-5-yl)benzo[d]thiazol-6-yl)ethyl pivalate was telescoped into the subsequent reaction. To the previous reaction mixture, methanol and 2M NaOH were added and reaction mixture was heated at 55° C. overnight. Reaction mixture was cooled to rt, diluted with ethyl acetate and washed with brine. The organic layer was dried (MgSO$_4$), filtered, concentrated and purified by CombiFlash (Hex/EtOAc) to give (S)-2-tert-butoxy-2-(7-(4-chlorophenyl)-5-methyl-2-(2-(1-methyl-1H-indazol-5-yl)pyridin-4-yl)benzo[d]thiazol-6-yl)ethanol. LCMS-ESI$^+$: calc'd for C$_{33}$H$_{32}$ClN$_4$O$_2$S: 583.2 (M+H$^+$); found: 583.2 (M+H$^+$).

(S)-2-tert-butoxy-2-(7-(4-chlorophenyl)-5-methyl-2-(1-methyl-1H-indazol-5-yl)benzo[d]thiazol-6-yl)ethanol was also isolated. LCMS-ESI$^+$: calc'd for C$_{28}$H$_{29}$ClN$_3$O$_2$S: 506.2 (M+H$^+$); found: 506.2 (M+H$^+$).

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.6 mL) was added to a solution of (S)-2-tert-butoxy-2-(7-(4-chlorophenyl)-5-methyl-2-(2-(1-methyl-1H-indazol-6-yl)pyridin-4-yl)benzo[d]thiazol-6-yl)ethanol (25 mg, 0.049 mmol) in ACN (3 mL) at room temperature and stirred for one hour. The reaction mixture was quenched with saturated Na$_2$SO$_3$ solution and extracted with EtOAc. The organic layer was dried (MgSO$_4$), filtered, concentrated and purified by reverse phase HPLC (H$_2$O/ACN+0.1% TFA) to give the desired product after lyophilization. LCMS-ESI$^+$: calc'd for C$_{33}$H$_{30}$ClN$_4$O$_3$S: 597.2 (M+H$^+$); found: 597.2, 599.2. $^1$H NMR (400 MHz, CD$_3$OD) δ 8.72 (d, J=5.3 Hz, 1H), 8.46 (s, 1H), 8.43 (s, 1H), 8.14-8.08 (m, 2H), 7.94-7.87 (m, 2H), 7.73-7.63 (m, 2H), 7.61-7.54 (m, 3H), 5.26 (s, 1H), 4.10 (s, 3H), 2.63 (s, 3H), 0.97 (s, 9H).

The preparation of (S)-2-tert-butoxy-2-(7-(4-chlorophenyl)-5-methyl-2-(1-methyl-1H-indazol-5-yl)benzo[d]thiazol-6-yl)acetic acid (114b) followed the procedure described above for (S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid. LCMS-ESI$^+$: calc'd for C$_{33}$H$_{30}$ClN$_4$O$_3$S: 520.05 (M+H$^+$); found: 520.2, 522.1. $^1$H NMR (400 MHz, CD$_3$OD) δ 8.38 (s, 1H), 8.09 (d, J=11.2 Hz, 2H), 7.78 (s, 1H), 7.68 (d, J=8.7 Hz, 1H), 7.63 (d, J=8.9 Hz, 1H), 7.60-7.53 (m, 3H), 5.24 (s, 1H), 4.08 (s, 3H), 2.59 (s, 3H), 0.97 (s, 9H).

Example 24

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)acetic acid (114)

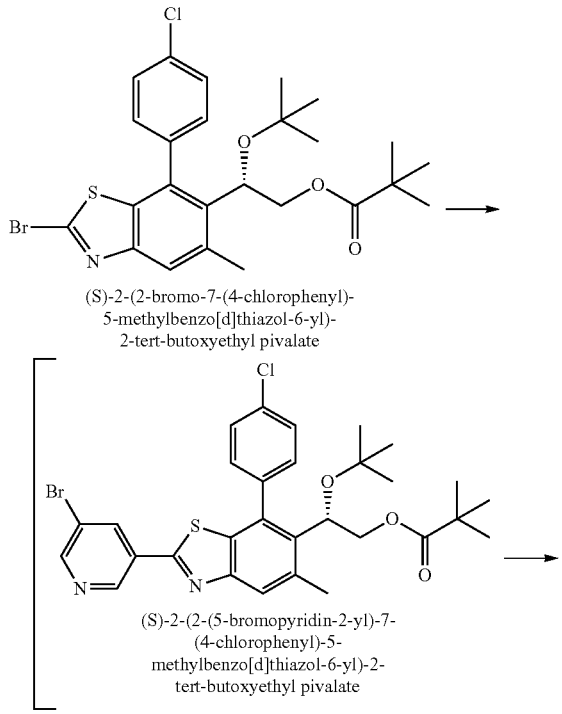

(S)-2-(2-bromo-7-(4-chlorophenyl)-5-methylbenzo[d]thiazol-6-yl)-2-tert-butoxyethyl pivalate (S)-2-(2-(5-bromopyridin-2-yl)-7-(4-chlorophenyl)-5-methylbenzo[d]thiazol-6-yl)-2-tert-butoxyethyl pivalate

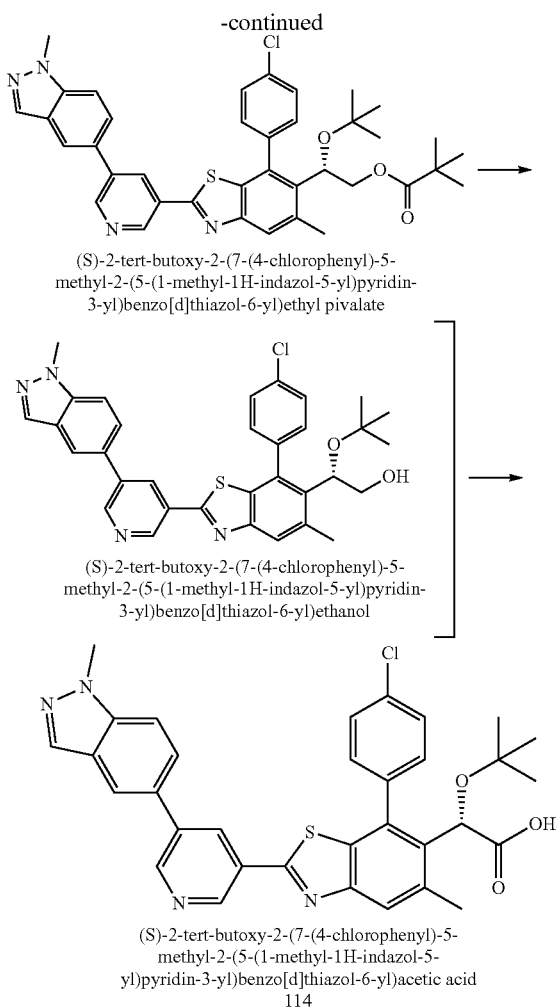

(S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate (S)-2-tert-butoxy-2-(7-(4-chlorophenyl)-5-methyl-2-(5-(1-methyl-1H-indazol-5-yl)pyridin-3-yl)benzo[d]thiazol-6-yl)ethanol (S)-2-tert-butoxy-2-(7-(4-chlorophenyl)-5-methyl-2-(5-(1-methyl-1H-indazol-5-yl)pyridin-3-yl)benzo[d]thiazol-6-yl)acetic acid
114

Preparation of (S)-2-(2-(5-bromopyridin-3-yl)-7-(4-chlorophenyl)-5-methylbenzo[d]thiazol-6-yl)-2-tert-butoxyethyl pivalate: A mixture of (S)-2-(2-bromo-7-(4-chlorophenyl)-5-methylbenzo[d]thiazol-6-yl)-2-tert-butoxyethyl pivalate (0.134 g, 0.25 mmol), 3-bromo-pyridin-5-ylboronic acid (0.55 g, 0.27 mmol), Pd(PPh$_3$)$_4$ (0.014 g, 0.013 mmol), aq. 2M potassium carbonate solution (0.5 mL, 1.0 mmol) in degassed dioxane (2.0 mL) was heated in microwave at 80° C. for 30 minutes to give (S)-2-(2-(5-bromopyridin-3-yl)-7-(4-chlorophenyl)-5-methylbenzo[d]thiazol-6-yl)-2-tert-butoxyethyl pivalate. LCMS-ESI$^+$: calc'd for C$_{30}$H$_{32}$BrClN$_2$O$_3$S: 617.1 (M+H$^+$); found: 617.2 (M+H$^+$).

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate: (S)-2-(2-(5-bromopyridin-3-yl)-7-(4-chlorophenyl)-5-methylbenzo[d]thiazol-6-yl)-2-tert-butoxyethyl pivalate was telescoped into the subsequent reaction. 1-Methyl-1H-indazol-5-ylboronic acid (0.024 g, 0.14 mmol) was added to the one-half of the previous reaction mixture and reaction heated in microwave at 115° C. for 30 minutes. Reaction mixture was portioned between ethyl acetate and H$_2$O, the organic layer removed and concentrated to give (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate. LCMS-ESI$^+$: calc'd for C$_{38}$H$_{40}$ClN$_4$O$_3$S: 667.2 (M+H$^+$); found: 667.3 (M+H$^+$).

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)ethanol: To a solution of (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate from above reaction was added THF:MeOH (1:1, 2 mL) and 2M NaOH (0.5 mL) were added and reaction mixture was heated at 55° C. for 3 h. Reaction mixture was cooled to rt, diluted with ethyl acetate and washed with saturated ammonium chloride solution. The organic layer was dried (MgSO$_4$), filtered, concentrated and purified by CombiFlash (EtOAC/Hex) to give (S)-2-tert-butoxy-2-(7-(4-chlorophenyl)-5-methyl-2-(5-(1-methyl-1H-indazol-5-yl)pyridin-3-yl)benzo[d]thiazol-6-yl)ethanol (15 mg). LCMS-ESI$^+$: calc'd for C$_{33}$H$_{32}$ClN$_4$O$_2$S: 583.2 (M+H$^+$); found: 583.3 (M+H$^+$).

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.3 mL) was added to a solution of (S)-2-tert-butoxy-2-(7-(4-chlorophenyl)-5-methyl-2-(2-(1-methyl-1H-indazol-6-yl)pyridin-5-yl)benzo[d]thiazol-6-yl)ethanol (15 mg, 0.027 mmol) in 0.75% H$_2$O in ACN (3 mL). The reaction mixture was stirred at rt for 45 minutes, quenched with saturated Na$_2$SO$_3$ solution and extracted with EtOAc. The organic layer was dried (MgSO$_4$), filtered, concentrated and purified by reverse phase HPLC (H$_2$O/ACN+0.1% TFA) to give the desired product after lyophilization. LCMS-ESI$^+$: calc'd for C$_{33}$H$_{30}$ClN$_4$O$_3$S: 597.2 (M+H$^+$); found: 597.2, 599.2. $^1$H NMR (400 MHz, CD$_3$OD) δ 9.13 (s, 1H), 8.98 (s, 1H), 8.67 (s, 1H), 8.16 (s, 1H), 8.12 (s, 1H), 7.92 (s, 1H), 7.83 (dd, J=8.8, 1.6 Hz, 1H), 7.73 (dd, J=13.4, 5.2 Hz, 2H), 7.60 (d, J=8.0 Hz, 3H), 5.27 (s, 1H), 4.11 (s, 3H), 2.63 (s, 3H), 0.98 (s, 9H) (115).

Example 25

Preparation of (S)-2-(2-(2-(1H-indazol-5-yl)pyridin-4-yl)-7-(4-chlorophenyl)-5-methylbenzo[d]thiazol-6-yl)-2-tert-butoxyacetic acid (115)

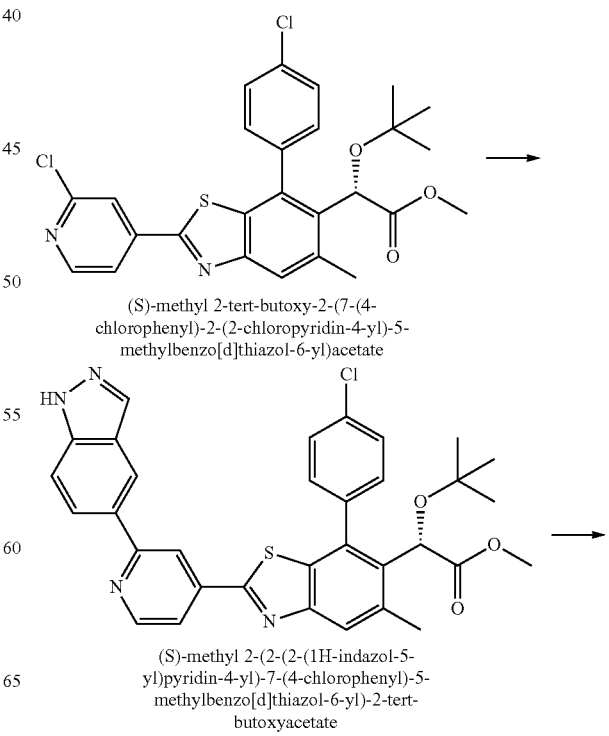

(S)-methyl 2-tert-butoxy-2-(7-(4-chlorophenyl)-2-(2-chloropyridin-4-yl)-5-methylbenzo[d]thiazol-6-yl)acetate (S)-methyl 2-(2-(2-(1H-indazol-5-yl)pyridin-4-yl)-7-(4-chlorophenyl)-5-methylbenzo[d]thiazol-6-yl)-2-tert-butoxyacetate -continued

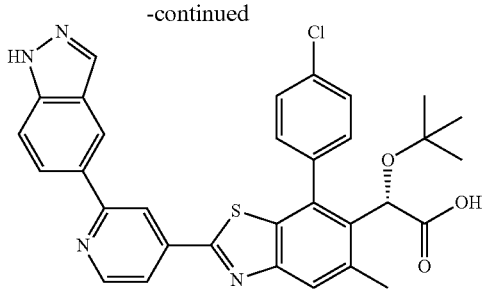

(S)-2-(2-(2-(1H-indazol-5-yl)pyridin-4-yl)-7-(4-chlorophenyl)-5-methylbenzo[d]thiazol-6-yl)-2-tert-butoxyacetic acid
115

Preparation of (S)-methyl 2-(2-(2-(1H-indazol-5-yl)pyridin-4-yl)-7-(4-chlorophenyl)-5-methylbenzo[d]thiazol-6-yl)-2-tert-butoxyacetate: A microwave tube was charged with (S)-methyl 2-tert-butoxy-2-(7-(4-chlorophenyl)-2-(2-chloropyridin-4-yl)-5-methylbenzo[d]thiazol-6-yl)acetate (25.0 mg, 48.5 µmol), 5-(4',4',5',5'-tetramethyl-1',3',2'-dioxaborolan-2'-yl)-1H-indazole (14.2 mg, 58.2 µmol, Pd(PPh$_3$)$_4$ (5.6 mg, 4.86 µmol), K$_2$CO$_3$ (27 mg, 0.19 mmol), H$_2$O (400 µL), and dioxane (1.6 mL). The reaction was sealed and heated to 110° C. The reaction failed to reach completion during the next 2 h (boronate ester was fully consumed (LCMS analysis), yet (S)-methyl 2-tert-butoxy-2-(7-(4-chlorophenyl)-2-(2-chloropyridin-4-yl)-5-methylbenzo[d]thiazol-6-yl)acetate remained.). The reaction was cooled to 23° C. and charged with more 5-(4',4',5',5'-tetramethyl-1',3',2'dioxaborolan-2'-yl)-1H-indazole (10 mg, 41 µmol). Heating to 110° C. was continued. Reaction progressed further, but was still incomplete after 1 h. Again, the reaction was cooled to 23° C. and this time charged with 1H-indazole-5-boronic acid (20 mg, 120 mop and K$_2$CO$_3$ (15 mg, 0.11 mmol); heating to 110° C. was resumed. Reaction reached completion in 1 h. The crude product (S)-methyl 2-(2-(2-(1H-indazol-5-yl)pyridin-4-yl)-7-(4-chlorophenyl)-5-methylbenzo[d]thiazol-6-yl)-2-tert-butoxyacetate was detected in solution. The solution was used crude in the next reaction. LCMS-ESI$^+$: calc'd for C$_{33}$H$_{29}$ClN$_4$O$_3$S: 597.2 and 599.2 (M+H$^+$); found: 597.3 and 599.3 (M+H$^+$).

Preparation of (S)-2-(2-(2-(1H-indazol-5-yl)pyridin-4-yl)-7-(4-chlorophenyl)-5-methylbenzo[d]thiazol-6-yl)-2-tert-butoxyacetic acid: The solution of crude (S)-methyl 2-(2-(2-(1H-indazol-5-yl)pyridin-4-yl)-7-(4-chlorophenyl)-5-methylbenzo[d]thiazol-6-yl)-2-tert-butoxyacetate from the previous reaction was treated directly with LiOH monohydrate (60 mg, 1.42 mmol), H$_2$O (500 µL), and MeOH (500 µL). The reaction was heated to 50° C. for 15 h. The reaction failed to reach completion (LCMS analysis). The reaction was then heated to 100° C. for 30 min and reached completion. The system was cooled to 23° C. and filtered (0.45 micron Teflon® filter). The filtrate was purified directly on a C-18 Gemini column using a Gilson liquid handler (Eluent H$_2$O/CH$_3$CN gradient with both mobile phase components spiked 0.1% v/v with TFA). The title compound was obtained as a mono-trifluoroacetic acid salt. LCMS-ESI$^+$: calc'd for C$_{32}$H$_{27}$ClN$_4$O$_3$S: 583.2 and 585.2 (M+H$^+$); Found: 583.3 and 585.3 (M+H$^+$). $^1$H NMR (400 MHz, CD$_3$OD) S: 8.78 (d, J=5.5 Hz, 1H), 8.58 (s, 1H), 8.51 (s, 1H), 8.22 (s, 1H), 8.11 (dd, J=8.6, 1.2 Hz, 1H), 8.04 (dd, J=5.4, 1.2 Hz, 1H), 7.99 (s, 1H), 7.74-7.70 (m, 2H), 7.65-7.60 (m, 3H), 5.23 (s, 1H), 2.65 (s, 3H), 0.99 (s, 9H).

Example 26

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)acetic acid (116)

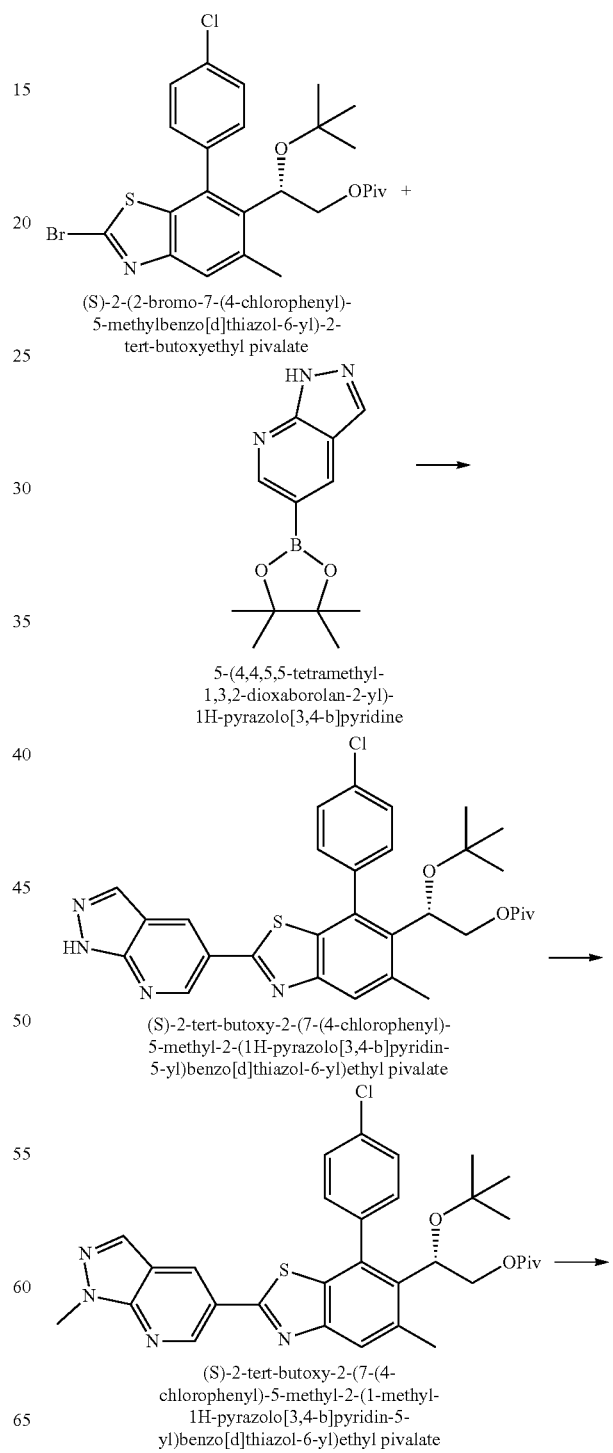

-continued

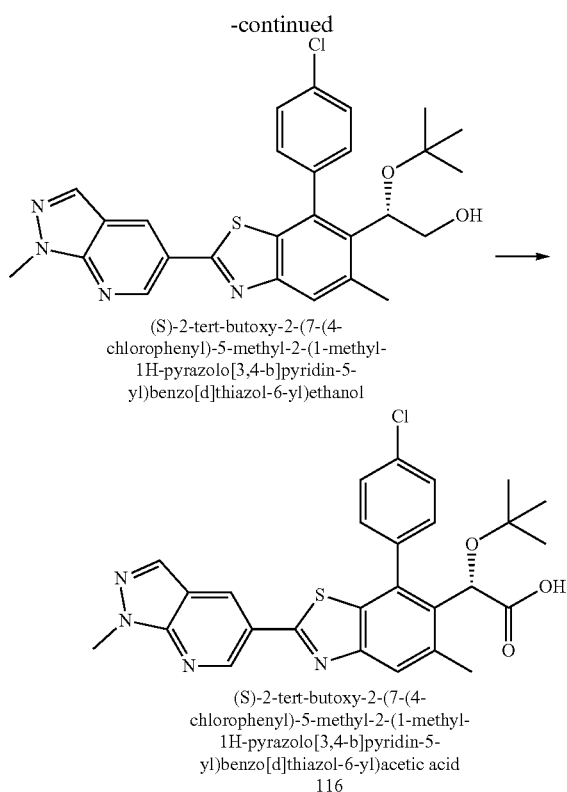

(S)-2-tert-butoxy-2-(7-(4-chlorophenyl)-5-methyl-2-(1-methyl-1H-pyrazolo[3,4-b]pyridin-5-yl)benzo[d]thiazol-6-yl)ethanol (S)-2-tert-butoxy-2-(7-(4-chlorophenyl)-5-methyl-2-(1-methyl-1H-pyrazolo[3,4-b]pyridin-5-yl)benzo[d]thiazol-6-yl)acetic acid 116

Preparation of (S)-2-tert-butoxy-2-(7-(4-chlorophenyl)-5-methyl-2-(1H-pyrazolo[3,4-b]pyridin-5-yl)benzo[d]thiazol-6-yl)ethyl pivalate: To a solution of (S)-2-(2-bromo-7-(4-chlorophenyl)-5-methylbenzo[d]thiazol-6-yl)-2-tert-butoxyethyl pivalate (51 mg, 0.095 mmol) and 5-(4,4,5,5-tetramethyl-1,3,2-dioxaborolan-2-yl)-1H-pyrazolo[3,4-b]pyridine (28 mg, 0.123 mmol) in degassed 1,4-dioxane (250 µL) and water (25 µL) was added aqueous K$_2$CO$_3$ (95 µL of a 2.0 M solution) and tetrakis(triphenylphosphine)palladium (0) (6 mg, 0.005 mmol). The reaction mixture was heated at 100° C. for 6 h, cooled and partitioned between ethyl acetate and brine. The organic layer was separated, dried over Na$_2$SO$_4$ and concentrated. The crude material was used without any further purification. LCMS-ESI$^+$: calc'd for C$_{31}$H$_{34}$ClN$_4$O$_3$S: 577.2 (M+H$^+$); Found: 577.3 (M+H$^+$).

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethyl pivalate: To a solution of the crude material from the previous reaction (assume 0.095 mmol) in dry DMF (1.0 mL) was added Cs$_2$CO$_3$ (60 mg, 0.185 mmol) at room temperature. After 15 min, neat methyl iodide (12 µL, 0.19 mmol) was added and the reaction was allowed to stir for 6 h. The reaction was then partitioned between ethyl acetate and water and extracted. The organic layer was washed sequentially with aqueous 5% LiCl, brine, dried over Na$_2$SO$_4$ and concentrated to give the desired product. Purification by flash column chromatography on silica gel using 30% ethyl acetate in hexanes provided a pale foam (14 mg, 25% for two steps). LCMS-ESI$^+$: calc'd for C$_{32}$H$_{36}$ClN$_4$O$_3$S: 591.2 (M+H$^+$); Found: 591.3 (M+H$^+$).

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethanol: To a solution of compound (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethyl pivalate (14 mg, 0.024 mmol) in THF (0.50 mL) and MeOH (0.50 mL) was added aqueous NaOH (0.10 mL of a 2 N solution). The reaction mixture was heated at 50° C. for 17 h, cooled, diluted with satd. aqueous NH$_4$Cl and extracted with ethyl acetate. The organic layer was dried and concentrated to give the desired product which was used without any further purification. LCMS-ESI$^+$: calc'd for C$_{27}$H$_{28}$ClN$_4$O$_2$S: 507.2 (M+H$^+$); 507.2 (M+H$^+$).

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)acetic acid: To a solution of (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethanol from previous reaction (assume 0.024 mmol) in 25% water/acetonitrile (0.70 mL) was added sequentially, a stock solution of CrO$_3$/H$_5$IO$_6$ (296 µL, 0.439 M solution) and CrO$_3$ (3 mg, 0.030 mmol) at room temperature. The reaction was stirred for 1 h, diluted with acetonitrile, filtered and purified by reverse phase HPLC. Fractions containing product were pooled and evaporated to the desired product. LCMS-ESI$^+$: calc'd for C$_{27}$H$_{26}$ClN$_4$O$_3$S: 521.1 (M+H$^+$); 521.2 (M+H$^+$); $^1$H NMR (400 MHz, CD$_3$OD): δ 9.26 (d, J=1.9 Hz, 1H), 8.79 (d, J=1.9 Hz, 1H), 8.20 (s, 1H), 7.87 (s, 1H), 7.69 (d, J=9.4 Hz, 1H), 7.61-7.59 (m, 3H), 5.26 (s, 1H), 4.15 (s, 3H), 2.61 (s, 3H), 0.97 (s, 9H).

Example 27

Preparation of (S)-2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetic acid (117)

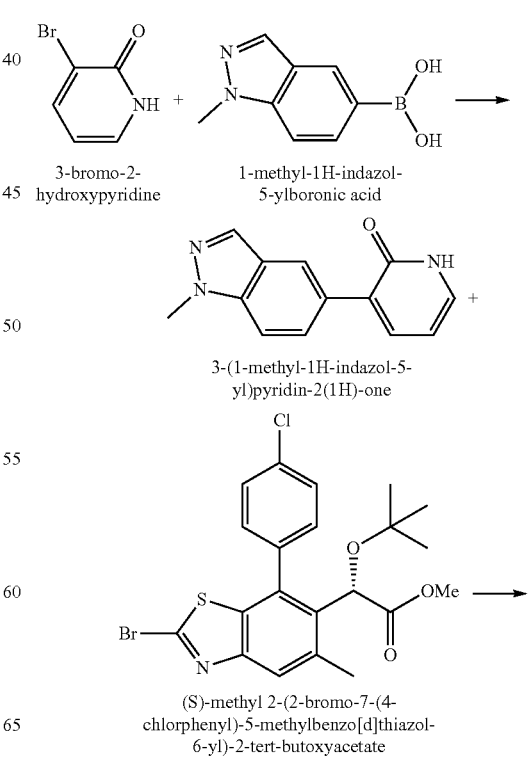

3-bromo-2-hydroxypyridine 1-methyl-1H-indazol-5-ylboronic acid 3-(1-methyl-1H-indazol-5-yl)pyridin-2(1H)-one (S)-methyl 2-(2-bromo-7-(4-chlorphenyl)-5-methylbenzo[d]thiazol-6-yl)-2-tert-butoxyacetate

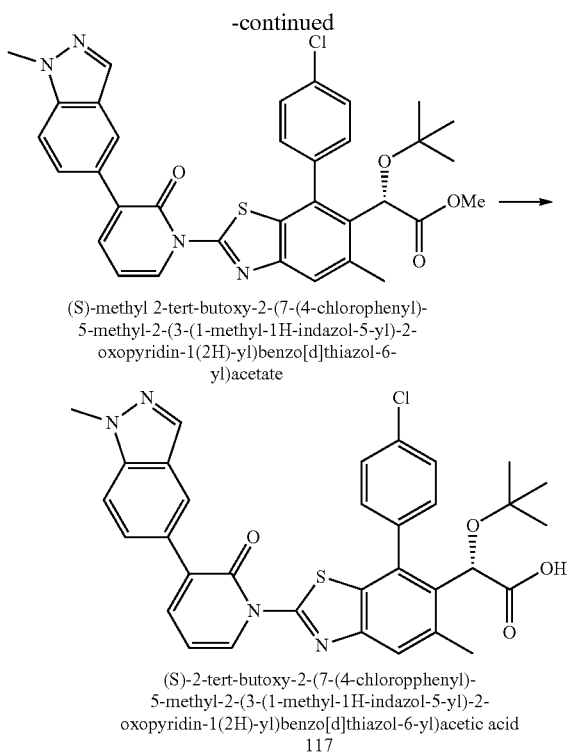

(S)-methyl 2-tert-butoxy-2-(7-(4-chlorophenyl)-
5-methyl-2-(3-(1-methyl-1H-indazol-5-yl)-2-
oxopyridin-1(2H)-yl)benzo[d]thiazol-6-
yl)acetate (S)-2-tert-butoxy-2-(7-(4-chloropphenyl)-
5-methyl-2-(3-(1-methyl-1H-indazol-5-yl)-2-
oxopyridin-1(2H)-yl)benzo[d]thiazol-6-yl)acetic acid
117

Preparation of 3-(1-methyl-1H-indazol-5-yl)pyridin-2 (1H)-one: The suspension of 3-bromo-2-hydroxypyridine (80 mg, 0.46 mmol), 1-methyl-1H-indazol-5-ylboronic acid (121 mg, 0.69 mmol) and sodium carbonate (146 mg, 1.38 mmol) in DMF (2.0 mL) and H$_2$O (0.4 mL) was degassed with N$_2$ for 5 minutes. To the mixture was added bis(triphenylphosphine)palladium (II) dichloride (67 mg, 0.09 mmol), and the resulting mixture was heated at 90° C. for 2 h. The reaction mixture was filtered and purified by reverse phase HPLC (Gemini, 5 to 100% ACN/H$_2$O+0.1% TFA) to give the product. LCMS-ESI$^+$ (m/z): [M+H]$^+$ calcd for C$_{13}$H$_{12}$N$_3$O: 226.25; Found: 226.2.

Preparation of (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetate: To a solution of 3-(1-methyl-1H-indazol-5-yl)pyridin-2(1H)-one (13.0 mg, 0.055 mmol), (S)-methyl 2-(2-bromo-7-(4-chlorophenyl)-5-methylbenzo[d]thiazol-6-yl)-2-tert-butoxyacetate (22 mg, 0.046 mmol), trans-N1,N2-dimethylcyclohexane-1,2-diamine (9 µL, 0.055 mmol) and potassium carbonate (13 mg, 0.091 mmol) in DMF (0.5 mL) was added copper(I) iodide (5.0 mg, 0.026 mmol). The mixture was degassed with N$_2$ for 5 minutes and then heated at 110° C. for 3 h. The mixture was then diluted with EtOAc, extracted with H$_2$O, brine, dried over Na$_2$SO$_4$, filtered and concentrated and purified by flash column chromatography (silica gel, 0 to 100% ethyl acetate/hexanes) to give the product. LCMS-ESI$^+$ (m/z): [M+H]$^+$ calcd for C$_{34}$H$_{32}$ClN$_4$O$_4$S: 627.18; Found: 627.2.

Preparation of (S)-2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetic acid: To a stirred solution of (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetate (12.6 mg, 0.020 mmol) in THF (1.2 mL) and methanol (0.5 mL) was added 1 M NaOH solution (0.3 mL, excess). The reaction mixture was stirred at 37° C. for 6 h. The reaction mixture was purified by reverse phase HPLC (Gemini, 5 to 100% ACN/H$_2$O+0.1% TFA) to give the product. LCMS-ESI$^+$ (m/z): [M+H]$^+$ calcd for C$_{33}$H$_{30}$ClN$_4$O$_4$S: 613.17; Found: 613.2; $^1$H-NMR: 400 MHz, (CD$_3$OD) δ 8.89 (dd, J=7.6, 2 Hz, 1H), 8.02 (s, 2H), 7.75 (s, 1H), 7.70-7.63 (m, 3H), 7.53-7.49 (m, 4H), 6.61 (t, J=7.2 Hz, 1H), 5.27 (s, 1H), 4.06 (s, 3H), 2.60 (s, 3H), 0.95 (s, 9H).

Example 28

Preparation of (S)-2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetic acid (118)

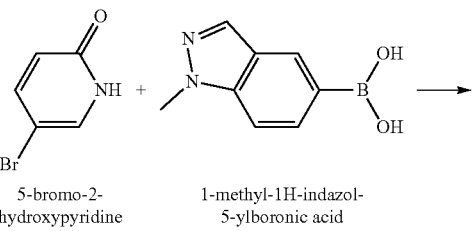

5-bromo-2-hydroxypyridine    1-methyl-1H-indazol-5-ylboronic acid

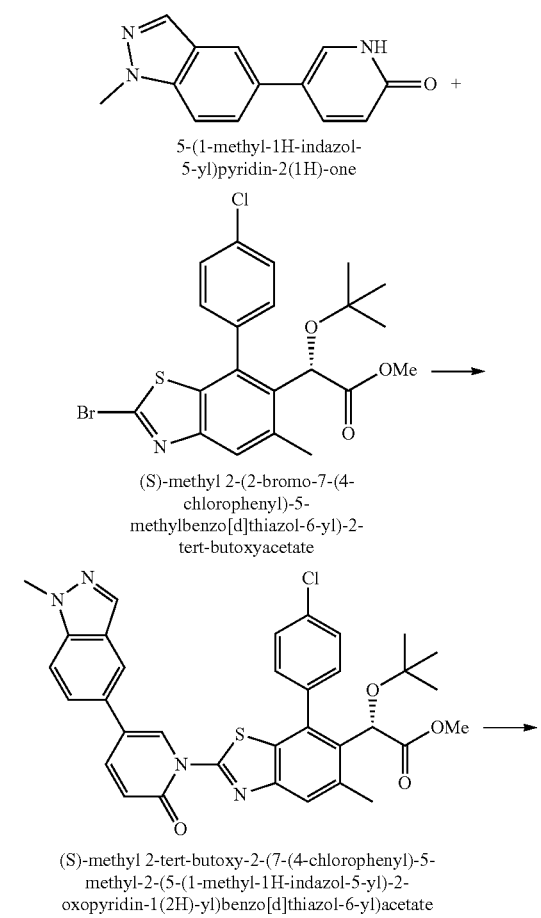

5-(1-methyl-1H-indazol-5-yl)pyridin-2(1H)-one (S)-methyl 2-(2-bromo-7-(4-chlorophenyl)-5-methylbenzo[d]thiazol-6-yl)-2-tert-butoxyacetate (S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate

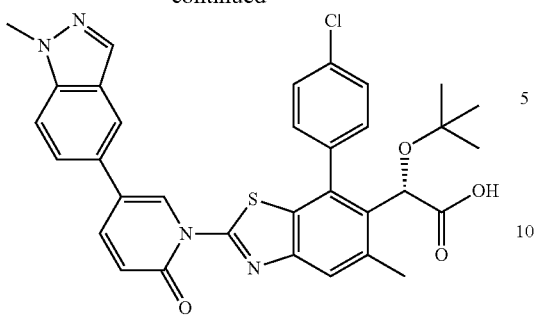

(S)-2-tert-butoxy-2-(7-(4-chlorophenyl)-5-
methyl-2-(5-(1-methyl-1H-indazol-5-yl)-2-
oxopyridin-1(2H)-yl)benzo[d]thiazol-6-yl)acetic acid
118

Preparation of 5-(1-methyl-1H-indazol-5-yl)pyridin-2 (1H)-one: The suspension of 5-bromo-2-hydroxypyridine (80 mg, 0.46 mmol), 1-methyl-1H-indazol-5-ylboronic acid (121 mg, 0.69 mmol) and 2N sodium carbonate solution (1.0 mL, 2 mmol) in DMF (2.1 mL) was degassed with $N_2$ for 5 minutes. To the mixture was added tetrakis(triphenylphosphine)palladium(0) (53 mg, 0.04 mmol), and the resulting mixture was heated at 80° C. overnight. The mixture was then diluted with $CH_2Cl_2$, extracted with $H_2O$, brine, dried over $Na_2SO_4$, filtered and concentrated and purified by reverse phase HPLC (Gemini, 5 to 100% ACN/$H_2O$+0.1% TFA) to give the product. LCMS-ESI$^+$ (m/z): [M+H]$^+$ calcd for $C_{13}H_{12}N_3O$: 226.25; Found: 226.3.

Preparation of (S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate: Compound (S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate was prepared following the procedure used to prepare (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetate of Example 27, except that 5-(1-methyl-1H-indazol-5-yl)pyridin-2(1H)-one was used instead of 3-(1-methyl-1H-indazol-5-yl)pyridin-2(1H)-one. LCMS-ESI$^+$ (m/z): [M+H]$^+$ calcd for $C_{34}H_{32}ClN_4O_4S$: 627.18; Found: 627.2.

Preparation of (S)-2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetic acid: Compound (S)-2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetic acid was prepared following the procedure used to (S)-2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetic acid of Example 27, except that (S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate was used instead of (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetate. $^1$H-NMR: 400 MHz, (CD$_3$OD) δ 9.07 (d, J=2.8 Hz, 1H), 8.04 (s, 1H), 7.97 (s, 1H), 7.93 (dd, J=9.2, 2.4 Hz, 1H), 7.69-7.62 (m, 4H), 7.55-7.51 (m, 3H), 6.72 (d, J=9.6 Hz, 1H), 5.25 (s, 1H), 4.09 (s, 3H), 2.56 (s, 3H), 0.96 (s, 9H); LCMS-ESI$^+$ (m/z): [M+H]$^+$ calcd for $C_{33}H_{30}ClN_4O_4S$: 613.17; Found: 613.2.

Example 29

Preparation of (2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)acetic acid (119)

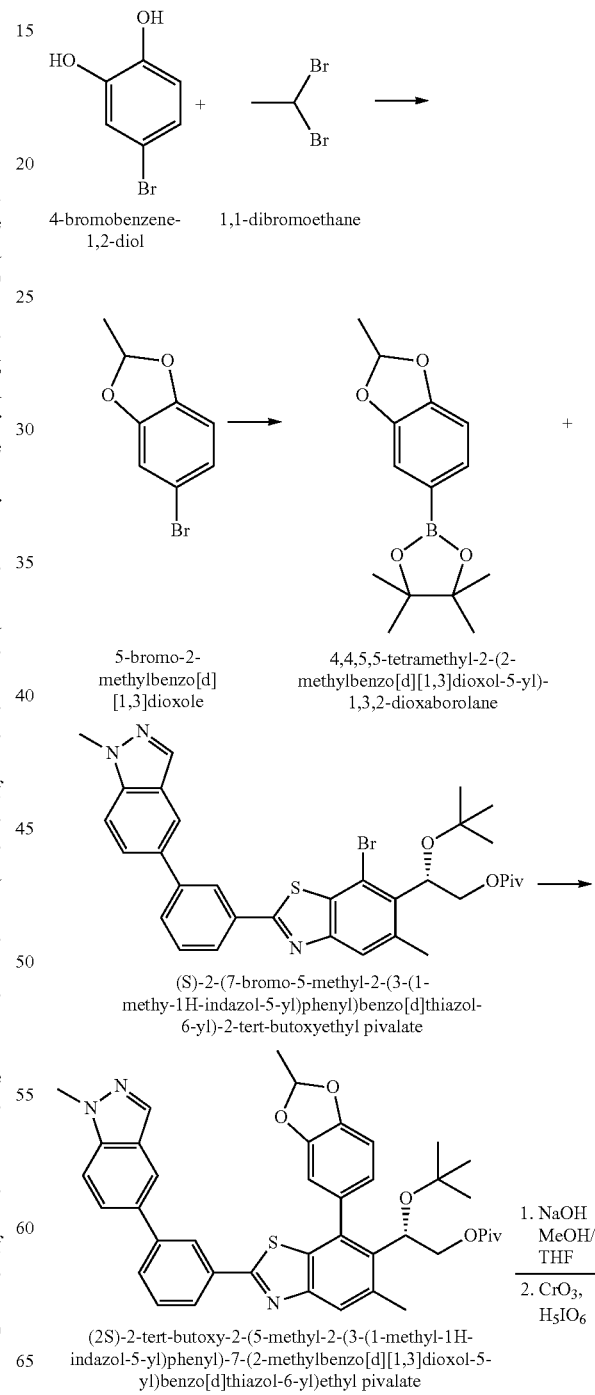

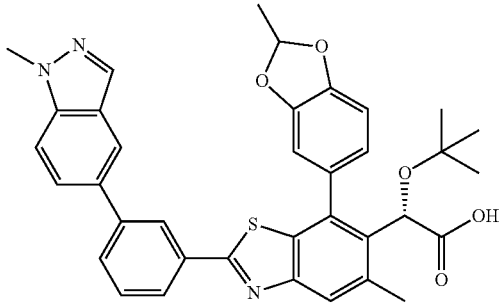

(2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)acetic acid
119

Preparation of 5-bromo-2-methylbenzo[d][1,3]dioxole: To a solution of 4-bromobenzene-1,2-diol (500 mg, 2.65 mmol) in acetone (4 mL) was added cesium carbonate (1.90 g, 5.82 mmol) and 1,1-dibromoethane (1.09 g, 5.82 mmol). The mixture was microwaved to 120° C. for 3 h. After cooling, the reaction mixture was diluted with EtOAc, extracted with H$_2$O, brine, dried over Na$_2$SO$_4$, filtered and concentrated and purified by flash column chromatography (silica gel, 0 to 10% ethyl acetate/hexanes) to give the product. $^1$H-NMR: 400 MHz, (CDCl$_3$) δ 6.93-6.89 (m, 2H), 6.63 (d, J=8 Hz, 1H), 6.27 (q, J=9.6 Hz, 1H), 1.67 (d, J=4.4 Hz, 3H).

Preparation of 4,4,5,5-tetramethyl-2-(2-methylbenzo[d][1,3]dioxol-5-yl)-1,3,2-dioxaborolane: The suspension of 5-bromo-2-methylbenzo[d][1,3]dioxole (36 mg, 0.17 mmol), bis(pinacolato)diboron (56 mg, 0.22 mmol) and potassium carbonate (50 mg, 0.51 mmol) in DME (0.4 mL) was degassed with N$_2$ for 5 minutes. To the mixture was added [1,1'-bis(diphenylphosphino)ferrocene]dichloropalladium (II) (12 mg, 0.02 mmol), and the resulting mixture was heated at 90° C. for 2 h. Concentrated in vacuo and then purified by flash column chromatography (silica gel, 0 to 50% ethyl acetate/hexanes) to give the product. $^1$H-NMR: 400 MHz, (CDCl$_3$) δ 7.34-7.32 (m, 1H), 7.19 (d, J=0.8 Hz, 1H), 6.78-6.75 (m, 1H), 6.29-6.23 (m, 1H), 1.68-1.64 (m, 3H), 1.32 (s, 12H).

Preparation of (2S)-2-tert-butoxy-2-(5-methyl-2-(3-(1-methyl-1H-indazol-5-yl)phenyl)-7-(2-methylbenzo[d][1,3] dioxol-5-yl)benzo[d]thiazol-6-yl)ethyl pivalate: To a solution of (S)-2-(7-bromo-5-methyl-2-(3-(1-methyl-1H-indazol-5-yl)phenyl)benzo[d]thiazol-6-yl)-2-tert-butoxyethyl pivalate (16 mg, 0.025 mmol) and 4,4,5,5-tetramethyl-2-(2-methylbenzo[d][1,3]dioxol-5-yl)-1,3,2-dioxaborolane (13 mg, 0.050 mmol) in 1,4-dioxane was added Pd(PPh$_3$)$_4$ (4 mg, 3.1×10$^{-3}$ mmol) and 2M K$_2$CO$_3$ (66 µL, 0.133 mmol). The reaction was degassed for 5 minutes with N$_2$ and then heated to 110° C. for 1 h. After cooling, the reaction mixture was diluted with EtOAc, extracted with saturated NaHCO$_3$, brine, dried over Na$_2$SO$_4$, filtered and concentrated and purified by flash column chromatography (silica gel, 0 to 10% ethyl acetate/hexanes) to give the product. LCMS-ESI+ (m/z): [M+H]+ calcd for C$_{41}$H$_{44}$N$_3$O$_5$S: 690.30; found: 690.4.

Preparation of (2S)-2-tert-butoxy-2-(5-methyl-2-(3-(1-methyl-1H-indazol-5-yl)phenyl)-7-(2-methylbenzo[d][1,3] dioxol-5-yl)benzo[d]thiazol-6-yl)acetic acid: prepared in a similar manner as (S)-2-tert-butoxy-2-(7-(4-chlorophenyl)-5-methyl-2-(3-(1-methyl-1H-indazol-5-yl)phenyl)benzo[d] thiazol-6-yl)acetic acid in Method G, except using (2S)-2-tert-butoxy-2-(5-methyl-2-(3-(1-methyl-1H-indazol-5-yl) phenyl)-7-(2-methylbenzo[d][1,3]dioxol-5-yl)benzo[d]thiazol-6-yl)ethyl pivalate instead of (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate. LCMS-ESI+ (m/z): [M+H]+ calcd for C$_{36}$H$_{34}$N$_3$O$_5$S: 620.2; Found: 620.3; $^1$H-NMR: 400 MHz, (CD$_3$OD) δ 8.34-8.32 (m, 1H), 8.08 (s, 2H), 8.00-7.94 (m, 1H), 7.85-7.84 (m, 3H), 7.66 (d, J=8.8 Hz, 1H), 7.59 (t, J=7.2 Hz, 1H), 7.17-7.11 (m, 1H), 7.06-7.00 (m, 1H), 6.97-6.94 (m, 1H), 6.43-6.37 (m, 1H), 5.46-5.36 (m, 1H), 4.10 (s, 3H), 2.60 (s, 3H), 1.74-1.68 (m, 3H), 0.99 (s, 9H).

Example 30

Preparation of (S)-2-tert-butoxy-2-(7-(4-chlorophenyl)-2-(3-(1,5-dimethyl-1H-pyrazol-4-yl)phenyl)-5-methylbenzo[d]thiazol-6-yl)acetic acid (120)

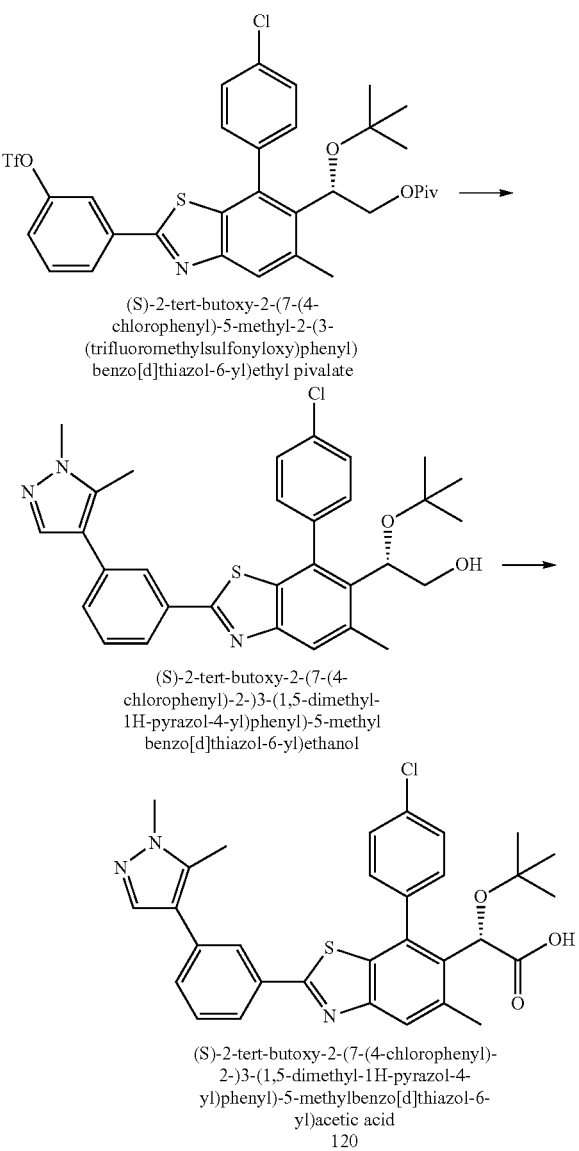

(S)-2-tert-butoxy-2-(7-(4-chlorophenyl)-5-methyl-2-(3-(trifluoromethylsulfonyloxy)phenyl)benzo[d]thiazol-6-yl)ethyl pivalate (S)-2-tert-butoxy-2-(7-(4-chlorophenyl)-2-)3-(1,5-dimethyl-1H-pyrazol-4-yl)phenyl)-5-methyl benzo[d]thiazol-6-yl)ethanol (S)-2-tert-butoxy-2-(7-(4-chlorophenyl)-2-)3-(1,5-dimethyl-1H-pyrazol-4-yl)phenyl)-5-methylbenzo[d]thiazol-6-yl)acetic acid
120

Preparation of (S)-2-tert-butoxy-2-(7-(4-chlorophenyl)-5-methyl-2-(3-(trifluoromethylsulfonyloxy)phenyl)benzo[d]

thiazol-6-yl)ethyl pivalate: The reaction mixture of (S)-2-tert-butoxy-2-(7-(4-chlorophenyl)-5-methyl-2-(3-(trifluoromethylsulfonyloxy)phenyl)benzo[d]thiazol-6-yl) ethyl pivalate (20 mg, 0.029 mmol), 1,5-dimethyl-1H-pyrazole-5-boronic acid pinnacle ester (13 mg, 0.058 mmol), 2N K$_2$CO$_3$ (80 µL), Pd(PPh$_3$)$_4$ (3.3 mg, 0.0029 mmol) in dioxane (1 mL) was heated at 120° C. in sealed tube for 2 hours. After the reaction finished, the reaction was cooled down, to the reaction mixture was added MeOH (1 mL), 2N NaOH (500 pt) and heated at 45° C. overnight. Then reaction mixture was washed by sat. NaHCO$_3$, extracted by EtOAc, the organic phase was dried over MgSO$_4$, filtered, concentrated down and purified by silica gel column, eluting by 0-100% EtOAc in hexanes to give the desired product. LCMS-ESI$^+$: calc'd for C$_{31}$H$_{32}$ClN$_3$O$_2$S: 546.2 (M+H$^+$); Found: 546.3 (M+H$^+$).

Preparation of (S)-2-tert-butoxy-2-(7-(4-chlorophenyl)-2-(3-(1,5-dimethyl-1H-pyrazol-4-yl)phenyl)-5-methylbenzo [d]thiazol-6-yl)acetic acid: To a solution of (S)-2-tert-butoxy-2-(7-(4-chlorophenyl)-2-(3-(1,5-dimethyl-1H-pyrazol-4-yl) phenyl)-5-methylbenzo[d]thiazol-6-yl)ethanol (11 mg, 0.020 mmol) in wet acetonitrile (0.75 w % H$_2$O, 1 mL), was added stock solution of H$_5$IO$_6$/CrO$_3$ (0.439 M in wet acetonitrile, 400 µt) at 0° C. for ½ hour. The reaction mixture was filtered and purified by reverse phase HPLC, eluting by 0-100% acetonitrile in H$_2$O with 0.1% TFA give the product. LCMS-ESI$^+$: calc'd for C$_{31}$H$_{30}$ClN$_3$O$_3$S: 560.2 (M+H$^+$); Found: 560.2 (M+H$^+$). $^1$H NMR (400 MHz, CD$_3$OD): δ 8.05 (s, 1H), 7.88 (d, J=3.4 Hz, 1H), 7.84 (s, 1H), 7.69-7.66 (m, 2H), 7.59-7.51 (m, 5H), 5.25 (s, 1H), 3.86 (s, 3H), 2.61 (s, 3H), 2.45 (s, 3H), 0.97 (S, 9H).

Example 31

Preparation of (S)-2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetic acid (121)

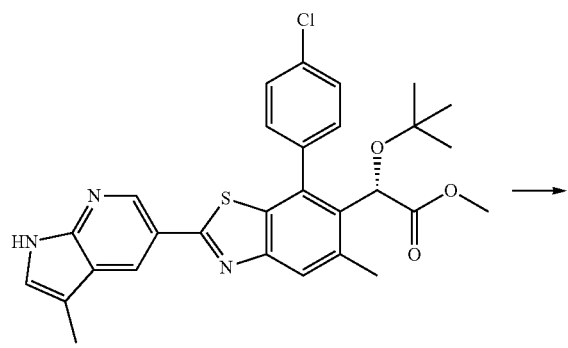

(S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate

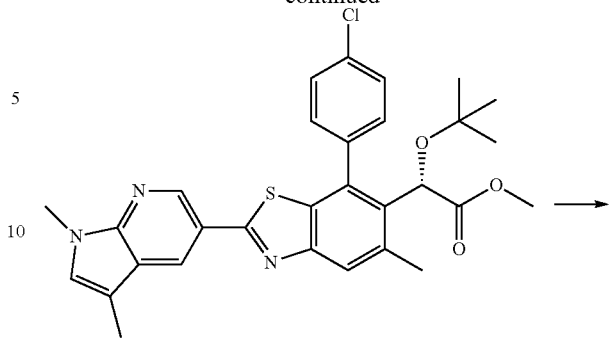

(S)-methyl 2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetate

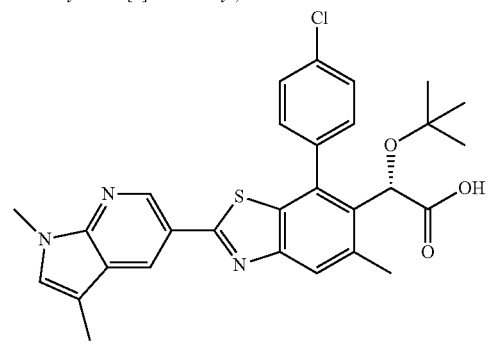

(S)-2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetic acid
121

Preparation (S)-methyl 2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetate: To a solution of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate (12 mg, 0.022 mmol) in DMF (5 mL) was added cesium carbonate (11 mg, 0.033 mmol). The reaction solution was stirred at room temperature for 5 minutes, iodomethane (4.7 mg, 0.033 mmol) was added. The reaction solution was stirred for 30 minutes and quenched with water. Volatiles were removed and the residue partitioned between ethyl acetate and water. The organic phase was washed with brine, dried (MgSO$_4$), filtered and concentrated to give crude product which was purified by chromatographic column to afford the desired product. LCMS-ESI$^+$: calc'd for C$_{30}$H$_{30}$ClN$_3$O$_3$S: 548.17 (M+H$^+$); Found: 548.4 (M+H$^+$).

Preparation (S)-2-tert-butoxy-2-(7-(4-chlorophenyl)-2-(1,3-dimethyl-1H-pyrrolo[2,3-b]pyridin-5-yl)-5-methylbenzo [d]thiazol-6-yl)acetic acid: To a solution of (S)-methyl 2-tert-butoxy-2-(7-(4-chlorophenyl)-2-(1,3-dimethyl-1H-pyrrolo [2,3-b]pyridin-5-yl)-5-methylbenzo[d]thiazol-6-yl)acetate: (4 mg, 0.0073 mmol) in THF/CH$_3$OH (0.5 mL/0.5 mL) was added 2N NaOH (37 uL, 0.073 mmol). The reaction mixture was heated at 50° C. for 2 h and the crude was purified by reverse phase HPLC, eluting with 5-100% acetonitrile in H$_2$O with 0.1% TFA to give desired product. LCMS-ESI$^+$: calc'd for C$_{29}$H$_{28}$ClN$_3$O$_3$S: 534.16 (M+H$^+$); Found: 534.2 (M+H$^+$). $^1$H NMR (400 MHz, CD$_3$OD): δ 8.88 (d, J=1 Hz, 1H), 8.51 (d, J=1 Hz, 1H), 7.82 (s, 1H), 7.71-7.58 (m, 4H), 7.21 (s, 1H), 5.26 (s, 1H), 3.83 (s, 3H), 2.61 (s, 3H), 2.34 (s, 3H), 0.97 (s, 9H).

Example 32

Preparation of (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyacetic acid (122)

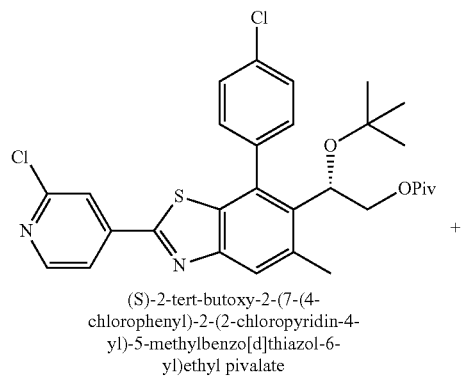

(S)-2-tert-butoxy-2-(7-(4-chlorophenyl)-2-(2-chloropyridin-4-yl)-5-methylbenzo[d]thiazol-6-yl)ethyl pivalate

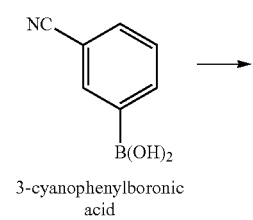

3-cyanophenylboronic acid

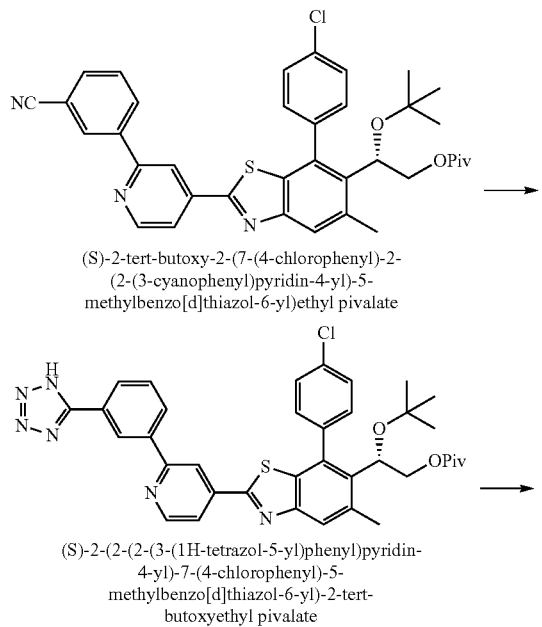

(S)-2-tert-butoxy-2-(7-(4-chlorophenyl)-2-(2-(3-cyanophenyl)pyridin-4-yl)-5-methylbenzo[d]thiazol-6-yl)ethyl pivalate (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethyl pivalate

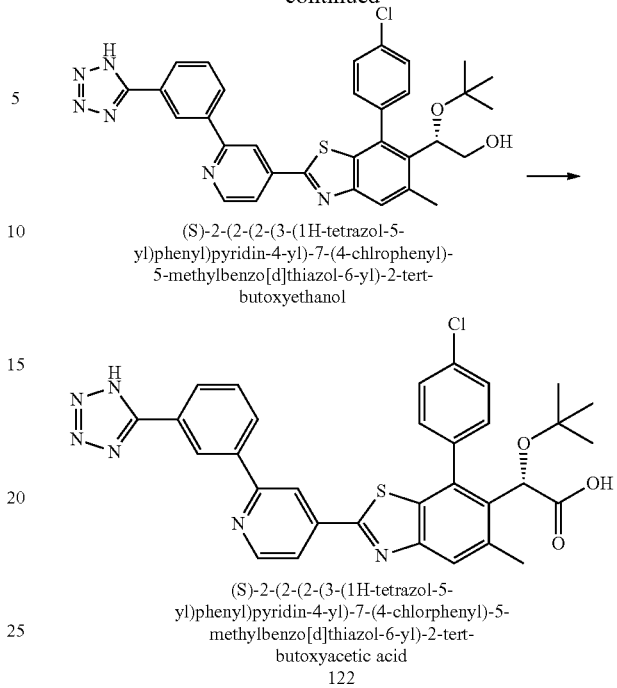

(S)-2-(2-(2-(3-(1H-tetrazol-5-yl)phenyl)pyridin-4-yl)-7-(4-chlrophenyl)-5-methylbenzo[d]thiazol-6-yl)-2-tert-butoxyethanol (S)-2-(2-(2-(3-(1H-tetrazol-5-yl)phenyl)pyridin-4-yl)-7-(4-chlorphenyl)-5-methylbenzo[d]thiazol-6-yl)-2-tert-butoxyacetic acid
122

Preparation of (S)-2-tert-butoxy-2-(7-(4-chlorophenyl)-2-(2-(3-cyanophenyl)pyridin-4-yl)-5-methylbenzo[d]thiazol-6-yl)ethyl pivalate: (S)-2-tert-butoxy-2-(7-(4-chlorophenyl)-2-(2-chloropyridin-4-yl)-5-methylbenzo[d]thiazol-6-yl)ethyl pivalate (19.7 mg, 0.034 mmol), 3-cyanophenylboronic acid (6.1 mg, 0.041 mmol), Pd(PPh$_3$)$_4$, and K$_2$CO$_3$ (14.3 mg, 0.103 mmol) were placed in a microwave vial and the vial was vacuum pumped and flushed with argon three times. To this mixture was added degassed 1,4-dioxane (0.4 mL) and degassed water (0.1 mL). The reaction mixture was heated at 110° C. for 1.5 h, cooled, diluted with ethyl acetate, filtered through Celite (ethyl acetate eluent), and concentrated. Purification by flash column chromatography on silica gel (hexanes/ethyl acetate eluent) provided the product. LCMS-ESI$^+$: calc'd for C$_{37}$H$_{37}$ClN$_3$O$_3$S: 638.2 (M+H$^+$); Found: 637.9 (M+H$^+$).

Preparation of (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethyl pivalate: To a solution of (S)-2-tert-butoxy-2-(7-(4-chlorophenyl)-2-(2-(3-cyanophenyl)pyridin-4-yl)-5-methylbenzo[d]thiazol-6-yl)ethyl pivalate (17.2 mg, 0.027 mmol) in DMF (0.5 mL) was added ammonium chloride (7.2 mg, 0.135 mmol) and sodium azide (9.4 mg, 0.144 mmol). The reaction mixture was heated at 120° C. for 6 h then cooled. The crude reaction mixture was passed through a silica gel plug (hexanes/ethyl acetate eluent) to remove the DMF and salts, concentrated, and used without further purification. LCMS-ESI$^+$: calc'd for C$_{37}$H$_{38}$ClN$_6$O$_3$S: 681.2 (M+H$^+$); Found: 680.9 (M+H$^+$).

Preparation of (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethanol: To a solution of crude (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethyl pivalate from the previous reaction (assume 0.027 mmol) in THF (0.4 mL) and methanol (0.4 mL) was added NaOH (0.4 mL of a 2N solution). The reaction mixture was heated at 40° C. for 2 h, cooled, quenched with NH$_4$Cl (sat. aq.), and extracted with ethyl acetate. The combined organic layers were dried over Na$_2$SO$_4$ and concentrated to give the crude product which was used without further purification. LCMS-ESI$^+$: calc'd for C$_{32}$H$_{30}$ClN$_6$O$_2$S: 597.2 (M+H$^+$); Found: 597.0 (M+H$^+$).

Preparation of (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyacetic acid: To a solution of crude (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethanol from the previous reaction (assume 0.023 mmol) in 25% water/acetonitrile (0.75 mL) was added sequentially, a stock solution of CrO$_3$/H$_5$IO$_6$ (0.27 mL, 0.439 M solution) and CrO$_3$ (3.5 mg, 0.035 mmol) at room temperature. The reaction was stirred for 2 h, filtered, and purified by reverse phase HPLC. Fractions containing the product were pooled and lyophilized to provide the TFA salt of the product. $^1$H NMR (400 MHz, CD$_3$OD) δ 8.84 (dd, J=5.2, 0.6 Hz, 1H), 8.80-8.77 (m, 1H), 8.58 (s, 1H), 8.37-8.31 (m, 1H), 8.19-8.14 (m, 1H), 8.01 (dd, J=5.2, 1.6 Hz, 1H), 7.98 (s, 1H), 7.77 (t, J=7.9 Hz, 1H), 7.73-7.68 (m, 1H), 7.65-7.59 (m, 3H), 5.29 (s, 1H), 2.65 (s, 3H), 0.99 (s, 9H). LCMS-ESI$^+$: calc'd for C$_{32}$H$_{28}$ClN$_6$O$_3$S: 611.2 (M+H$^+$); Found: 610.9 (M+H$^+$).

Example 33

Preparation of (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid (123)

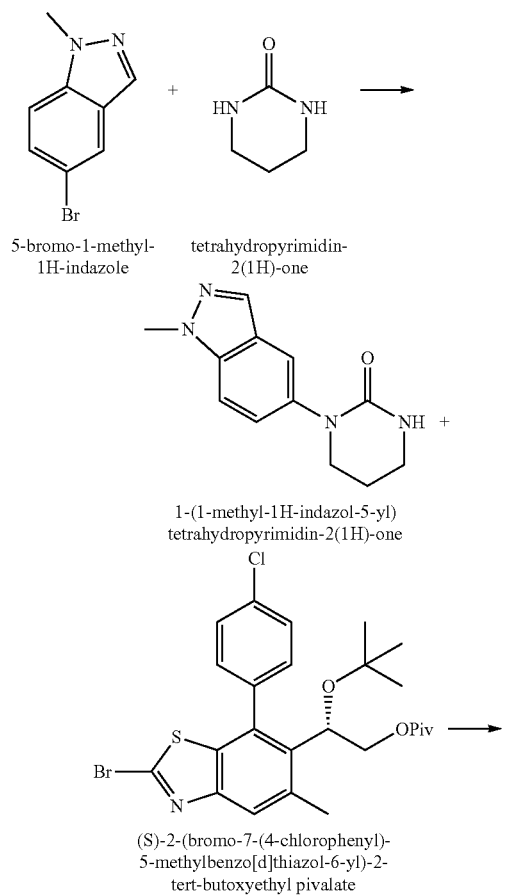

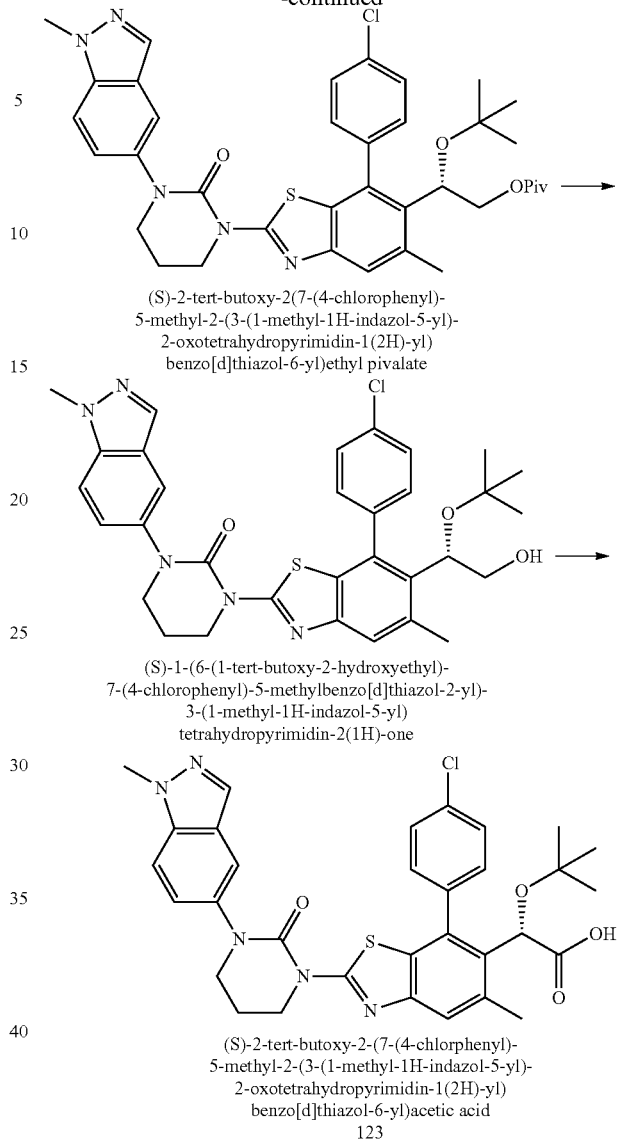

Preparation of 1-(1-methyl-1H-indazol-5-yl)tetrahydropyrimidin-2(1H)-one: To a solution of 5-bromo-1-methyl-1H-indazole (76 mg, 0.36 mmol) in 1,4-dioxane (5 mL) was added tetrahydropyrimidin-2(1H)-one (Aldrich, 216 mg, 2.16 mmol), followed by Pd$_2$(dba)$_3$ (16 mg, 0.02 mmol), 4,5-bis(diphenylphosphino)-9,9-dimethylxanthene (31 mg, 0.06 mmol) and cesium carbonate (176 mg, 0.54 mmol). The reaction mixture was degassed with nitrogen and heated at 100° C. for 16 hours. The mixture was diluted with ethyl acetate, washed with water and brine, and dried over Na$_2$SO$_4$ and filtered. Concentration and purification by flash column chromatography (hexanes/EtOAc) yielded 1-(1-methyl-1H-indazol-5-yl)tetrahydropyrimidin-2(1H)-one. LCMS-ESI$^+$: calc'd for C$_{12}$H$_{14}$N$_4$O: 231.2 (M+H$^+$); Found: 231.2 (M+H$^+$).

Preparation of ((S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)ethyl pivalate: To a solution of (S)-2-(2-bromo-7-(4-chlorophenyl)-5-methylbenzo[d]thiazol-6-yl)-2-tert-butoxyethyl pivalate (27 mg, 0.05 mmol) in 1,4-dioxane (1.5 mL) was added 1-(1-methyl- 1H-indazol-5-yl)tetrahydropyrimidin-2(1H)-one (23 mg, 0.1 mmol), followed by Pd$_2$(dba)$_3$ (5 mg, 0.006 mmol), 4,5-bis(diphenylphosphino)-9,9-dimethylxanthene (10 mg, 0.02 mmol) and cesium carbonate (60 mg, 0.18 mmol). The reaction mixture was degassed with nitrogen and heated at 100° C. for 16 hours. The mixture was diluted with ethyl acetate, washed with water and brine, and dried over Na$_2$SO$_4$ and filtered. Concentration and purification by flash column chromatography (hexanes/EtOAc) yielded ((S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)ethyl pivalate. LCMS-ESI$^+$: calc'd for C$_{37}$H$_{42}$ClN$_5$O$_4$S: 688.3 (M+H$^+$); Found: 688.4 (M+H$^+$).

Preparation of (S)-1-(6-(1-tert-butoxy-2-hydroxyethyl)-7-(4-chlorophenyl)-5-methylbenzo[d]thiazol-2-yl)-3-(1-methyl-1H-indazol-5-yl)tetrahydropyrimidin-2(1H)-one: To the solution of ((S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)ethyl pivalate (20 mg) in THF/MeOH (1 mL/1 mL) was added sodium hydroxide solution (1 mL, 1 N, 1 mmol). The mixture was heated at 50° C. for 12 hours. The mixture was diluted with water, and extracted with ethyl acetate. The organic phase was washed with water and brine, dried over sodium sulfate and filtered. Concentration gave (S)-1-(6-(1-tert-butoxy-2-hydroxyethyl)-7-(4-chlorophenyl)-5-methylbenzo[d]thiazol-2-yl)-3-(1-methyl-1H-indazol-5-yl)tetrahydropyrimidin-2(1H)-one. LCMS-ESI$^+$: calc'd for C$_{32}$H$_{34}$ClN$_5$O$_3$S: 604.2 (M+H$^+$); Found: 604.3 (M+H$^+$).

Preparation of (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O, 114 mL). To a solution of (S)-1-(6-(1-tert-butoxy-2-hydroxyethyl)-7-(4-chlorophenyl)-5-methylbenzo[d]thiazol-2-yl)-3-(1-methyl-1H-indazol-5-yl)tetrahydropyrimidin-2(1H)-one (16 mg) in wet acetonitrile (1.0 mL, 0.75% H$_2$O) at 0° C. was added the above stock solution (0.6 mL) at 0° C. Filtration and purification by reverse phase HPLC gave (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid. LCMS-ESI$^+$: calc'd for C$_{32}$H$_{32}$ClN$_5$O$_4$S: 618.2 (M+H$^+$); Found: 618.3 (M+H$^+$), 615.8 (M+H$^+$); $^1$H-NMR 400 MHz, (CD$_3$OD) δ 7.99 (s, 1H), 7.70 (s, 1H), 7.62-7.50 (m, 3H), 7.50-7.47 (m, 3H), 7.37 (m, 1H), 5.20 (s, 1H), 4.40 (m, 2H), 4.07 (s, 3H), 3.85 (m, 2H), 2.55 (s, 3H), 2.34 (m, 2H), 0.94 (s, 9H).

Example 34

Preparation of (S)-2-tert-butoxy-2-(7-(4-chlorophenyl)-5-methyl-2-(3-(1-methyl-1H-indazol-5-yl)-2-oxoimidazolidin-1-yl)benzo[d]thiazol-6-yl)acetic acid (124)

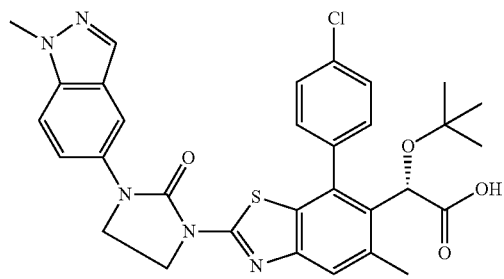

(S)-2-tert-butoxy-2-(7-(4-chlorophenyl)-5-methyl-2-(3-(1-methyl-1H-indazol-5-yl)-2-oxoimidazolidin-1-yl)benzo[d]thiazol-6-yl)acetic acid Preparation of (S)-2-tert-butoxy-2-(7-(4-chlorophenyl)-5-methyl-2-(3-(1-methyl-1H-indazol-5-yl)-2-oxoimidazolidin-1-yl)benzo[d]thiazol-6-yl)acetic acid: (S)-2-tert-butoxy-2-(7-(4-chlorophenyl)-5-methyl-2-(3-(1-methyl-1H-indazol-5-yl)-2-oxoimidazolidin-1-yl)benzo[d]thiazol-6-yl)acetic acid (1.3 mg) was prepared in a similar manner as compound (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid except using imidazolidin-2-one instead of tetrahydropyrimidin-2(1H)-one. LCMS-ESI$^+$: calc'd for C$_{31}$H$_{30}$ClN$_5$O$_4$S: 604.2 (M+H$^+$); Found: 604.2 (M+H$^+$); $^1$H-NMR 400 MHz, (CD$_3$OD) δ 7.99 (s, 1H), 7.82 (m, 1H), 7.66 (m, 1H), 7.60-7.48 (m, 5H), 7.42 (m, 1H), 5.21 (s, 1H), 4.33 (m, 1H), 4.22 (m, 2H), 4.06 (s, 3H), 3.64 (m, 1H), 2.55 (s, 3H), 0.96 (s, 9H).

Example 35

Preparation of (2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid (125)

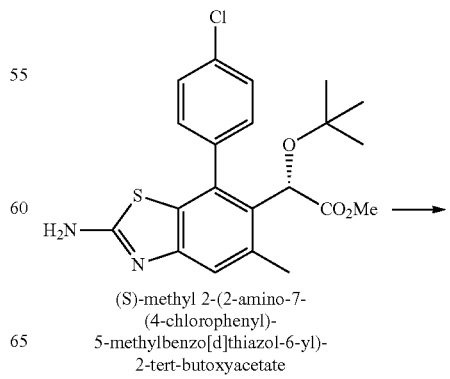

(S)-methyl 2-(2-amino-7-(4-chlorophenyl)-5-methylbenzo[d]thiazol-6-yl)-2-tert-butoxyacetate -continued

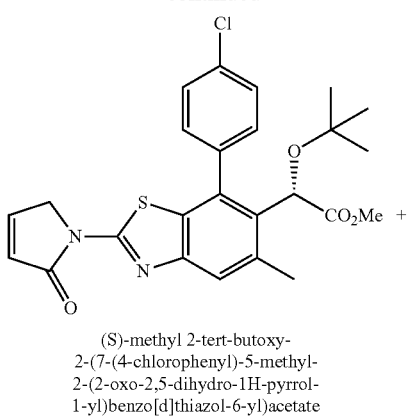

(S)-methyl 2-tert-butoxy-
2-(7-(4-chlorophenyl)-5-methyl-
2-(2-oxo-2,5-dihydro-1H-pyrrol-
1-yl)benzo[d]thiazol-6-yl)acetate

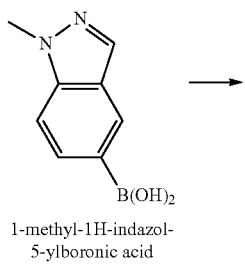

1-methyl-1H-indazol-
5-ylboronic acid

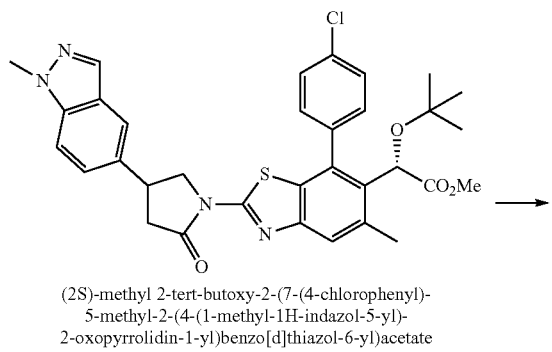

(2S)-methyl 2-tert-butoxy-2-(7-(4-chlorophenyl)-
5-methyl-2-(4-(1-methyl-1H-indazol-5-yl)-
2-oxopyrrolidin-1-yl)benzo[d]thiazol-6-yl)acetate

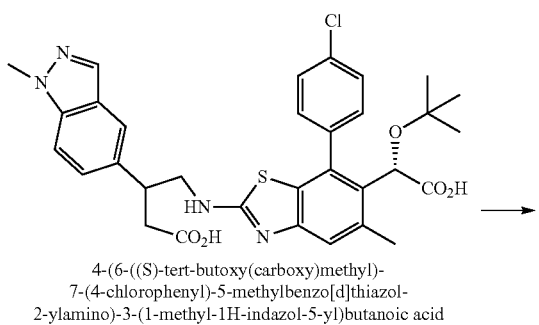

4-(6-((S)-tert-butoxy(carboxy)methyl)-
7-(4-chlorophenyl)-5-methylbenzo[d]thiazol-
2-ylamino)-3-(1-methyl-1H-indazol-5-yl)butanoic acid -continued

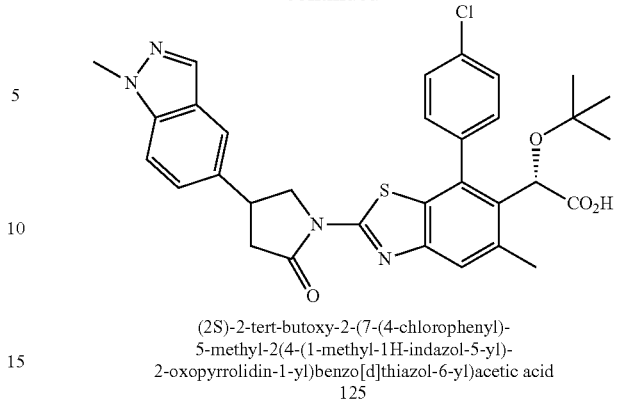

(2S)-2-tert-butoxy-2-(7-(4-chlorophenyl)-
5-methyl-2(4-(1-methyl-1H-indazol-5-yl)-
2-oxopyrrolidin-1-yl)benzo[d]thiazol-6-yl)acetic acid
125

Preparation of (S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate: To a solution of (S)-methyl 2-(2-amino-7-(4-chlorophenyl)-5-methylbenzo[d]thiazol-6-yl)-2-tert-butoxyacetate (40 mg, 0.1 mmol) in acetonitrile (1 mL) was added 2,5-dimethoxy-2,5-dihydrofuran (26 µL, 0.2 mmol), followed by hydrochloric acid (0.2 N, 0.8 mL, 0.16 mmol). The mixture was stirred for 24 hours, and was diluted with EtOAc and quenched with saturated sodium bicarbonate solution. The organic layer was separated, and was washed with water and brine, dried with sodium sulfate and filtered. Concentration and purification by flash column chromatography (hexanes/EtOAc) gave (S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate. LCMS-ESI$^+$: calc'd for $C_{25}H_{25}ClN_2O_4S$: 485.1 (M+H$^+$); Found: 485.2 (M+H$^+$).

Preparation of (2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate: To a solution of (S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate (12 mg, 0.025 mmol) in 1,4-dioxane/water (0.5 mL/50 µL) was added 1-methyl-1H-indazol-5-ylboronic acid (8 mg, 0.050 mmol), followed by chloro(1,5-cyclooctadiene) rhodium (I) dimer (1 mg), BINAP (5 mg), and potassium carbonate solution (2 N, 6 µL). The mixture was purged with nitrogen and heated at 80° C. for 24 hours. The mixture was diluted with EtOAc, and was washed with water and brine, dried with sodium sulfate and filtered. Concentration and purification by flash column chromatography (hexanes/EtOAc) gave (2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate. LCMS-ESI$^+$: calc'd for $C_{33}H_{33}ClN_4O_4S$: 617.2 (M+H$^+$); Found: 617.2 (M+H$^+$).

Preparation of 4-(6-((S)-tert-butoxy(carboxy)methyl)-7-(4-chlorophenyl)-5-methylbenzo[d]thiazol-2-ylamino)-3-(1-methyl-1H-indazol-5-yl)butanoic acid: To a solution of (2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate (5 mg) in THF/MeOH (0.5 mL/0.5 mL) was added sodium hydroxide solution (1.0 N, 0.5 mL). The mixture was stirred at 25° C. for 2 hours and heated at 50° C. for 16 hours. The mixture was cooled and neutralized with 0.1 N hydrochloric acid until pH=5. The reaction mixture was freeze-dried and used for next step without further purification. LCMS-ESI$^+$: calc'd for $C_{32}H_{33}ClN_4O_5S$: 621.2 (M+H$^+$); Found: 621.2 (M+H$^+$).

Preparation of (2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid: To a solution of 4-(6-((S)-tert-butoxy(carboxy)methyl)-7-(4-chlorophenyl)-5-methylbenzo[d]thiazol-2-ylamino)-3-(1-methyl-1H-indazol-5-yl)butanoic acid in DMF (1 mL) was added di-isopropylethylamine (86 followed by N-(3-dimethylaminopropyl)-N-ethylcarbodiimide hydrochloride (19 mg). The mixture was stirred for 2 hours and purified with reverse phase HPLC to give an intermediate (6 mg). The intermediate was dissolved in pyridine (1 mL), water (1 mL) and 1-hydroxybenzotriazole hydrate (1 mg) were added. The mixture was heated at 100° C. for 48 hours. Concentration and purification by reverse phase HPLC gave (2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid. LCMS-ESI$^+$: calc'd for $C_{32}H_{31}ClN_4O_4S$: 603.2 (M+H$^+$); Found: 603.4 (M+H$^+$); $^1$H-NMR 400 MHz, (CD$_3$OD) δ 7.97 (m, 1H), 7.74 (m, 1H), 7.60-7.47 (m, 7H), 5.22 (s, 1H), 4.68 (m, 1H), 4.19 (m, 1H), 4.06 (m, 3H), 4.0 (m, 1H), 3.10 (m, 1H), 2.95 (m, 1H), 2.55 (s, 3H), 0.95 (s, 9H).

Example 36

Preparation of (2S)-2-tert-butoxy-2-(7-(4-chlorophenyl)-5-methyl-2-(3-phenoxypyrrolidin-1-yl)benzo[d]thiazol-6-yl)acetic acid (126)

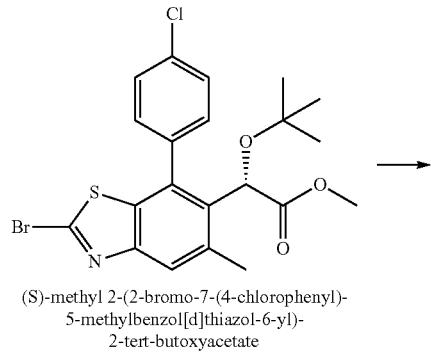

(S)-methyl 2-(2-bromo-7-(4-chlorophenyl)-5-methylbenzol[d]thiazol-6-yl)-2-tert-butoxyacetate

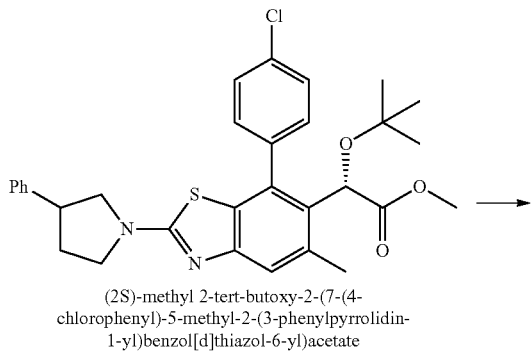

(2S)-methyl 2-tert-butoxy-2-(7-(4-chlorophenyl)-5-methyl-2-(3-phenylpyrrolidin-1-yl)benzol[d]thiazol-6-yl)acetate -continued

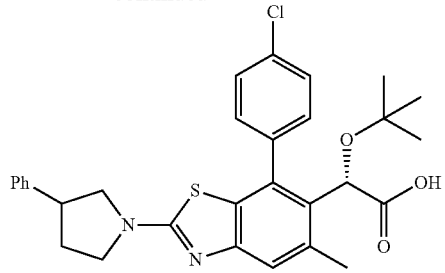

(2S)-2-tert-butoxy-2-(7-(4-chlorophenyl)-5-methyl-2-(3-phenylpyrrolidin-1-yl)benzol[d]thiazol-6-yl)acetic acid
126

Preparation of (2S)-methyl 2-tert-butoxy-2-(7-(4-chlorophenyl)-5-methyl-2-(3-phenylpyrrolidin-1-yl)benzo[d]thiazol-6-yl)acetate: To a solution of (9-methyl 2-(2-bromo-7-(4-chlorophenyl)-5-methylbenzo[d]thiazol-6-yl)-2-tert-butoxyacetate (46.1 mg, 0.095 mmol) in THF (2 mL) was added 3-phenylpyrrolidine (16.9 mg, 0.115 mmol) and diethylpropylamine (24.8 µL, 0.143 mmol). The resulting reaction mixture was heated at 50° C. for 16 hr then evaporated to dryness. The residue was purified via chromatography on silica gel (4 g "gold" ISCO column; 0-60% EtOAc/Hex) to give (2S)-methyl 2-tert-butoxy-2-(7-(4-chlorophenyl)-5-methyl-2-(3-phenylpyrrolidin-1-yl)benzo[d]thiazol-6-yl)acetate. LCMS-ESI$^+$: calc'd for $C_{31}H_{34}ClN_2O_3S$: 548.2 550.2 (M+H$^+$); found: 549.3, 551.3 (M+H$^+$).

Preparation of (2S)-2-tert-butoxy-2-(7-(4-chlorophenyl)-5-methyl-2-(3-phenoxypyrrolidin-1-yl)benzo[d]thiazol-6-yl)acetic acid: To a solution of (2S)-methyl 2-tert-butoxy-2-(7-(4-chlorophenyl)-5-methyl-2-(3-phenylpyrrolidin-1-yl)benzo[d]thiazol-6-yl)acetate (29.3 mg, 0.653 mmol) in CH$_3$OH (1 mL) was added NaOH (1N, 1 mL, 1 mmol), the resulting mixture was heated at 50 C for 10 hr. The mixture was acidified to pH 3 and evaporated to a small volume, and the residue was partitioned between CH$_2$Cl$_2$ and brine. The organic layer was separated, dried, filtered and evaporated to dryness. The residue was purified on TLC (50% EtOAc/Hex) to give (2S)-2-tert-butoxy-2-(7-(4-chlorophenyl)-5-methyl-2-(3-phenoxypyrrolidin-1-yl)benzo[d]thiazol-6-yl)acetic acid. LCMS-ESI$^+$: calc'd for $C_{30}H_{32}ClN_2O_3S$: 534.2, 536.2 (M+H$^+$); found: 535.2, 537.2 (M+H$^+$). $^1$H-NMR: 400 MHz, (CD$_3$OD) δ: 7.63 (dd, J=2.0, 7.2 Hz, 1H), 7.49-7.52 (m, 3H), 7.30-7.34 (m, 5H), 7.24 (m, 1H), 5.13 (s, 1H), 3.94 (m, 1H), 3.70 (m, 1H), 3.52-3.63 (m, 4H), 2.48 (s, 3H), 2.46 (m, 1H), 2.20 (m, 1H), 0.94 (s, 9H).

Example 37

Preparation of 6-(3-bromophenyl)-1-methyl-1H-pyrazolo[4,3-b]pyridine: To a solution of 6-bromo-1-methyl-1H-pyrazolo[4,3-b]pyridine (127)

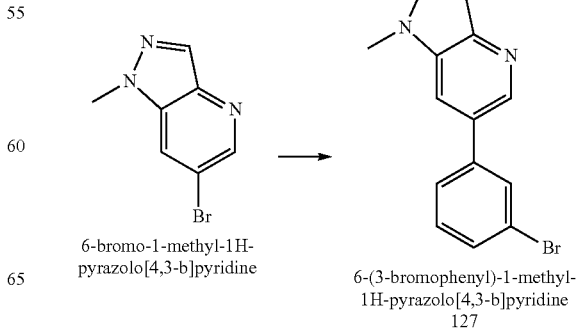

6-bromo-1-methyl-1H-pyrazolo[4,3-b]pyridine 6-(3-bromophenyl)-1-methyl-1H-pyrazolo[4,3-b]pyridine
127

Preparation of 6-(3-bromophenyl)-1-methyl-1H-pyrazolo[4,3-b]pyridine: To a solution of 6-bromo-1-methyl-1H-pyrazolo[4,3-b]pyridine (120 mg, 0.566 mmol) and 3-bromophenylboronic acid (136 mg, 0.679 mmol) in degassed 1,4-dioxane (6 mL) and water (2 mL) was added $K_2CO_3$ (391 mg, 2.83 mmol) and tetrakis(triphenylphosphine)palladium(0) (32 mg, 0.028 mmol). The reaction mixture was heated at 90° C. for 1 h, cooled and partitioned between ethyl acetate and brine. The organic layer was separated, dried over $Na_2SO_4$ and concentrated to give crude which was purified by chromatographic column to afford the desired product. LCMS-ESI$^+$: calc'd for $C_{13}H_{10}BrN_3$: 288.01 (M+H$^+$); Found: 288.2 (M+H$^+$).

Example 38

Representative procedure for the synthesis of stannane intermediates used in Method H. Preparation of 1-methyl-5-(4-(tributylstannyl)pyrimidin-2-yl)-1H-indazole (128)

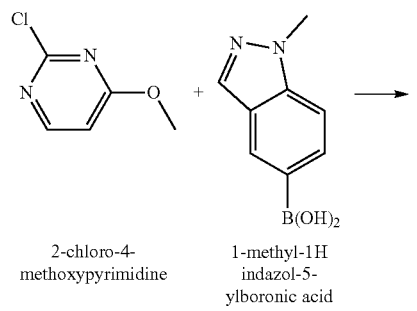

2-chloro-4-methoxypyrimidine 1-methyl-1H-indazol-5-ylboronic acid

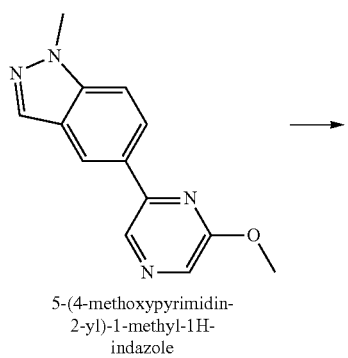

5-(4-methoxypyrimidin-2-yl)-1-methyl-1H-indazole

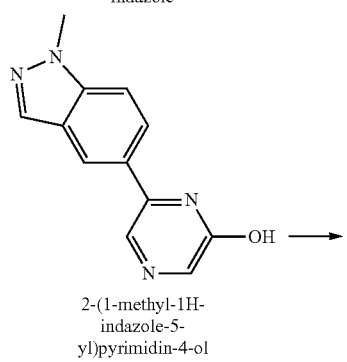

2-(1-methyl-1H-indazole-5-yl)pyrimidin-4-ol

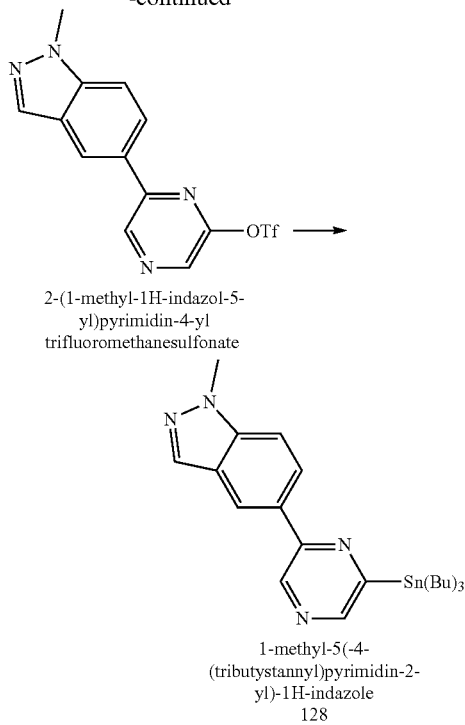

2-(1-methyl-1H-indazol-5-yl)pyrimidin-4-yl trifluoromethanesulfonate 1-methyl-5-(4-(tributystannyl)pyrimidin-2-yl)-1H-indazole 128

Preparation of 5-(4-methoxypyrimidin-2-yl)-1-methyl-1H-indazole: 2-chloro-4-methoxypyrimidine (100.0 mg, 0.69 mmol), 1-methyl-1H-indazol-5-ylboronic acid (133.9 mg, 0.76 mmol), Pd(PPh$_3$)$_4$ (79.9 mg, 0.069 mmol), and $K_2CO_3$ (286.8 mg, 2.075 mmol) were taken in a microwave vial and the vial was vacuum pumped and flushed with argon three times. To this mixture was added degassed toluene (2.5 mL) and DMF (0.28 mL). The reaction mixture was heated in a microwave at 185° C. for 30 min, diluted with ethyl acetate, filtered through Celite (ethyl acetate eluent), and concentrated. Purification by flash column chromatography on silica gel (hexanes/ethyl acetate eluent) provided the product. $^1$H NMR (400 MHz, CDCl$_3$) δ 8.92 (s, 1H), 8.56 (dd, J=8.9, 1.3 Hz, 1H), 8.52 (d, J=5.8 Hz, 1H), 8.10 (s, 1H), 7.47 (d, J=8.9 Hz, 1H), 6.64 (d, J=5.8 Hz, 1H), 4.14 (s, 3H), 4.12 (s, 3H). LCMS-ESI$^+$: calc'd for $C_{13}H_{13}N_4O$: 241.1 (M+H$^+$); Found: 241.2 (M+H$^+$).

Preparation of 2-(1-methyl-1H-indazol-5-yl)pyrimidin-4-ol: 5-(4-methoxypyrimidin-2-yl)-1-methyl-1H-indazole (30.2 mg, 0.126 mmol) was suspended in hydrochloric acid (1.25 mL of a 2N solution) and heated at 85° C. for 14 h, cooled, and neutralized by dropwise addition of NaOH (2N solution). The mixture was extracted six times with 1:1 chloroform/isopropanol and the combined organic layers were dried over $Na_2SO_4$ and concentrated to provide the crude product which was used without further purification. LCMS-ESI$^+$: calc'd for $C_{12}H_{11}N_4O$: 227.1 (M+H$^+$); Found: 227.2 (M+H$^+$).

Preparation of 2-(1-methyl-1H-indazol-5-yl)pyrimidin-4-yl trifluoromethanesulfonate:

To a solution of crude 2-(1-methyl-1H-indazol-5-yl)pyrimidin-4-ol (41.5 mg, 0.183 mmol) in DCM (2.0 mL) was added triethylamine (0.15 mL, 1.101 mmol) followed by trifluoromethanesulfonic anhydride (91.3 µL, 0.550 mmol) at −78° C. The reaction mixture was stirred for 16 h and allowed to slowly warm to room temperature during this time then concentrated. Purification by flash column chromatography on silica gel (hexanes/ethyl acetate eluent) provided the product. ¹H NMR (400 MHz, CDCl₃). δ 8.92 (d, J=5.4 Hz, 1H), 8.90 (s, 1H), 8.49 (dd, J=8.9, 1.5 Hz, 1H), 8.13 (s, 1H), 7.49 (d, J=8.9 Hz, 1H), 7.00 (d, J=5.4 Hz, 1H), 4.13 (s, 3H). LCMS-ESI⁺: calc'd for C$_{13}$H$_{10}$F$_3$N$_4$O$_3$S: 359.0 (M+H⁺); Found: 359.1 (M+H⁺).

Preparation of 1-methyl-5-(4-(tributylstannyl)pyrimidin-2-yl)-1H-indazole: 2-(1-methyl-1H-indazol-5-yl)pyrimidin-4-yl trifluoromethanesulfonate (43.4 mg, 0.121 mmol), Pd(PPh₃)₄ (7.0 mg, 0.006 mmol), and lithium chloride (25.6 mg, 0.604 mmol) were taken in a microwave vial and the vial was vacuum pumped and flushed with argon three times. To this mixture was added degassed toluene (2.0 mL) and bis (tributyltin) (61 μt, 0.121 mmol). The reaction mixture was heated at 110° C. for 16 h, cooled, quenched with water, and diluted with ethyl acetate. The aqueous layer was removed and twice extracted with ethyl acetate. The combined organic layers were dried over Na₂SO₄ and concentrated. Purification by flash column chromatography on silica gel (hexanes/ethyl acetate eluent) provided the product. LCMS-ESI⁺: calc'd for C$_{24}$H$_{37}$N$_4$Sn: 501.2 (M+H⁺); Found: 501.3 (M+H⁺).

Example 39

The compounds in the table below were prepared by the general method noted (e.g. Method B (example 14), Method C (example 15), Method D (example 16), Method E (example 17), Method F (example 18), Method G (example 19), Method H (example 20), Method I (example 21) and Method J (example 22))

| Compound Number | Structure | Method | Parent MW | LCMS-ESI+ | 1H NMR |
|---|---|---|---|---|---|
| 129 | 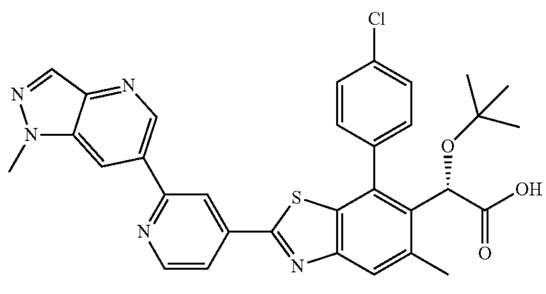 [SMILES: Cc1cc2nc(-c3ccnc(-c4cnc5cnn(C)c5c4)c3)sc2c(-c2ccc(Cl)cc2)c1[C@H](OC(C)(C)C)C(=O)O] | C | 598.1 | 598.2 | ¹H NMR (400 MHz, CD₃OD): δ 9.31 (s, 1H), 8.85-8.84 (m, 2H), 8.64 (s, 1H), 8.25 (s, 1H), 8.01-7.954 (m, 2H), 7.71-7.60 (m, 4H), 5.28 (s, 1H), 4.22 (d, J = 1 Hz, 3H), 2.64 (s, 3H), 0.97 (s, 9H) |
| 130 | 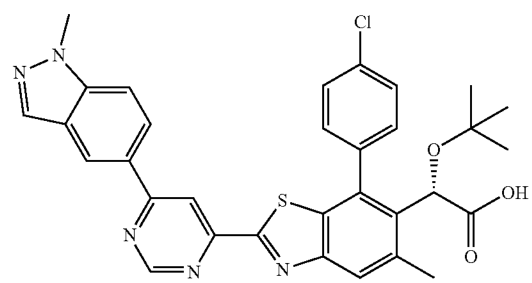 [SMILES: Cc1cc2nc(-c3cc(-c4ccc5c(cnn5C)c4)ncn3)sc2c(-c2ccc(Cl)cc2)c1[C@H](OC(C)(C)C)C(=O)O] | H | 598.1 | 597.9 | ¹H NMR (400 MHz, CD₃OD): δ 9.19 (d, J = 0.9 Hz, 1H), 8.84 (d, J = 1.0 Hz, 1H), 8.78 (s, 1H), 8.38 (dd, J = 8.9, 1.6 Hz, 1H), 8.21 (s, 1H), 7.98 (s, 1H), 7.75 (s, J = 9.2 Hz, 1H), 7.72-7.69 (m, 1H), 7.65-7.59 (m, 3H), 5.30 (s, 1H), 4.14 (s, 3H), 2.65 (s, 3H), 0.98 (s, 9H). |
| 131 | 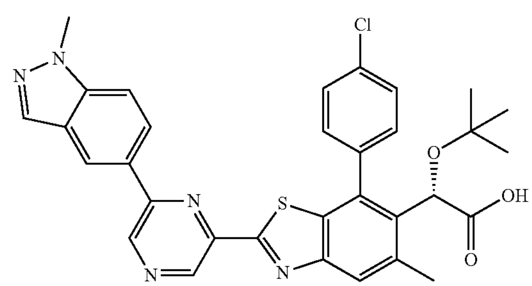 [SMILES: Cc1cc2nc(-c3cncc(-c4ccc5c(cnn5C)c4)n3)sc2c(-c2ccc(Cl)cc2)c1[C@H](OC(C)(C)C)C(=O)O] | H | 598.1 | 598 | ¹H NMR (400 MHz, CD₃OD): δ 9.37 (s, 1H), 9.29 (s, 1H), 8.62 (s, 1H), 8.28 (dd, J = 8.9, 1.6 Hz, 1H), 8.16 (s, 1H), 7.94 (s, 1H), 7.73-7.72 (m, 1H), 7.71-7.69 (m, 1H), 7.67-7.60 (m, 3H), 5.29 (s, 1H), 4.11 (s, 3H), 2.64 (s, 3H), 0.99 (s, 9H). |
| 132 | 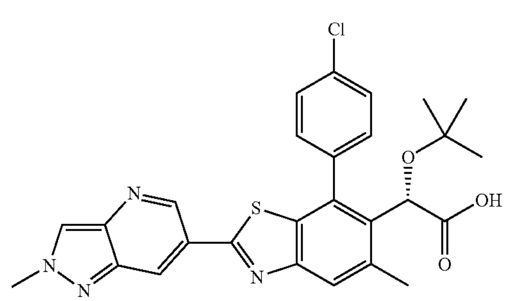 [SMILES: Cc1cc2nc(-c3cnc4cn(C)nc4c3)sc2c(-c2ccc(Cl)cc2)c1[C@H](OC(C)(C)C)C(=O)O] | I | 521 | 521.3 | ¹H NMR (400 MHz, CD₃OD): δ 9.23 (d, J = 1 Hz, 1H), 8.65 (s, 1H), 8.54 (s, 1H), 7.90 (s, 1H), 7.71-7.59 (m, 4H), 5.27 (s, 1H), 4.31 (s, 3H), 2.62 (s, 3H), 0.97 (s, 9H). |

-continued

| Compound Number | Structure | Method | Parent MW | LCMS-ESI+ | 1H NMR |
|---|---|---|---|---|---|
| 133 | 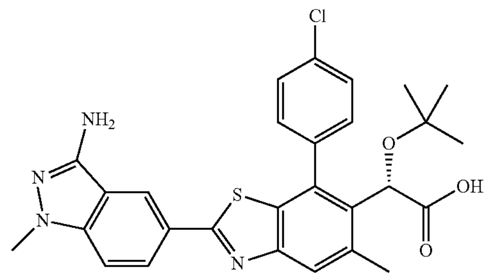 [SMILES: Cc1cc2nc(-c3ccc4c(c3)c(N)nn4C)sc2c(-c2ccc(Cl)cc2)c1[C@H](OC(C)(C)C)C(=O)O] | J | 535.1 | 535.3 | ¹H NMR (400 MHz, CD₃OD): δ 8.40 (s, 1H), 8.09-8.07 (m, 1H), 7.79 (s, 1H), 7.69 (d, J = 4.2 Hz, 1H), 7.60-7.41 (m, 4H), 5.25 (s, 1H), 3.83 (s, 3H), 2.60 (s, 3H), 0.97 (s, 9H). |
| 134 | 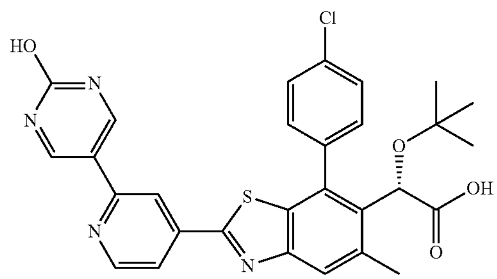 [SMILES: Cc1cc2nc(-c3ccnc(-c4cnc(O)nc4)c3)sc2c(-c2ccc(Cl)cc2)c1[C@H](OC(C)(C)C)C(=O)O] | F | 561.13 | 561.1 | ¹H NMR (400 MHz, CD₃OD): δ 9.13 (bs, 2H), 8.72 (bs, 1H), 8.36 (bs, 1H), 7.92-7.90 (m, 2H), 7.69-7.56 (m, 4H), 5.27 (s, 1H), 2.62 (s, 3H), 0.97 (s, 9H). |
| 135 | 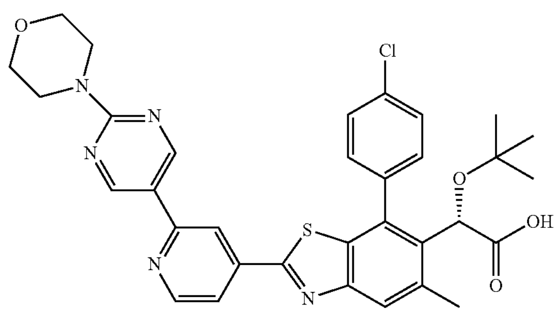 [SMILES: Cc1cc2nc(-c3ccnc(-c4cnc(N5CCOCC5)nc4)c3)sc2c(-c2ccc(Cl)cc2)c1[C@H](OC(C)(C)C)C(=O)O] | F | 630.29 | 630.2 | ¹H NMR (400 MHz, CD₃OD): δ 9.03 (s, 2H), 8.71 (d, J = 2.4 Hz, 1H), 8.43 (s, 1H), 7.95-7.93 (m, 2H), 7.70-7.68 (m, 1H), 7.60 (s, 3H), 5.27 (s, 1H), 3.92-3.89 (m, 4H), 3.78-3.75 (m, 4H), 2.63 (s, 3H), 0.97 (s, 9H). |
| 136 | 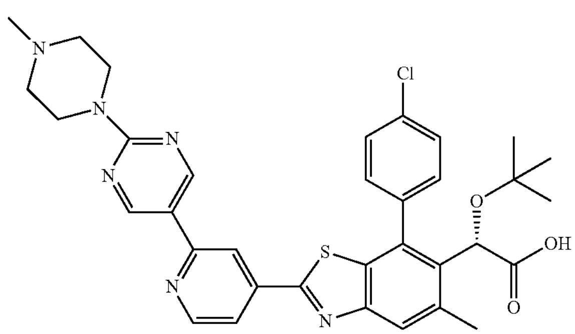 [SMILES: Cc1cc2nc(-c3ccnc(-c4cnc(N5CCN(C)CC5)nc4)c3)sc2c(-c2ccc(Cl)cc2)c1[C@H](OC(C)(C)C)C(=O)O] | F | 643.22 | 643.2 | ¹H NMR (400 MHz, CD₃OD): δ 9.10 (s, 2H), 8.72 (d, J = 2.6 Hz, 1H), 8.38 (s, 1H), 7.92 (s, 1H), 7.87-7.7.86 (m, 1H), 7.70-7.68 (m, 1H), 7.62-7.58 (m, 3H), 5.27 (s, 1H), 5.10-5.04 (m, 2H), 3.61-3.34 (m, 4H), 3.29-3.18 (m, 2H), 2.97 (s, 3H), 2.62 (s, 3H), 0.97 (s, 9H). |
| 137 | 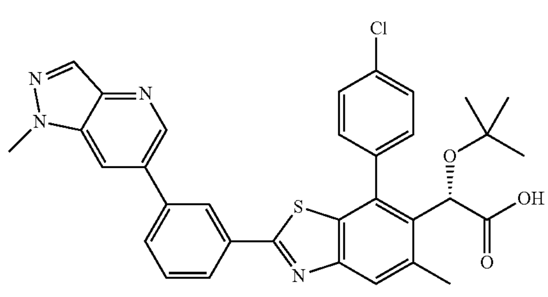 [SMILES: Cc1cc2nc(-c3cccc(-c4cnc5cnn(C)c5c4)c3)sc2c(-c2ccc(Cl)cc2)c1[C@H](OC(C)(C)C)C(=O)O] | I | 597.1 | 597.2 | ¹H NMR (400 MHz, CD₃OD): δ 8.92 (s, 1H), 8.51-8.45 (m, 2H), 8.25 (s, 1H), 8.10-7.94 (m, 2H), 7.87-7.58 (m, 6H), 5.26 (s, 1H), 4.20 (s, 3H), 2.62 (s, 3H), 0.98 (s, 9H). |

-continued

| Compound Number | Structure | Method | Parent MW | LCMS-ESI+ | 1H NMR |
|---|---|---|---|---|---|
| 138 | 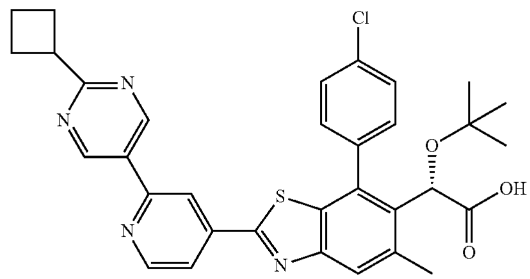 [SMILES: Cc1cc2nc(-c3ccnc(-c4cnc(C5CCC5)nc4)c3)sc2c(-c2ccc(Cl)cc2)c1[C@H](OC(C)(C)C)C(=O)O] | F | 599.15 | 599.1 | ¹H NMR (400 MHz, CD₃OD): δ 9.43 (s, 1H), 8.83 (d, J = 2.4 Hz, 1H), 8.57 (s, 1H), 8.02-8.8.00 (m, 1H), 7.95 (s, 1H), 7.70-7.68 (m, 1H), 7.60-7.59 (m, 3H), 5.27 (s, 1H), 3.92-3.31 (m, 1H), 2.63 (s, 3H), 2.59-2.42 (m, 4H), 2.20-2.2.12 (m, 2H), 2.03-1.97 (m, 2H), 0.97 (s, 9H). |
| 139 | 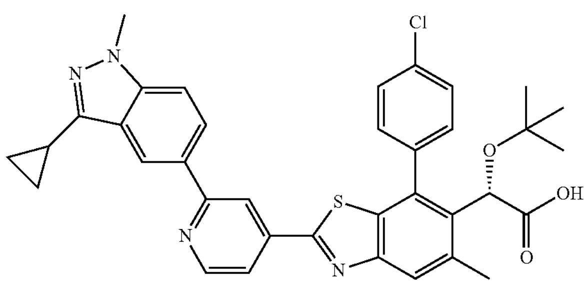 [SMILES: Cc1cc2nc(-c3ccnc(-c4ccc5c(c4)c(C4CC4)nn5C)c3)sc2c(-c2ccc(Cl)cc2)c1[C@H](OC(C)(C)C)C(=O)O] | F | 637.2 | 637.2 | ¹H NMR (400 MHz, CD₃OD): δ 8.60 (d, J = 2.6 Hz, 1H), 8.40 (s, 1H), 8.34 (s, 1H), 7.93-7.91 (m, 1H), 7.86-7.83 (m, 2H), 7.61-7.59 (m, 1H), 7.50-7.45 (m, 4H), 5.28 (s, 1H), 3.86 (s, 3H), 2.53 (s, 3H), 2.24-2.21 (m, 1H), 0.99-0.97 (m, 4H), 0.88 (s, 9H). |
| 140 | 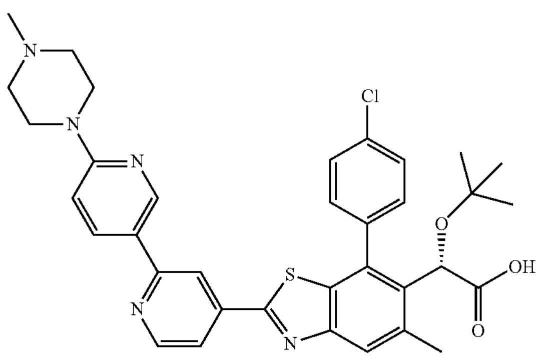 [SMILES: Cc1cc2nc(-c3ccnc(-c4ccc(N5CCN(C)CC5)nc4)c3)sc2c(-c2ccc(Cl)cc2)c1[C@H](OC(C)(C)C)C(=O)O] | F | 642.22 | 642.2 | ¹H NMR (400 MHz, CD₃OD): δ 8.79 (d, J = 1.2 Hz, 1H), 8.61 (d, J = 2.8 Hz, 1H), 8.29 (s, 1H), 8.23-8.21 (m, 1H), 7.83 (s, 1H), 7.77-7.76 (m, 1H), 7.61-7.58 (m, 1H), 7.52-7.48 (m, 3H), 6.98 (d, J = 4.4 Hz, 1H), 5.18 (s, 1H), 4.55-4.52 (m, 2H), 3.39-3.21 (m, 6H), 2.88 (s, 3H), 2.53 (s, 3H), 0.87 (s, 9H). |
| 141 | 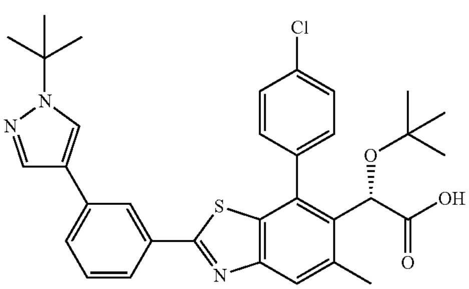 [SMILES: Cc1cc2nc(-c3cccc(-c4cnn(C(C)(C)C)c4)c3)sc2c(-c2ccc(Cl)cc2)c1[C@H](OC(C)(C)C)C(=O)O] | B | 588.17 | 588.3 | ¹H NMR (400 MHz, CD₃OD): δ (8.23-8.22 (m, 2H), 7.93 (s, 1H), 7.83-7.80 (m, 2H), 7.74-7.67 (m, 2H), 7.58 (m, 3H), 7.48-7.45 (m, 1H), 5.25 (s, 1H), 2.61 (s, 3H), 1.64 (s, 9H), 0.97 (s, 9H). |
| 142 | 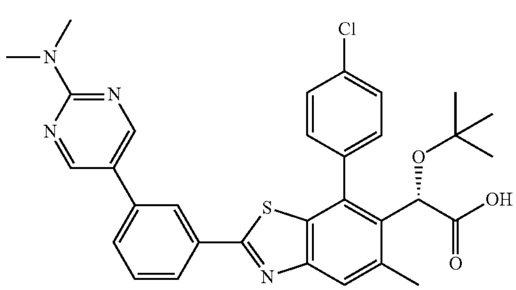 [SMILES: Cc1cc2nc(-c3cccc(-c4cnc(N(C)C)nc4)c3)sc2c(-c2ccc(Cl)cc2)c1[C@H](OC(C)(C)C)C(=O)O] | D | 587.14 | 587.2 | ¹H NMR (400 MHz, CD₃OD): δ 8.57 (s, 2H), 8.10 (s, 1H), 7.81 (d, J = 4 Hz, 1H), 7.72 (s, 1H), 7.58 (d, J = 4 Hz, 1H), 7.47-7.42 (m, 4H), 5.16 (s, 1H), 3.14 (s, 6H), 2.61 (s, 3H), 0.97 (s, 9H). |

-continued

| Compound Number | Structure | Method | Parent MW | LCMS-ESI+ | 1H NMR |
|---|---|---|---|---|---|
| 143 | 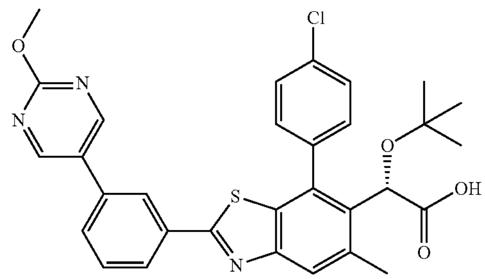 [SMILES: COc1ncc(-c2cccc(-c3nc4cc(C)c([C@H](OC(C)(C)C)C(=O)O)c(-c5ccc(Cl)cc5)c4s3)c2)cn1] | D | 574.1 | 574.2 | ¹H NMR (400 MHz, CD₃OD): δ 0.89 (s, 2H), 8.29 (s, 1H), 8.02 (d, J = 3.8 Hz, 1H), 7.85 (s, 1H), 7.78 (d, J = 4 Hz, 1H), 7.68 (d, J = 4.2 Hz, 1H), 7.63-7.58 (m, 4H), 5.26 (s, 1H), 4.06 (s, 3H), 2.61 (s, 3H), 0.97 (s, 9H). |
| 144 | 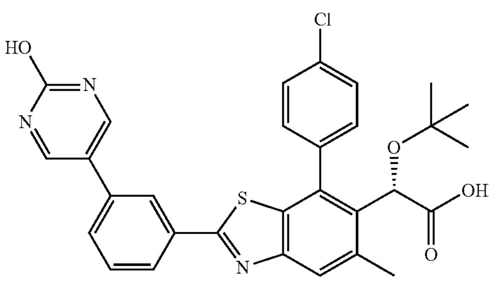 [SMILES: Cc1cc2nc(-c3cccc(-c4cnc(O)nc4)c3)sc2c(-c2ccc(Cl)cc2)c1[C@H](OC(C)(C)C)C(=O)O] | D | 560.07 | 560.2 | ¹H NMR (400 MHz, CD₃OD): δ 8.65 (s, 2H), 8.14 (s, 1H), 7.91 (d, J = 4 Hz, 1H), 7.74 (s, 1H), 7.65-7.46 (m, 6H), 5.26 (s, 1H), 2.51 (s, 3H), 0.87 (s, 9H). |
| 145 | 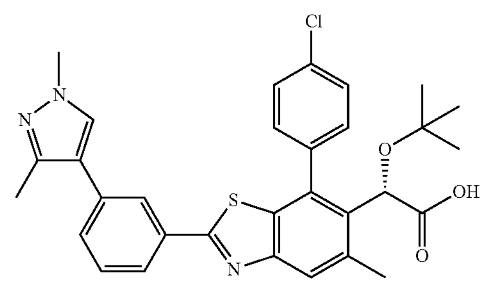 [SMILES: Cc1cc2nc(-c3cccc(-c4cn(C)nc4C)c3)sc2c(-c2ccc(Cl)cc2)c1[C@H](OC(C)(C)C)C(=O)O] | B | 560.12 | 560.2 | ¹H NMR (400 MHz, CD₃OD): δ 7.98 (s, 1H), 7.79-7.73 (m, 3H), 7.60-7.587 (m, 3H), 7.50-7.48 (m, 4H), 7.43-7.39 (m, 1H), 5.16 (s, 1H), 3.78 (s, 3H), 2.52 (s, 3H), 2.31 (s, 3H), 0.88 (s, 9H). |
| 146 | 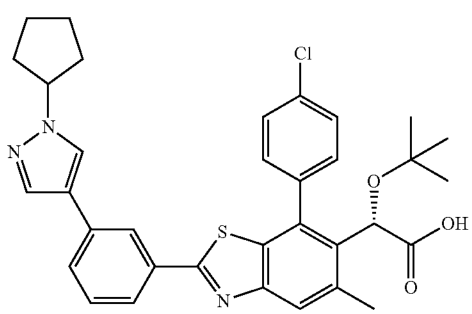 [SMILES: Cc1cc2nc(-c3cccc(-c4cnn(C5CCCC5)c4)c3)sc2c(-c2ccc(Cl)cc2)c1[C@H](OC(C)(C)C)C(=O)O] | B | 600.18 | 600.2 | ¹H NMR (400 MHz, CD3OD): δ 8.22 (s, 1H), 8.15 (s, 1H), 7.92 (s, 1H), 7.85-7.82 (m, 2H), 7.73-7.7.67 (m, 2H), 7.60-7.58 (m, 3H), 7.50-7.46 (m, 1H), 5.26 (s, 1H), 4.76-4.72 (m, 1H), 2.62 (s, 3H), 2.22-2.19 (m, 2H), 2.07-2.03 (m, 2H), 1.93-1.91 (m, 2H), 1.78-1.73 (m, 2H), 0.97 (s, 9H). |
| 147 | 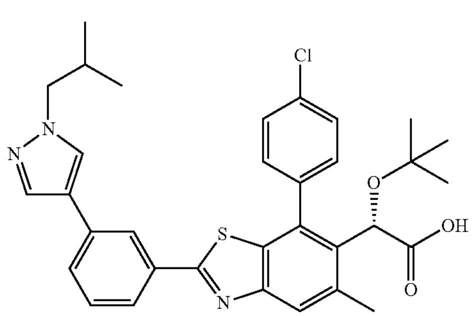 [SMILES: Cc1cc2nc(-c3cccc(-c4cnn(CC(C)C)c4)c3)sc2c(-c2ccc(Cl)cc2)c1[C@H](OC(C)(C)C)C(=O)O] | B | 588.17 | 588.2 | ¹H NMR (400 MHz, CD₃OD): δ 8.21 (s, 1H), 8.09 (s, 1H), 7.92 (s, 1H), 7.83-7.81 (m, 2H), 7.72-7.67 (m, 2H), 7.59-7.58 (m, 3H), 7.49-7.45 (m, 1H), 5.25 (s, 1H), 3.98 (d, J = 3.6 Hz, 2H), 2.61 (s, 3H), 2.24-2.20 (m, 1H), 0.97 (s, 9H), 0.94 (d, J = 3.4 Hz, 6H). |

-continued

| Compound Number | Structure | Method | Parent MW | LCMS-ESI+ | 1H NMR |
|---|---|---|---|---|---|
| 148 | 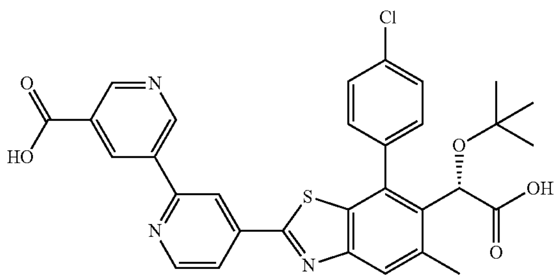 [SMILES: Cc1cc2nc(-c3ccnc(-c4cncc(C(=O)O)c4)c3)sc2c(-c2ccc(Cl)cc2)c1[C@H](OC(C)(C)C)C(=O)O] | C | 588.08 | 588.1 | ¹H NMR (400 MHz, CD₃OD): δ 9.49 (s, 1H), 9.22 (s, 1H), 9.14-9.10 (m, 1H), 8.86 (d, J = 5.1 Hz, 1H), 8.62 (s, 1H), 8.02 (dd, J = 5.1, 1.3 Hz, 1H), 7.97 (s, 1H), 7.73-7.68 (m, 1H), 7.64-7.59 (m, 3H), 5.28 (s, 1H), 2.64 (s, 3H), 0.98 (s, 9H). |
| 149 | 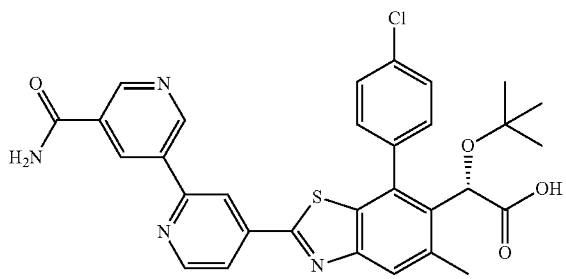 [SMILES: Cc1cc2nc(-c3ccnc(-c4cncc(C(N)=O)c4)c3)sc2c(-c2ccc(Cl)cc2)c1[C@H](OC(C)(C)C)C(=O)O] | C | 587.1 | 587.2 | ¹H NMR (400 MHz, CD₃OD): δ 9.49 (s, 1H), 9.14 (s, 1H), 9.10 (s, 1H), 8.86 (d, J = 5.1 Hz, 1H), 8.63 (s, 1H), 8.04 (d, J = 5.2 Hz, 1H), 7.95 (s, 1H), 7.73-7.67 (m, 1H), 7.63-7.58 (m, 3H), 5.28 (s, 1H), 2.64 (s, 3H), 0.99 (s, 9H). |
| 150 | 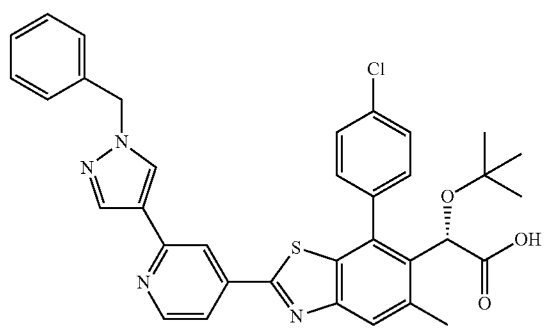 [SMILES: Cc1cc2nc(-c3ccnc(-c4cnn(Cc5ccccc5)c4)c3)sc2c(-c2ccc(Cl)cc2)c1[C@H](OC(C)(C)C)C(=O)O] | B | 622.19 | 622.2 | ¹H NMR (400 MHz, CD₃OD): δ 8.21 (s, 1H), 8.17 (s, 1H), 7.96 (s, 1H), 7.83-7.28 (m, 13H), 5.38 (s, 2H), 5.25 (s, 1H), 2.61 (s, 3H), 0.97 (s, 9H). |
| 151 | 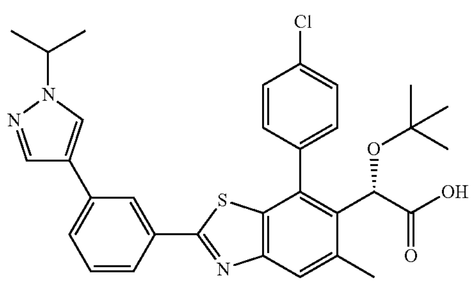 [SMILES: Cc1cc2nc(-c3cccc(-c4cnn(C(C)C)c4)c3)sc2c(-c2ccc(Cl)cc2)c1[C@H](OC(C)(C)C)C(=O)O] | B | 574.14 | 574.2 | ¹H NMR (400 MHz, CD3OD): δ 8.22 (s, 1H), 8.16 (s, 1H), 7.92 (s, 1H), 7.84-7.82 (m, 2H), 7.73-7.59 (m, 5H), 7.50-7.46 (m, 1H), 5.26 (s, 1H), 4.59-4.55 (m, 1H), 2.61 (s, 3H), 1.54 (d, J = 3.2 Hz, 6H), 0.97 (s, 9H). |
| 152 | 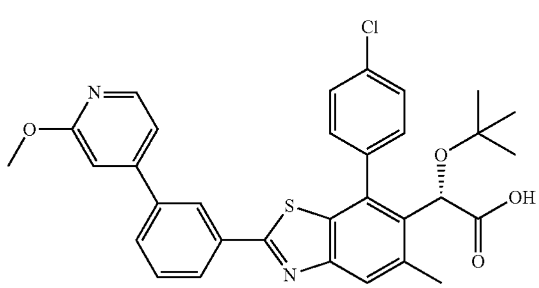 [SMILES: COc1cc(-c2cccc(-c3nc4cc(C)c([C@H](OC(C)(C)C)C(=O)O)c(-c5ccc(Cl)cc5)c4s3)c2)ccn1] | B | 573.11 | 573.2 | ¹H NMR (400 MHz, CD₃OD): δ 8.38 (s, 1H), 8.22 (d, J = 2.8 Hz, 1H), 8.08-8.06 (m, 1H), 7.89-7.87 (m, 2H), 7.70-7.58 (m, 5H), 7.35-7.34 (m, 1H), 7.18 (s, 1H), 5.26 (s, 1H), 3.99 (s, 3H), 2.62 (s, 3H), 0.97 (s, 9H). |

-continued

| Compound Number | Structure | Method | Parent MW | LCMS-ESI+ | 1H NMR |
|---|---|---|---|---|---|
| 153 | 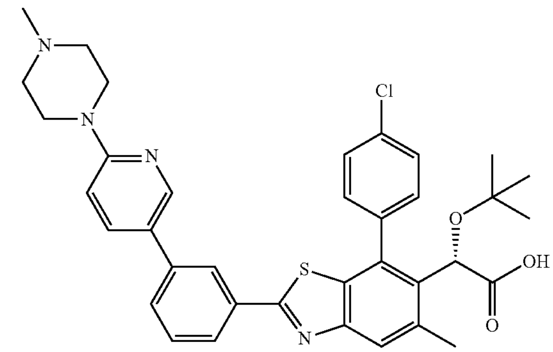 [SMILES: Cc1cc2nc(-c3cccc(-c4ccc(N5CCN(C)CC5)nc4)c3)sc2c(-c2ccc(Cl)cc2)c1[C@H](OC(C)(C)C)C(=O)O] | B | 641.23 | 641.2 | ¹H NMR (400 MHz, CD₃OD): δ 8.54 (d, J = 1 Hz, 1H), 8.27 (s, 1H), 8.02-7.94 (m, 2H), 7.87 (s, 1H), 7.77-7.68 (m, 2H), 7.60-7.58 (m, 4H), 7.07 (d, J = 4.4 Hz), 5.26 (s, 1H), 4.0-4.50 (m, 2H), 3.65-3.55 (m, 2H), 3.3-3.15 (m, 4H), 2.98 (s, 3H), 2.62 (s, 3H), 0.97 (s, 9H). |
| 154 | 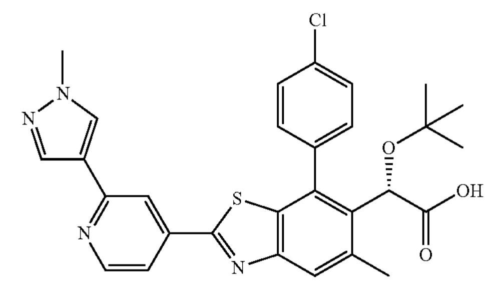 | C | 547.08 | 547.2 | ¹H NMR (400 MHz, CD₃OD): δ 8.64 (d, J = 5.7 Hz, 1H), 8.41 (s, 1H), 8.40 (s, 1H), 8.18 (s, 1H), 8.02 (d, J = 5.5 Hz, 1H), 7.98 (s, 1H), 7.70 (d, J = 7.8 Hz, 1H), 7.65-7.58 (m, 3H), 5.28 (s, 1H), 3.99 (s, 3H), 2.64 (s, 3H), 0.98 (s, 9H). |
| 155 | 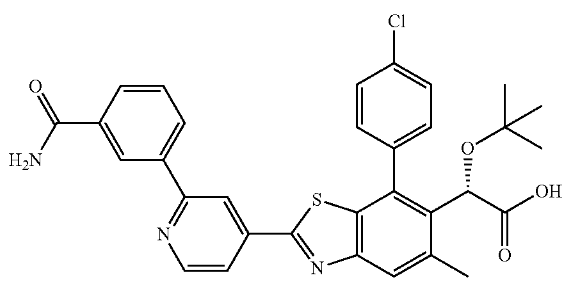 | C | 586.11 | 586.1 | ¹H NMR (400 MHz, CD₃OD): δ 8.79 (d, J = 5.3 Hz, 1H), 8.57 (s, 1H), 8.53 (s, 1H), 8.26 (d, J = 7.7 Hz, 1H), 8.04-7.99 (m, 2H), 7.94 (s, 1H), 7.72-7.68 (m, 1H), 7.67-7.58 (m, 4H), 5.28 (s, 1H), 2.63 (s, 3H), 0.98 (s, 9H). |
| 156 | 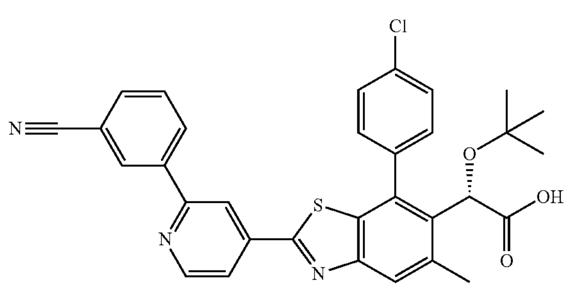 [SMILES: Cc1cc2nc(-c3ccnc(-c4cccc(C#N)c4)c3)sc2c(-c2ccc(Cl)cc2)c1[C@H](OC(C)(C)C)C(=O)O] | C | 568.1 | 568.1 | ¹H NMR (400 MHz, CD₃OD): δ 8.77 (d, J = 5.2 Hz, 1H), 8.47 (s, 1H), 8.45 (s, 1H), 8.36 (d, J = 7.9 Hz, 1H), 7.95-7.88 (m, 2H), 7.82 (d, J = 7.6 Hz, 1H), 7.73-7.65 (m, 2H), 7.62-7.57 (m, 3H), 5.28 (s, 1H), 2.63 (s, 3H), 0.98 (s, 9H). |
| 157 | 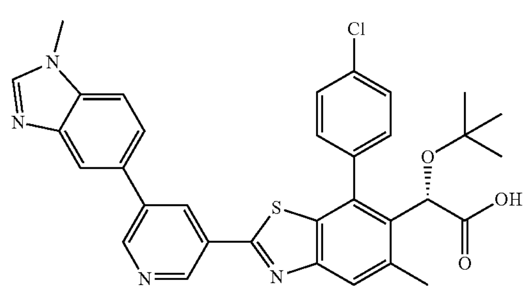 [SMILES: Cc1cc2nc(-c3cncc(-c4ccc5c(c4)ncn5C)c3)sc2c(-c2ccc(Cl)cc2)c1[C@H](OC(C)(C)C)C(=O)O] | | 597.14 | 597.2, 599.2 | ¹H NMR (400 MHz, CD₃OD): δ 9.48 (s, 1H), 9.26 (s, 1H), 9.07 (s, 1H), 8.82 (s, 1H), 8.24 (s, 1H), 8.10 (s, 2H), 7.93 (s, 1H), 7.69 (d, J = 8.9 Hz, 1H), 7.60 (d, J = 6.0 Hz, 3H), 5.27 (s, 1H), 4.21 (s, 3H), 2.63 (s, 3H), 0.98 (s, 9H). |

-continued

| Compound Number | Structure | Method | Parent MW | LCMS-ESI+ | 1H NMR |
|---|---|---|---|---|---|
| 158 | 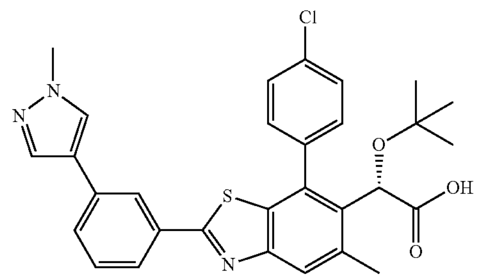 [SMILES: Cc1cc2nc(-c3cccc(-c4cnn(C)c4)c3)sc2c(-c2ccc(Cl)cc2)c1[C@H](OC(C)(C)C)C(=O)O] | B | 546.09 | 546.1 | ¹H NMR (400 MHz, CD₃OD): δ 8.20 (s, 1H), 8.06 (s, 1H), 7.90 (s, 1H), 7.84-7.82 (m, 2H), 7.17-7.59 (m, 5H), 7.50-7.48 (s, 1H), 5.26 (s, 1H), 3.94 (s, 3H), 2.61 (s, 3H), 0.97 (s, 9H). |
| 159 | 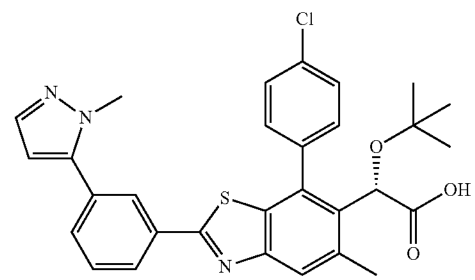 [SMILES: Cc1cc2nc(-c3cccc(-c4ccnn4C)c3)sc2c(-c2ccc(Cl)cc2)c1[C@H](OC(C)(C)C)C(=O)O] | B | 546.09 | 546.2 | ¹H NMR (400 MHz, CD₃OD): δ 8.16 (s, 1H), 8.07 (d, J = 3.6 Hz, 1H), 7.86 (s, 1H), 7.69-7.854 (m, 7H), 6.47 (d, J = 0.8 Hz, 1H), 5.25 (s, 1H), 3.92 (s, 3H), 2.61 (s, 3H), 0.97 (s, 9H). |
| 160 | 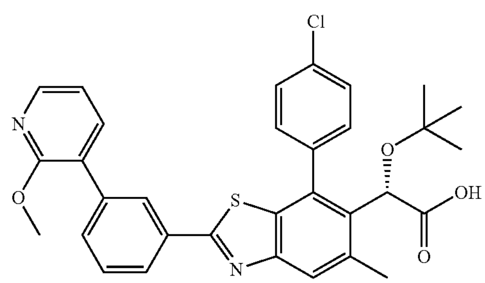 [SMILES: COc1ncccc1-c1cccc(-c2nc3cc(C)c([C@H](OC(C)(C)C)C(=O)O)c(-c4ccc(Cl)cc4)c3s2)c1] | B | 573.11 | 573.1 | ¹H NMR (400 MHz, CD₃OD): δ 8.21-8.16 (m, 3H), 7.99-7.85 (m, 2H), 7.79-7.67 (m, 3H), 7.59-7.53 (m, 4H), 7.10-7.07 (m, 1H), 5.25 (s, 1H), 3.96 (s, 3H), 2.61 (s, 3H), 0.97 (s, 9H). |
| 161 | 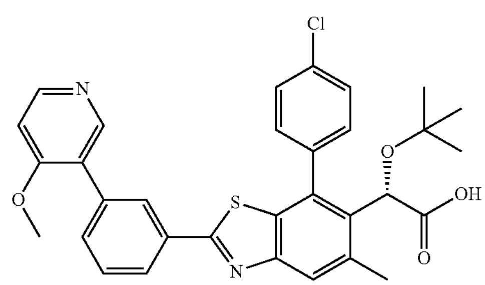 [SMILES: COc1ccncc1-c1cccc(-c2nc3cc(C)c([C@H](OC(C)(C)C)C(=O)O)c(-c4ccc(Cl)cc4)c3s2)c1] | B | 573.11 | 573.2 | ¹H NMR (400 MHz, CD₃OD): δ 8.63-8.60 (m, 2H), 8.16 (s, 1H), 8.03 (d, J = 4 Hz, 1H), 7.77 (s, 1H), 7.66-7.49 (m, 7H), 5.16 (s, 1H), 4.07 (s, 3H), 2.52 (s, 3H), 0.88 (s, 9H). |
| 162 | 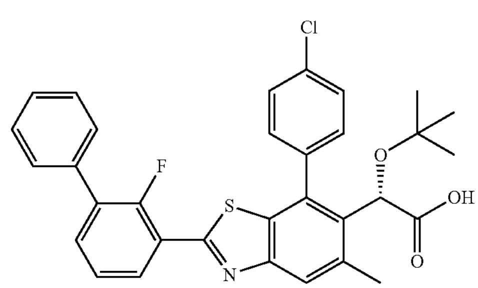 [SMILES: Cc1cc2nc(-c3cccc(-c4ccccc4)c3F)sc2c(-c2ccc(Cl)cc2)c1[C@H](OC(C)(C)C)C(=O)O] | G | 560.09 | 560.2 | ¹H NMR (400 MHz, CD₃OD): δ 8.22 (t, J = 7.2 Hz, 1H), 7.82 (s, 1H), 7.60-7.48 (m, 7H), 7.40-7.311 (m, 4H), 5.17 (s, 1H), 2.35 (s, 3H), 0.87 (s, 9H). |

-continued

| Compound Number | Structure | Method | Parent MW | LCMS-ESI+ | 1H NMR |
|---|---|---|---|---|---|
| 163 | 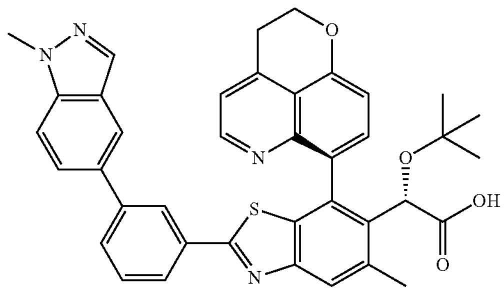 | G | 654.79 | 655.1 | ¹H NMR (400 MHz, CD₃OD): δ 8.77 (d, J = 2.8 Hz, 1H), 8.27-8.26 (m, 1H), 8.09 (s, 1H), 8.05 (d, J = 0.4 Hz, 1H), 8.03-8.02 (m, 1H), 7.94-7.90 (m, 2H), 7.84-7.82 (m, 1H), 7.78-7.73 (m, 2H), 7.65-7.63 (m, 1H), 7.58-7.54 (m, 1H), 7.41 (d, J = 4.2 Hz, 1H), 5.26 (s, 1H), 4.71-4.70 (m, 2H), 4.09 (s, 3H), 3.63 (t, J = 5.8 Hz, 2H), 2.79 (s, 3H), 0.93 (s, 9H). |
| 164 | 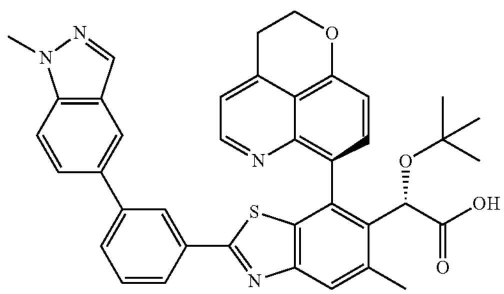 | G | 654.79 | 655.1 | ¹H NMR (400 MHz, CD₃OD): δ 8.64 (d, J = 2.6 Hz, 1H), 8.24-8.18 (m, 2H), 8.05-8.04 (m, 2H), 8.013-8.01 (m, 2H), 7.90-7.88 (m, 1H), 7.82-7.80 (m, 1H), 7.75-7.72 (m, 1H), 7.64-7.62 (m, 2H), 7.57-7.53 (m, 1H), 7.40 (d, J = 4.2 Hz, 1H), 5.31 (s, 1H), 4.67-4.66 (m, 2H), 4.09 (s, 3H), 3.57-3.56 (m, 2H), 2.74 (s, 3H), 0.91 (s, 9H). |
| 165 | 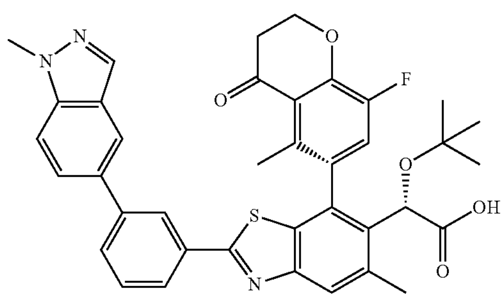 | G | 663.77 | 664.2 | ¹H NMR (400 MHz, CD₃OD): δ 8.32 (s, 1H), 8.08 (s, 2H), 7.97-7.7.79 (m, 4H), 7.65-7.53 (m, 3H), 5.20 (s, 1H), 4.71 (t, J = 6.4 Hz, 2H), 4.11 (s, 3H), 2.94 (t, J = 6.4 Hz, 2H), 2.67 (s, 3H), 2.30 (s, 3H), 1.06 (s, 9H). |
| 166 | 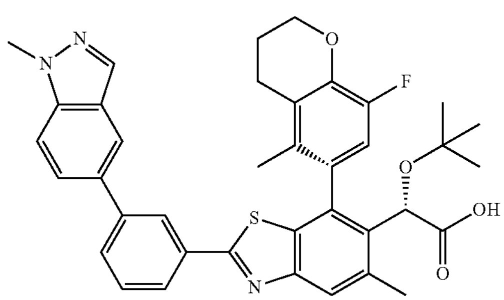 | G | 649.78 | 650.2 | ¹H NMR (400 MHz, CD₃OD): δ 8.32 (s, 1H), 8.09 (s, 2H), 7.97 (d, J = 4 Hz, 1H), 7.85-7.79 (m, 3H), 7.68-7.57 (m, 2H), 7.17 (d, J = 5.8 Hz, 1H), 5.27 (s, 1H), 4.30-4.25 (m, 2H), 4.11 (s, 3H), 2.78-2.69 (m, 2H), 2.63 (s, 3H), 2.16-2.13 (m, 2H), 1.92 (s, 3H), 1.02 (s, 9H). |
| 167 | 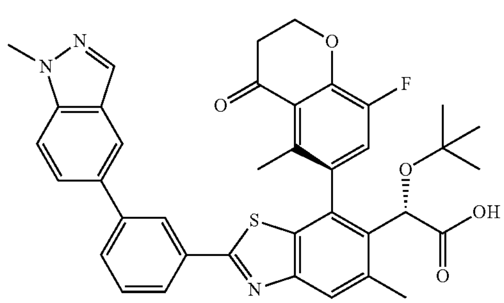 | G | 663.77 | 664.2 | ¹H NMR (400 MHz, CD₃OD): δ 8.21 (s, 1H), 7.98-7.97 (m, 2H), 7.85 (d, J = 3.8 Hz, 1H), 7.80 (s, 1H), 7.75-7.68 (m, 2H), 7.57-7.50 (m, 2H), 7.10 (d, J = 5.4 Hz), 5.11 (s, 1H), 4.60 (t, J = 6.6 Hz, 2H), 4.01 (s, 3H), 2.85 (t, J = 6.4 Hz, 2H), 2.63 (s, 3H), 2.24 (s, 3H), 1.04 (s, 9H). |

-continued

| Compound Number | Structure | Method | Parent MW | LCMS-ESI+ | 1H NMR |
|---|---|---|---|---|---|
| 168 | 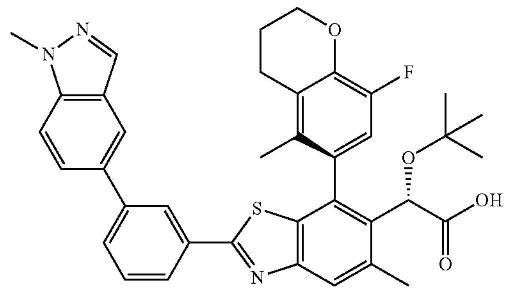 | G | 649.78 | 650.2 | ¹H NMR (400 MHz, CD₃OD): δ 8.31 (s, 1H), 8.08-8.07 (m, 2H), 7.95 (d, J = 4 Hz), 7.85-7.78 (m, 3H), 7.67-7.58 (m, 2H), 6.81 (d, J = 5.6 Hz), 5.19 (s, 1H), 4.27 (t, J = 2.6 Hz, 2H), 4.10 (s, 3H), 2.77-2.75 (m, 2H), 2.69 (s, 3H), 2.15-2.14 (m, 2H), 1.91 (s, 3H), 1.14 (s, 9H). |
| 169 | 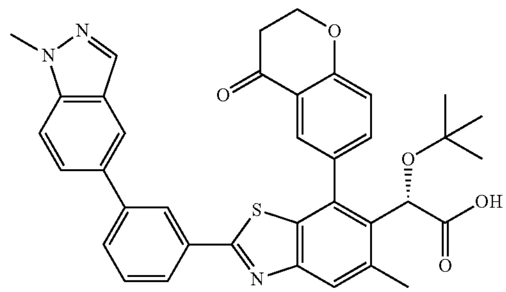 [SMILES: Cc1cc2nc(-c3cccc(-c4ccc5c(cnn5C)c4)c3)sc2c(-c2ccc3c(c2)C(=O)CCO3)c1[C@H](OC(C)(C)C)C(=O)O] | G | 631.75 | 632.2 | ¹H NMR (300 MHz, CD₃OD): δ 8.30 (s, 1H), 8.19-7.94 (m, 3H), 7.85-7.7.57 (m, 6H), 7.22-7.19 (m, 1H), 5.28 (s, 0.5H), 5.24 (s, 0.5H), 4.66-4.64 (m, 2H), 4.01 (s, 3H), 2.90-2.88 (m, 2H), 2.63 (s, 3H), 0.99 (s, 9H). |
| 170 | 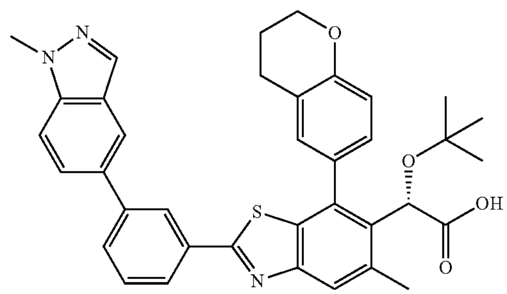 [SMILES: Cc1cc2nc(-c3cccc(-c4ccc5c(cnn5C)c4)c3)sc2c(-c2ccc3c(c2)CCCO3)c1[C@H](OC(C)(C)C)C(=O)O] | G | 617.77 | 618.2 | ¹H NMR (300 MHz, CD₃OD): δ 8.23 (s, 1H), 7.98 (s, 2H), 7.81-7.70 (m, 3H), 7.57-7.48 (m, 2H), 7.28-7.16 (m, 2H), 6.82 (s, 1H), 5.30 (s, 1H), 4.17-1.15 (m, 2H), 4.01 (s, 3H), 2.78-2.74 (m, 2H), 2.50 (s, 3H), 1.97 (M, 2H), 0.88 (s, 9H). |

Example 40

The following illustrate representative pharmaceutical dosage forms, containing a compound of formula I ('Compound X'), for therapeutic or prophylactic use in humans.

| | mg/tablet |
|---|---|
| (i) Tablet 1 | |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/ml |
|---|---|
| (iv) Injection 1 (1 mg/ml) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |

-continued

| | |
|---|---|
| Water for injection (v) Injection 2 (10 mg/ml) | q.s. ad 1 mL |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound, or a pharmaceutically acceptable salt thereof, of formula I':

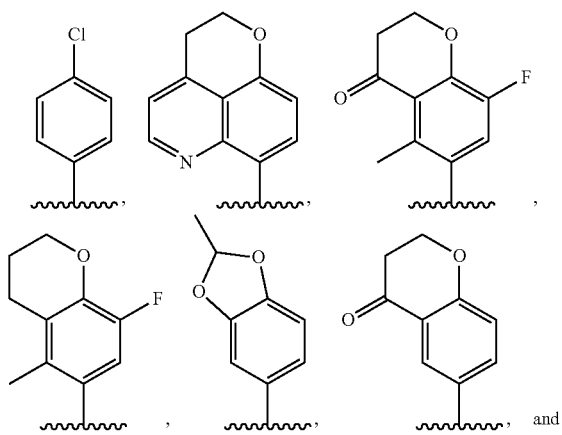

wherein:

$R^4$ is selected from the group consisting of:

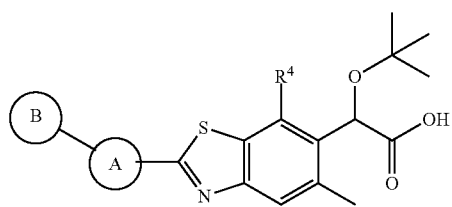

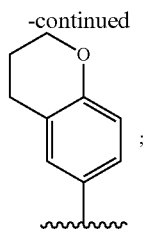

A is selected from the group consisting of phenyl, monocyclic heteroaryl and monocyclic heterocycle, wherein A is optionally substituted with 1 to 5 $Z^{1a}$ groups;

B is selected from the group consisting of $(C_6-C_{20})$aryl, heteroaryl and hetereocycle, wherein B is optionally substituted with 1 to 5 $Z^{1b}$ groups; or A and B together form a substituent selected from the group consisting of bicyclic $(C_9-C_{14})$aryl, bicyclic heteroaryl and bicyclic heterocycle, wherein each bicyclic $(C_9-C_{14})$aryl, bicyclic heteroaryl or bicyclic heterocycle is optionally substituted with 1 to 5 $Z^{1b}$ groups;

each $Z^{1a}$ is independently selected from the group consisting of halo, $(C_1-C_3)$alkyl, $(C_2-C_3)$alkenyl, $(C_2-C_3)$alkynyl, $(C_1-C_3)$haloalkyl, $(C_3-C_7)$carbocycle, 3-7 membered monocyclic heterocycle, —O$(C_1-C_3)$alkyl, —O$(C_2-C_3)$alkenyl, —O$(C_2-C_3)$alkynyl, —NR$_c$R$_d$, —NR$_a$C(O)R$_a$, —C(O)OR$_b$ and —C(O)NR$_c$R$_d$, wherein any $(C_3-C_7)$carbocycle or 3-7 membered monocyclic heterocycle of $Z^{1a}$ is optionally independently substituted with 1 to 5 halogen or $(C_1-C_6)$alkyl;

each $Z^{1b}$ is independently selected from the group consisting of halo, CN, $(C_1-C_6)$alkyl, $(C_2-C_6)$alkenyl, $(C_2-C_6)$alkynyl, $(C_1-C_6)$haloalkyl, $(C_3-C_7)$carbocycle, heteroaryl, 3-7 membered monocyclic heterocycle, $(C_6-C_{20})$aryl$(C_1-C_6)$alkyl-, —OH, —O$(C_1-C_6)$alkyl, —O$(C_2-C_6)$alkenyl, —O$(C_2-C_6)$alkynyl, —NR$_c$R$_d$, —NR$_a$C(O)R$_a$, —C(O)OR$_b$ and —C(O)NR$_c$R$_d$, wherein any $(C_3-C_7)$carbocycle or 3-7 membered monocyclic heterocycle of $Z^{1b}$ is optionally independently substituted with 1 to 5 halogen or $(C_1-C_6)$alkyl; and $R_a$, $R_b$, $R_c$ and $R_d$ are each independently H or $(C_1-C_6)$ alkyl;

wherein each heteroaryl, as a monocyclic ring or portion of a 2 to 3 ring system, has 1 to 6 carbon atoms and 1 to 4 heteroatoms selected from the group consisting of oxygen, nitrogen and sulfur, and each heterocycle, as a monocyclic ring or portion of a 2 to 3 ring system, has 1 to 6 carbon atoms and 1 to 3 heteroatoms selected from the group consisting of oxygen, nitrogen and sulfur.

2. The compound of claim 1, or a pharmaceutically acceptable salt thereof, wherein:

A is selected from the group consisting of phenyl, monocyclic heteroaryl and monocyclic heterocycle wherein A is optionally substituted with 1 to 5 $Z^{1a}$ groups; and B is selected from the group consisting of $(C_6-C_{20})$aryl, heteroaryl and hetereocycle wherein B is optionally substituted with 1 to 5 $Z^{1b}$ groups.

3. The compound of claim 2, or a pharmaceutically acceptable salt thereof, wherein A is selected from the group consisting of phenyl, monocyclic N-heteroaryl and monocyclic heterocycle, wherein A is optionally substituted with 1 to 5 $Z^{1a}$ groups.

4. The compound of claim 2, or a pharmaceutically acceptable salt thereof, wherein A is monocyclic N-heteroaryl, wherein monocyclic N-heteroaryl is optionally substituted with 1 to 5 $Z^{1a}$ groups.

5. The compound of claim 2, or a pharmaceutically acceptable salt thereof, wherein A is selected from the group consisting of phenyl, pyridinyl, pyrimidinyl, pyrazinyl, pyridinyl-2-one, tetrahydropyrimidinyl-2-one, imidazolidinyl-2-one, pyrrolidinyl-2-one and pyrrolidinyl, wherein A is optionally substituted with 1 to 5 $Z^{1a}$ groups.

6. The compound of claim 1, or a pharmaceutically acceptable salt thereof, wherein:
   A is selected from the group consisting of pyridinyl, pyrimidinyl, pyrazinyl, pyridinyl-2-one, tetrahydropyrimidinyl-2-one, imidazolidinyl-2-one, pyrrolidinyl-2-one and pyrrolidinyl, wherein A is optionally substituted with 1 to 5 $Z^{1a}$ groups; and
   B is selected from the group consisting of phenyl, pyridinyl, pyrazolyl, pyrimidinyl, indazolyl, pyrazolopyridine and benzimidazolyl, wherein B is optionally substituted with 1 to 5 $Z^{1b}$ groups.

7. The compound of claim 1, or a pharmaceutically acceptable salt thereof, wherein:
   A is selected from the group consisting of pyridinyl, pyrimidinyl, and pyrazinyl; and
   B is selected from the group consisting of phenyl, pyridinyl, pyrazolyl, pyrimidinyl, indazolyl, pyrazolopyridine and benzimidazolyl, wherein B is optionally substituted with 1 to 5 $Z^{1b}$ groups.

8. The compound of claim 1, or a pharmaceutically acceptable salt thereof, wherein A and B together form a substituent selected from the group consisting of bicyclic $(C_9-C_{14})$aryl, bicyclic heteroaryl and bicyclic heterocycle wherein each bicyclic $(C_9-C_{14})$aryl, bicyclic heteroaryl or bicyclic heterocycle is optionally substituted with 1 to 5 $Z^{1b}$ groups.

9. The compound of claim 2, or a pharmaceutically acceptable salt thereof, wherein A is selected from the group consisting of pyridinyl, pyrimidinyl and pyrazinyl, wherein A is optionally substituted with 1 to 5 $Z^{1a}$ groups.

10. The compound of claim 9, or a pharmaceutically acceptable salt thereof, wherein A is selected from the group consisting of pyridinyl, pyrimidinyl and pyrazinyl.

11. The compound of claim 1, or a pharmaceutically acceptable salt thereof, wherein A is not substituted with $Z^{1a}$.

12. The compound of claim 1, or a pharmaceutically acceptable salt thereof, wherein each $Z^{1b}$ is independently $C_1-C_6$ alkyl.

13. The compound of claim 1, or a pharmaceutically acceptable salt thereof, wherein A-B is selected from the group consisting of:

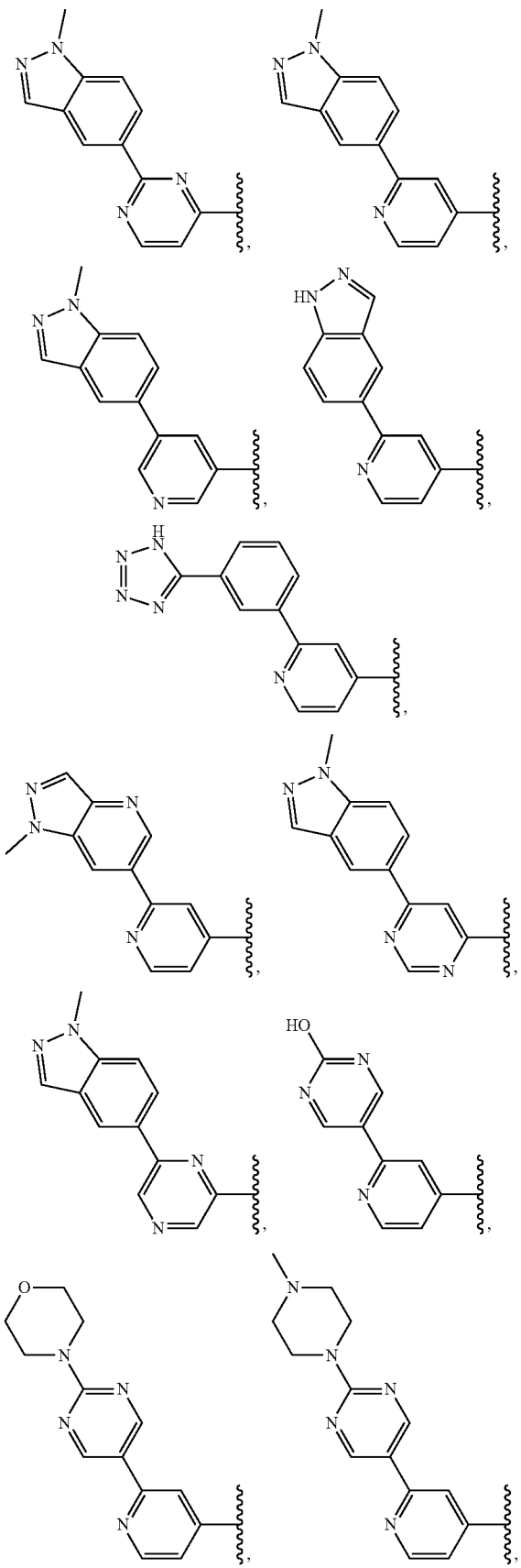

205
-continued
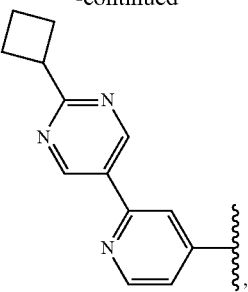
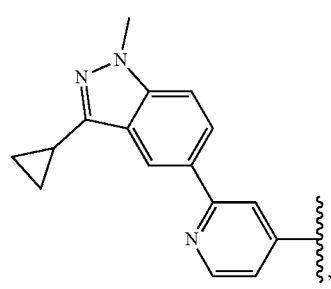
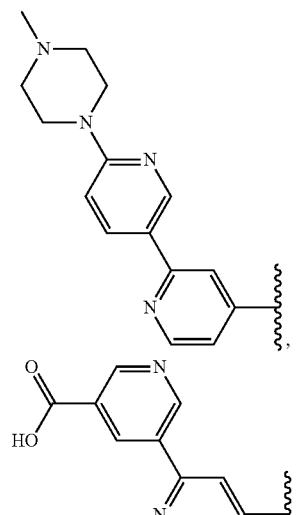
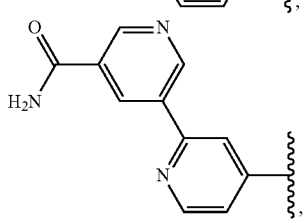
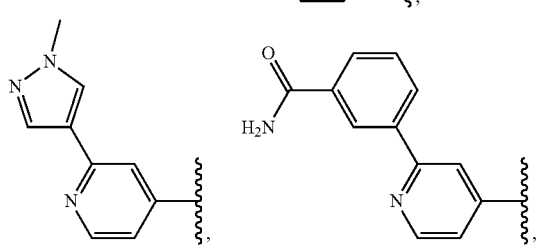
206
-continued
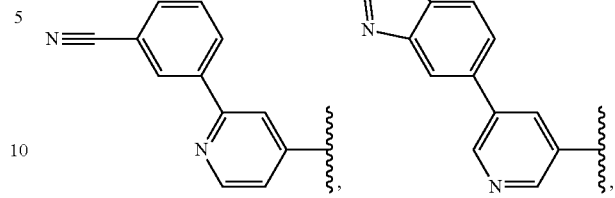
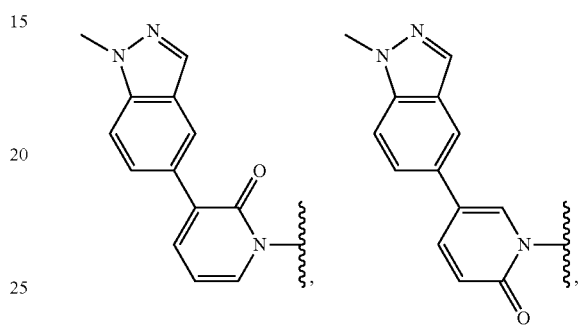
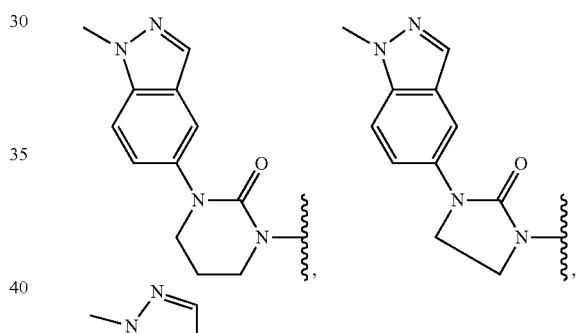
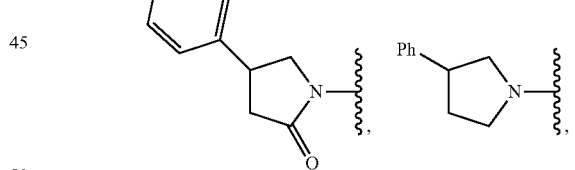
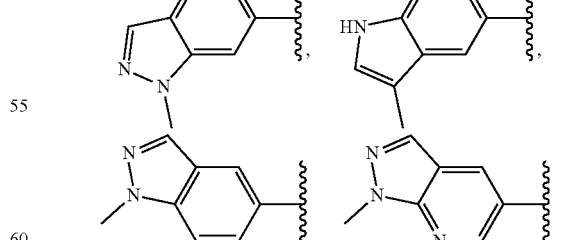
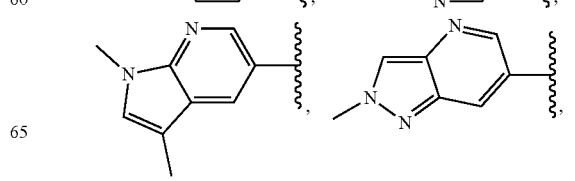

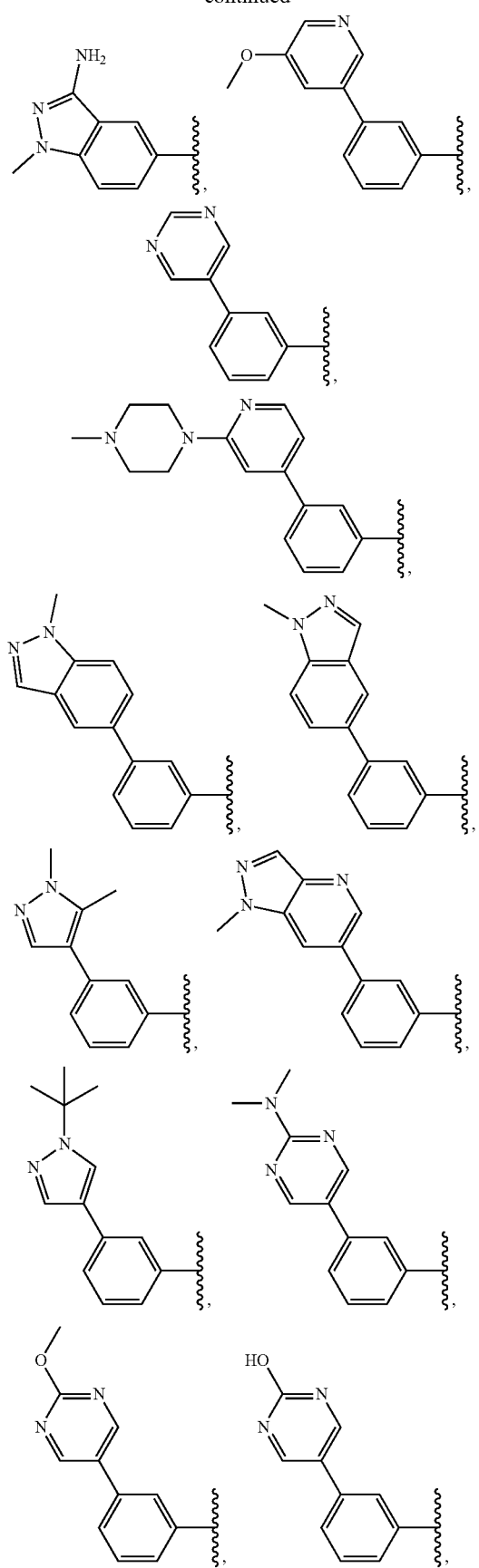
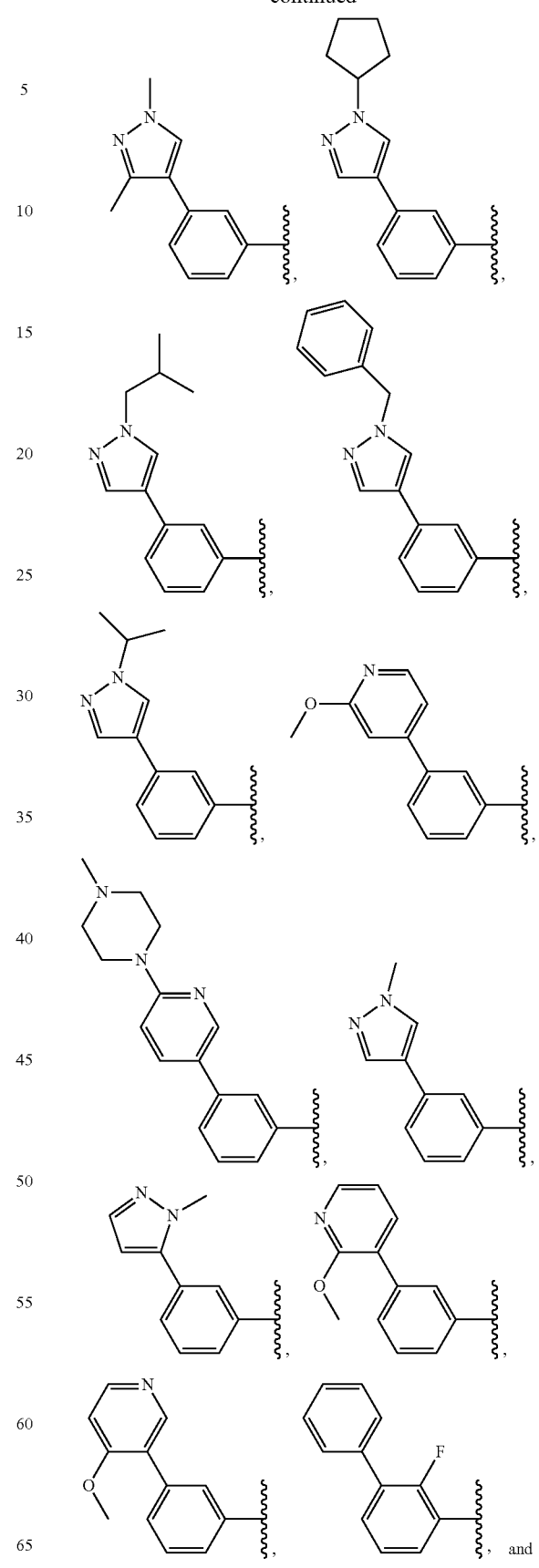

14. The compound of claim 1, or a pharmaceutically acceptable salt thereof, wherein R⁴ is selected from the group consisting of:
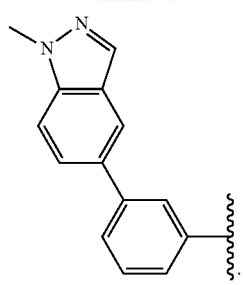
15. The compound of claim 1, or a pharmaceutically acceptable salt thereof, wherein R⁴ is selected from the group consisting of:
16. The compound of claim 1, or a pharmaceutically acceptable salt thereof, which is selected from the group consisting of:
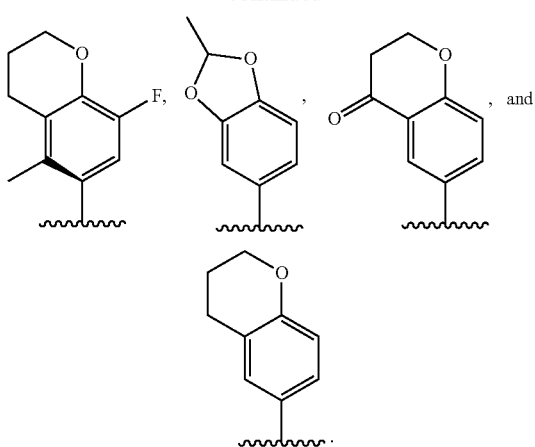

211
-continued
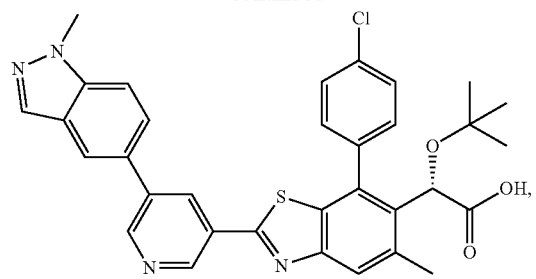
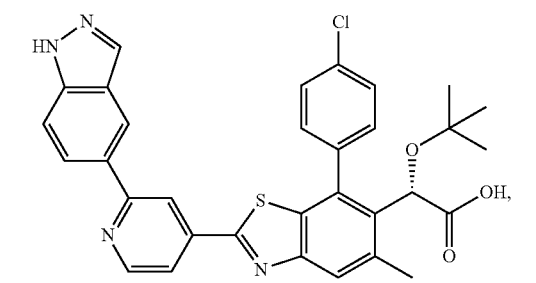
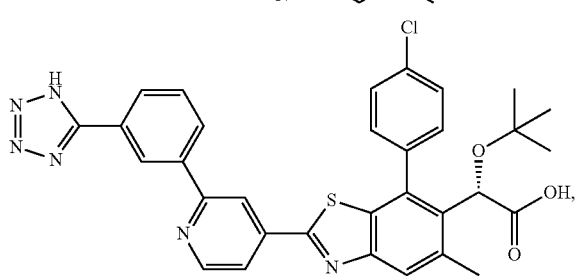
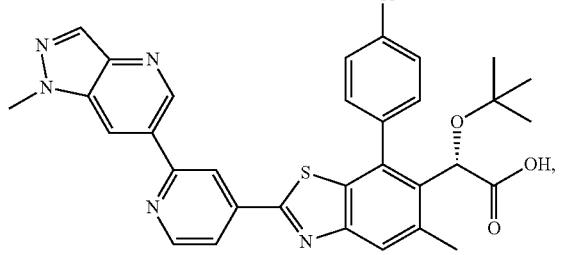
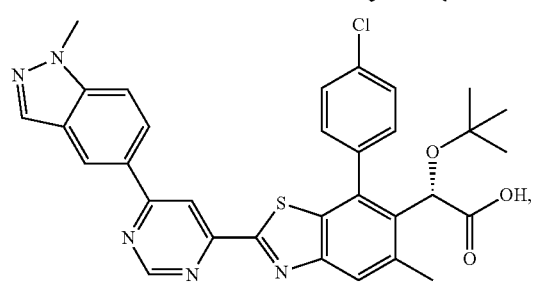
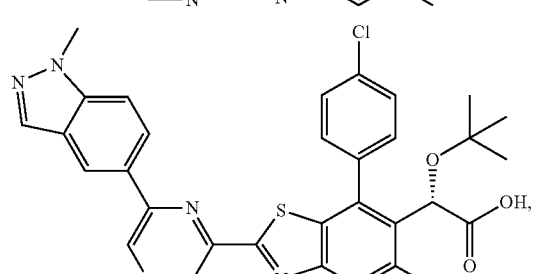
212
-continued
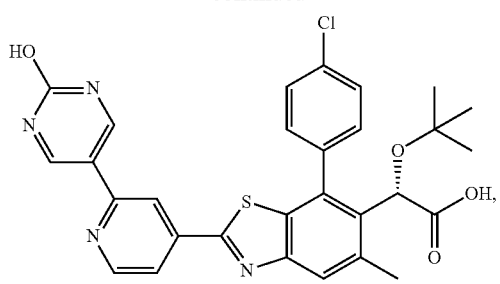
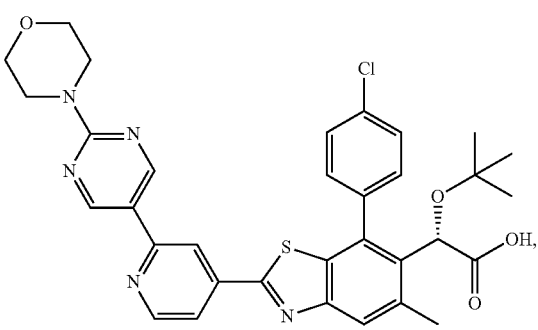
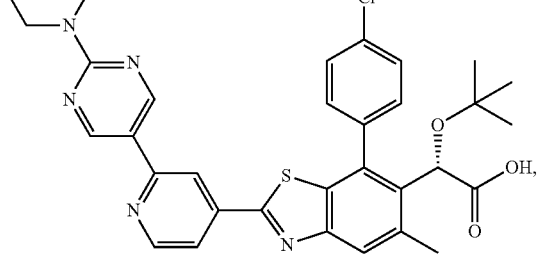
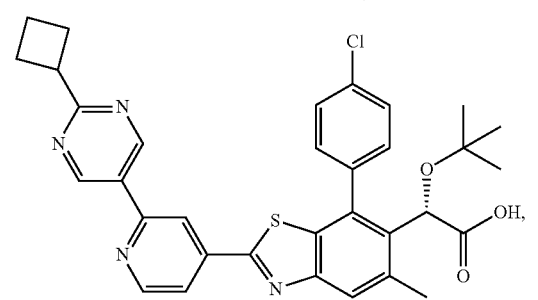
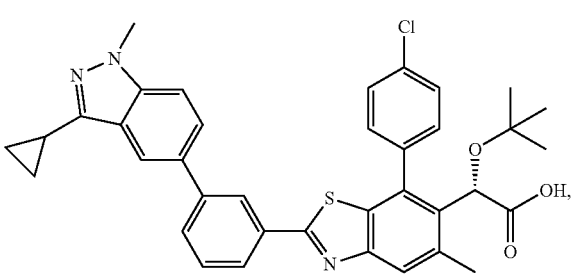

213
-continued
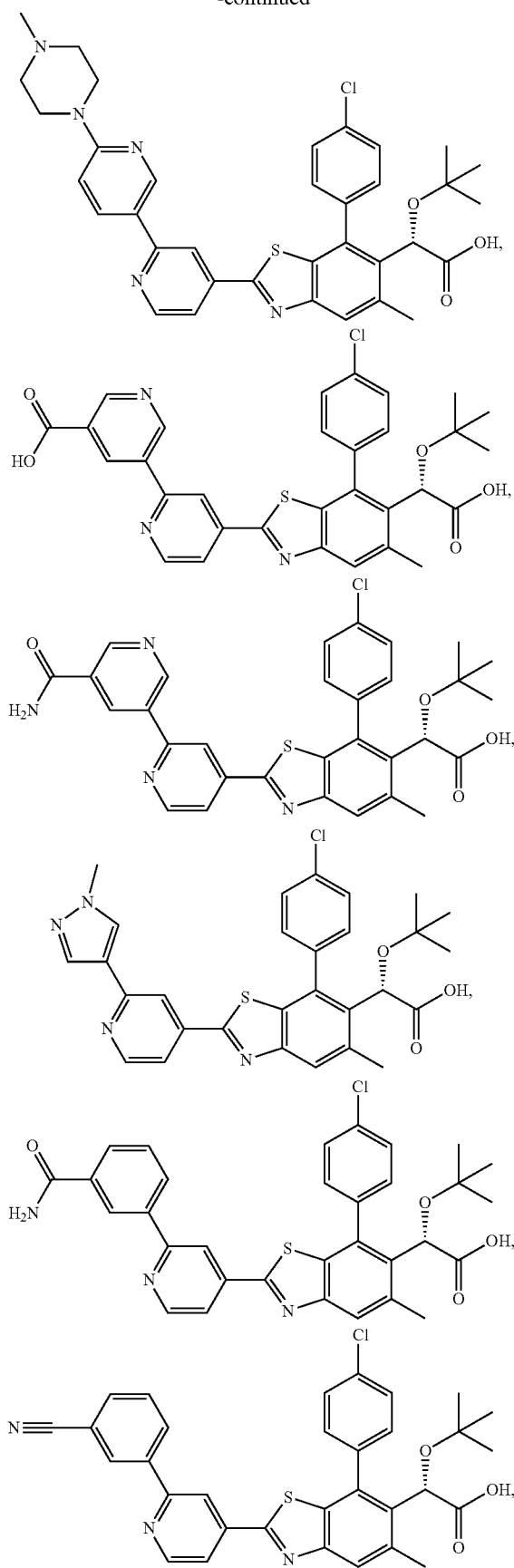
214
-continued
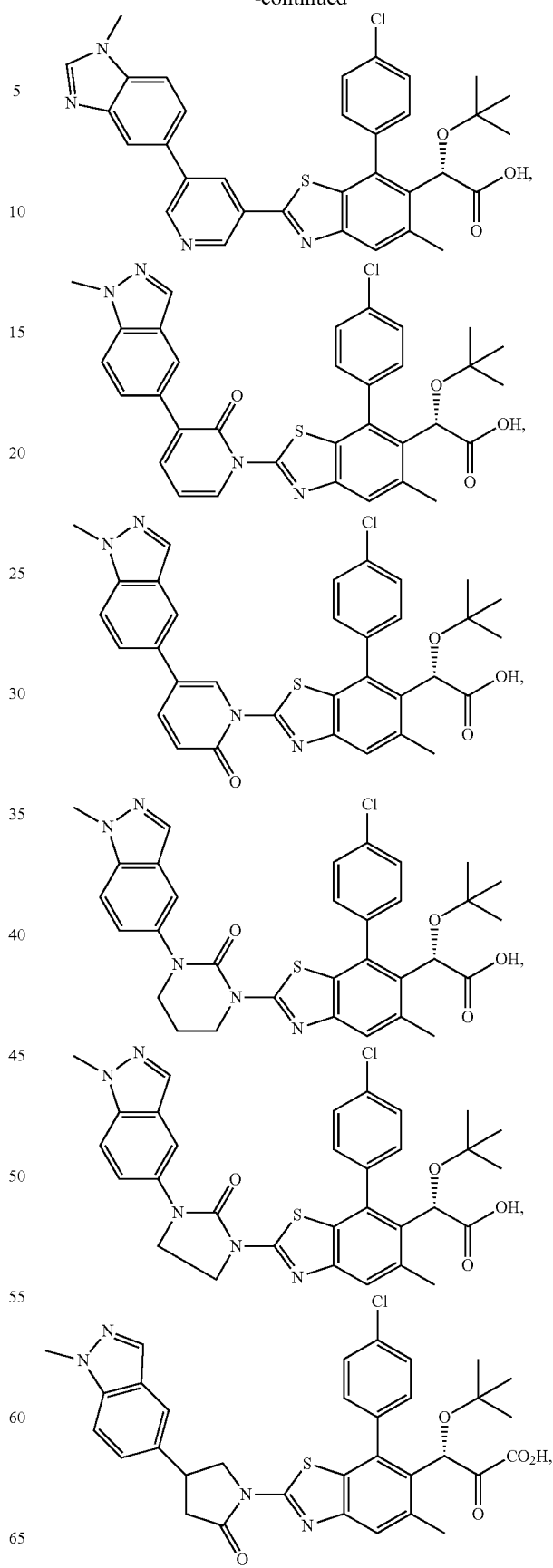

215
-continued
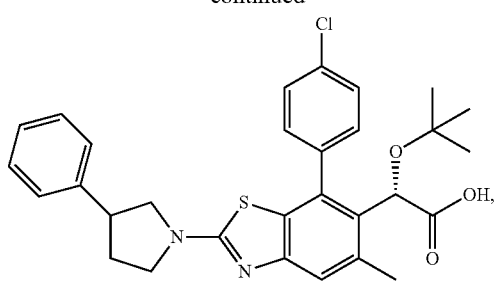
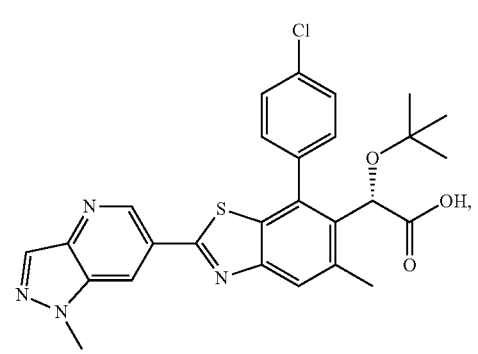
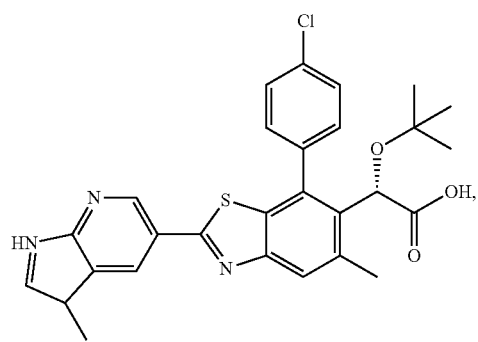
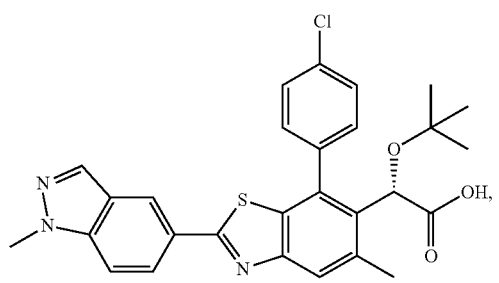
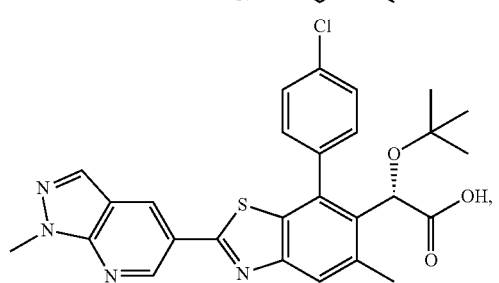
216
-continued
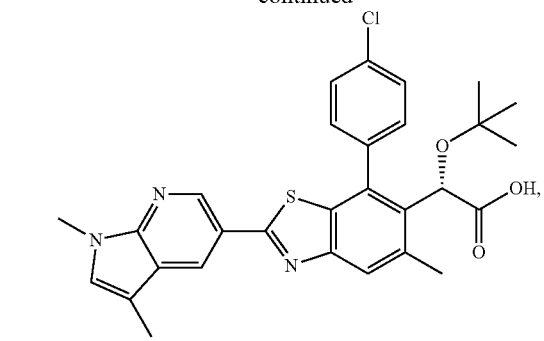
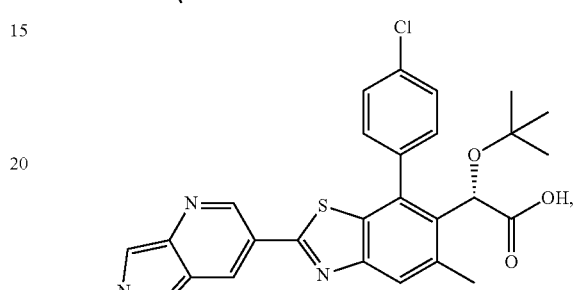
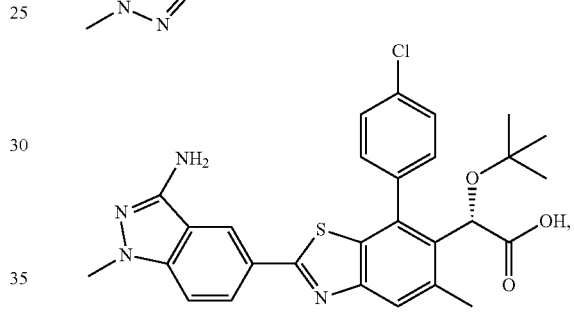
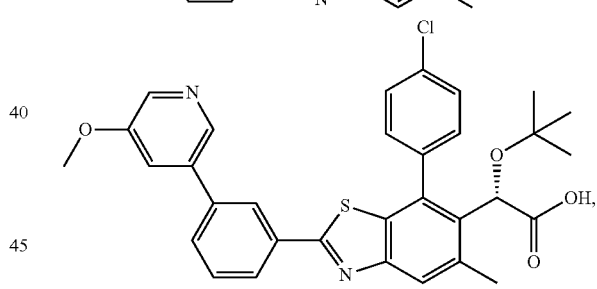
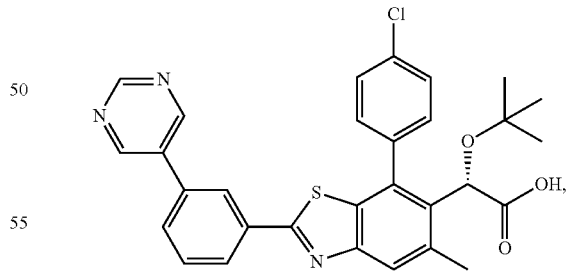
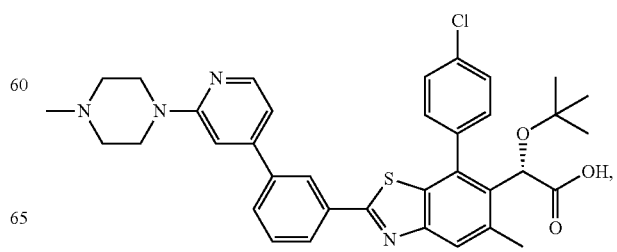

217
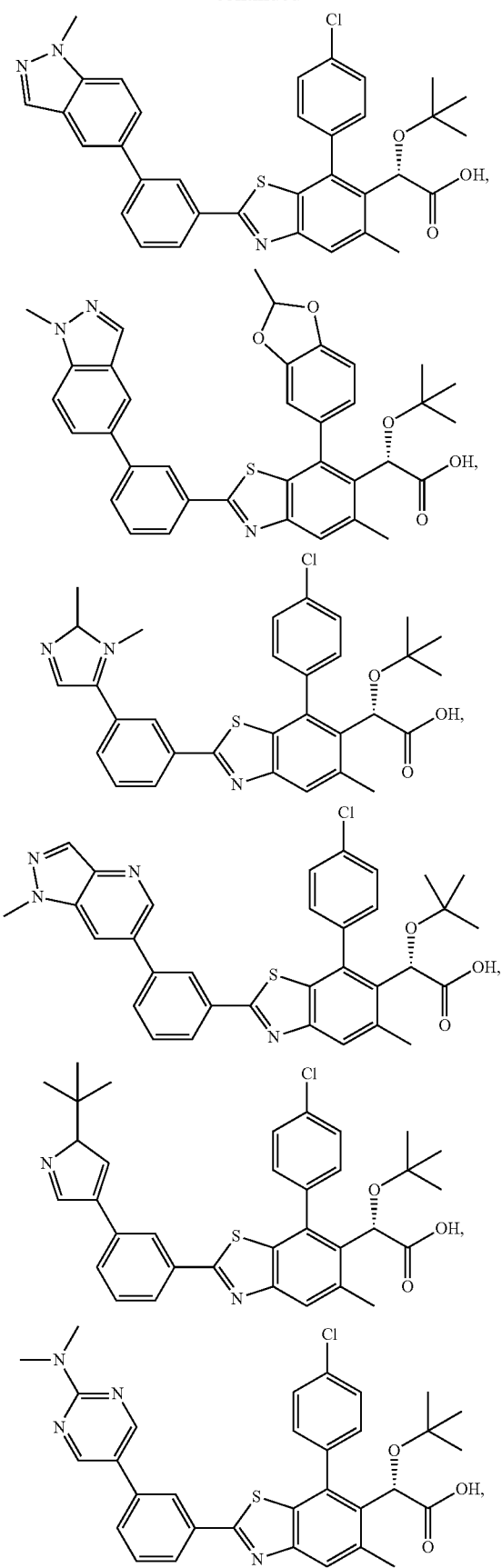
218
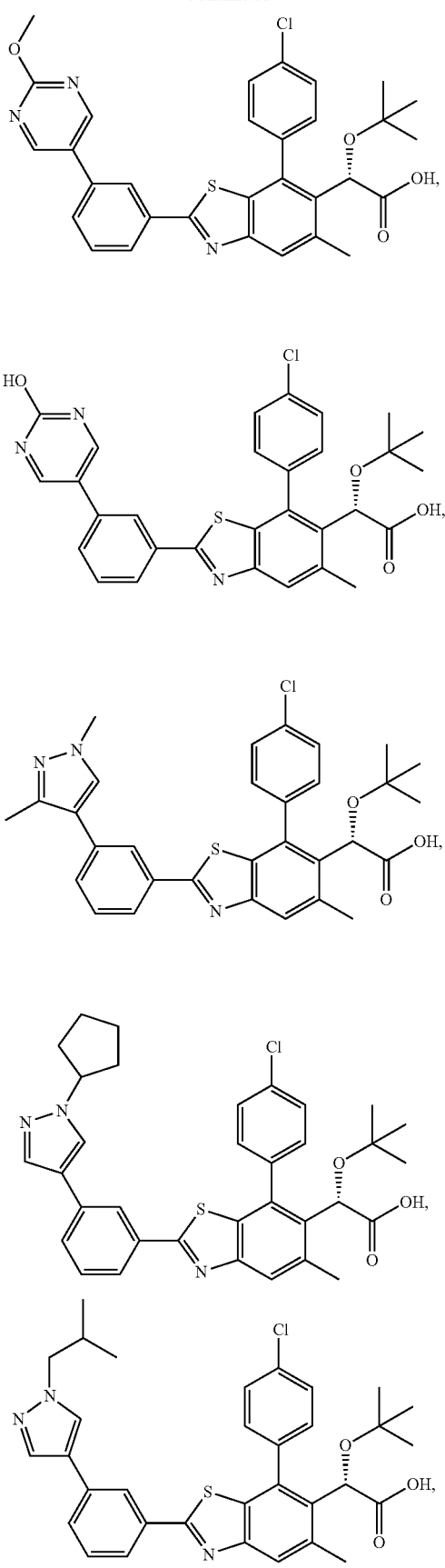

219
-continued
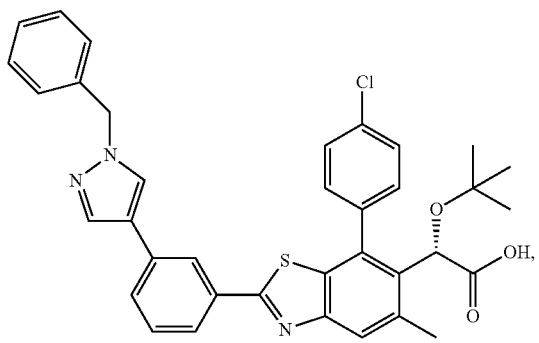
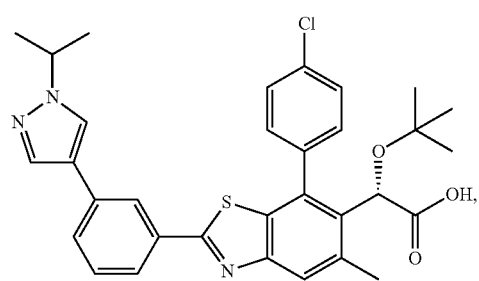
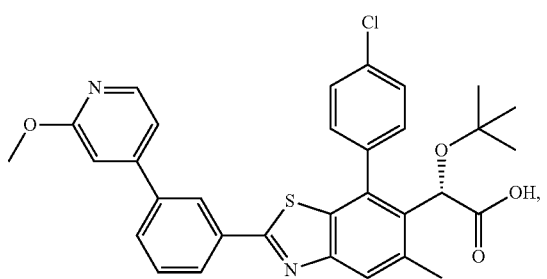
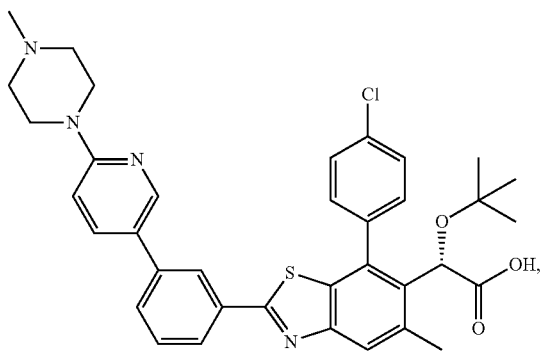
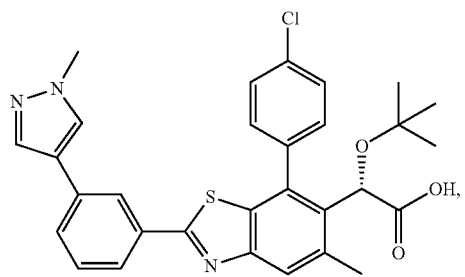
220
-continued
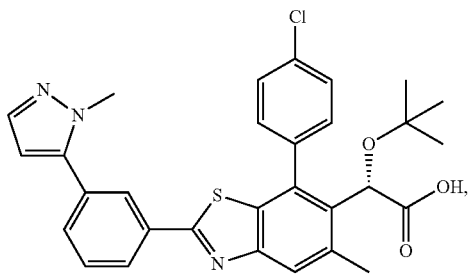
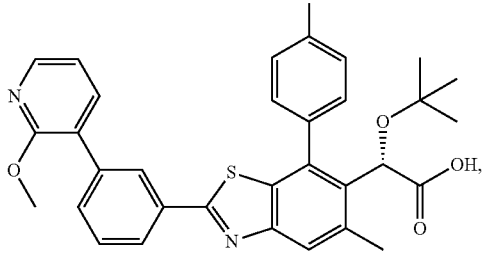
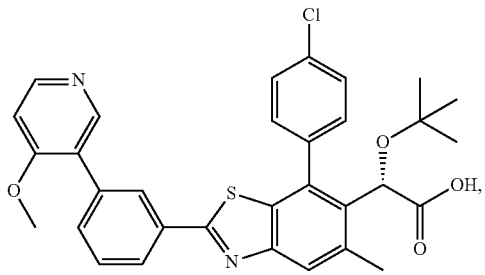
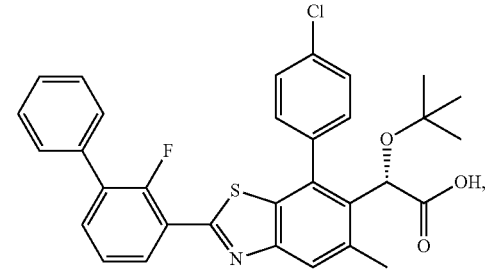
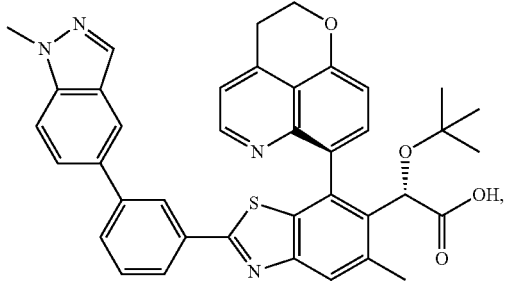
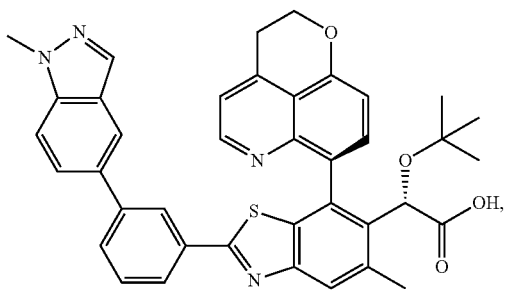

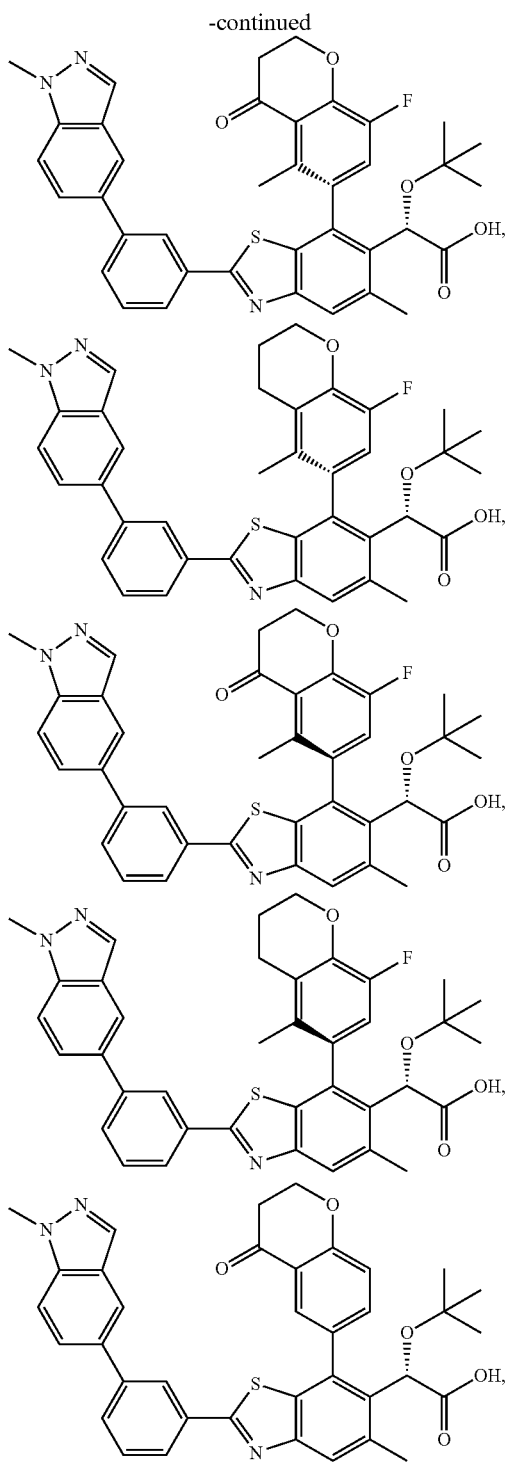

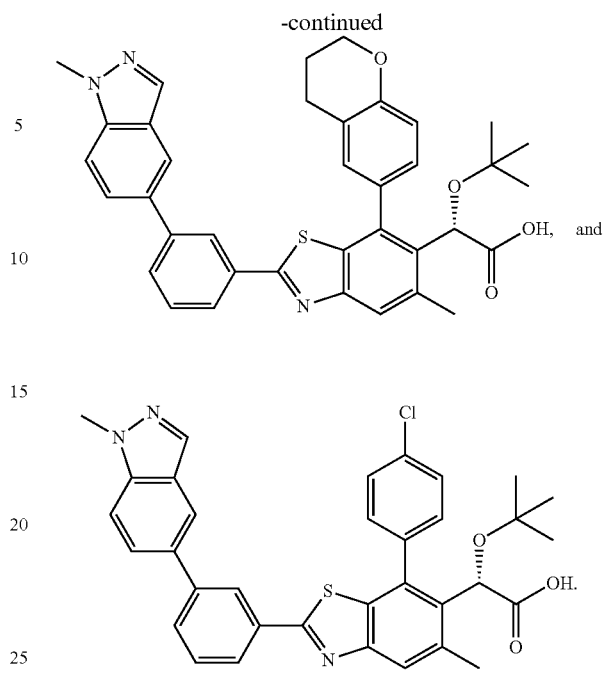

17. The compound of claim 1, or a pharmaceutically acceptable salt thereof, wherein each $Z^{1b}$ is independently selected from the group consisting of CN, $(C_2-C_6)$alkenyl, $(C_2-C_6)$alkynyl, $(C_1-C_6)$haloalkyl, $(C_3-C_7)$carbocycle, heteroaryl, 3-7 membered monocyclic heterocycle, $(C_6-C_{20})$aryl $(C_1-C_6)$alkyl-, —OH, —O$(C_1-C_6)$alkyl, —O$(C_2-C_6)$alkenyl, —O$(C_2-C_6)$alkynyl, —NR$_c$R$_d$, —NR$_a$C(O)R$_a$, and —C(O)NR$_c$R$_d$.

18. A pharmaceutical composition comprising the compound of claim 1, or a pharmaceutically acceptable salt thereof, and a pharmaceutically acceptable carrier.

19. A method for treating an HIV infection in a human comprising administering the compound of claim 1, or a pharmaceutically acceptable salt thereof, to the human.

20. A method for treating an HIV infection in a human comprising administering to the human in need thereof a therapeutically effective amount of the compound of claim 1, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV.

\* \* \* \* \*